United States Patent
Meerpoel et al.

(10) Patent No.: US 7,816,360 B2
(45) Date of Patent: *Oct. 19, 2010

(54) MTP INHIBITING ARYL PIPERIDINES OR PIPERAZINES SUBSTITUTED WITH 5-MEMBERED HETEROCYCLES

(75) Inventors: Lieven Meerpoel, Beerse (BE); Leo Jacobus Jozef Backx, Arendonk (BE); Libuse Jaroskova, Vosselaar (BE); Peter Walter Maria Roevens, Malle (BE); Louis Jozef Elisabeth Van Der Veken, Vosselaar (BE); Marcel Viellevoye, Breda (NL); Joannes Theodorus Maria Linders, Eindhoven (NL)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 12/341,567

(22) Filed: Dec. 22, 2008

(65) Prior Publication Data

US 2010/0004263 A1 Jan. 7, 2010

Related U.S. Application Data

(63) Continuation of application No. 10/589,515, filed as application No. PCT/EP2005/051010 on Mar. 7, 2005, now Pat. No. 7,504,400.

(60) Provisional application No. 60/556,336, filed on Mar. 25, 2004.

(30) Foreign Application Priority Data

Mar. 10, 2004 (EP) .................................. 04075771

(51) Int. Cl.
*A61K 31/496* (2006.01)
*A61K 31/454* (2006.01)
*C07D 401/04* (2006.01)
*C07D 401/10* (2006.01)
*C07D 401/12* (2006.01)
*C07D 401/14* (2006.01)
*C07D 405/12* (2006.01)
*C07D 417/12* (2006.01)
*C07D 487/04* (2006.01)
*C07D 233/74* (2006.01)
*C07D 249/12* (2006.01)

(52) U.S. Cl. .......................... 514/253.04; 514/253.09; 514/254.02; 514/254.05; 514/326; 544/362; 544/363; 544/364; 544/366; 544/369; 546/210

(58) Field of Classification Search .................. None
See application file for complete search history.

(56) References Cited

FOREIGN PATENT DOCUMENTS

| WO | WO 00/32582 A1 | 6/2000 |
|---|---|---|
| WO | WO 01/96327 A1 | 12/2001 |
| WO | WO 02/20501 A1 | 3/2002 |

OTHER PUBLICATIONS

Chan et al., "New N-and O-Arylations with Phenylboronic Acids and Cupric Acetate1.", Tetrahedron Letters, 1998, pp. 2933-2936, 39, Elsevier Science Ltd.
Hudson, Derek, "Methodological Implications of Simultaneous Solid-Phase Peptide Synthesis. 1. Comparison of Different Coupling Procedures.", J.Org. Chem., 1998, pp. 617-624, 53.
Sharp et al., "Cloning and gene defects in microsomal triglyceride transfer protein associated with abetalipoproteinaemia.", Letters to Nature, 1993, pp. 65-69, 365.
Willoughby et al., "Solid Phase Synthesis of Aryl Amines.", Tetrahedron Letters, 1996, pp. 7181-7184, 37(40), Elsevier Science Ltd.
Wolfe et al., "An Improved Catalyst System for Aromatic Carbon-Nitrogen Bond Formation: The Possible Involvement of Bis(Phosphine) Palladium Complexes as key Intermediates.", J.Am. Chem.Soc., 1996, pp. 7215-7216, 118.
PCT International Search Report dated Jul. 19, 2005 for PCT Application. No. PCT/EP2005/051010 which relates to U.S. Appl. No. 12/341,567.
Written Opinion of the International Searching Authority for PCT Application No. PCT/EP2005/051010.
Wetterau et al, "Purification and characterization of microsomal triglyceride and cholesteryl ester transfer protein from bovine liver microsomes.", Chemistry and Physics of Lipids, 1985, pp. 205-222, vol. 38.

*Primary Examiner*—Emily Bernhardt

(57) ABSTRACT

The present invention is concerned with novel aryl piperidine or piperazine compounds substituted with certain 5-membered heterocycles having apoB secretion/MTP inhibiting activity and concomitant lipid lowering activity. The invention further relates to methods for preparing such compounds, pharmaceutical compositions comprising said compounds as well as the use of said compounds as a medicine for the treatment of hyperlipidemia, obesity and type II diabetes.

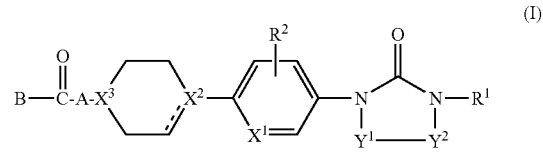

(I)

The invention further relates to methods for preparing such compounds, pharmaceutical compositions comprising said compounds as well as the use of said compounds as a medicine for the treatment of atherosclerosis, pancreatitis, obesity, hypertriglyceridemia, hypercholesterolemia, hyperlipidemia, diabetes and type II diabetes.

23 Claims, No Drawings

MTP INHIBITING ARYL PIPERIDINES OR PIPERAZINES SUBSTITUTED WITH 5-MEMBERED HETEROCYCLES

CROSS REFERENCE TO RELATED APPLICATIONS

This application is a continuation application of U.S. Ser. No. 10/589,515, filed Aug. 16, 2006, now U.S. Pat. No. 7,504,400 the disclosure of which is hereby incorporated by reference in its entirety, which is a US national stage of Application No. PCT/EP2005/051010, filed Mar. 7, 2005, which application claims priority from EP 04075771.8 filed Mar. 10, 2004, and U.S. Provisional Application No. 60/556,336 filed Mar. 25, 2004.

The present invention is concerned with novel aryl piperidine or piperazine compounds substituted with certain 5-membered heterocycles having apoB secretion/MTP inhibiting activity and concomitant lipid lowering activity. The invention further relates to methods for preparing such compounds, pharmaceutical compositions comprising said compounds as well as the use of said compounds as a medicine for the treatment of atherosclerosis, pancreatitis, obesity, hypertriglyceridemia, hypercholesterolemia, hyperlipidemia, diabetes and type II diabetes.

Obesity is the cause of a myriad of serious health problems like the adult onset of diabetes and heart disease. In addition, losing weight is getting an obsession among an increasing proportion of the human population.

The causal relationship between hypercholesterolemia, particularly that associated with increased plasma concentrations of low density lipoproteins (hereinafter referred as LDL) and very low density lipoproteins (hereinafter referred as VLDL), and premature atherosclerosis and/or cardiovascular disease is now widely recognized. However, a limited number of drugs are presently available for the treatment of hyperlipidemia.

Drugs primarily used for the management of hyperlipidemia include bile acid sequestrant resins such as cholestyramine and colestipol, fibric acid derivatives such as bezafibrate, clofibrate, fenofibrate, ciprofibrate and gemfibrozil, nicotinic acid and cholesterol synthesis inhibitors such as HMG Co-enzyme-A reductase inhibitors. There still remains a need for new lipid lowering agents with improved efficiency and/or acting via other mechanisms than the above mentioned drugs.

Plasma lipoproteins are water-soluble complexes of high molecular weight formed from lipids (cholesterol, triglyceride, phospholipids) and apolipoproteins. Five major classes of lipoproteins that differ in the proportion of lipids and the type of apolipoprotein, all having their origin in the liver and/or the intestine, have been defined according to their density (as measured by ultracentrifugation). They include LDL, VLDL, intermediate density lipoproteins (hereinafter referred as IDL), high density lipoproteins (hereinafter referred as HDL) and chylomicrons. Ten major human plasma apolipoproteins have been identified. VLDL, which is secreted by the liver and contains apolipoprotein B (hereinafter referred as Apo-B), undergoes degradation to LDL which transports 60 to 70% of the total serum cholesterol. Apo-B is also the main protein component of LDL. Increased LDL-cholesterol in serum, due to oversynthesis or decreased metabolism, is causally related to atherosclerosis. In contrast high density lipoproteins (hereinafter referred as HDL), which contain apolipoprotein A1, have a protective effect and are inversely correlated with the risk of coronary heart disease. The HDL/LDL ratio is thus a convenient method of assessing the atherogenic potential of an individual's plasma lipid profile.

The two isoforms of apolipoprotein (apo) B, apo B-48 and apo B-100, are important proteins in human lipoprotein metabolism. Apo B-48, is about 48% the size of apo B-100 on sodium dodecyl sulfate-polyacrylamide gels, is synthesized by the intestine in humans. Apo B-48 is necessary for the assembly of chylomicrons and therefore has an obligatory role in the intestinal absorption of dietary fats. Apo B-100, which is produced in the liver in humans, is required for the synthesis and secretion of VLDL. LDL, which contain about ⅔ of the cholesterol in human plasma, are metabolic products of VLDL. Apo B-100 is virtually the only protein component of LDL. Elevated concentrations of apo B-100 and LDL cholesterol in plasma are recognized risk factors for developing atherosclerotic coronary artery disease.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias have also been classified into common hypercholesterolaemia, familial combined hyperlipidaemia, familial hypercholesterolaemia, remnant hyperlipidaemia, chylomicronaemia syndrome and familial hypertriglyceridaemia.

Microsomal triglyceride transfer protein (hereinafter referred as MTP) is known to catalyze the transport of triglyceride and cholesteryl ester by preference to phospholipids such as phosphatidylcholine. It was demonstrated by D. Sharp et al., *Nature* (1993) 365:65 that the defect causing abetalipoproteinemia is in the MTP gene. This indicates that MTP is required for the synthesis of Apo B-containing lipoproteins such as VLDL, the precursor to LDL. It therefore follows that an MTP inhibitor would inhibit the synthesis of VLDL and LDL, thereby lowering levels of VLDL, LDL, cholesterol and triglyceride in humans.

MTP inhibitors have been disclosed in WO-00/32582, WO-01/96327 and WO-02/20501.

The present invention is based on the unexpected discovery that a group of novel aryl piperidine or piperazine compounds substituted with certain 5-membered heterocycles have apoB secretion/MTP inhibiting activity. These compounds of formula (I) can act systemically and/or as selective MTP inhibitors, i.e. is able to selectively block MTP at the level of the gut wall in mammals.

The present invention relates to a family of novel compounds of formula (I)

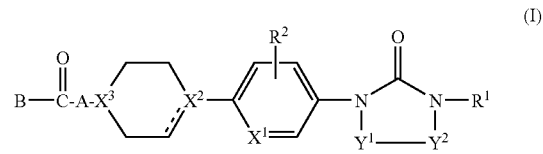

the N-oxides, the pharmaceutically acceptable acid addition salts and the stereochemically isomeric forms thereof, wherein the dotted line is an optional bond and is absent when $X^2$ represents nitrogen; the radical —$Y^1$—$Y^2$— is a radical of formula $$-N=CH-\qquad(a\text{-}1),$$

$$-CH=N-\qquad(a\text{-}2),$$

$$-CH_2-CH_2-\qquad(a\text{-}3),$$

$$-CH=CH-\qquad(a\text{-}4),$$

wherein in the bivalent radicals of formula (a-1) or (a-2) the hydrogen atom may optionally be replaced by $C_{1-6}$alkyl or phenyl; or in the bivalent radicals of formula (a-3) or (a-4) one or two hydrogen atoms may optionally be replaced by $C_{1-6}$alkyl or phenyl;

$X^1$ is carbon or nitrogen;

at least one of $X^2$ or $X^3$ represents nitrogen and the other $X^2$ or $X^3$ represents CH or carbon when the dotted line represents a bond, or both $X^2$ and $X^3$ represent nitrogen;

$R^1$ is $C_{1-6}$alkyl;
   aryl$^1$;
   $C_{1-6}$alkyl substituted with hydroxy, $C_{3-6}$cycloalkyl, aryl$^1$ or naphthalenyl;
   $C_{3-6}$cycloalkyl;
   $C_{3-6}$cycloalkenyl;
   $C_{3-6}$alkenyl;
   $C_{3-6}$alkenyl substituted with aryl$^1$;
   $C_{3-6}$alkynyl;
   $C_{3-6}$alkynyl substituted with aryl$^1$;
   $C_{1-4}$alkyloxy$C_{1-4}$alkanediyl optionally substituted with aryl$^1$;
   or when —$Y^1$—$Y^2$— is a radical of formula (a-1) than $R^1$ may be taken together with $Y^2$ to form a radical of formula —CH=CH—CH=CH— wherein each hydrogen may optionally be replaced by a substituent independently selected from $C_{1-4}$alkyl, $C_{1-4}$alkyloxy, polyhalo$C_{1-4}$alkyl, halo, cyano, trifluoromethyl or aryl$^1$;
   wherein aryl$^1$ is phenyl; or phenyl substituted with from one or five substituents each independently selected from $C_{1-4}$alkyl, $C_{1-4}$alkyloxy, polyhalo$C_{1-4}$alkyl, halo, cyano, or trifluoromethyl;

$R^2$ is hydrogen, $C_{1-4}$alkyl, or halo;

A is $C_{1-6}$alkanediyl;
   $C_{1-6}$alkanediyl substituted with one or two groups selected from aryl$^2$, heteroaryl$^1$ and $C_{3-8}$cycloalkyl;
   or provided $X^3$ represents CH said radical A may also represent NH optionally substituted with aryl$^2$, heteroaryl$^1$ or $C_{3-8}$cycloalkyl;
   wherein aryl$^2$ is phenyl; or phenyl substituted with from one to five substituents each independently selected from $C_{1-4}$alkyl, $C_{1-4}$alkyloxy, halo, cyano or trifluoromethyl;
   heteroaryl$^1$ is furanyl, thienyl, pyridinyl, pyrazinyl, pyrimidinyl, or pyridazinyl; and said heteroaryl$^1$ is optionally substituted with one or two substituents each independently selected from $C_{1-4}$alkyl, $C_{1-4}$alkyloxy, halo, cyano or trifluoromethyl;

B is $NR^3R^4$; or
   $OR^9$;
   wherein each $R^3$ and $R^4$ are independently selected from hydrogen,
      $C_{1-8}$alkyl,
      $C_{1-8}$alkyl substituted with one, two or three substituents each independently from one another selected from hydroxy, halo, cyano, $C_{1-4}$alkyloxy, $C_{1-4}$alkyloxycarbonyl, $C_{3-8}$cycloalkyl, polyhalo$C_{1-4}$alkyl, $NR^5R^6$, $CONR^7R^8$, aryl$^3$, polycyclic aryl, or heteroaryl$^2$;
      $C_{3-8}$cycloalkyl;
      $C_{3-8}$cycloalkenyl;
      $C_{3-8}$alkenyl;
      $C_{3-8}$alkynyl;
      aryl$^3$;
      polycyclic aryl;
      heteroaryl$^2$; or $R^3$ and $R^4$ combined with the nitrogen atom bearing $R^3$ and $R^4$ may form an azetidinyl, pyrrolidinyl, piperidinyl, morpholinyl, azepanyl, or azocanyl ring wherein each of these rings may optionally be substituted by $C_{1-4}$alkyloxycarbonyl, $C_{1-4}$alkyloxycarbonyl$C_{1-4}$alkyl, carbonylamino, $C_{1-4}$alkylcarbonylamino, $CONR^7R^8$ or $C_{1-4}$alkyl$CONR^7R^8$;

wherein
$R^5$ is hydrogen, $C_{1-4}$alkyl, aryl$^3$, polycyclic aryl, or heteroaryl$^2$;
$R^6$ is hydrogen or $C_{1-4}$alkyl;
$R^7$ is hydrogen, $C_{1-4}$alkyl or phenyl;
$R^8$ is hydrogen, $C_{1-4}$alkyl or phenyl; or
$R^9$ is $C_{1-6}$alkyl, or $C_{1-6}$alkyl substituted with one, two or three substituents each independently from one another selected from hydroxy, halo, cyano, $C_{1-4}$alkyloxy, $C_{1-4}$alkyloxycarbonyl, $C_{3-8}$cycloalkyl, $C_{3-8}$cycloalkenyl, trifluoromethyl, $NR^5R^6$, $CONR^7R^8$, aryl$^3$, polycyclic aryl, or heteroaryl$^2$;
wherein
   aryl$^3$ is phenyl; phenyl substituted with one to five substituents each independently selected from $C_{1-4}$alkyl, $C_{1-4}$alkyloxy, halo, hydroxy, trifluoromethyl, cyano, $C_{1-4}$alkyloxycarbonyl, $C_{1-4}$alkyloxycarbonyl$C_{1-4}$alkyl, methylsulfonylamino, methylsulfonyl, $NR^5R^6$, $C_{1-4}$alkyl$NR^5R^6$, $CONR^7R^8$ or $C_{1-4}$alkyl$CONR^7R^8$;
   polycyclic aryl is naphthalenyl, indanyl, fluorenyl, or 1,2,3,4-tetrahydronaphtalenyl, and said polycyclic aryl is optionally substituted with one or two substituents each independently selected from $C_{1-6}$alkyl, $C_{1-6}$alkyloxy, phenyl, halo, cyano, $C_{1-4}$alkylcarbonyl, $C_{1-4}$alkyloxycarbonyl, $C_{1-4}$alkyloxycarbonyl$C_{1-4}$alkyl, $NR^5R^6$, $C_{1-4}$alkyl$NR^5R^6$, $CONR^7R^8$, $C_{1-4}$alkyl$CONR^7R^8$ or $C_{1-4}$alkyloxycarbonylamino, and
   heteroaryl$^2$ is pyridinyl, pyrazinyl, pyrimidinyl, pyridazinyl, triazinyl, triazolyl, imidazolyl, pyrazolyl, thiazolyl, isothiazolyl, oxazolyl, pyrrolyl, furanyl, thienyl; quinolinyl; isoquinolinyl; 1,2,3,4-tetrahydro-isoquinolinyl; benzothiazolyl; benzo[1,3]dioxolyl; 2,3-dihydro-benzo[1,4]dioxinyl; indolyl; 2,3-dihydro-1H-indolyl; 1H-benzoimidazolyl; and said heteroaryl$^2$ is optionally substituted with one or two substituents each independently selected from $C_{1-6}$alkyl, $C_{1-6}$alkyloxy, phenyl, halo, cyano, $C_{1-4}$alkylcarbonyl, $C_{1-4}$alkyloxycarbonyl, $C_{1-4}$alkyloxycarbonyl$C_{1-4}$alkyl, $NR^5R^6$, $C_{1-4}$alkyl$NR^5R^6$, $CONR^7R^8$ or $C_{1-4}$alkyl$CONR^7R^8$.

As used in the foregoing definitions:
halo is generic to fluoro, chloro, bromo and iodo
$C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like
—$C_{1-6}$alkyl is meant to include $C_{1-4}$alkyl and the higher homologues thereof having 5 or 6 carbon atoms, such as, for example, 2-methylbutyl, pentyl, hexyl and the like;
$C_{1-8}$alkyl is meant to include $C_{1-6}$alkyl and the higher homologues thereof having 7 to 8 carbon atoms, such as for instance heptyl, ethylhexyl, octyl, and the like;
polyhalo$C_{1-4}$alkyl is defined as polyhalosubstituted $C_{1-4}$alkyl, in particular $C_{1-4}$alkyl (as hereinabove defined) substituted with 2 to 6 halogen atoms such as difluoromethyl, trifluoromethyl, trifluoroethyl, and the like;
$C_{3-6}$cycloalkyl is generic to cyclopropyl, cyclobutyl, cyclopentyl, and cyclohexyl;

$C_{3-8}$cycloalkyl is generic to cyclopropyl, cyclobutyl, cyclopentyl, cyclohexyl, cycloheptyl and cyclooctyl;

$C_{3-6}$cycloalkenyl is generic to cyclopropenyl, cyclobutenyl, cyclopentenyl and cyclohexenyl;

$C_{3-8}$cycloalkenyl is generic to cyclopropenyl, cyclobutenyl, cyclopentenyl, cyclohexenyl, cycloheptenyl and cyclooctenyl;

$C_{1-4}$alkanediyl defines bivalent straight or branched chain hydrocarbon radicals containing from 1 to 4 carbon atoms such as, for example, methanediyl, 1,2-ethanediyl, 1,3-propanediyl, and 1,4-butanediyl;

$C_{1-6}$alkanediyl defines bivalent straight or branched chain hydrocarbon radicals containing from 1 to 6 carbon atoms such as, for example, methanediyl, 1,2-ethanediyl, 1,3-propanediyl, 1,4-butanediyl, 1,5-pentanediyl, 1,6-hexanediyl, and the branched isomers thereof;

$C_{3-6}$alkenyl defines straight and branched chain hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl, 3-hexenyl, 2-hexenyl and the like;

$C_{3-8}$alkenyl is meant to include $C_{3-6}$alkenyl and the higher homologues thereof having 7 to 8 carbon atoms, such as 2-pentenyl, 2-octenyl and the like;

$C_{3-6}$alkynyl defines straight and branched chain hydrocarbon radicals containing one triple bond and having from 3 to 6 carbon atoms such as, for example, 2-propynyl, 3-butynyl, 2-butynyl, 2-pentynyl, 3-pentynyl, 3-methyl-2-butynyl, 3-hexynyl, 2-hexynyl and the like;

$C_{3-8}$alkynyl is meant to include $C_{3-6}$alkynyl and the higher homologues thereof having 7 to 8 carbon atoms, such as 2-pentynyl, 2-octynyl and the like.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

The absolute stereochemical configuration of the compounds of formula (I) and of the intermediates used in their preparation may easily be determined by those skilled in the art while using well-known methods such as, for example, X-ray diffraction.

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

The pharmaceutically acceptable acid addition salts as mentioned hereinabove are meant to comprise the therapeutically active non-toxic acid addition salt forms which the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

Some of the compounds of formula (I) may also exist in their tautomeric form. Such forms although not explicitly indicated in the above formula are intended to be included within the scope of the present invention. For instance, when an aromatic heterocyclic ring is substituted with hydroxy the keto-form may be the mainly populated tautomer.

In an embodiment, the present invention relates to those compounds of formula (I) wherein the definitions of aryl$^3$, polycyclic aryl and heteroaryl$^2$ read as follows: aryl$^3$ is phenyl; phenyl substituted with one to five substituents each independently selected from $C_{1-4}$alkyl, $C_{1-4}$alkyloxy, halo, hydroxy, trifluoromethyl, cyano, $C_{1-4}$alkyloxycarbonyl, $C_{1-4}$alkyloxycarbonyl$C_{1-4}$alkyl, methylsulfonylamino, NR$^5$R$^6$, $C_{1-4}$alkylNR$^5$R$^6$, CONR$^7$R$^8$ or $C_{1-4}$alkylCONR$^7$R$^8$; and polycyclic aryl is naphthalenyl, indanyl, fluorenyl, or 1,2,3,4-tetrahydronaphtalenyl, and said polycyclic aryl is optionally substituted with one or two substituents each independently selected from $C_{1-6}$alkyl, $C_{1-6}$alkyloxy, phenyl, halo, cyano, $C_{1-4}$alkylcarbonyl, $C_{1-4}$alkyloxycarbonyl, $C_{1-4}$alkyloxycarbonyl$C_{1-4}$alkyl, NR$^5$R$^6$, $C_{1-4}$alkylNR$^5$R$^6$, CONR$^7$R$^8$, or $C_{1-4}$alkylCONR$^7$R$^8$, and heteroaryl$^2$ is pyridinyl, pyrazinyl, pyrimidinyl, pyridazinyl, triazinyl, triazolyl, imidazolyl, pyrazolyl, thiazolyl, isothiazolyl, oxazolyl, pyrrolyl, furanyl, thienyl; quinolinyl; isoquinolinyl; benzo[1,3]dioxolyl; 2,3-dihydro-benzo[1,4]dioxinyl; indolyl; 2,3-dihydro-1H-indolyl; 1H-benzoimidazolyl; and said heteroaryl$^2$ is optionally substituted with one or two substituents each independently selected from $C_{1-6}$alkyl, $C_{1-6}$alkyloxy, phenyl, halo, cyano, $C_{1-4}$alkylcarbonyl, $C_{1-4}$alkyloxy-carbonyl, $C_{1-4}$alkyloxycarbonyl$C_{1-4}$alkyl, NR$^5$R$^6$, $C_{1-4}$alkylNR$^5$R$^6$, CONR$^7$R$^8$ or $C_{1-4}$alkylCONR$^7$R$^8$.

In another embodiment, the present invention relates to those compounds of formula (I) the dotted line is an optional bond and is absent when X$^2$ represents nitrogen; the radical —Y$^1$—Y$^2$— is a radical of formula $$-N=CH- \qquad (a\text{-}1),$$

$$-CH=N- \qquad (a\text{-}2),$$

$$-CH_2-CH_2- \qquad (a\text{-}3),$$

$$-CH=CH- \qquad (a\text{-}4),$$

wherein in the bivalent radicals of formula (a-1) or (a-2) the hydrogen atom may optionally be replaced by $C_{1-6}$alkyl or phenyl;

X$^1$ is carbon or nitrogen;

X$^2$ presents CH and X$^3$ represents nitrogen; or X$^2$ represents nitrogen and X$^3$ represents CH; or X$^2$ and X$^3$ represent nitrogen;

R$^1$ is $C_{1-6}$alkyl;
aryl$^1$;
$C_{1-6}$alkyl substituted with hydroxy, $C_{3-6}$cycloalkyl, aryl$^1$ or naphthalenyl;
$C_{3-6}$alkenyl;
$C_{3-6}$alkenyl substituted with aryl$^1$;

$C_{1-4}$alkyloxy$C_{1-4}$alkanediyl optionally substituted with aryl$^1$;

or when —Y$^1$—Y$^2$— is a radical of formula (a-1) than R$^1$ may be taken together with Y$^2$ to form a radical of formula —CH═CH—CH═CH— wherein each hydrogen may optionally be replaced by a substituent independently selected from $C_{1-4}$alkyl, $C_{1-4}$alkyloxy, trifluoromethyl or aryl$^1$;

wherein aryl$^1$ is phenyl; or phenyl substituted with from one or two substituents each independently selected from $C_{1-4}$alkyl, $C_{1-4}$alkyloxy, halo, or trifluoromethyl;

R$^2$ is hydrogen, $C_{1-4}$alkyl, or halo;

A is $C_{1-6}$alkanediyl;
$C_{1-6}$alkanediyl substituted with one or two groups selected from aryl$^2$ and heteroaryl$^1$;
wherein aryl$^2$ is phenyl; or phenyl substituted with from one or two substituents each independently selected from $C_{1-4}$alkyl or halo;
heteroaryl$^1$ is thienyl or pyridinyl;

B is NR$^3$R$^4$; or OR$^9$;
wherein each R$^3$ and R$^4$ are independently selected from
hydrogen,
$C_{1-8}$alkyl,
$C_{1-8}$alkyl substituted with one or two substituents each independently from one another selected from hydroxy, cyano, $C_{1-4}$alkyloxy, $C_{1-4}$alkyloxycarbonyl, polyhalo$C_{1-4}$alkyl, NR$^5$R$^6$, aryl$^3$, polycyclic aryl, or heteroaryl$^2$;
$C_{3-8}$cycloalkyl;
$C_{3-8}$alkenyl;
aryl$^3$;
polycyclic aryl;
heteroaryl$^2$; or
R$^3$ and R$^4$ combined with the nitrogen atom bearing R$^3$ and R$^4$ may form a piperidinyl ring optionally substituted by $C_{1-4}$alkyloxycarbonyl;
wherein
R$^5$ is hydrogen, $C_{1-4}$alkyl, or aryl$^3$;
R$^6$ is hydrogen or $C_{1-4}$alkyl;
R$^9$ is $C_{1-6}$alkyl;
wherein
aryl$^3$ is phenyl; phenyl substituted with one to three substituents each independently selected from $C_{1-4}$alkyl, $C_{1-4}$alkyloxy, halo, hydroxy, trifluoromethyl, $C_{1-4}$alkyloxycarbonyl, methylsulfonyl, or NR$^5$R$^6$;
polycyclic aryl is naphthalenyl, indanyl, or fluorenyl, and said polycyclic aryl is optionally substituted with one substituent independently selected from $C_{1-4}$alkyloxycarbonylamino, and
heteroaryl$^2$ is pyridinyl, thiazolyl, furanyl, quinolinyl; 1,2,3,4-tetrahydro-isoquinolinyl; benzothiazolyl; benzo[1,3]dioxolyl; 2,3-dihydro-benzo[1,4]dioxinyl; indolyl; 2,3-dihydro-1H-indolyl; 1H-benzoimidazolyl; and said heteroaryl$^2$ is optionally substituted with one or two substituents each independently selected from $C_{1-6}$alkyl, phenyl, $C_{1-4}$alkylcarbonyl, $C_{1-4}$alkyloxycarbonyl, or $C_{1-4}$alkyloxycarbonyl$C_{1-4}$alkyl.

Interesting compounds of formula (I) are those compounds of formula (I) wherein one or more of the following restrictions apply:
a) the dotted line is absent;
b) the dotted line represents a bond and X$^2$ represents carbon;
c) R$^1$ is $C_{1-6}$alkyl or aryl$^1$ or $C_{1-6}$alkyl substituted with aryl$^1$;
d) A is $C_{1-6}$alkanediyl or $C_{1-6}$alkanediyl substituted with aryl$^2$, in particular A is —CH$_2$— or —CH(C$_6$H$_5$)—;
e) A is $C_{1-6}$alkanediyl substituted with heteroaryl$^1$;
f) B is OR$^9$ wherein R$^9$ is $C_{1-6}$alkyl;
g) B is NR$^3$R$^4$ wherein each R$^3$ and R$^4$ are independently selected from hydrogen, $C_{1-8}$alkyl, $C_{1-8}$alkyl substituted with one, two or three substituents selected from $C_{1-4}$alkyloxycarbonyl, aryl$^3$, polycyclic aryl, or heteroaryl$^2$.

A first particular group of compounds are those compounds of formula (I) wherein X$^2$ represents nitrogen and X$^3$ represents CH.

A second particular group of compounds are those compounds of formula (I) wherein X$^2$ represents CH and X$^3$ represents nitrogen.

A third particular group of compounds are those compounds of formula (I) wherein both X$^2$ and X$^3$ represent nitrogen.

A fourth particular group of compounds are those compounds of formula (I) wherein the dotted line is a bond, X$^2$ represents carbon and X$^3$ represents nitrogen.

A fifth particular group of compounds are those compounds of formula (I) wherein X$^1$ is carbon.

A sixth particular group of compounds are those compounds of formula (I) wherein X$^1$ is nitrogen.

A seventh particular group of compounds are those compounds of formula (I) wherein radical A represents $C_{1-6}$alkanediyl substituted with aryl$^2$.

An eight particular group of compounds are those compounds of formula (I) wherein radical B represents $C_{1-6}$alkyloxy.

An eight particular group of compounds are those compounds of formula (I) wherein radical B represents NR$^3$R$^4$ wherein R$^3$ is hydrogen.

A ninth particular group of compounds are those compounds of formula (I) wherein radical A represents —C(CH$_3$)$_2$— or —C(CH$_3$)(C$_6$H$_5$)— or —C(C$_6$H$_5$)$_2$)— in particular radical A represents —C(CH$_3$)(C$_6$H$_5$)—.

Preferred compounds of formula (I) are compounds (187), (192), (196), (204), (223), (224), (227), (228), (271), (272), (278)-(295), (298)-(302), (314), (343)-(346), (361), and (362) as listed in Table 1.

In general compounds of formula (I) can be prepared by reacting an intermediate of formula (III) with an intermediate of formula (II) wherein Q is selected from bromo, iodo, trifluoromethylsulfonate, B(OH)$_2$, alkylboronates and cyclic analogues thereof, in at least one reaction-inert solvent and optionally in the presence of at least one transition metal coupling reagent and/or at least one suitable catalyst such as palladium associated with triphenylphosphine, triphenylarsine and the like. More information on these Buchwald reaction conditions can be found below.

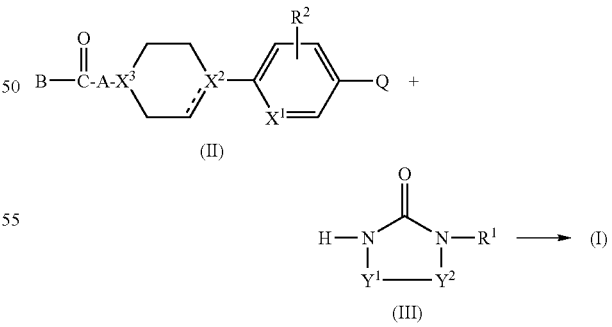

Compounds of formula (I-a), defined as compounds of formula (I) wherein X$^2$ is nitrogen, can generally be prepared by reacting an intermediate of formula (V), wherein Z is selected from halo, B(OH)$_2$, alkylboronates and cyclic analogues thereof, with an intermediate of formula (IV) in at least one reaction-inert solvent and optionally in the presence of at least one transition metal coupling reagent and/or at least one suitable ligand, the said process further optionally comprising converting a compound of formula (I) into an addition salt thereof, and/or preparing stereochemically isomeric forms thereof. This type of reaction being known in the art as the Buchwald reaction, reference to the applicable metal coupling reagents and/or suitable ligands, e.g. palladium compounds such as palladium tetra(triphenyl-phosphine), tris (dibenzylidene-acetone dipalladium, 2,2'-bis (diphenylphosphino)-1,1'-binaphtyl and the like, may be found for instance in *Tetrahedron Letters* (1996) 37(40) 7181-7184 and *J. Am. Chem. Soc.* (1996) 118:7216. If Z is B(OH)$_2$, an alkylboronate or a cyclic analogue thereof, then cupric acetate or cupric alkanoate should be used as the coupling reagent, according to *Tetrahedron Letters* (1998) 39:2933-6.

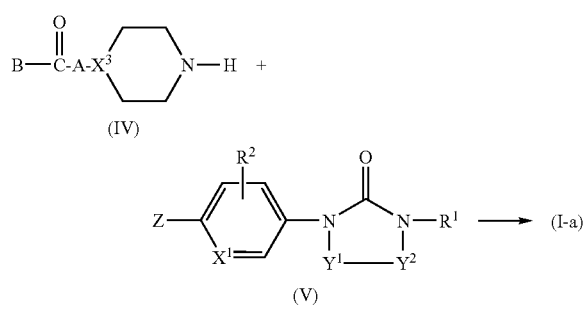

(IV)

(I-a)

(V)

An alternative procedure for preparing the compounds of formula (I-a) uses intermediates of formula (IV) wherein $X^3$ represents nitrogen and wherein the B—(C=O)-A- moiety has been replaced by a hydrogen or a suitable protecting group such as, e.g. benzyl or tert-butoxy-carbonyl. Said protecting group is removed after the Buchwald reaction which is then followed by an N-alkylation reaction with intermediate (VI).

Compounds of formula (I-b), defined as compounds of formula (I) wherein $X^3$ is nitrogen, can generally be prepared by N-alkylating an intermediate of formula (VII) with an intermediate of formula (VI), wherein W is an appropriate leaving group such as, for example, halo, e.g. fluoro, chloro, bromo, iodo, or in some instances W may also be a sulfonyloxy group, e.g. methanesulfonyloxy, trifluoromethanesulfonyloxy, benzenesulfonyloxy and the like reactive leaving groups. The reaction can be performed in a reaction-inert solvent such as, for example, acetonitrile, 2-pentanol, isobutanol, dimethyl acetamide or DMF, and optionally in the presence of a suitable base such as, for example, sodium carbonate, potassium carbonate, N-methyl-pyrrolidone or triethylamine. Stirring may enhance the rate of the reaction. The reaction may conveniently be carried out at a temperature ranging between room temperature and the reflux temperature of the reaction mixture.

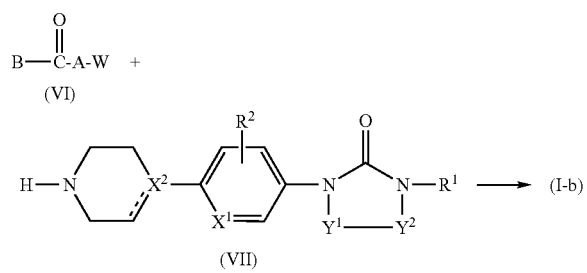

(VI)

(I-b)

(VII)

Compounds of formula (I-c), defined as compounds of formula (I) wherein radical B represents NR$^3$R$^4$, can generally be prepared by reacting an intermediate of formula (VIII) with an intermediate of formula (IX), in at least one reaction-inert solvent and optionally in the presence of at least one suitable coupling reagent and/or a suitable base, the said process further optionally comprising converting a compound of formula (I) into an addition salt thereof, and/or preparing stereochemically isomeric forms thereof.

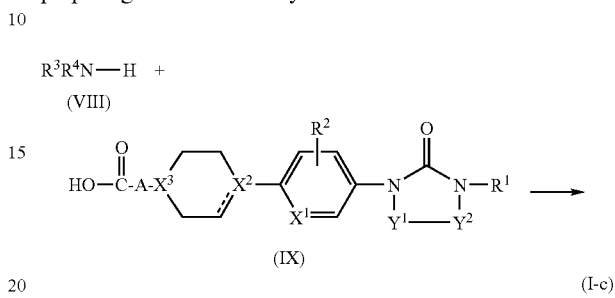

(VIII)

(IX)

(I-c)

It may be convenient to activate the carboxylic acid of formula (IX) by adding an effective amount of a reaction promoter. Non-limiting examples of such reaction promoters include carbonyldiimidazole, diimides such as N,N'-dicyclohexyl-carbodiimide or 1-(3-dimethylaminopropyl)-3-ethyl-carbodiimide, and functional derivatives thereof. In case a chirally pure reactant of formula (VIII) is used, a fast and enantiomerization-free reaction of the intermediate of formula (VIII) with the said intermediate (IX) may be performed in the further presence of an effective amount of a compound such as hydroxybenzotriazole, benzotriazolyloxytris (dimethylamino)-phosphonium hexafluorophosphate, tetrapyrrolidinophosphonium hexafluorophosphate, bromotripyrrolidinophosphonium hexafluorophosphate, or a functional derivative thereof such as disclosed by D. Hudson, *J. Org. Chem.* (1988), 53:617.

Compounds of formula (I-d), defined as compounds of formula (I) wherein radical B represents OR$^9$, can generally be prepared by reacting an intermediate of formula (X) with an intermediate of formula (IX), in at least one reaction-inert solvent and optionally in the presence of at least one suitable coupling reagent and/or a suitable base, the said process further optionally comprising converting a compound of formula (I) into an addition salt thereof, and/or preparing stereochemically isomeric forms thereof.

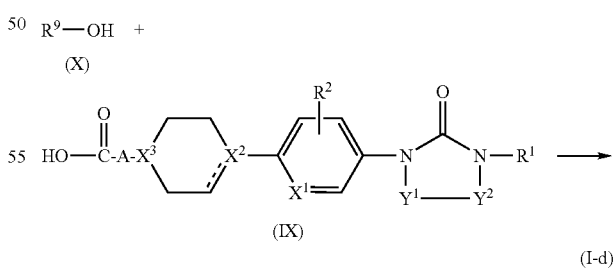

(X)

(IX)

(I-d)

It may be convenient to activate the carboxylic acid of formula (IX) by adding an effective amount of a reaction promoter. Non-limiting examples of such reaction promoters include carbonyldiimidazole, diimides such as N,N'-dicyclohexyl-carbodiimide or 1-(3-dimethylaminopropyl)-3-ethyl-carbodiimide, and functional derivatives thereof.

Compounds of formula (I-e), defined as compounds of formula (I) wherein the dotted bond represents a bond and $X^2$ is carbon, can generally be prepared by reacting an intermediate of formula (XI) with an intermediate of formula (XII) wherein one of L and Q is selected from bromo, iodo and trifluoromethylsulfonate and the other of L and Q is selected from tri($C_{1-4}$alkyl) tin, $B(OH)_2$, alkylboronates and cyclic analogues thereof, in at least one reaction-inert solvent and optionally in the presence of at least one transition metal coupling reagent and/or at least one suitable catalyst such as palladium associated with triphenylphosphine, triphenylarsine and the like. This type of reaction being known in the art as the Stille reaction or the Suzuki reaction.

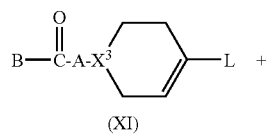

(XI)

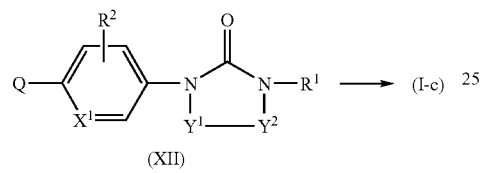

(XII) → (I-c)

An alternative procedure for preparing the compounds of formula (I-d) uses intermediates of formula (XI) wherein $X^3$ represents nitrogen and wherein the B—(C=O)-A- moiety has been replaced by a suitable protecting group such as, e.g. benzyl or tert-butoxy-carbonyl. Said protecting group is removed after the coupling reaction which is then followed by an N-alkylation reaction with intermediate (VI).

The starting materials and some of the intermediates are known compounds and are commercially available or may be prepared according to conventional reaction procedures generally known in the art.

Intermediates of formula (IX-a), defined as intermediates of formula (IX) wherein $X^3$ represents nitrogen, can be prepared as set out below. An intermediate of formula (XIII) is reacted with an intermediate of formula (V) under Buchwald reaction conditions and the resulting intermediate of formula (XIV) is then converted into an intermediate of formula (IX-a) using art-known acid or base catalyzed hydrolysis procedures.

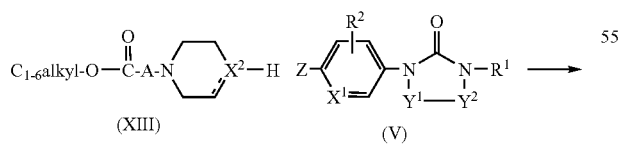

(XIII)

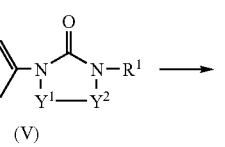

(V)

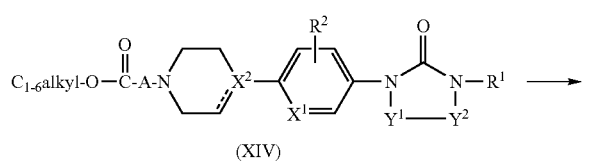

(XIV)

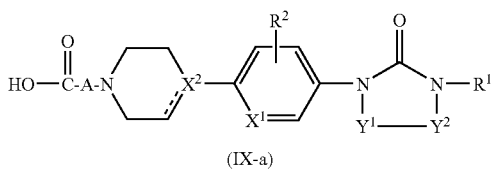

(IX-a)

Intermediates of formula (VII) can be prepared by reacting an intermediate of formula (III) with an intermediate of formula (XV) wherein PG is a protecting group such as e.g. benzyl or tert-butoxy-carbonyl, and Q is selected from bromo, iodo and trifluoromethylsulfonate, in at least one reaction-inert solvent and optionally in the presence of at least one transition metal coupling reagent and/or at least one suitable catalyst such as palladium associated with triphenylphosphine, triphenylarsine and the like; followed by removal of the protecting group.

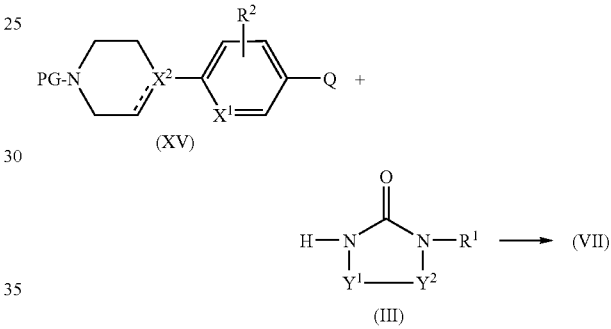

(XV)

(III) → (VII)

Intermediates of formula (VII-a), defined as intermediates of formula (VII) wherein —$Y^1$—$Y^2$— represents —CH=N— and $R^1$ hydrogen, can be prepared as outlined below. PG is a protecting group such as e.g. benzyl or tert-butoxy-carbonyl, which is removed in the final step.

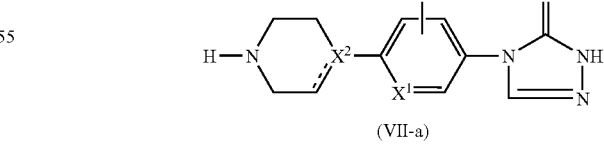

(XVII)

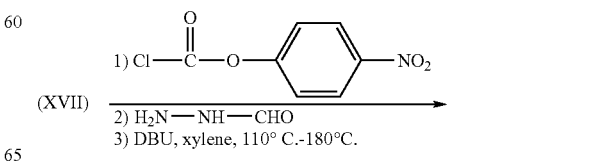

(VII-a)

(XVII)
1) Cl—C(=O)—O—⟨phenyl⟩—$NO_2$
2) $H_2N$—NH—CHO
3) DBU, xylene, 110° C.-180°C.

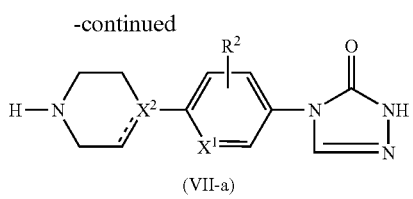

Intermediates of formula (VII-b), defined as intermediates of formula (VII) wherein —Y$^1$—Y$^2$— represents —CH=N— wherein a hydrogen is replaced by C$_{1-6}$alkyl or phenyl and R$^1$ hydrogen, can be prepared as outlined below. PG is a protecting group such as e.g. benzyl or tert-butoxy-carbonyl, which is removed in the final step.

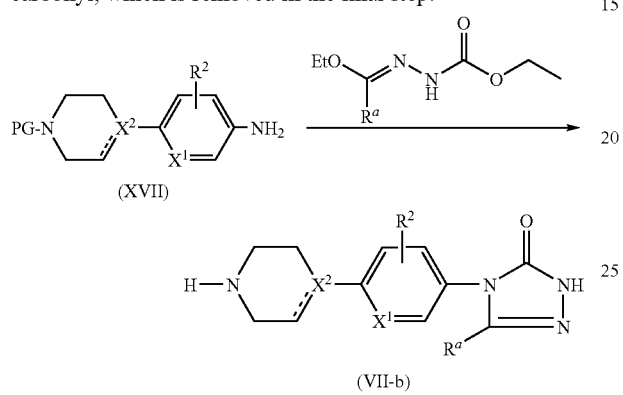

R$^a$ represents C$_{1-6}$alkyl or phenyl

Intermediates of formula (VII-c), defined as intermediates of formula (VII) wherein —Y$^1$—Y$^2$— represents —CH=N— wherein a hydrogen is replaced by C$_{1-6}$alkyl or phenyl, can be prepared as outlined below. PG is a protecting group such as e.g. benzyl or tert-butoxy-carbonyl, which is removed in the final step.

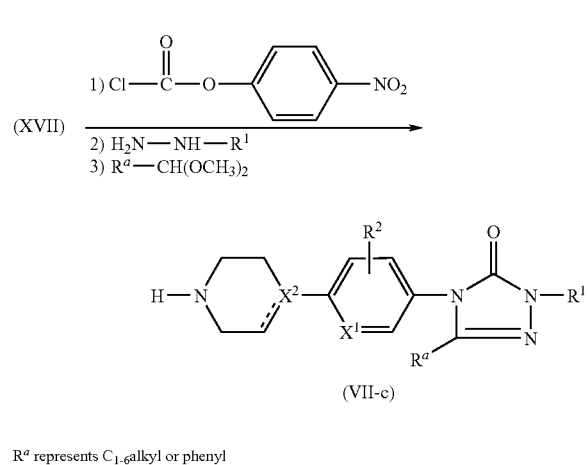

R$^a$ represents C$_{1-6}$alkyl or phenyl

Other intermediates of formula (VII) can be prepared as outlined below. PG is a protecting group such as e.g. benzyl or tert-butoxy-carbonyl, which is removed in the final step.

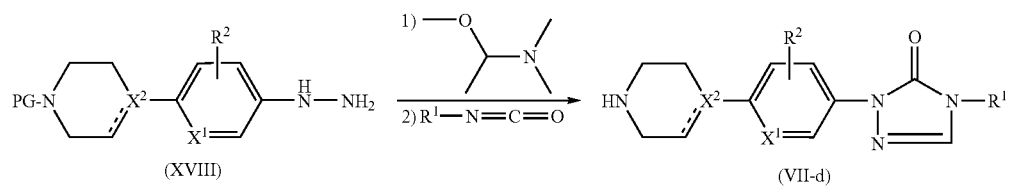

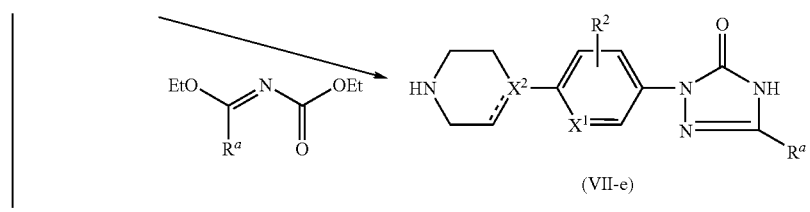

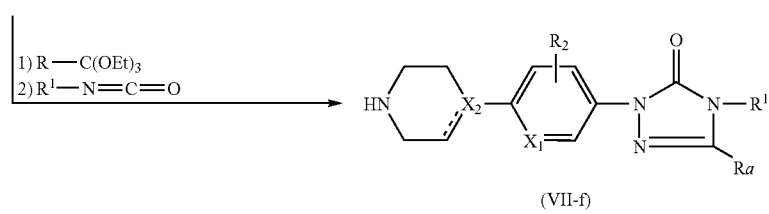

R$^a$ represents C$_{1-6}$alkyl or phenyl

Intermediates of formula (IV-a), defined as intermediates of formula (IV) wherein X³ represents nitrogen, can be prepared by N-alkylating piperazine with an intermediate of formula (VI). The reaction can be performed in a reaction-inert solvent such as, for example, acetonitrile, and optionally in the presence of a suitable base such as, for example, sodium carbonate, potassium carbonate or triethylamine. Stirring may enhance the rate of the reaction. The reaction may conveniently be carried out at a temperature ranging between room temperature and the reflux temperature of the reaction mixture.

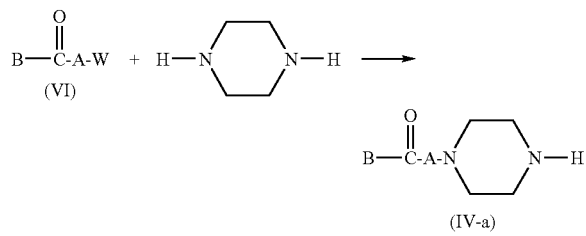

Intermediates of formula (V), defined as intermediates of formula (V) wherein Z represents halo, can be prepared by reacting an intermediate of formula (III) with an intermediate of formula (XVI) wherein Q is selected from bromo, iodo and trifluoromethylsulfonate, in at least one reaction-inert solvent and optionally in the presence of at least one transition metal coupling reagent and/or at least one suitable catalyst such as palladium associated with triphenylphosphine, triphenylarsine.

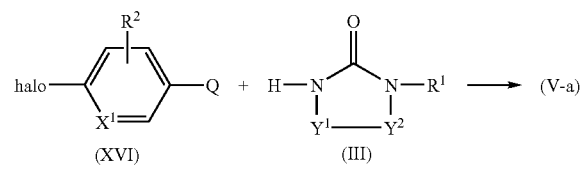

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the N-oxide forms, the pharmaceutically acceptable salts and stereoisomeric forms thereof possess favourable apoB secretion and MTP inhibiting activity and concomitant lipid lowering activity. Therefore the present compounds of formula (I) are useful as a medicine especially in a method of treating patients suffering from hyperlipidemia, obesity, atherosclerosis or type II diabetes.

Subsequently the present compounds may be used for the manufacture of a medicine for treating disorders caused by an excess of very low density lipoproteins (VLDL) or low density lipoproteins (LDL), and especially disorders caused by the cholesterol associated with said VLDL and LDL. In particular the present compounds may be used for the manufacture of a medicament for the treatment of hyperlipidemia, obesity, atherosclerosis or type II diabetes.

The principal mechanism of action of the compounds of formula (I) appears to involve inhibition of MTP (microsomial triglyceride transfer protein) activity in hepatocytes and intestinal epithelial cells, resulting in decreased VLDL and chylomicron production, respectively. This is a novel and innovative approach to hyperlipidemia, and is expected to lower LDL-cholesterol and triglycerides through reduced hepatic production of VLDL and intestinal production of chylomicrons.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias are common hypercholesterolaemia, familial combined hyperlipidaemia, familial hypercholesterolaemia, remnant hyperlipidaemia, chylo-micronaemia syndrome, familial hypertriglyceridaemia. The present compounds may also be used to prevent or treat patients suffering from obesitas or from atherosclerosis, especially coronary atherosclerosis and more in general disorders which are related to atherosclerosis, such as ischaemic heart disease, peripheral vascular disease, cerebral vascular disease. The present compounds may cause regression of atherosclerosis and inhibit the clinical consequences of atherosclerosis, particularly morbidity and mortality.

In view of the utility of the compounds of formula (I), it follows that the present invention also provides a method of treating warm-blooded animals, including humans, (generally called herein patients) suffering from disorders caused by an excess of very low density lipoproteins (VLDL) or low density lipoproteins (LDL), and especially disorders caused by the cholesterol associated with said VLDL and LDL. Consequently a method of treatment is provided for relieving patients suffering from conditions, such as, for example, hyperlipidemia, obesity, atherosclerosis or type II diabetes.

Apo B-48, synthetized by the intestine, is necessary for the assembly of chylomicrons and therefore has an obligatory role in the intestinal absorption of dietary fats. The present invention provides compounds which are acting as selective MTP inhibitors at the level of the gut wall.

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

The compounds of formula (I) may be used in conjunction with other pharmaceutical agents, in particular the pharmaceutical compositions of the present invention may further comprise at least one additional lipid-lowering agent, thus leading to a so-called combination lipid-lowering therapy. The said additional lipid-lowering agent may be, for instance, a known drug conventionally used for the management of hyperlipidaemia such as e.g. a bile acid sequestrant resin, a fibric acid derivative or nicotinic acid as previously mentioned in the background of the invention. Suitable additional lipid-lowering agents also include other cholesterol biosynthesis inhibitors and cholesterol absorption inhibitors, especially HMG-CoA reductase inhibitors and HMG-CoA synthase inhibitors, HMG-CoA reductase gene expression inhibitors, CETP inhibitors, ACAT inhibitors, squalene synthetase inhibitors, CB-1 antagonists, cholesterol absorption inhibitors such as ezetimibe, and the like.

Any HMG-CoA reductase inhibitor may be used as the second compound in the combination therapy aspect of this invention. The term "HMG-CoA reductase inhibitor" as used herein, unless otherwise stated, refers to a compound which inhibits the biotransformation of hydroxymethylglutaryl-coenzyme A to mevalonic acid as catalyzed by the enzyme HMG-CoA reductase. Such "HMG-CoA reductase inhibitors" are, for example, lovastatin, simvastatin, fluvastatin, pravastatin, rivastatin, and atorvastatin.

Any HMG-CoA synthase inhibitor may be used as the second compound in the combination therapy aspect of this invention. The term "HMG-CoA synthase inhibitor" as used herein, unless otherwise stated, refers to a compound which inhibits the biosynthesis of hydroxymethylglutaryl-coenzyme A from acetyl-coenzyme A and acetoacetyl-coenzyme A, catalyzed by the enzyme HMG-CoA synthase Any HMG-CoA reductase gene expression inhibitor may be used as the second compound in the combination therapy aspect of this invention. These agents may be HMG-CoA reductase transcription inhibitors that block the transcription of DNA or translation inhibitors that prevent translation of mRNA coding for HMG-CoA reductase into protein. Such inhibitors may either affect transcription or translation directly or may be biotransformed into compounds having the above-mentioned attributes by one or more enzymes in the cholesterol biosynthetic cascade or may lead to accumulation of a metabolite having the above-mentioned activities.

Any CETP inhibitor may be used as the second compound in the combination therapy aspect of this invention. The term "CETP inhibitor" as used herein, unless otherwise stated, refers to a compound which inhibits the cholesteryl ester transfer protein (CETP) mediated transport of various cholesteryl esters and triglycerides from HDL to LDL and VLDL.

Any ACAT inhibitor may be used as the second compound in the combination therapy aspect of this invention. The term "ACAT inhibitor" as used herein, unless otherwise stated, refers to a compound which inhibits the intracellular esterification of dietary cholesterol by the enzyme acyl CoA:cholesterol acyltransferase.

Any squalene synthetase inhibitor may be used as the second compound in the combination therapy aspect of this invention. The term "squalene synthetase inhibitor" as used herein, unless otherwise stated, refers to a compound which inhibits the condensation of two molecules of farnesylpyrophosphate to form squalene, catalyzed by the enzyme squalene synthetase.

Those of skill in the treatment of hyperlipidemia will easily determine the therapeutically effective amount of a compound of formula (I) from the test results presented hereinafter. In general it is contemplated that a therapeutically effective dose will be from about 0.001 mg/kg to about 50 mg/kg of body weight, more preferably from about 0.01 mg/kg to about 5 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 350 mg, more particularly from about 1 to about 200 mg, of the active ingredient per unit dosage form.

The exact dosage and frequency of administration depends on the particular compound of formula (I) used, the particular condition being treated, the severity of the condition being treated, the age, weight and general physical condition of the particular patient as well as the other medication (including the above-mentioned additional lipid-lowering agents), the patient may be taking, as is well known to those skilled in the art. Furthermore, said effective daily amount may be lowered or increased depending on the response of the treated patient and/or depending on the evaluation of the physician prescribing the compounds of the instant invention. The effective daily amount ranges mentioned hereinabove are therefore only guidelines.

EXPERIMENTAL PART

In the procedures described hereinafter the following abbreviations were used: "DMSO" stands for dimethylsulfoxide, "THF" stands for tetrahydrofuran; "DCM" stands for dichloromethane; "DIPE" stands for diisopropylether; "DMF" means N,N-dimethyl-formamide; "TFFH" stands for tetramethylfluoroformamidinium hexafluorophosphate; "NMP" means N-methyl-2-pyrrolidone and; "DIPEA" means diisopropylethylamine; "TFA" means trifluoroacetic acid; "TIS" means triisopropylsilane, and "BINAP" stands for 2,2'-bis(diphenylphosphino)-1,1'-binaphthyl. "PyBOP®" means a complex of (T-4)-hexafluorophosphate(1$^-$) (1-hydroxy-1H-benzotriazolato-O)tri-1-pyrrolidinyl-phosphorus (1$^+$).

Extrelut™ is a product of Merck KgaA (Darmstadt, Germany) and is a short column comprising diatomaceous earth.

Methylisocyanate polystyrene resin (Novabiochem 01-64-0169); 4-benzyloxy-benzaldehyde polystyrene resin (Novabiochem 01-64-0182); 2-(3,5-dimethoxy-4-formylphenoxy) ethoxymethyl polystyrene resin (Novabiochem 01-64-0261); (±)-1-glycerol polystyrene resin (Novabiochem 01-64-0408); and N-hydroxy-benzotriazole-6-carboxamidomethyl polystyrene resin (Novabiochem 01-64-0425) can be obtained from Calbiochem-Novabiochem AG, Weidenmattweg 4, CH-4448 Läufelfingen, Switzerland.

A. Synthesis of the Intermediates

Example A.1 a) Preparation of

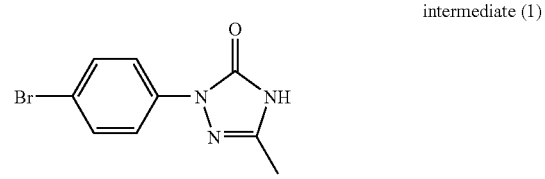

intermediate (1)

4-Bromophenylhydrazine hydrochloride(1:1) (0.11 mol) was converted into the free base with $CH_2Cl_2/H_2O/Na_2CO_3$. Ethyl N-ethoxycarbonylacetimidate (0.13 mol) and 4-dimethylaminopyridine (2 g) in triethylamine (22 ml) and xylene (200 ml) were added. The mixture was stirred and refluxed overnight and then stirred at room temperature over the weekend, filtered and dried, yielding 16 g of intermediate (1).

b) Preparation of

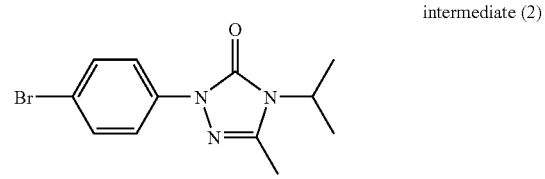

intermediate (2)

A mixture of intermediate (1) (0.063 mol) and potassium hydroxide (0.69 mol) in DMF (300 ml) was stirred for 20 minutes. 2-Bromopropane (0.126 mol) was added. The mixture was stirred at 60° C. overnight. The solvent was evaporated. The residue was dissolved in DCM and washed with water. The organic layer was dried, filtered and the solvent was evaporated. The residue was purified by column chromatography over silica gel (eluent: $CH_2Cl_2$). The pure fractions were collected and the solvent was evaporated, yielding 7 g of intermediate (2).

Example A.2 a) Preparation of

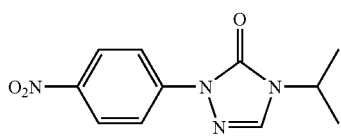

intermediate (3)

A mixture of N,N-dimethyl-N'-(4-nitrophenyl)methanehydrazonamide (0.17 mol), 2-isocyanatopropane (23 g) and N,N-dimethyl-4-pyridinamine (2 g) in dichloromethane (200 ml) was stirred and refluxed overnight. 2-Isocyanatopropane (20 g) was added and the reaction mixture was stirred and refluxed for 2 hours. The solvent was evaporated. The residue was stirred and refluxed for 2 hours in xylene (300 ml). The mixture was cooled and the resulting precipitate was filtered off and recrystallized from toluene. The precipitate was filtered off and dried, yielding 29 g of intermediate (3).

b) Preparation of

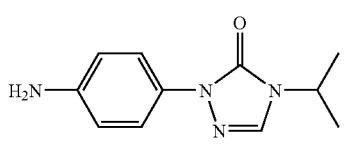

intermediate (4)

A mixture of intermediate (3) (0.11 mol) in methanol (500 ml) was hydrogenated with palladium-on-carbon (10%, 4 g) as a catalyst in the presence of a thiophene solution (2 ml). After uptake of hydrogen (3 equivalents), the catalyst was filtered off and the filtrate was evaporated. The residue was crystallised from MIK/DIPE, yielding 18 g of intermediate (4) (mp. 132.5° C.).

Example A.3 a) Preparation of

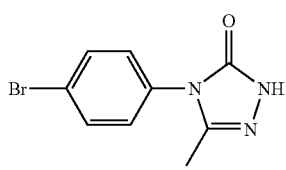

intermediate (5)

A mixture of 4-bromobenzenamine (0.2 mol) and (1-ethoxyethylidene)hydrazine-carboxylic acid, ethyl ester (0.4 mol) was stirred on an oil bath at 130-140° C. under nitrogen for 4 hours, then the reaction mixture was cooled and triturated under ether (150 ml). The resulting solids were filtered off and dried, yielding 21.5 g of crude product. A part (3.5 g) of the crude product was crystallised from 2-propanol, then the resulting product was collected and dried for 18 hours at 50° C., yielding 2.60 g of intermediate (5) (m.p. 88-90° C.).

b) Preparation of

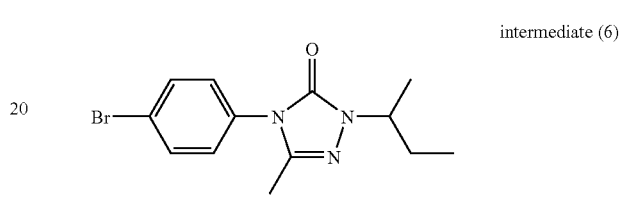

intermediate (6)

A mixture of intermediate (5) (0.01 mol), 2-bromobutane (0.02 mol) and potassium hydroxide (0.02 mol) in DMF (50 ml) was reacted for 2 hours at 120° C. The reaction mixture was cooled and poured out into ice water (500 ml). The resulting precipitate was filtered off and dried, yielding 2.20 g of crude product which was purified by flash column chromatography over silica gel (eluent 1: $CH_2Cl_2$; eluent 2: $CH_2Cl_2$/(10% $NH_4OH/CH_3OH$) 99/1). The pure product fractions were collected and the solvent was evaporated, yield 1.56 g of intermediate (6) (m.p. 168-170° C.).

Example A.4

Preparation of

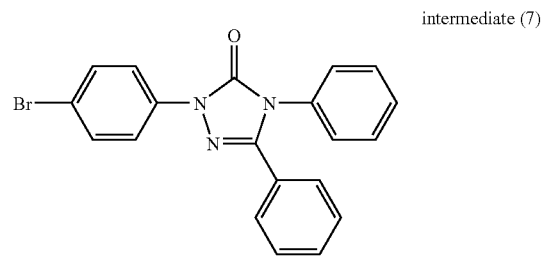

intermediate (7)

Triethylamine (0.040 mol) was added to a suspension of 2,4-dihydro-4,5-diphenyl-3H-1,2,4-triazol-3-one (0.013 mol), 4-bromophenylboronic acid (0.026 mol) and copper(II) acetate (0.0209 mol) in DCM (150 ml under $N_2$ flow. Molecular sieves (3 g) were added. The mixture was stirred at room temperature over the weekend, then filtered through dicalite, washed with 10% $NH_4OH$ solution (150 ml), washed twice with water (100 ml) and washed with a saturated NaCl solution. The resulting precipitate was filtered over dicalite and the filtrate was evaporated. The residue was triturated in methanol. The precipitate was filtered off and dried, yielding 1.8 g of intermediate (7).

Example A.5

Preparation of

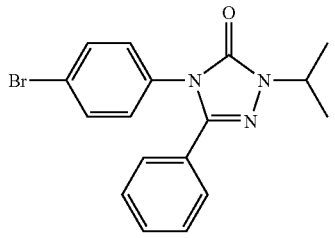

intermediate (8)

2-Bromopropane (0.03 mol) was added at room temperature to a stirring solution of 4-(p-bromophenyl)-5-phenyl-4H-1,2,4-triazol-3-ol (0.01 mol) and potassium hydroxide (0.011 mol) in DMF (40 ml). The mixture was stirred at 60° C. for 16 hours and then stirred at 70° C. for 6 hours. The mixture was poured out into cold water (200 ml). The resulting precipitate was filtered off, washed with water and DIPE and dried in vacuo. The filtrate was extracted twice with DIPE (2 times 75 ml). The combined organic layer was dried, filtered and the solvent was evaporated. The residue was triturated in methanol. The precipitate was filtered off and dried, yielding intermediate (8).

Example A.6

Preparation of

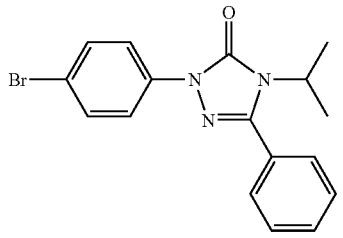

intermediate (9)

A solution of N-(4-bromophenyl)benzenecarbohydrazonic acid, ethyl ester (0.00063 mol) in THF (3 ml) was cooled to −40° C. Lithium hexamethyldisilazane (1M in THF) (0.0007 mol) was added dropwise. The mixture was stirred at −40° C. for 30 minutes. A mixture of isopropyl isocyanate (0.001 mol) in THF (2 ml) was added. The mixture was stirred for 3 hours while the temperature was brought to room temperature, then stirred at room temperature for 1 hour and poured out into water and HCl (1N). The organic layer was separated, diluted with DCM, washed with water and a saturated NaCl solution, dried, filtered and the solvent was evaporated. This fraction was triturated in DIPE. The precipitate was filtered off and dried. The residue was purified by column chromatography over silica gel (eluent: $CH_2Cl_2$/hexane 10/1). The pure fractions were collected and the solvent was evaporated, yielding 0.065 g of intermediate (9).

Example A.7 a) Preparation of

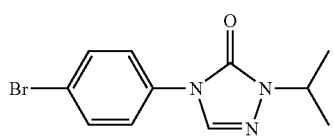

intermediate (10)

A mixture of 4-(4-bromophenyl)-2,4-dihydro-3H-1,2,4-triazol-3-one (0.062 mol) and potassium hydroxide (0.07 mol) in DMF (200 ml) was stirred for 15 minutes. 2-Bromopropane (0.2 mol) was added and the reaction mixture was stirred overnight at 60° C. The reaction mixture was cooled, poured out into water, then stirred for one hour. The reaction mixture was filtered. The precipitate was dissolved in DCM. The organic solution was washed, dried, filtered and the solvent evaporated. The residue was triturated under DIPE, filtered off and dried, yielding 11.2 g of intermediate (10).

b) Preparation of

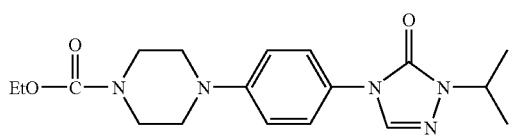

intermediate (11)

A mixture of intermediate (10) (0.001 mol), $Pd_2$(dibenzylideneacetone)$_3$ complex (0.0000025 mol), BINAP (0.000005 mol) and sodium pivalate (0.00116 mol) in toluene (4 ml) was stirred under Ar flow for 5 minutes. A mixture of 1-piperazine-carboxylic acid ethyl ester (0.00116 mol) in toluene (1 ml) was added. The mixture was stirred at 100° C. for 16 hours, evaporated and purified by HPLC (eluent: (0.5% $NH_4OAc$ in $H_2O/CH_3CN$ 90/10)/$CH_3CN$ 85/15, 10/90 and 0/100; column: Hyperprep C18 8 μm). The pure fractions were collected and the solvent was evaporated, yielding 0.076 g of intermediate (11).

c) Preparation of

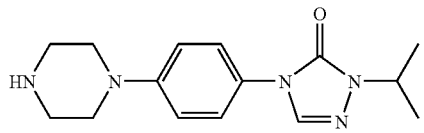

intermediate (12)

A mixture of intermediate (11) (0.05 mol) and sodium hydrogen sulfite (3 g) in a solution of hydrobromic acid in water (48%) (125 ml) was stirred and refluxed for 5 hours. The mixture was cooled and evaporated. The residue was dissolved in DCM and neutralized with $NH_4OH$. The organic layer was dried, filtered off and evaporated.

The residue was crystallized from ethyl acetate. The precipitate was filtered off and dried in vacuo at 75° C., yielding 12.9 g of intermediate (12) (mp. 125.3° C.).

Example A.8

Preparation of intermediate (13)

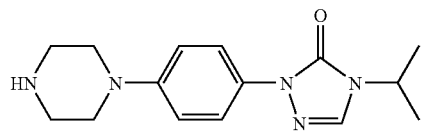

A mixture of intermediate (4) (0.17 mol) and 2-chloro-N-(2-chloroethyl)ethanamine hydrochloride (0.35 mol) in 2-butanol (400 ml) was stirred and refluxed. Potassium carbonate (7×15 g) was added each hour and the mixture was stirred and refluxed overnight. The mixture was cooled and filtered off. The precipitate was dissolved in water and extracted with DCM. The organic layer was evaporated and the residue was stirred up in DIPE. The precipitate was filtered off and dried in vacuo at 65° C., yielding 29 g of intermediate (13) (m.p. 130.2° C.).

Example A.9

Preparation of intermediate (14)

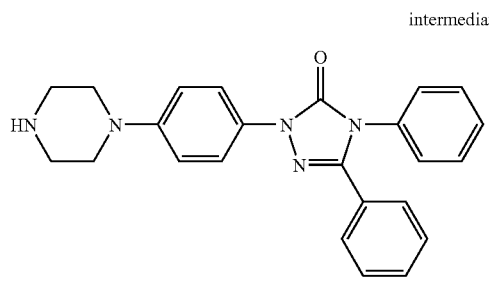

A suspension of intermediate (7) (0.010 mol), Pd$_2$(dibenzylideneacetone)$_3$ complex (0.0002 mol), BINAP (0.0004 mol) and sodium butoxide (0.025 mol) in anhydrous toluene (100 ml) was stirred at room temperature for 15 minutes. Piperazine (0.050 mol) was added. The mixture was stirred at 110° C. for 16 hours, filtered over dicalite and the filtrate was washed three times with water, washed with concentrated brine, dried, filtered and the solvent was evaporated. The residue was purified by column chromatography over silica gel (eluent: CH$_2$Cl$_2$/CH$_3$OH/NH$_3$ 90/10/1). The pure fractions were collected and the solvent was evaporated. The residue was triturated in methanol, filtered off and dried, yielding 1.1 g of intermediate (14).

Intermediates (15), (16) and (17) were prepared in an analogous way.

intermediate (15)

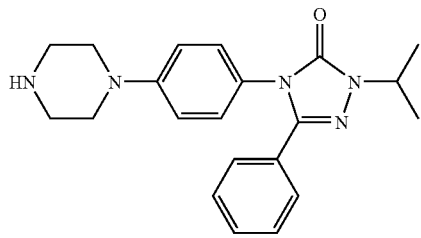

intermediate (16)

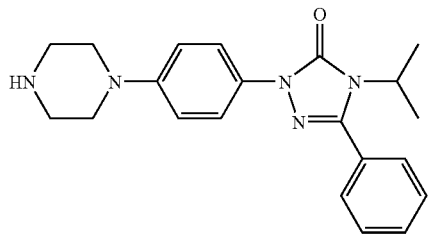

intermediate (17)

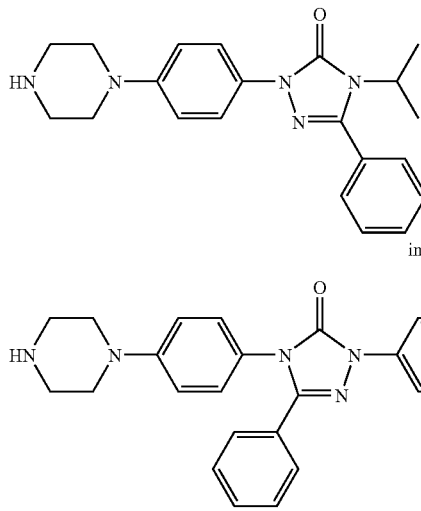

Example A.10

Preparation of intermediate (18)

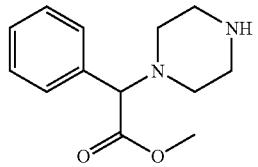

Piperazine (0.2 mol) in DMF (150 ml) was stirred until complete dissolution. Methyl 2-bromophenylacetate (0.043 mol) was added dropwise. The mixture was stirred overnight. The solvent was evaporated. The residue was dissolved in DCM and washed with water. The organic layer was dried, filtered and the solvent was evaporated, yielding 10 g of intermediate (18).

Example A.11

Preparation of intermediate (19)

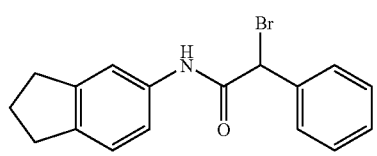

Thionyl chloride (81 ml) was added to a stirring solution of 2-bromo-2-phenylacetic acid (0.54 mol) in dry chloroform (450 ml). The reaction mixture was stirred and refluxed for 2.5 hours. The mixture was distilled off and the residue was dissolved in tetrahydrofuran (200 ml), and the resulting solution was slowly added to a stirring solution of 1H-2,3-dihydro-inden-5-amine (0.42 mol) and triethylamine (80 ml) in tetrahydrofuran (300 ml) cooled with ice-water for 15 minutes. The reaction mixture was stirred overnight and extracted from water (100 ml) with DCM (3 times 250 ml). The extracts were combined, washed with a diluted HCl solution and with brine, then the mixture was dried and filtered. The residue was crystallised 2 times from ethyl acetate (250 ml) and then the product was collected, yielding 65.0 g of intermediate (19) (mp.: 112-114° C.).

Example A.12

Preparation of

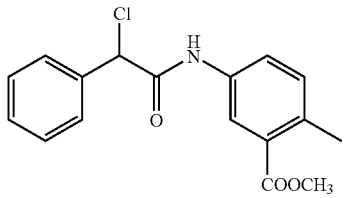

intermediate (20)

Chlorophenyl acetyl chloride (0.0015 mol) was added to a solution of 5-amino-2-methyl-benzoic acid, methyl ester hydrochloride (0.0010 mol) and triethylamine (0.0030 mol) in DCM (25 ml) and the reaction mixture was stirred for 70 hours at 20° C., then water (5 ml) was added and the mixture was stirred for 3 hours at 20° C. The organic layer was separated and the solvent was evaporated. The crude residue was purified by high-performance liquid chromatography. The product fractions were collected and the solvent was evaporated. The residue was dissolved in DCM (20 ml) and washed with an aqueous sodium carbonate solution, then the organic layer was separated and the solvent was evaporated, yielding 0.160 g of intermediate (20).

Example A.13 a) Preparation of

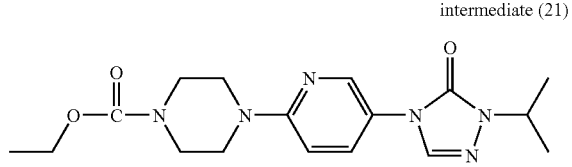

intermediate (21)

A mixture of 4-[5-(1,5-dihydro-5-oxo-4H-1,2,4-triazol-4-yl)-2-pyridinyl]-1-piperazinecarboxylic acid, ethyl ester (0.005 mol), 2-iodopropane (0.0066 mol) and potassium hydroxyde (0.0062 mol) in DMF (50 ml) was stirred at 50° C. overnight. The mixture was cooled, poured into water and the aqueous layer was extracted with DCM. The organic layer was washed, dried, filtered off and evaporated (residue 1). The reaction was started again with 4-[5-(1,5-dihydro-5-oxo-4H-1,2,4-triazol-4-yl)-2-pyridinyl]-1-piperazinecarboxylic acid, ethyl ester (0.0144 mol) and the same procedure to give residue (2). Residue (1) and (2) were put together and purified by column chromatography over silica gel (eluent: CH$_2$Cl$_2$/(CH$_3$OH/NH$_3$) 99.5/0.5). The pure fractions were collected and evaporated. The residue was crystallized from isopropano, yielding 0.5 g of intermediate (21) (m.p. 157.4° C.).

b) Preparation of

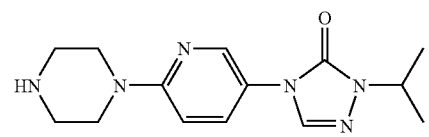

intermediate (22)

A mixture of intermediate (21) (0.056 mol) in a solution of hydrobromic acid in water (48%) (250 ml) was stirred and refluxed for 5 hours. The mixture was evaporated, ice and DCM were added to the residue and the aqueous layer was alkalized with concentrated NH$_4$OH. The organic layer was separated, dried, filtered and the solvent was evaporated. The residue was crystallized from DIPE. The precipitate was filtered off and dried, yielding 9 g of intermediate (22).

In an analogous way, intermediate (23) was prepared starting from 4-[4-(1,5-dihydro-5-oxo-4H-1,2,4-triazol-4-yl) phenyl]-1-piperazinecarboxylic acid, ethyl ester.

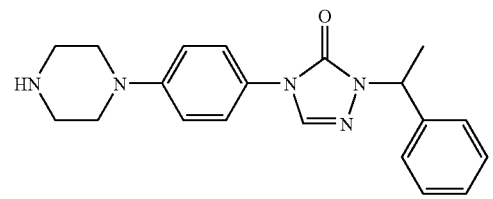

intermediate (23)

Example A.14 a) Preparation of

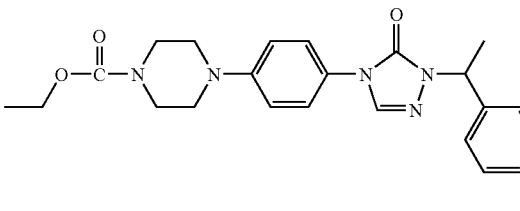

intermediate (24)

A dispersion of sodium hydride in mineral oil (60%) (0.011 mol) was stirred in DMF, dry (50 ml). 4-[4-(1,5-Dihydro-5-oxo-4H-1,2,4-triazol-4-yl)phenyl]-1-piperazine-carboxylic acid, ethyl ester (0.01 mol) was added and then extra DMF was added to facilitate the stirring. 1-Chloro-1-(4-fluorophenyl)ethane (0.015 mol) was added and the reaction mixture was heated overnight at 70° C. The organic solvent was evaporated and the concentrate was stirred in water, extracted with DCM, then dried. The crude was purified by flash chromatography (eluent:ethyl acetate/hexane 1/2). The product fractions were collected and the solvent was evaporated, yielding 2.6 g of intermediate (24) (m.p. 140-141° C.).

b) Preparation of

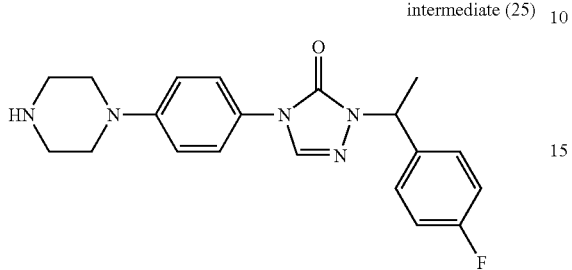

intermediate (25)

A mixture of intermediate (24) (0.0056 mol) and potassium hydroxide (0.011 mol) in 2-methoxyethanol (20 ml) was stirred and refluxed overnight, then the solvent was evaporated. The residue was purified by flash column chromatography on silica gel (eluent: methanol). The product fractions were collected and the solvent was evaporated, yielding 1.3 g of intermediate (25) (m.p. 199-201° C.).

Example A.15 a) Preparation of

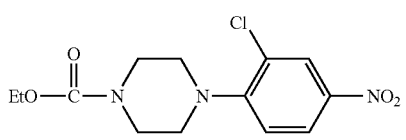

intermediate (26)

A mixture of 1-piperazinecarboxylic acid, ethyl ester (0.16 mol), 3-chloro-4-fluoronitrobenzene (0.14 mol) and sodium carbonate (0.2 mol) in DMF (200 ml) was stirred overnight at room temperature. The mixture was filtered and the filtrate was evaporated. The residue was crystallized from DIPE. The precipitate was filtered off and dried, yielding 41.8 g of intermediate (26).

b) Preparation of

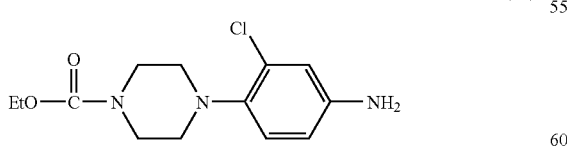

intermediate (27)

A mixture of intermediate (26) (0.13 mol) and triethylamine (15 g) in methanol (500 ml) was hydrogenated overnight at 50° C. with palladium on activated carbon (10%, 3 g) as a catalyst in the presence of a solution of thiophene in methanol (4%, 3 ml). After uptake of hydrogen (3 equivalents), the catalyst was filtered off and the filtrate was evaporated. The residue was triturated in DIPE. The precipitate was filtered off and dried, yielding 27.3 g of intermediate (27).

c) Preparation of

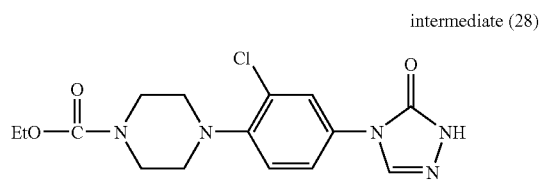

intermediate (28)

Reaction under $N_2$ flow. A mixture of intermediate (27) (0.096 mol) and ethyl [(dimethylamino)methylene]hydrazinecarboxylate (0.29 mol) in sulfolane (50 ml) was stirred for one hour at 180° C., then cooled, poured out into water, stirred for one hour, and decanted. The residue was dissolved in DCM. The organic solution was washed, dried, filtered and the solvent was evaporated. The residue was triturated in DIPE and ethyl acetate, filtered off and dried, yielding 17 g of intermediate (28).

d) Preparation of

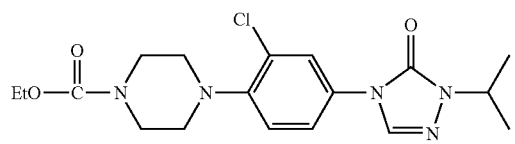

intermediate (29)

A mixture of intermediate (28) (0.025 mol) and 2-bromopropane (0.050 mol) in DMF (50 ml) was stirred at room temperature and potassium hydroxide (80%) (0.050 mol) was added. The reaction mixture was stirred and refluxed for 6 hours, then cooled. The mixture was diluted with water, the water was decanted off and fresh water was added. The mixture was extracted with DCM (4 times 100 ml) and the extracts were dried and concentrated. The residual oil was purified by flash column chromatography (eluent: EtOAc/hexane 1/2). The product fractions were collected and the solvent was evaporated. The residue was crystallised from diethyl ether and the resulting precipitate was collected, yielding 8.63 g of intermediate (29) (mp.: 108-110° C.).

e) Preparation of

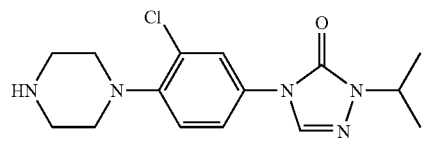

intermediate (30)

A mixture of intermediate (29) (0.01 mol) and sodium hydrogen sulfite (0.009 mol) in hydrobromic acid (48%) (40 ml) was stirred and refluxed for 5 hours. Then the reaction mixture was cooled and the solvent was evaporated. The residue was dissolved in DCM and neutralised with $NH_4OH$. The organic layer was separated, dried, filtered off and the solvent was evaporated. The residue was crystallised from ethyl acetate, then the resulting precipitate was filtered off and dried, yielding 4.3 g of intermediate (30) (m.p. 152-153° C.).

In an analogous way, intermediates (31) was prepared starting from 1,2-difluoro-4-nitrobenzene and ethyl N-piperazinecarboxylate.

intermediate (31)

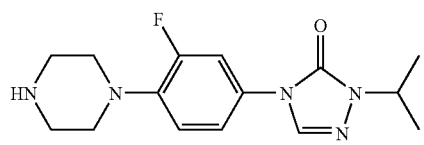

Example A.16 a) Preparation of intermediate (32)

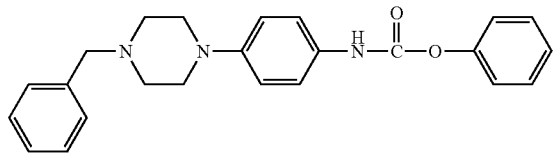

Phenyl chloroformate (0.33 mol) was added dropwise to a mixture of 4-[1-(phenylmethyl)-1-piperazinyl]benzenamine (0.3 mol) in DMA (300 ml) and the reaction mixture was stirred at room temperature for 1 hour. The mixture was poured out into water, then the resulting precipitate was filtered off and dried, yielding 118 g of intermediate (32) (m.p. 160.0° C.).

b) Preparation of intermediate (33)

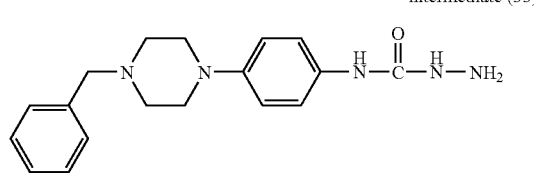

A mixture of intermediate (32) (0.15 mol) and hydrazine hydrate (1:1) (0.62 mol) in 1,4-dioxane (300 ml) was stirred at room temperature overnight. Water was added, the precipitate was filtered off and dried, yielding 35 g of intermediate (33).

c) Preparation of intermediate (34)

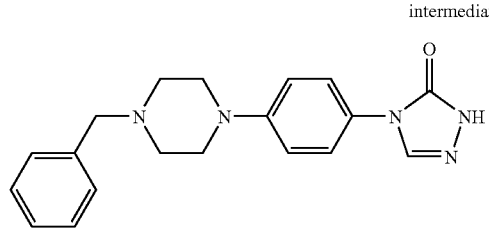

A mixture of intermediate (33) (0.107 mol) and methanimidamide monoacetate (0.55 mol) in 1-butanol (300 ml) was stirred and refluxed for 4 hours. The mixture was cooled and the product was crystallized out. The precipitate was filtered off, washed with ethyl acetate on a filter and dried, yielding 23.5 g of intermediate (34).

d) Preparation of intermediate (35)

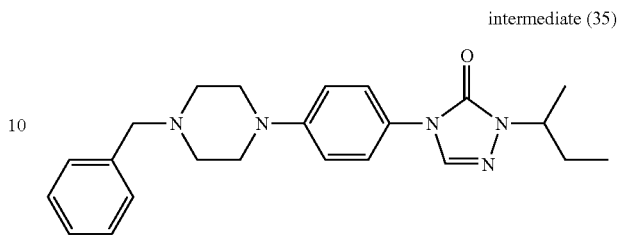

A mixture of intermediate (34) (0.178 mol), 2-bromobutane (0.36 mol) and sodium hydroxide (0.36 mol) in DMF (250 ml) was stirred at 80° C. under nitrogen flow overnight. Sodium hydroxide (3 g) and 2-bromobutane (10 g) were added. The mixture was stirred at 100° C. for 2 hours, then cooled and poured out into water. The precipitate was filtered off and dried. The residue was crystallized from 2-propanol, yielding 40 g of intermediate (35).

e) Preparation of intermediate (36)

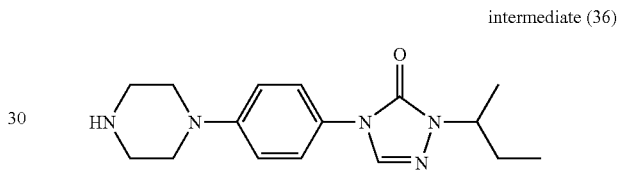

A mixture of intermediate (35) (0.03 mol) in methanol (250 ml) was hydrogenated under atmospheric conditions with palladium on activated carbon (10%) (3 g) as a catalyst. After uptake of hydrogen (1 equivalent), the catalyst was filtered off and the filtrate was evaporated. The residue was dissolved in methanol and converted into the hydrochloric acid salt (1:1) with HCl/2-propanol. The solvent was evaporated. The solid residue was stirred in 2-propanone, filtered off and dried, yielding 11.5 g of intermediate (36).

In an analogous way, intermediate (37) was prepared starting from 4-[1-(phenylmethyl)-4-piperidinyl]benzenamine.

intermediate (37)

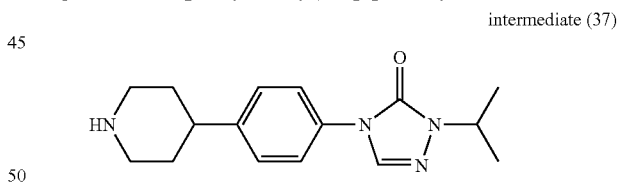

Example A.17 a) Preparation of intermediate (38)

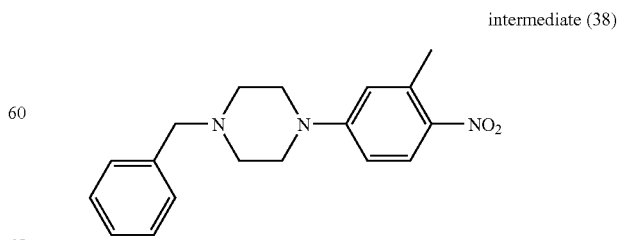

A mixture of 1-(phenylmethyl)piperazine (0.32 mol), 4-fluoro-2-methylnitrobenzene (0.32 mol) and sodium carbonate (1.27 mol) in DMF (35 ml) was heated to 60° C. and then stirred overnight. The reaction mixture was poured out into water. The resulting precipitate was filtered off and dried, yielding 78.64 g of intermediate (38).

b) Preparation of intermediate (39)

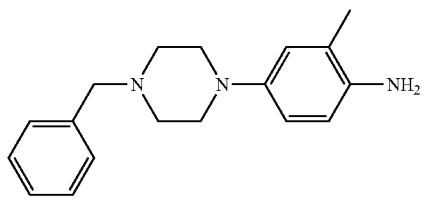

A mixture of intermediate (38) (0.08 mol) in ethanol (250 ml) was hydrogenated with hydrogen (50 bar=5.0 M.Pa) at 40° C. for 90 minutes with palladium-on-carbon (5%, 0.8 g) as a catalyst in the presence of a solution of thiophene in ethanol (0.6 ml). After uptake of hydrogen (3 equivalents), the reaction mixture was filtered over dicalite and the filtrate was evaporated. The residue was triturated under DCM and then the resulting precipitate was filtered off, yielding 20 g of intermediate (39).

c) Preparation of intermediate (40)

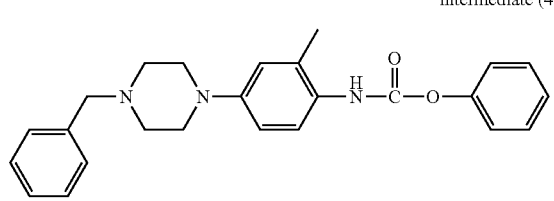

Carbonochloridic acid, phenyl ester (0.048 mol) was added dropwise at below 5° C. to a suspension of intermediate (39) (0.048 mol) and sodium carbonate (0.068 mol) in DCM (40 ml) and the reaction mixture was stirred for 3 hours at a temperature ranging between 3 and 5° C. Water (60 ml) was added and the layers were separated. The product was extracted with DCM (2 times 140 ml). The organic layers were combined, washed with water (125 ml), dried and evaporated. The residue was purified by column chromatography (eluent:ethyl acetate/hexane 1/2). Two product fractions were collected and the solvent was evaporated, yielding 4.42 g of intermediate (40) (m.p.: 106-108° C.).

d) Preparation of intermediate (41)

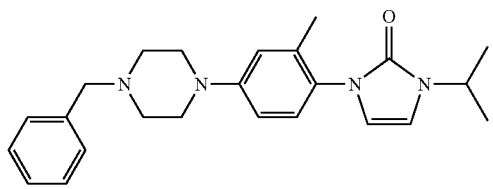

A mixture of intermediate (40) (0.042 mol), N-(2,2-dimethoxyethyl)-2-propanamine (0.063 mol), triethylamine (0.042 mol) and N,N-dimethyl-4-pyridinamine (0.042 mol) in 1,4-dioxane (200 ml) was stirred and refluxed for 2 hours. The reaction mixture was left to stand overnight. Water (200 ml) was added and the mixture was stirred for 1 hour followed by extraction with DCM (3 times 100 ml). The organic layers were combined, washed with water (200 ml), dried and distilled off. Formic acid (25 ml) was added and the resulting mixture was stirred and refluxed for 2 hours, then distilled off and extracted from an aqueous NaHCO$_3$ solution (300 ml) with DCM (3 times 80 ml). The extracts were combined, dried and distilled off. The residue was purified by column chromatography over silica gel (eluent: ethyl acetate). Two product fractions were collected and the solvent was evaporated, yielding 7.97 g of intermediate (41) (m.p. 135-137° C.).

e) Preparation of intermediate (42)

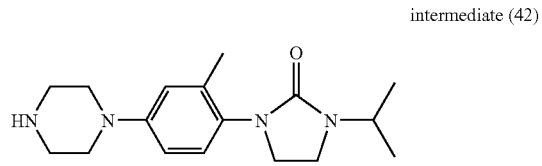

A mixture of intermediate (41) (0.0072 mol) in acetic acid (40 ml) was hydrogenated for 6 hours at 10 Bar (1.0 M.Pa) with palladium-on-carbon (10%, 0.4 g) as a catalyst. After uptake of hydrogen, the reaction mixture was filtered over celite. The celite path was washed with ethanol and the filtrate was evaporated. The residue was extracted from NaOH (2N, 70 ml) with DCM (2 times 75 ml). Then the extracts were combined, dried and evaporated. The residue was purified by column chromatography (eluent: CH$_2$Cl$_2$/CH$_3$OH 99/1). Two product fractions were collected and the solvent was evaporated. Both fractions were fully debenzylated (but only partially reduced) and combined, to give residue (I). Residue (I) was subjected a second time to the same reaction procedure, yielding 0.81 g of intermediate (42).

Example A.18

Preparation of intermediate (43)

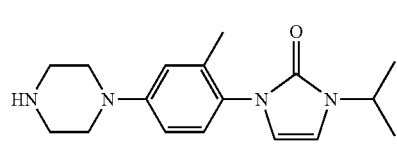

A mixture of 1-chloroethyl chloroformate (0.017 mol) in dry dichloromethane (10 ml) was added dropwise to a stirring solution of intermediate (41) (0.013 mol) in dry DCM (50 ml) at 0° C. The reaction mixture was stirred for 24 hours and distilled off. Methanol (75 ml) was added to the residue and the mixture was stirred and refluxed for 1 hour. The mixture was distilled off, diethyl ether (80 ml) was added and the ground solids were filtered off, yielding 4.53 g of intermediate (43) (mp.: 232-234° C.).

Example A.19 a) Preparation of

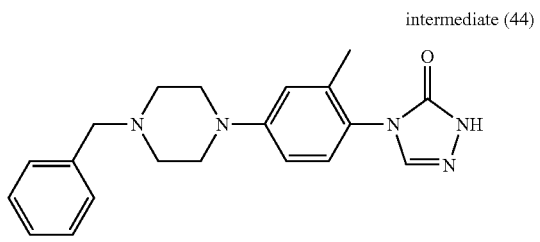

intermediate (44)

Methyl 2-[(dimethylamino)methylene]hydrazinecarboxylate was added to a stirring solution of intermediate (39) (0.025 mol) in 1,3-dimethyl-2-imidazolidinone (15 ml) at 160° C. The reaction mixture was kept at 160° C. over 1 hour (some $CH_3OH$ was distilled off). The rest of 2-[(dimethylamino)methylene]-hydrazine-carboxylate (q.s.) was added and the mixture was kept at 160° C. The resulting mixture was cooled to room temperature and extracted from water (100 ml) with diethyl ether (3 times 150 ml). The diethyl ether-layer was evaporated dry and the residue was filtered off, then washed with ether (2 times 50 ml), yielding 3.56 g of intermediate (44) (m.p. 124.5-126.5° C.).

b) Preparation of

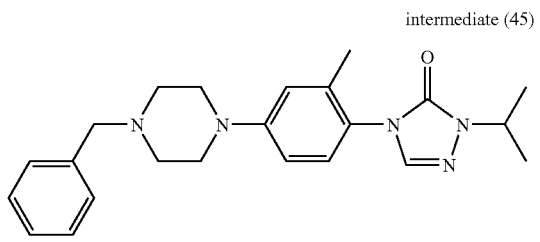

intermediate (45)

A mixture of intermediate (44) (0.010 mol), 2-bromopropane (0.020 mol) and potassium hydroxide (0.012 mol) in DMF (25 ml) was stirred for 42 hours at room temperature and then water (200 ml) was added. The resulting solids were filtered off and washed with water (3 times 60 ml), yielding 3.39 g of intermediate (45) (m.p. 145.5-146.5° C.).

c) Preparation of

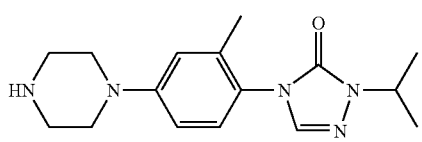

intermediate (46)

A mixture of 1-chloroethyl chloroformate (0.011 mol) in dichloromethane (10 ml) was added dropwise to a stirring solution of intermediate (45) (0.0082 mol) in DCM (30 ml, dry) at 0° C., then the reaction mixture was stirred at 0° C. for 2 hours and distilled off. Methanol (50 ml) was added and the resulting mixture was stirred and refluxed for 1 hour. The mixture was distilled off and ground up with ether. The residue was dissolved in methanol (50 ml) and the solution was extracted from a saturated $NaHCO_3$ solution with DCM (3 times 100 ml). The extracts were combined, dried and distilled off. The residue was purified by column chromatography (eluent: $CH_2Cl_2/CH_3OH$ 9/1). The product fractions were collected and the solvent was evaporated, to give 1.6 g of intermediate (46) (m.p. 140-142° C.).

Example A.20 a) Preparation of

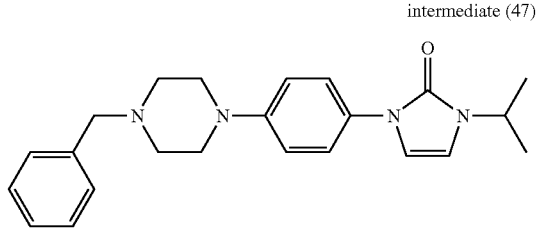

intermediate (47)

A mixture of intermediate (74) (0.073 mol), N-(2,2-dimethoxyethyl)-2-propanamine (0.116 mol), N,N-dimethyl-4-pyridinamine (0.073 mol) and triethylamine (0.073 mol) in 1,4-dioxane (360 ml) was stirred and refluxed for 2 hours. The reaction mixture was cooled to room temperature. Water (360 ml) was added. The mixture was stirred for 15 minutes and extracted with DCM (3 times 200 ml). The organic extracts were combined, dried and evaporated. The residue was stirred and refluxed in formic acid (290 ml) for 2 hours, then the mixture was cooled and the solvent was distilled off, yielding 67 g of product. The resulting residue was dissolved in DCM, washed with a saturated $NaHCO_3$ solution, dried and evaporated. This residue was washed with $NaHCO_3$ and purified by flash column chromatography, yielding intermediate (47).

b) Preparation of

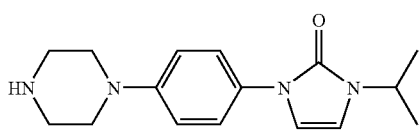

intermediate (48)

A mixture of 1-chloroethyl chloroformate (0.00346 mol) in dry DCM (3 ml) was added dropwise to a stirring solution of intermediate (47) (0.00266 mol) in dry DCM (10 ml) at 0° C. The reaction mixture was stirred for 1 hour at 0° C. The solvent was distilled off and the residue was dissolved in methanol (20 ml). The solution was stirred and refluxed for 1 hour, then the mixture was cooled to room temperature and the solvent was evaporated off. The residue was triturated under diethyl ether (20 ml) and the resulting product was collected, yielding 0.55 g of intermediate (48) (m.p. 196-198° C.).

Example A.21

Preparation of

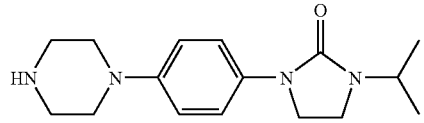
intermediate (49)

A mixture of intermediate (47) (0.053 mol) in acetic acid (200 ml) was hydrogenated for 6 hours at 30° C. under hydrogen (2 bar=0.2 M.Pa) with palladium-on-carbon (10%, 2 g) as a catalyst, then the reaction mixture was heated under hydrogen at 30° C. for another 7 hours and stirred overnight at room temperature. After uptake of hydrogen (2 equivalents), the mixture was filtered over celite and distilled off. The residue was extracted from NaOH (2N, 200 ml) with DCM (2 times 250 ml), then the extracts were combined, dried and evaporated, yielding 14.4 g of intermediate (49) (m.p. 159-161° C.).

Example A.22 a) Preparation of

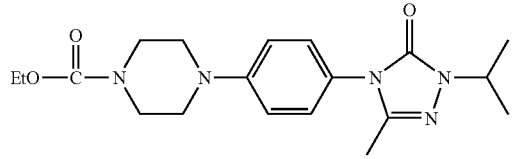
intermediate (50)

A mixture of 4-[4-(1,5-dihydro-3-methyl-5-oxo-4H-1,2,4-triazol-4-yl)phenyl]-1-piperazinecarboxylic acid ethyl ester (0.0078 mol), 2-bromopropane (0.023 mol) and sodium carbonate (0.023 mol) in DMF (250 ml) was stirred at 80° C. overnight. Potassium hydroxide (1.4 g) was added. The mixture was stirred for 5 minutes. 2-Bromopropane (0.023 mol) was added again. The mixture was stirred at 80° C. overnight. The solvent was evaporated. The residue was dissolved in DCM, washed with water, dried, filtered and the solvent was evaporated. Potassium hydroxide (1.4 g), 2-bromopropane (3 g) and DMF (250 ml) were added to the residue. The mixture was stirred at 80° C. for 5 hours. The solvent was evaporated. The residue was dissolved in DCM, washed, dried, filtered and the solvent was evaporated. The residue was purified by column chromatography over silica gel (eluent: CH$_2$Cl$_2$/CH$_3$OH 99/1). The pure fractions were collected and the solvent was evaporated, yielding 2.1 g of intermediate (50).

b) Preparation of

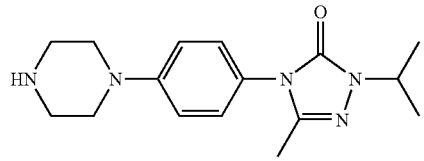
intermediate (51)

A mixture of intermediate (50) (0.0053 mol) and potassium hydroxide (3 g) in 2-propanol (50 ml) was stirred and refluxed overnight, stirred at room temperature over the weekend and then stirred and refluxed overnight. The solvent was evaporated. The residue was dissolved in DCM, washed, dried, filtered and the solvent was evaporated, yielding 1.6 g of intermediate (51).

Example A.23 a) Preparation of

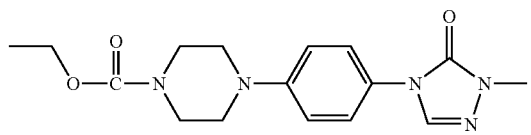
intermediate (52)

A mixture of 4-[4-(1,5-dihydro-5-oxo-4H-1,2,4-triazol-4-yl)phenyl]-1-piperazine-carboxylic acid ethyl ester (0.016 mol), dimethyl sulfate (0.02 mol) and potassium hydroxide (0.02 mol) in DMF (100 ml) was stirred at room temperature for 2 hours. The mixture was filtered off, the filtrate was poured into water (400 ml), crystallized out and stirred for 10 minutes. The precipitate was filtered off, dissolved in DCM and purified by column chromatography over silica gel (eluent: CH$_2$Cl$_2$/CH$_3$OH 99/1). The pure fractions were collected and evaporated. The residue was crystallized from ethyl acetate, yielding 2.5 g of intermediate (52) (mp. 169.7° C.).

b) Preparation of

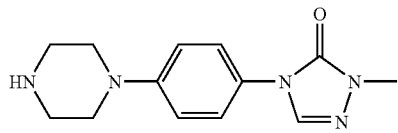
intermediate (53)

A mixture of intermediate (52) (0.076 mol) in a mixture of hydrogen bromide in water (48%) (25 0 ml) was stirred and refluxed for 5 hours. The solvent was evaporated. Ice and DCM were added. The mixture was basified with a concentrated NH$_4$OH solution and separated into its layers. The organic layer was dried, filtered and the solvent was evaporated. The residue was crystallized from DIPE. The precipitate was filtered off and dried, yielding 18 g of intermediate (53).

Example A.24

Preparation of

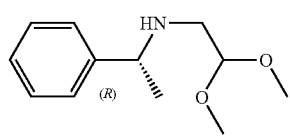
intermediate (54)

(+)-(R)-α-methylbenzenemethanamine (0.1 mol) was stirred in THF (200 ml) at room temperature, then dimethoxyacetaldehyde 0.2 mol, 45% in 2-methoxy-2-methylpropane, was added followed by titanium(IV) isopropoxide (0.11 mol). The mixture was reacted for 2 hours at room temperature and methanol (80 ml) was added, then sodium tetrahydroborate (0.2 mol) was added portionwise and the reaction mixture was stirred for 2 hours at room temperature. Water (80 ml) was added and then the resulting precipitate was filtered off over dicalite and washed 3 times with THF. The filtrate was evaporated until THF and methanol were removed and the residue was extracted with DCM. The organic layer was separated, dried, filtered off and the solvent was evaporated. The residue was purified by column chromatography over silica gel (eluent: CH$_2$Cl$_2$/CH$_3$OH 100/0, 98/2). The product fractions were collected and the solvent was evaporated, yielding 17 g of intermediate (54).

Example A.25

Preparation of

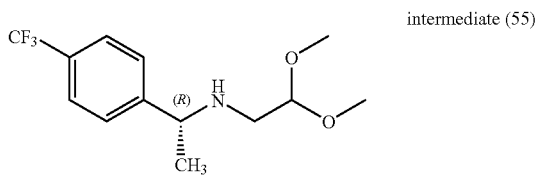

intermediate (55)

Mp-Triacetoxyborohydride resin (polystyrene-linked-CH$_2$—N$^+$Et$_3$-B$^-$H(Oac)$_3$ resin obtained from Argonaut (New Road, Hengoed, Mid Glamorgan CF82 8AU, United Kingdom) with product code 800414) (0.500 g) was added to a solution of (R)-α-methyl-4-(trifluoromethyl)benzenemethanamine (0.00082) and dimethoxy-acetaldehyde (0.0010 mol) in THF (5 ml) and the reaction mixture was shaken for 30 minutes at 100° C., then the mixture was cooled to room temperature and shaken for 24 hours at room temperature. Extra dimethoxy-acetaldehyde (0.0010 mol) and extra Argonaut 800414 triacetoxyborohydride resin (0.250 g) were added and the resulting mixture was shaken for 24 hours at room temperature. 2-(4-Toluenesulfonylhydrazino)-ethyl-functionalized silica gel (obtained from Sigma-Aldrich Corporation with Aldrich code 55, 259-3) (0.200 g, 1 mmol/g) was added and then Novabiochem 01-64-0182 4-benzyloxy-benzaldehyde polystyrene resin (0.300 g) was added. The reaction mixture was shaken for 24 hours and extra Novabiochem 01-64-0182 resin (0.300 g) was added. The mixture was shaken for 24 hours, filtered, washed with DCM (5 ml) and the filtrate was evaporated, yielding 0.181 g of intermediate (55).

Example A.26

Preparation of

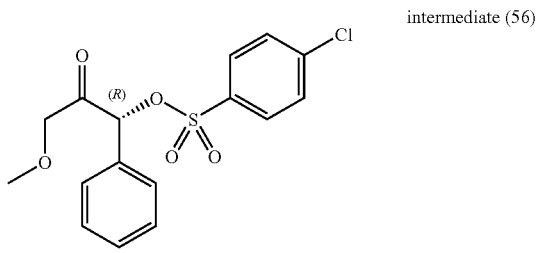

intermediate (56)

A mixture of (R)-ethyl (hydroxy)(phenyl)acetate (0.139 mol), 1,2-lutidine (21 g) and N,N-dimethyl-4-pyridinamine (1 g) was stirred in DCM (200 ml) and the mixture was cooled in an ice bath, then a mixture of 4-chlorobenzenesulfonyl chloride (0.153 mol) in DCM (50 ml) was added dropwise and the reaction mixture was stirred overnight at room temperature. Triethylamine (q.s.) was added (exothermic reaction) and the mixture was stirred for 2 hours at room temperature. The resulting mixture was washed with diluted HCl, dried and the solvent was evaporated. The residue was further crystallised from hexane with a small amount of DIPE and the resulting precipitate was collected, yielding 20.1 g of intermediate (56) (mp. 46.3-48.8° C.).

Example A.27

Preparation of

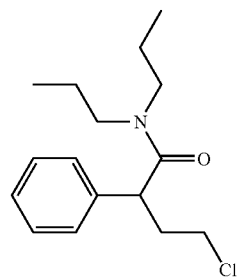

intermediate (57)

Thionyl chloride (1 mol) was added to a mixture of dihydro-3-phenyl-2(3H)-furanone (0.4 mol) and zinc chloride (5 g) and then the reaction mixture was stirred and refluxed overnight. The polymerised product was dissolved in CHCl$_3$ and the solvent was evaporated. The residue was distilled and the product was collected, yielding 7 g of 4-chloro-2-phenyl-butyryl chloride. The obtained 4-chloro-2-phenyl-butyryl chloride was added dropwise at a temperature below 10° C. to a solution of dipropylamine (1 mol) in DCM (500 ml) and the reaction mixture was stirred overnight. The mixture was washed with water, dried and the solvent was evaporated, yielding 75 g of intermediate (57).

Example A.28

Preparation of

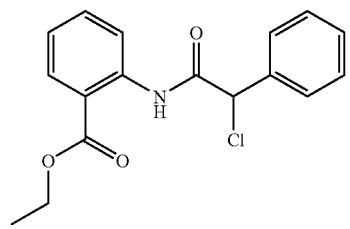

intermediate (58)

Triethylamine (0.040 mol) and chlorophenylacetyl chloride (0.0333 mol) were added dropwise under stirring to a mixture of 2-aminobenzoic acid, ethyl ester (0.0333 mol) in THF (50 ml) and the reaction mixture was stirred for 15 minutes, then the organic solvent was removed and the residue was taken up in CH$_2$Cl$_2$/H$_2$O (25/50). The organic layer was separated and the aqueous layer was extracted with DCM (25 ml). The organic layers were combined, dried, filtered and the solvent was removed, yielding 10.5 g of intermediate (58) (m.p. 55-59.5° C.).

Example A.29 a) Preparation of

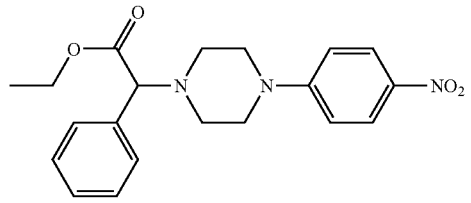
intermediate (59)

A mixture of 1-(4-nitrophenyl)piperazine (0.024 mol), α-bromobenzeneacetic acid ethyl ester (0.024 mol) and sodium carbonate (0.036 mol) in dry DMF (25 ml) was stirred overnight at room temperature and then the organic solvent (DMF) was evaporated. The residue was stirred in water and extracted with DCM. The organic layer was separated and dried, then the solvent was evaporated and the residue was stirred in hexane. Finally, the desired product was collected, yielding intermediate (59) (m.p. 101-104° C.).

b) Preparation of

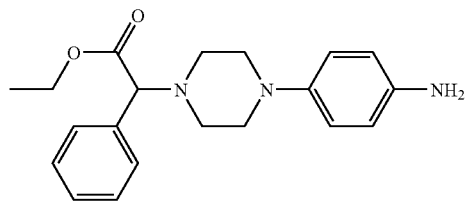
intermediate (60)

A mixture of intermediate (59) (0.01 mol) in cyclohexene (5 ml) and ethanol (25 ml) was hydrogenated for 36 hours with palladium-on-carbon (10%, 0.12 g) as a catalyst. After uptake of hydrogen (3 equivalents), the catalyst was filtered off and the filtrate was evaporated. The residue was purified by flash column chromatography (eluent: ethyl acetate/hexane 1/4, 1/1). The product fractions were collected and the solvent was evaporated, yielding intermediate (60).

Example A.30 a) Preparation of

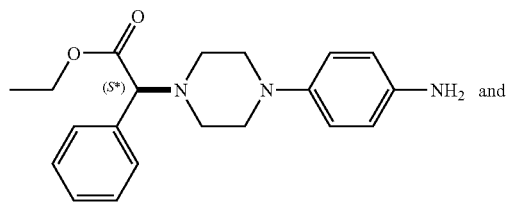
intermediate (61)

and

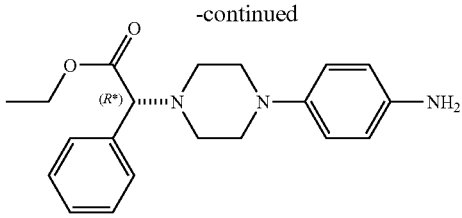
intermediate (62)

Intermediate (60) (0.088 mol) was separated and purified by Chiral high-performance liquid chromatography (Prochrom D.A.C. column; 500 g Chiralcel OJ 20 µm; eluent: ethanol (isocratic)). Two product fractions were collected and, after evaporation of the solvent, converted into their hydrochloric acid addition salt (1:2) with HCl/2-propanol, yielding 13.7 g of intermediate (61) (mp. 214.5-214.6° C.; $[\alpha]_D^{20}=-54.58°$ (c=10.26 mg/5 ml in DMF)), isolated as its hydrochloric acid salt and 11.7 g of intermediate (62) (mp. 222-222.1° C.; $[\alpha]_D^{20}=+54.90°$ (c=10.11 mg/5 ml in DMF)), isolated as its hydrochloric acid salt.

b) Preparation of

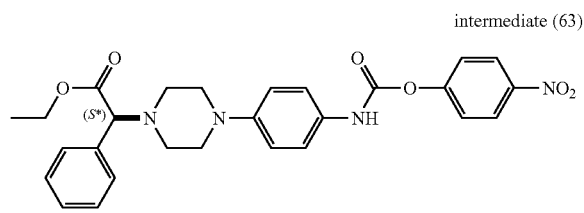
intermediate (63)

4-Nitrophenyl chloroformate was stirred in DCM (100 ml) and the mixture was cooled on an ice-salt bath. Then intermediate (61), followed by a saturated sodium hydrogen carbonate solution (100 ml) was added. The reaction mixture was stirred and cooled for 1 hour, then stirred for 1 hour at room temperature. The organic layer was separated, dried and the solvent was evaporated. The residue was triturated under ether/DIPE (50/50), filtered off and the desired product was collected, yielding 1.76 g of intermediate (63).

In an analogous way, intermediate (64) was prepared starting from intermediate (62).

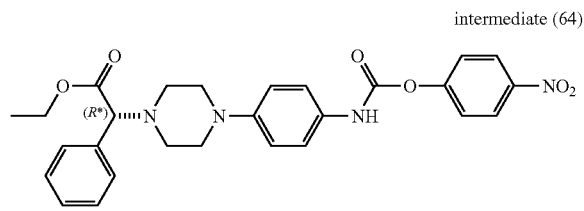
intermediate (64)

Example A.31 a) Preparation of

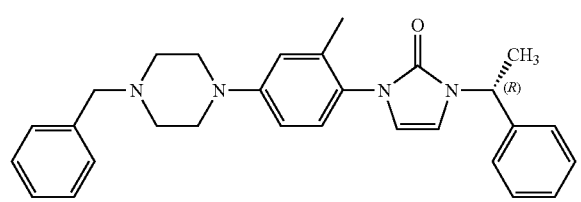
intermediate (65)

A mixture of intermediate (40) (0.029 mol), (R)—N-(2,2-dimethoxyethyl)-benzenemethanamine (0.029 mol) and N,N-dimethyl-4-pyridinamine (0.029 mol) in dioxane was stirred and refluxed for 24 hours, then the reaction mixture was cooled, poured out into water and extracted with DCM. The extract was washed with water and the solvent was evaporated. The oily residue was treated with a (1:1) mixture of trifluoroacetic acid and methanol and heated at 60° C. for 4 hours, then the resulting mixture was cooled and filtered. The residue was taken up in DCM, washed with water and with sodium carbonate and dried, yielding intermediate (65).

b) Preparation of intermediate (66)

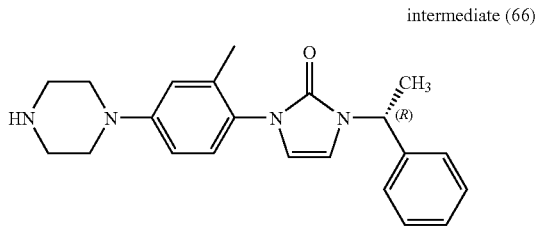

A solution of intermediate (65) (0.015 mol) in dry DCM was stirred at 0° C. and a mixture of 1-chloroethyl chloroformate (0.0195 mol) in DCM was added dropwise, then the reaction mixture was stirred at 0° C. for 1 hour and the solvent was evaporated. The residue was dissolved in methanol (140 ml) and the resulting solution was heated at reflux temperature for 1 hour. The mixture was cooled to room temperature and evaporated to dryness, then the residue was triturated with ether and the desired product was collected, yielding intermediate (66).

Example A.32 a) Preparation of intermediate (67)

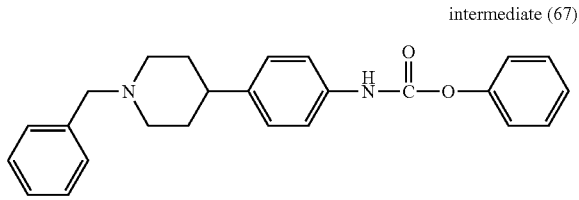

Phenyl chloroformate (0.33 mol) was added dropwise to a cooled mixture on ice of 4-[1-(phenylmethyl)-4-piperidinyl]-benzenamine (0.33 mol) in DMA (500 ml) and the mixture was stirred for 1 hour. The mixture was poured into water, the precipitate was filtered off and dried, yielding 128 g of intermediate (67).

b) Preparation of intermediate (68)

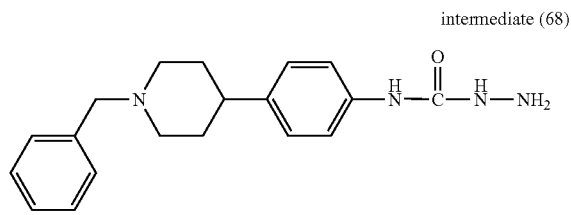

A mixture of intermediate (67) (0.33 mol) and hydrazine monohydrate (1.6 mol) in 1,4-dioxane (1 l) was stirred at room temperature for 48 hours and then at 60° C. overnight. The mixture was poured into water. The precipitate was filtered off and crystallized from 1-butanol, yielding 61 g of intermediate (68).

c) Preparation of intermediate (69)

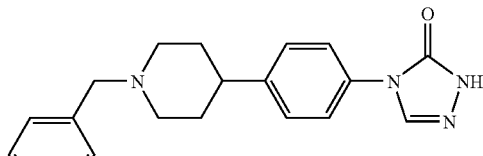

A mixture of intermediate (68) (0.12 mol) and methanimidamide, monoacetate (0.5 mol) in 1-butanol (250 ml) was stirred and refluxed for 48 hours. The mixture was cooled, DIPE was added and crystallized out. The precipitate was filtered off and dried. The residue was purified by column chromatography over silica gel (eluent: $CH_2Cl_2/CH_3OH$ 98/2). The pure fractions were collected and evaporated. The residue was triturated in DIPE, yielding 18.7 g of intermediate (69).

d) Preparation of intermediate (70)

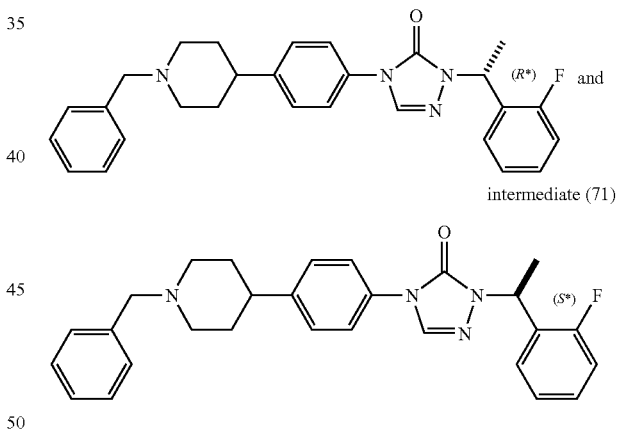

intermediate (71)

Intermediate (69) (0.04 mol) was stirred in DMF (200 ml) at room temperature and then sodium hydride (60%) (0.04 mol) was added and the mixture was stirred for 1 hour at room temperature. The mixture was heated at 70° C. and after 30 minutes 1-(1-chloroethyl)-2-fluorobenzene (0.062 mol) was added. The reaction mixture was stirred for 20 hours at 70° C. and then water (500 ml) and DIPE (50 ml) were added. The resulting mixture was stirred for 1 hour at room temperature and the product was filtered off, then purified by liquid chromatography over silica gel (eluent: $CH_2Cl_2/CH_3OH$ 99/1). The product fractions were collected and the solvent was evaporated, yielding 13 g of product which was separated into its enantiomers by liquid chromatography on a chiral AD-column (eluent: $CH_3OH/CH_3CN$ 65/35). Two product fractions were collected and the solvent was evaporated. Each residue was triturated under DIPE and the desired products were filtered off, yielding 5.1 g of intermediate (70) and 5.1 g of intermediate (71).

e) Preparation of

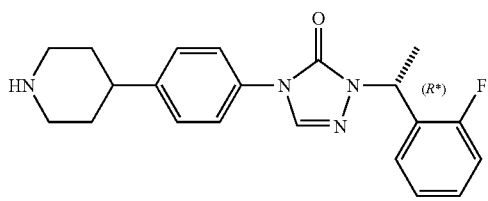

intermediate (72)

A mixture of intermediate (70) (0.011 mol) in methanol (100 ml) was hydrogenated at room temperature for 24 hours with palladium-on-carbon (1 g) as a catalyst. Extra hydrogen and palladium-on-carbon (10%) (catalytic quantity) were added and the mixture was further hydrogenated for 24 hours. After uptake of hydrogen (1 equivalent), the catalyst was filtered off and the filtrate was evaporated. The residue was triturated under DIPE and the desired product was filtered off, yielding 3.3 g of intermediate (72).

In an analogous way, intermediate (73) was prepared starting from intermediate (71).

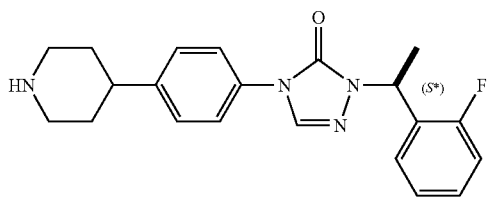

intermediate (73)

Example A.33 a) Preparation of

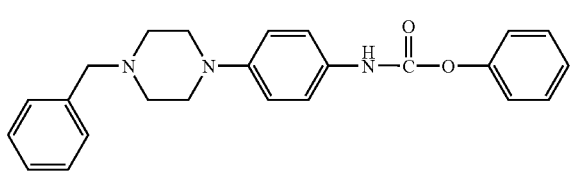

intermediate (74)

Phenyl chloroformate (0.33 mol) was added dropwise to a mixture of 4-[4-(phenylmethyl)-1-piperazinyl]benzenamine (0.3 mol) in DMA (300 ml) and the reaction mixture was stirred at room temperature for 1 hour. The mixture was poured out into water, then the resulting precipitate was filtered off and dried, yielding 118 g of intermediate (74) (mp. 160.0° C.).

b) Preparation of

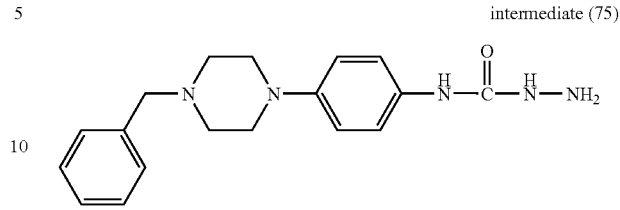

intermediate (75)

A mixture of intermediate (74) (0.15 mol) and hydrazine monohydrate (0.62 mol) in 1,4-dioxane (300 ml) was stirred at room temperature overnight. Water was added, the precipitate was filtered off and dried, yielding 35 g of intermediate (75).

c) Preparation of

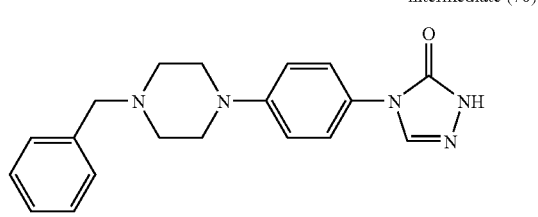

intermediate (76)

A mixture of intermediate (75) (0.107 mol) and methanimidamide, monoacetate (0.55 mol) in 1-butanol (300 ml) was stirred and refluxed for 4 hours. The mixture was cooled and the product was crystallized out. The precipitate was filtered off, washed with ethyl acetate on a filter and dried, yielding 23.5 g of intermediate (76).

d) Preparation of

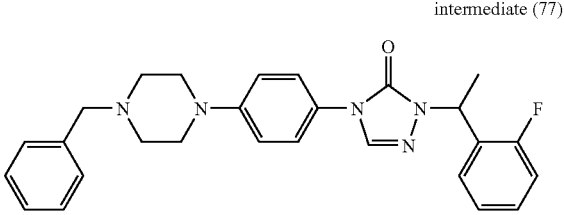

intermediate (77)

Intermediate (76) (0.30 mol) and 1-(1-chloroethyl)-2-fluorobenzene (0.38 mol) were added to a solution of potassium hydroxide (0.38 mol) in DMF (500 ml) and then the reaction mixture was stirred for 6 hours at 60° C. and cooled. The mixture was poured out into water and extracted with DCM. The organic layer was separated, dried and filtered over a Büchi filter. The filtrate was evaporated and the residue was purified by column chromatography over silica gel. The product fractions were collected and the solvent was evaporated, yielding 3 g of intermediate (77).

e) Preparation of

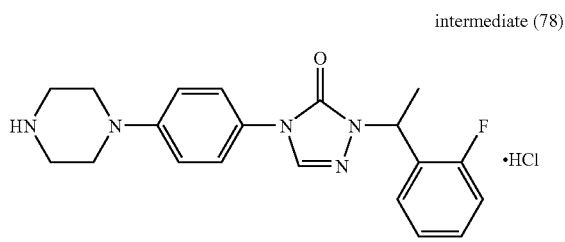

intermediate (78)

A solution of intermediate (77) (0.06 mol) in DCM was stirred at 0° C. and then a mixture of 1-chloroethyl chloroformate (0.077 mol) in DCM was added dropwise. The reaction mixture was stirred for 1 hour at 0° C. and extra 1-chloroethyl chloroformate (2 ml) was added. The mixture was stirred overnight and again extra 1-chloroethyl chloroformate (2 ml) was added. The resulting mixture was stirred for 48 hours at room temperature and concentrated, then the resulting residue was dissolved in methanol (540 ml). The solution was stirred and refluxed for 1 hour, then cooled to room temperature and distilled. The residue was triturated under ether and the desired product was collected, yielding 21 g of intermediate (78) (mp. 190-192° C.).

Example A.34 a) Preparation of

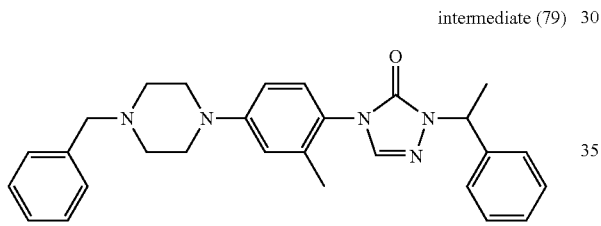

intermediate (79)

Intermediate (44) (0.039 mol) and 1-chloro-1-phenylethane (0.049 mol) were added to a solution of potassium hydroxide (2.7 g) in DMF (100 ml) and then the reaction mixture was stirred overnight at 60° C. The mixture was poured out into water and filtered. The product was extracted with DCM, dried and filtered over a Buchi-filter. The filter residue was purified by column chromatography (eluent: hexane/ethyl acetate 90/10->60/40). The product fractions were collected and the solvent was evaporated, yielding 7.5 g of intermediate (79) (mp. 80-82° C.).

b) Preparation of

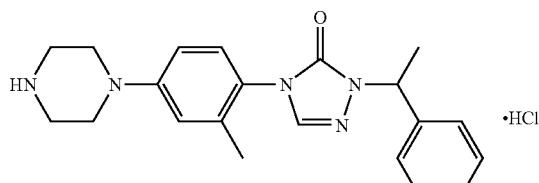

intermediate (80)

A mixture of 1-chloroethyl chloroformate (0.022 mol) in DCM was added dropwise to a mixture of intermediate (79) (0.017 mol) in DCM at 0° C. and then the reaction mixture was stirred for 1 hour at 0° C. The solvent was distilled off and the obtained product was dissolved in methanol (150 ml). The solution was stirred and refluxed for 1 hour, then cooled to room temperature and distilled off. The dry residue was stirred in ether, filtered off and dried, yielding intermediate (80).

Example A.35 a) Preparation of

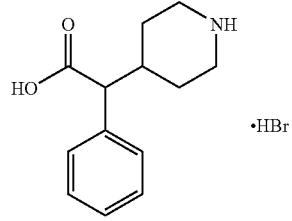

intermediate (81)

A mixture of α-phenyl-4-piperidineacetonitrile monohydrochloride (0.038 mol) in hydrobromic acid (100 ml) was stirred and refluxed for 5 hours. The solvent was evaporated. 2-Propanol was added to the residue twice and the solvent was evaporated. The residue was triturated with 2-propanol and DIPE. The precipitate was filtered off and dried, yielding 8.6 g of intermediate (81) isolated as its hydrobromic acid salt.

b) Preparation of

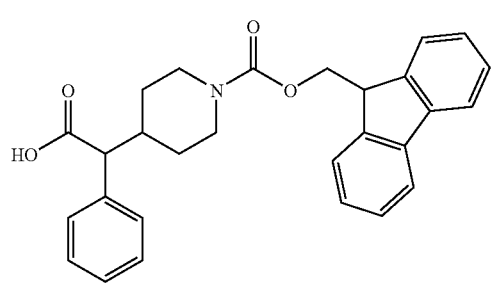

intermediate (82)

Dioxane (150 ml) was added to a solution of intermediate (81) (0.028 mol) and sodiumcarbonate (0.06 mol) in water (100 ml). The mixture was cooled on ice. 9-Fluorenylmethyl chloroformate (0.03 mol) was added. The mixture was brought to room temperature and then stirred for 2 hours. Water (500 ml) was added. The mixture was extracted 3 times with DIPE (200 ml). The aqueous layer was acidified with HCl 1N and extracted with DCM. The combined organic layer was dried, filtered and the solvent was evaporated. The residue was triturated with DIPE. The precipitate was filtered off and air-dried, yielding 5.2 g of intermediate (82).

Example A.36 a) Preparation of

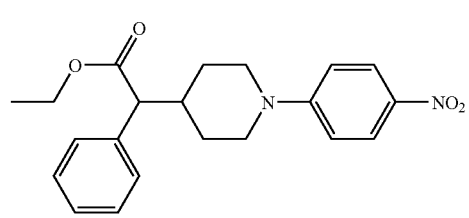

intermediate (83)

A mixture of 1-(4-nitrophenyl)-α-phenyl-4-piperidineacetic acid (0.01469 mol) and concentrated sulfuric acid (catalytic amount) in ethanol (dry, 50 ml) was heated at reflux temperature for 45 hours and the reaction mixture was allowed to cool. The resulting precipitate was collected and dissolved in chloroform to which an aqueous NaHCO₃ solution was added. The organic layer was separated, dried, filtered off and the solvent was evaporated. The residual oil was triturated unded hexane, yielding 1.92 g of intermediate (83) (mp. 93-97° C.).

b) Preparation of intermediate (84)

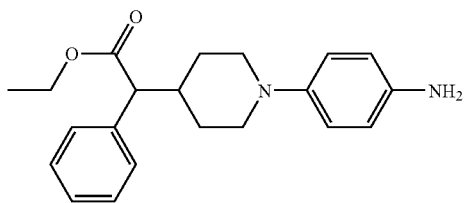

A mixture of intermediate (83) (0.1 mol) in methanol (400 ml) was hydrogenated at 50° C. for 18 hours with palladium-on-carbon (10%, 0.6 g) as a catalyst. After uptake of hydrogen (3 equivalents), the catalyst was filtered over celite and the celite path was washed with methanol (50 ml). The filtrate was evaporated and then co-evaporated with toluene (15 ml). The residue solidified at room temperature after two days, yielding intermediate (84) (m.p. 20.5-21.5° C.).

Example A.37 a) Preparation of intermediate (85)

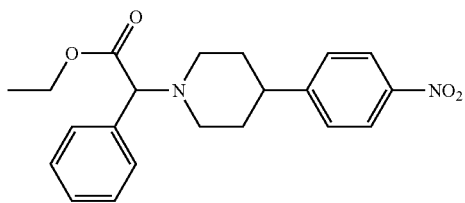

A mixture of 4-(4-nitrophenyl)-piperidine (0.1455 mol), α-bromobenzeneacetic acid ethyl ester (0.1455 mol) and Na₂CO₃ (15.4 g) in DMF (220 ml) was stirred overnight, then the reaction mixture was poured out into cold water (500 ml) and extracted three times with ether. The organic layers were combined, washed with brine, dried and the solvent was evaporated. The residual oil was triturated under ethanol and the suspension was left to stand overnight at 5° C. The resulting solid was filtered off and dried, yielding 31 g of intermediate (72-a). The filtrate was evaporated and the residual oil was purified by column chromatography over silica gel (eluent:ethyl acetate/hexane 50:50). The product fractions were collected and the solvent was evaporated. The oily residue was solidified at room temperature and triturated under a small amount of ethanol, filtered off and dried, yielding an additional 9 g of intermediate (85) (mp. 102-104° C.).

b) Preparation of intermediate (86)

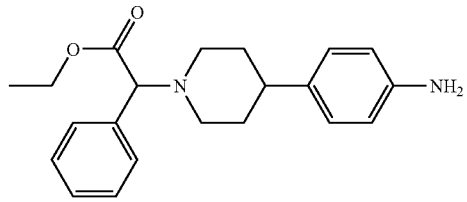

A mixture of intermediate (85) (0.0841 mol) in THF (dry, 300 ml) was hydrogenated in autoclave at 40 bar with palladium-on-carbon (10%, 3 g) as a catalyst. After uptake of hydrogen (3 equivalents), the reaction mixture was filtered and the solid was washed with THF (300 ml). The filtrates solvent was evaporated and the crude residue was stirred in ether (300 ml), then filtered off and washed with ether (100 ml). The desired product was collected and dried, yielding 22 g of intermediate (86) (m.p. 132-135° C.).

Example A.38

Preparation of intermediate (87)

A suspension of intermediate (84) (0.0030 mol) and potassium carbonate (0.580 g) in DCM (15 ml) was stirred and cooled, then phenyl chloroformate (0.0030 mol) was added dropwise and the reaction mixture was stirred overnight. The organic layer was separated and washed with water (3×10 ml), then dried and concentrated. yielding 1.22 g of intermediate (87).

In an analogous way, intermediate (88) was prepared starting from intermediate (86).

intermediate (88)

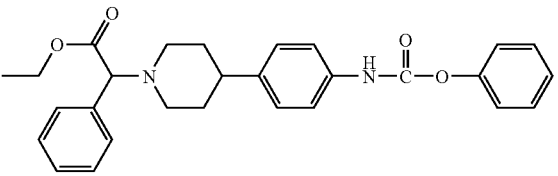

Example A.39 a) Preparation of

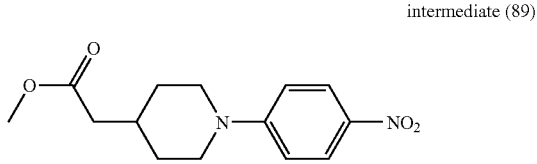

intermediate (89)

A mixture of 4-piperidineacetic acid, methyl ester, hydrochloride (0.019 mol), 1-fluoro-4-nitrobenzene (0.022 mol) and sodium carbonate (0.044 mol) in DMF (100 ml) was stirred at room temperature for 20 hours, then water and DIPE were added and the reaction mixture was stirred for 1 hour. The product was filtered off, washed with water and with DIPE and finally dried, yielding 2.1 g intermediate (89).

b) Preparation of

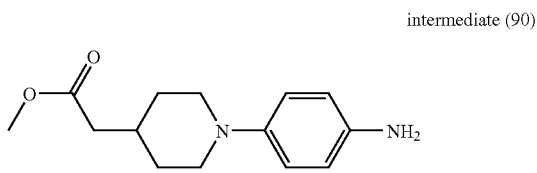

intermediate (90)

A mixture of intermediate (89) (0.0075 mol) in THF (50 ml) was hydrogenated at room temperature with palladium-on-carbon (0.5 g) as a catalyst in the presence of thiophene solution (0.5 ml). After uptake of hydrogen (3 equivalents), the catalyst was filtered off and 2-propanol/HCl (3 ml) was added to the filtrate. Ethanol and DCM were added and the resulting solution was evaporated. The residue was triturated under ethanol/DIPE (50/50), then the desired product was filtered off and dried, yielding 1.8 g of intermediate (90) isolated as its hydrochloric acid salt.

c) Preparation of

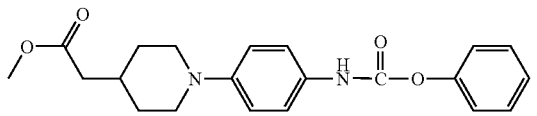

intermediate (91)

Phenyl chloroformate (0.006 mol) was stirred in DCM (100 ml) at room temperature and intermediate (90) (0.0056 mol), followed by sodium hydrogen carbonate (50 ml) was added. The reaction mixture was stirred for 4 hours and the layers were separated, then the organic layer was dried and the solvent was evaporated. The residue was triturated under DIPE and the desired product was filtered off, yielding 2.06 g of intermediate (91).

d) Preparation of

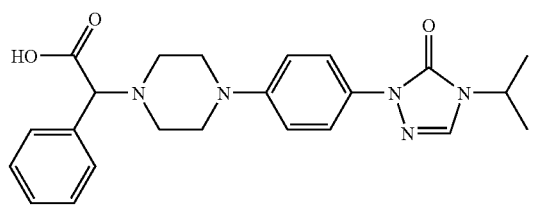

intermediate (92)

A mixture of intermediate (91) (0.00027 mol), (O)—N-(2, 2-dimethoxyethyl)-α-methyl-benzenemethanamine (0.0005 mol) and N,N-dimethyl-4-pyridinamine (0.00027 mol) was shaken and heated over the weekend at 96° C. and the solvent was evaporated under a stream of nitrogen. DCM (5 ml) was added, followed by Novabiochem 01-64-0169 methylisocyanate polystyrene resin (0.200 g), and the reaction mixture was shaken for 4 hours, filtered and the solvent was evaporated, yielding intermediate (92).

Example A.40

Preparation of

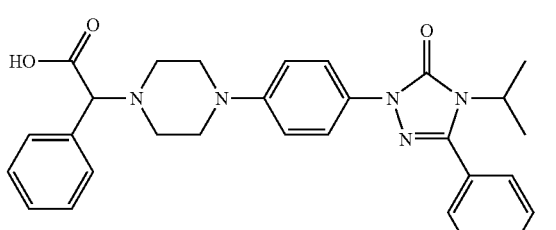

intermediate (93)

A mixture of compound (36) (0.02 mol) in hydrochloric acid (36%, 50 ml) was stirred and refluxed for 4 hours and then stirred at room temperature overnight. The precipitate was filtered off. The residue was triturated in DIPE. The precipitate was filtered off and dried, yielding 5.5 g of intermediate (93) isolated as its hydrochloric acid salt.

In an analogous way, intermediate (94) to intermediate (129) were prepared in the form of their hydrochloric acid salts.

intermediate (94)

intermediate (95)
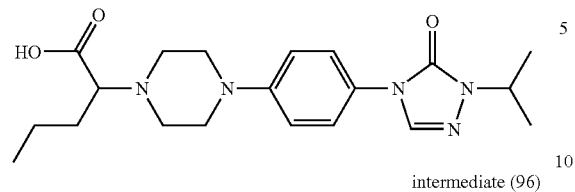
intermediate (96)
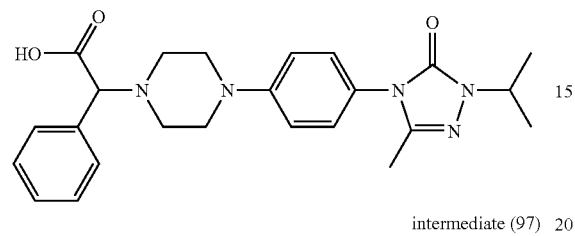
intermediate (97)
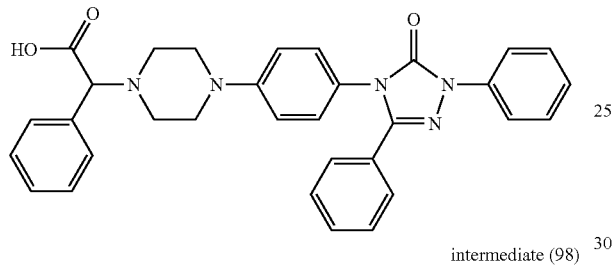
intermediate (98)
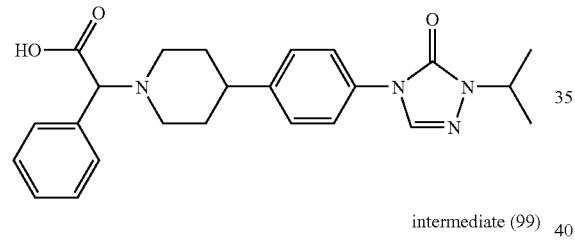
intermediate (99)
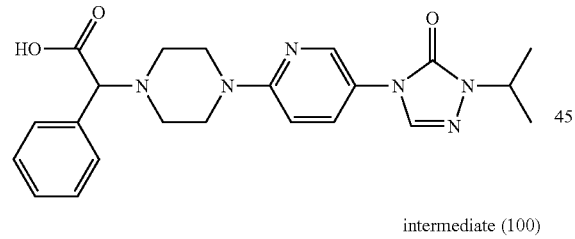
intermediate (100)
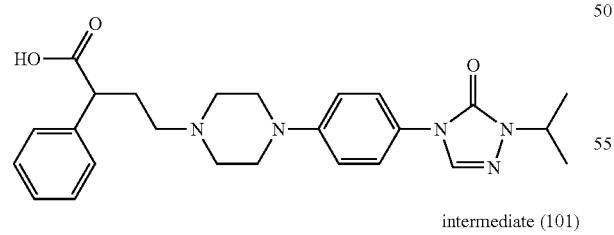
intermediate (101)
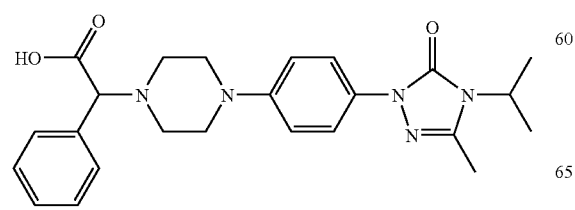
intermediate (102)
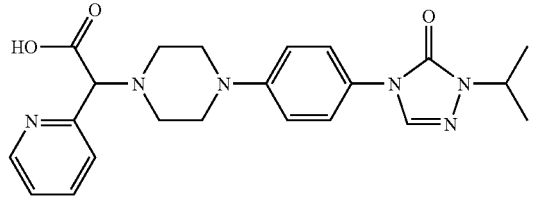
intermediate (103)
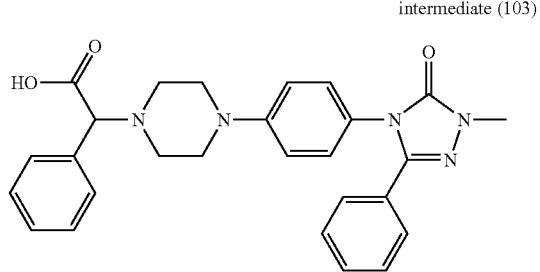
intermediate (104)
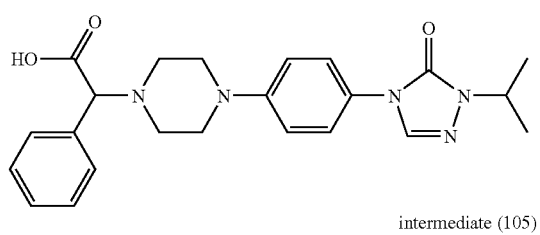
intermediate (105)
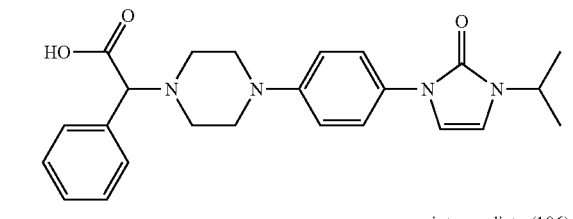
intermediate (106)
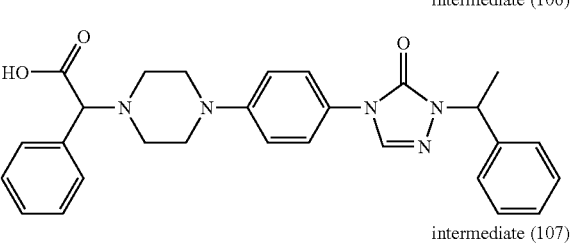
intermediate (107)
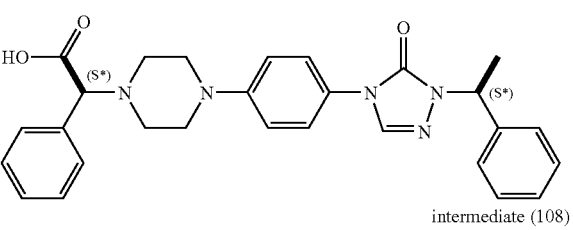
intermediate (108)
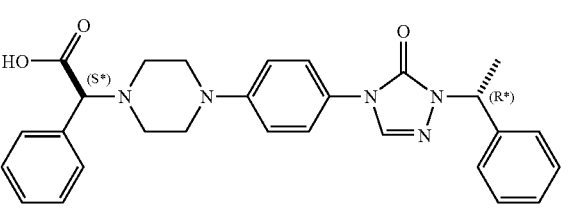

-continued
intermediate (109)
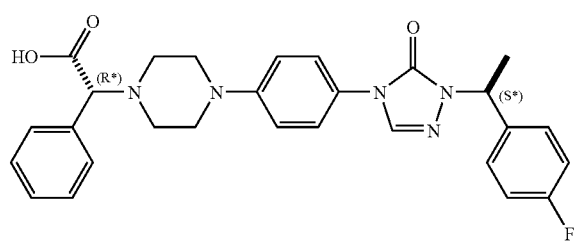
intermediate (110)
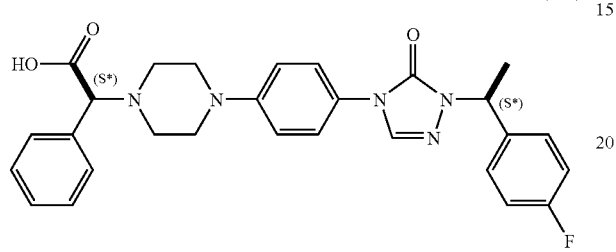
intermediate (111)
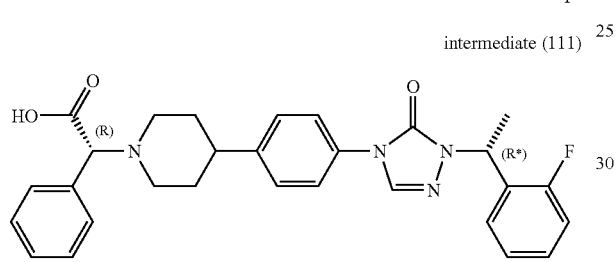
intermediate (112)
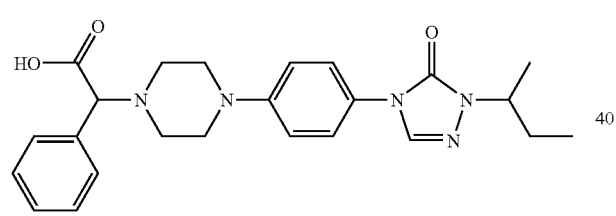
intermediate (113)
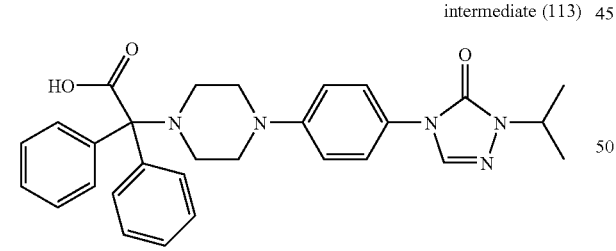
intermediate (114)
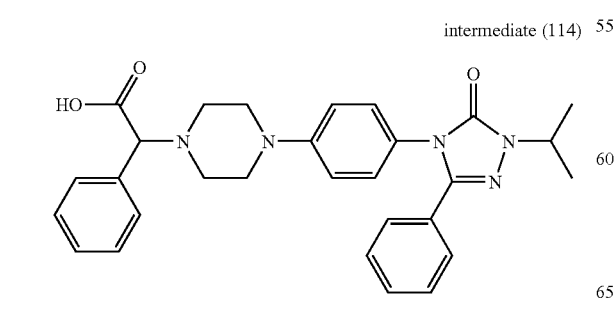
-continued
intermediate (115)
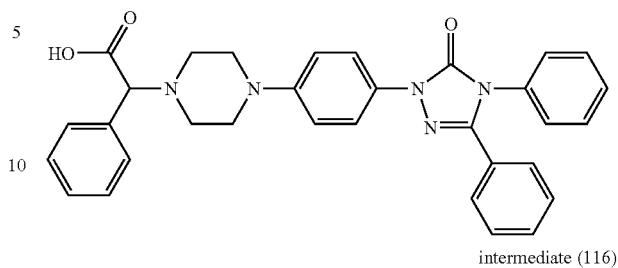
intermediate (116)
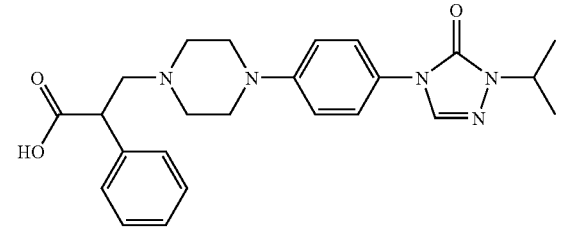
intermediate (117)
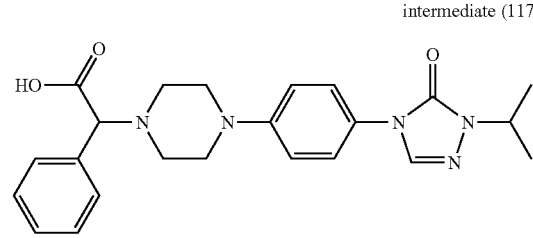
intermediate (118)
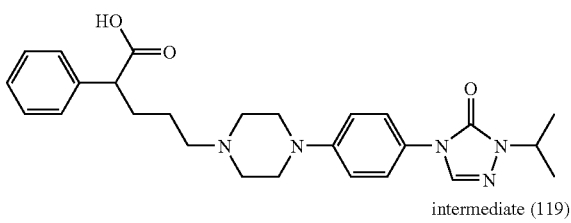
intermediate (119)
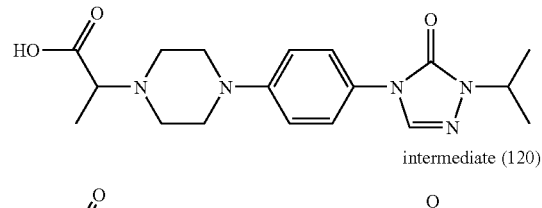
intermediate (120)
intermediate (121)
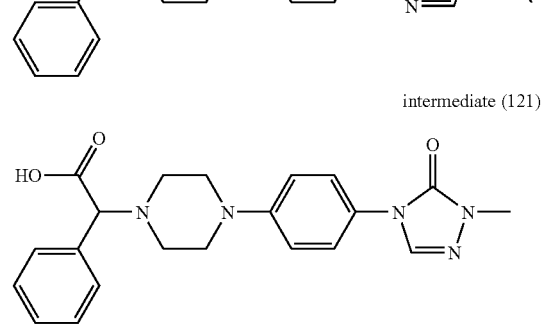

-continued

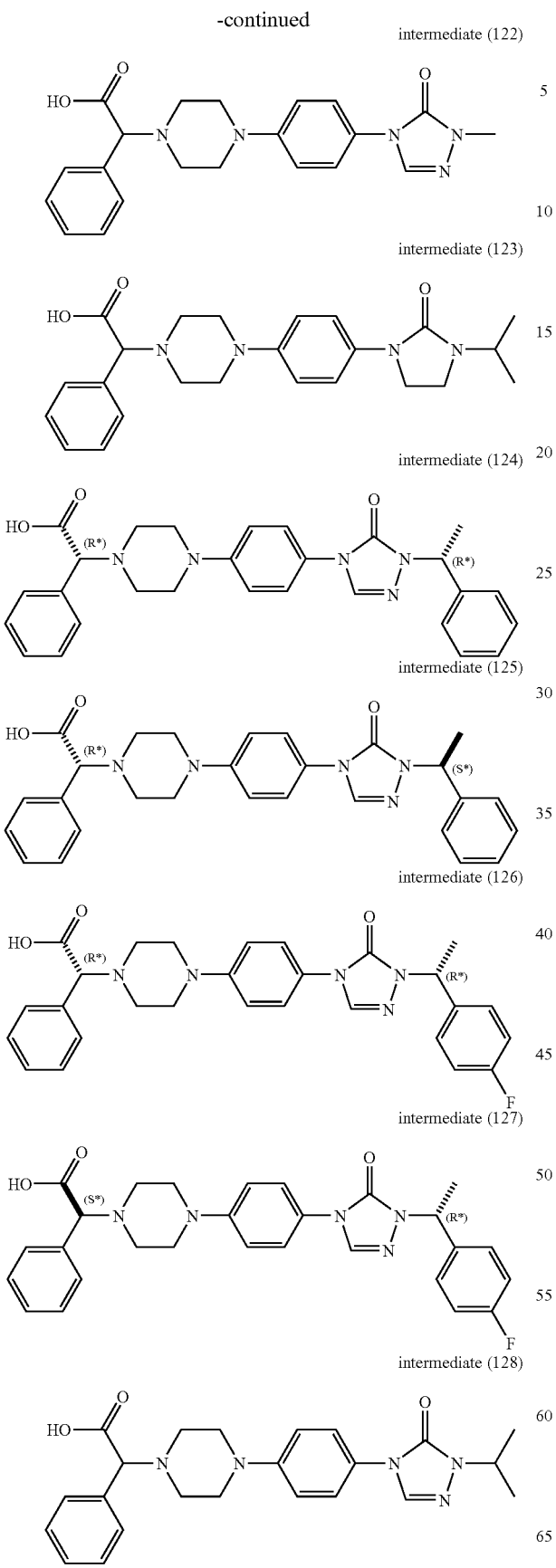

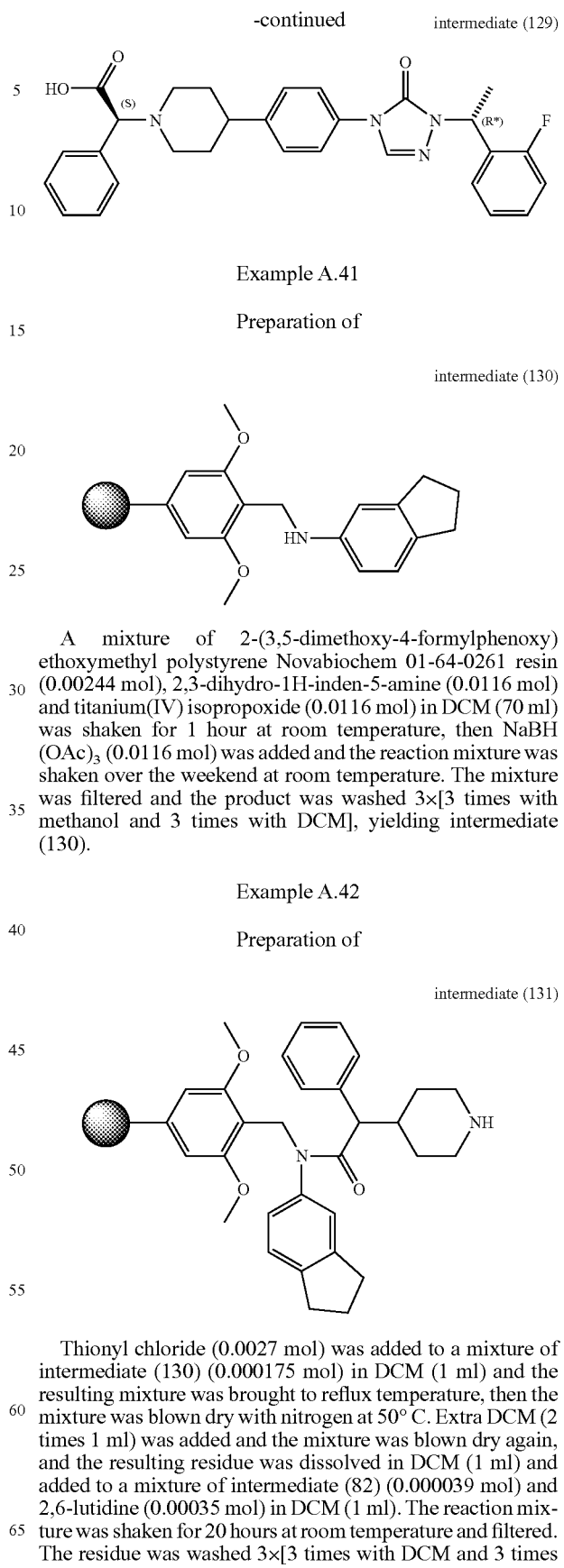

Example A.41

Preparation of intermediate (130)

A mixture of 2-(3,5-dimethoxy-4-formylphenoxy) ethoxymethyl polystyrene Novabiochem 01-64-0261 resin (0.00244 mol), 2,3-dihydro-1H-inden-5-amine (0.0116 mol) and titanium(IV) isopropoxide (0.0116 mol) in DCM (70 ml) was shaken for 1 hour at room temperature, then NaBH(OAc)$_3$ (0.0116 mol) was added and the reaction mixture was shaken over the weekend at room temperature. The mixture was filtered and the product was washed 3×[3 times with methanol and 3 times with DCM], yielding intermediate (130).

Example A.42

Preparation of intermediate (131)

Thionyl chloride (0.0027 mol) was added to a mixture of intermediate (130) (0.000175 mol) in DCM (1 ml) and the resulting mixture was brought to reflux temperature, then the mixture was blown dry with nitrogen at 50° C. Extra DCM (2 times 1 ml) was added and the mixture was blown dry again, and the resulting residue was dissolved in DCM (1 ml) and added to a mixture of intermediate (82) (0.000039 mol) and 2,6-lutidine (0.00035 mol) in DCM (1 ml). The reaction mixture was shaken for 20 hours at room temperature and filtered. The residue was washed 3×[3 times with DCM and 3 times with methanol] and again 3 times with DCM, then once with DMF. A 20% mixture of piperidine in DMF (4 ml) was added and the mixture was shaken for 2.5 hours, then the product was filtered off and washed 3×[3 times DCM and 3 times methanol], yielding intermediate (131).

In an analogous way, intermediate (132) and intermediate (133) were prepared by reacting intermediate (130) with 1-[(9H-fluoren-9-ylmethoxy)carbonyl]-4-piperidineacetic acid or 1-(9H-fluoren-9-ylmethyl) 1,4-piperidinedicarboxylic acid ester.

intermediate (132)

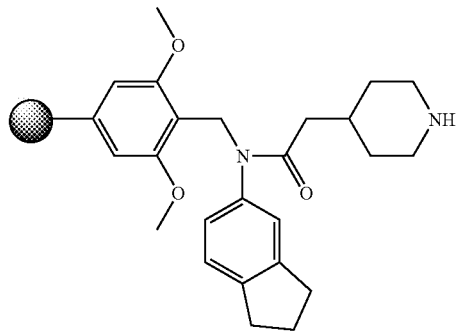

intermediate (133)

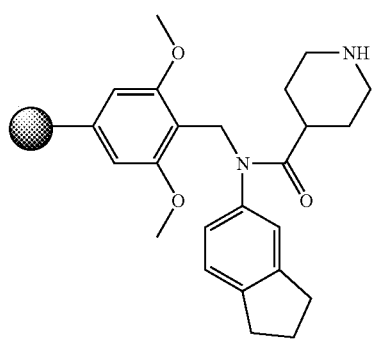

Example A.43 a) Preparation of intermediate (134)

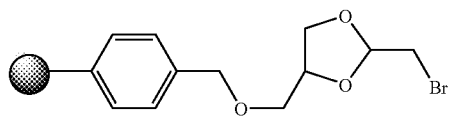

A mixture of 2-bromo-1,1-diethoxy-ethane (0.0012 mol) in DCM dry (1 ml) was added to a mixture of (±)-1-glycerol polystyrene Novabiochem 01-64-0408 resin (0.00012 mol) in DCM dry (2 ml), then a mixture of DL-10-camphorsulfonic acid (0.00012 mol) in DCM dry (1 ml) was added and the reaction mixture was shaken for 20 hours at room temperature. The desired product was filtered off, washed 2×[3 times with DCM and 3 times with DMF] and finally 6 times with DCM again, yielding intermediate (134).

b) Preparation of intermediate (135)

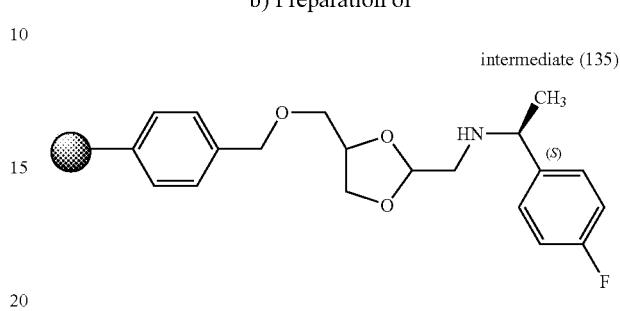

A mixture of 4-fluoro-α-methyl-benzenemethanamine (0.0012 mol) in 1-methyl-2-pyrrolidinone (1 ml) was added to a mixture of intermediate (134) (0.00012 mol) in 1-methyl-2-pyrrolidinone (3 ml) and the reaction mixture was heated at 80° C. for 20 hours, then the reaction mixture was cooled and filtered. The desired product was collected and washed 2×[3 times with DCM and 3 times with DMF] and finally 6 times with DCM, yielding intermediate (135).

In an analogous way, intermediates (136) and intermediate (137) were prepared.

intermediate (136)

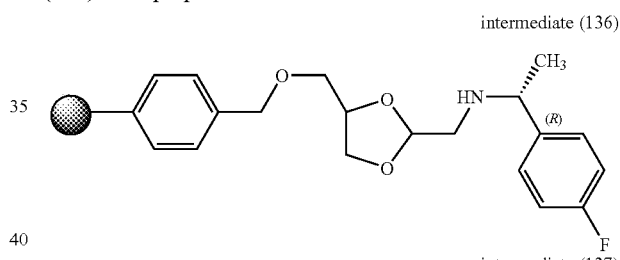

intermediate (137)

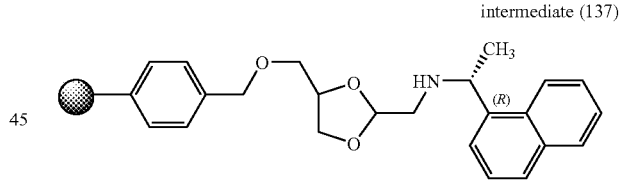

Example A.44

Preparation of intermediate (138)

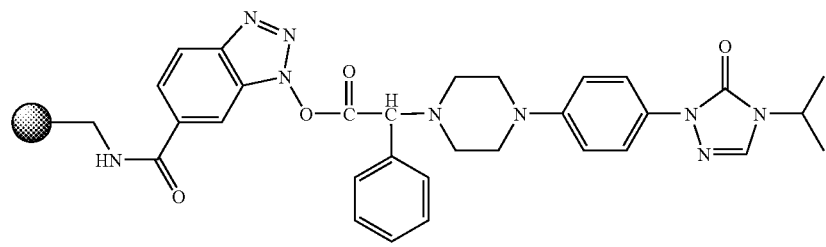

A Novabiochem 01-64-0425 N-hydroxybenzotriazole-6-carboxamidomethyl polystyrene resin (0.1 g) was washed with DCM, DCM (2 ml) was added, giving mixture (I). DCM (1 ml), then 1,3-diisopropylcarbodiimide (0.00005 mol) was added to a solution of intermediate (93) (0.0004 mol), lutidine (0.0008 mol) and N,N-dimethyl-4-pyridinamine (0.00008 mol) in DMF (1 ml) and DCM (1 ml), giving mixture (II). Mixtures (I) and (II) were combined and stirred for 4 hours at room temperature. The reaction mixture was filtered, washed (3 times) with DCM, washed (3 times) with DMF, again washed (3 times) with DCM and then dried (50° C.), yielding 0.126 g of intermediate (138).

Example A.45 a) Preparation of

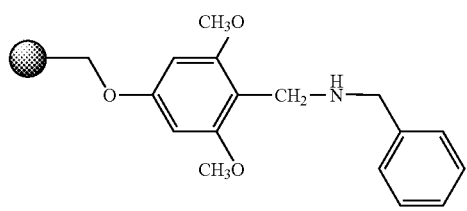

intermediate (139)

A mixture of 2-(3,5-dimethoxy-4-formylphenoxy) ethoxymethyl polystyrene resin (Novabiochem 01-64-0261) (0.00112 mol), benzenemethanamine (0.0056 mol) and titanium(IV) isopropoxide (0.0056 mol) in DCM (20 ml) was shaken for 2 hours at room temperature. Sodium triacetoxyborohydride (0.0056 mol) was added and the reaction mixture was shaken for 24 hours at room temperature. Methanol (2 ml) was added. The mixture was shaken for a while, filtered and the filter residue was washed with three times with DCM, then three time with (DCM followed by methanol), and again three times with DCM. Reaction was done 4 times in parallel, yielding intermediate (139).

b) Preparation of

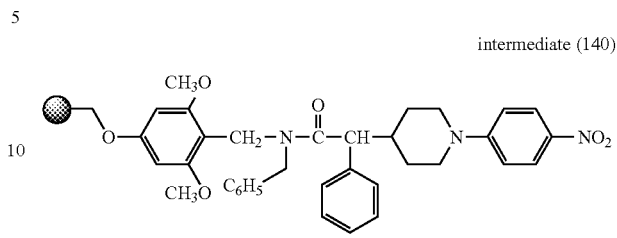

intermediate (140)

1-(4-Nitrophenyl)-α-phenyl-4-piperidineacetic acid (0.0056 mol) was added to intermediate (139) (0.00112 mol). A solution of PyBOP® (2.9 g) in DCM (15 ml) and DMF (5 ml) was added. N,N-diisopropylethylamine (0.0112 mol) was added and the reaction mixture was shaken for 24 hours at room temperature, filtered and the filter residue was washed with DMF (5×20 ml), then 5× with $CH_2Cl_2/CH_3OH$ (50/50; 20 ml), 5× with $CH_2Cl_2/CH_3COOH$ (95/5; 20 ml), 5× with DMF (20 ml) and 3× with NMP (20 ml). Reaction was done 4 times in parallel, yielding intermediate (140).

c) Preparation of

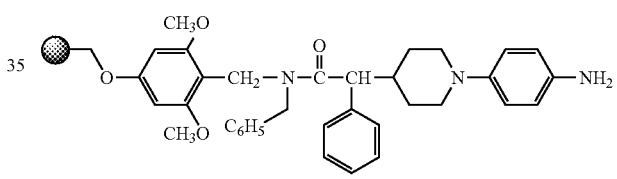

intermediate (141)

A mixture of intermediate (140) (0.00112 mol) and tin(II) chloride dihydrate (0.0224 mol) in 1-methyl-2-pyrrolidinone (20 ml) was shaken for 6 days at 55° C., then cooled, filtered and the filter residue was washed with DMF (3×), with DMF/DIPEA (90/10, 2 x), with DMF (3×), and then 3 times with (DCM, followed by methanol), then dried, yielding intermediate (141).

d) Preparation of

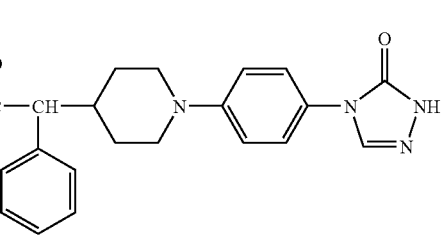

intermediate (142)

A solution of [(dimethylamino)methylene]hydrazinecarboxylic acid, ethyl ester (0.044 mol) in NMP (8 ml) was added to intermediate (141) (0.00112 mol) and the reaction mixture was shaken for 24 hours at 120° C., then the mixture was cooled and filtered. The filter residue was washed 3 times with DMF, 3 times with DCM and with methanol and then dried to give residue (I).

A solution of [(dimethylamino)methylene]hydrazinecarboxylic acid, ethyl ester (0.019 mol) in NMP (8 ml) was added to intermediate (102) (0.00112 mol) and the reaction mixture was shaken over the weekend at 120° C., then the mixture was cooled and filtered. The filter residue was washed 3 times with DMF, 3 times with (DCM followed by methanol), and then dried to give residue (II).

Residue (I) and residue (II) were combined and then [(dimethylamino)methylene]-hydrazinecarboxylic acid, ethyl ester (0.038 mol) and NMP (15 ml) were added. The reaction mixture was heated overnight at 125° C. and cooled. The mixture was washed 3 times with DMF, 3 times with DCM and with methanol, then 3×[washed again with DMF, shaken for 30 minutes and then washed with DCM and with methanol], finally the desired product was dried, yielding 2.68 g of intermediate (142).

Example A.46 a) Preparation of intermediate (143)

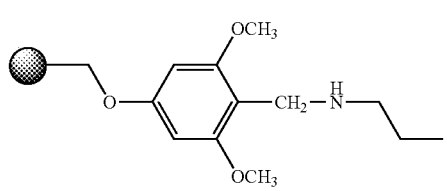

A mixture of 2-(3,5-dimethoxy-4-formylphenoxy) ethoxymethyl polystyrene resin (Novabiochem 01-64-0261) (0.0056 mol), 1-propanamine (0.028 mol) and titanium(IV) isopropoxide (0.028 mol) in dichloromethane (100 ml) was shaken for 2 hours at room temperature. Sodium triacetoxyborohydride (0.028 mol) was added and the reaction mixture was shaken for 20 hours at room temperature. Methanol (30 ml) was added. The mixture was filtered and the filter residue was washed with $CH_2Cl_2/CH_3OH$ 50/50 (3×), DMF (3×), then 3× with [DCM followed by methanol]; yielding 5.280 g of intermediate (143).

b) Preparation of

Intermediate (82) (0.0005 mol) and PYBOP® (2.6 g) were dissolved in DCM (20 ml). This mixture was added to intermediate (143) (0.00106 mol). N,N-diisopropyl-ethylamine (0.010 mol) was added and the reaction mixture was shaken for 4 hours at room temperature, then stood over the weekend, filtered and the filter residue was washed with $CHDCM_2Cl_2$ (3×), then 3× with [DCM followed by methanol], then dried, yielding 1.365 g of intermediate (144).

c) Preparation of intermediate (145)

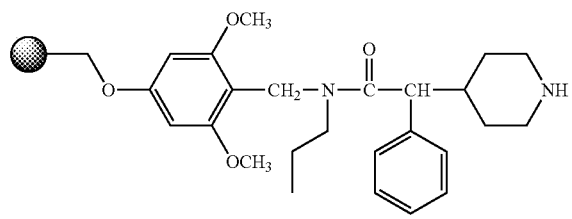

Intermediate (144) (0.00085 mol) in a mixture of piperidine and DMF (20/80) (15 ml) was shaken for 3 hours at room temperature, then filtered and the filter residue was washed with DMF. The reaction was done again (overnight at room temperature), then filtered and the filter residue was washed with DMF (3×), then 3 times with [(CH2Cl2, followed by CH3OH], then dried, yielding 1.164 g of intermediate (145).

intermediate (144)

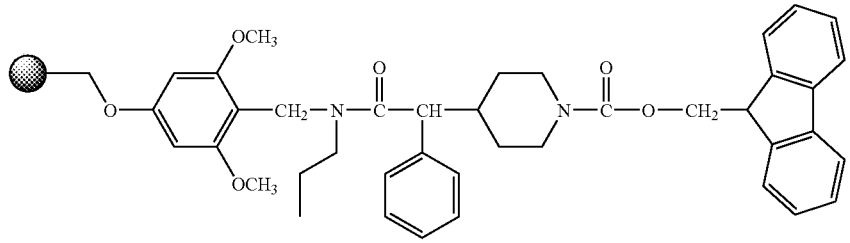

d) Preparation of

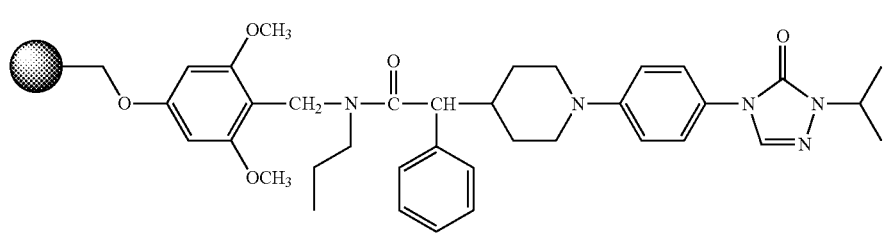

intermediate (146)

A mixture of intermediate (145) (0.000054 mol) and intermediate (10) (0.001 mol) in toluene (3 ml) was bubbled through with argon for 5 minutes to give mixture (I). Toluene (3 ml) was bubbled through with argon for 5 minutes, and a mixture of Pd$_2$(dibenzylideneacetone)$_3$ complex (0.0000136 mol), BINAP (0.000054 mol) and 2-methyl-2-propanol sodium salt (0.0012 mol) was added. The mixture was treated with Argon for 5 more minutes, to give mixture (II).

Mixture (I) was combined with mixture (II) and the whole was shaken for 6 hours at 80° C. The reaction mixture was cooled, filtered, washed with DMF (3×), with water (3×), DMF (3×), DCM (3×), DCM/acetic acid (96/4) (3×), and then 3× with [DCM followed by methanol], then dried, yielding 0.111 g of intermediate (146).

Example A.47

Preparation of

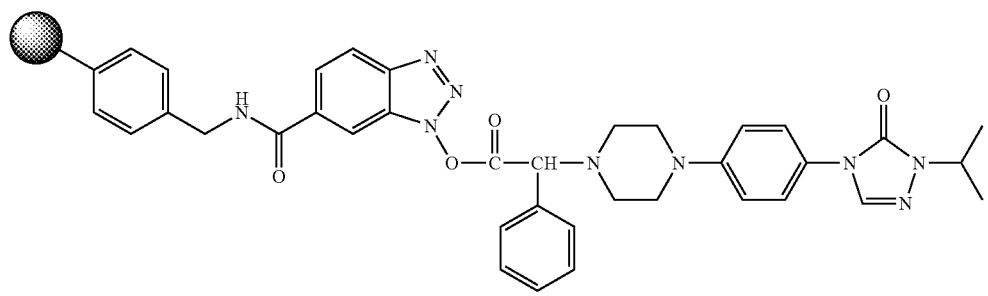

intermediate (147)

A solution of intermediate (117) (0.020 mol), 2,6-dimethylpyridine (0.086 mol) and N,N-dimethyl-4-pyridinamine (0.5 g) in a mixture of DCM (120 ml) and DMF (40 ml) was added to N-hydroxy-benzotriazole-6-carboxamidomethyl polystyrene resin (Novabiochem 01-64-0425) (0.0065 mol), then N,N'-methanetetraylbis-2-propanamine (0.0325 mol) was added and the reaction mixture was shaken for 3 hours at room temperature. The mixture was filtered, washed with DCM and DMF, then washed 2 times with DCM, twice with (3 times with DMF, 3 times with DCM). The product was dried overnight in a vacuum oven at 50° C., to give 5.450 g of reaction product. A part (5.250 g) of said reaction product was re-reacted with intermediate (117), 2,6-dimethylpyridine, N,N-dimethyl-4-pyridinamine, dichloromethane and DMF and N,N'-methanetetraylbis-2-propanamine and the resulting mixture was shaken for 3 hours and filtered off. The residue was washed with DCM, then [3 times with DMF and 3 times with DCM]×2. The product was dried overnight at 50° C., yielding 6.946 g of intermediate (147).

Example A.48 a) Preparation of

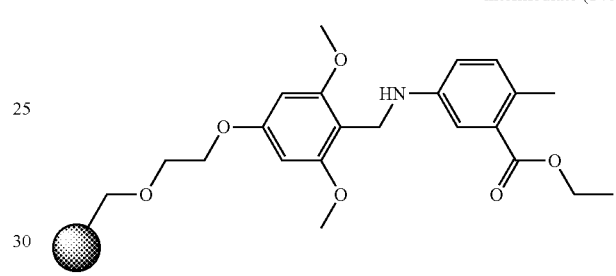

intermediate (148)

5-Amino-2-methyl-benzoic acid ethyl ester hydrochloride (0.0035 mol) was dissolved in 1-methyl-2-pyrrolidinone (10 ml). This solution was added to a mixture of 2-(3,5-dimethoxy-4-formylphenoxy)ethoxymethyl polystyrene resin (Novabiochem 01-64-0261) (0.00072 mol) in DCM (15 ml). Titanium(IV) isopropoxide (0.0035 mol) was added and the mixture was agitated for 2 hours at room temperature. Sodium triacetoxyborohydride (0.0035 mol) was added and the reaction mixture was shaken for 72 hours at room temperature. The reaction mixture was drained, washed with DCM (3×), CH$_2$Cl$_2$/DIPEA 90/10 (3×), methanol (3×), DCM (3×), methanol (3×), then DCM (3×), yielding intermediate (148) (used in next reaction step, without further purification).

b) Preparation of

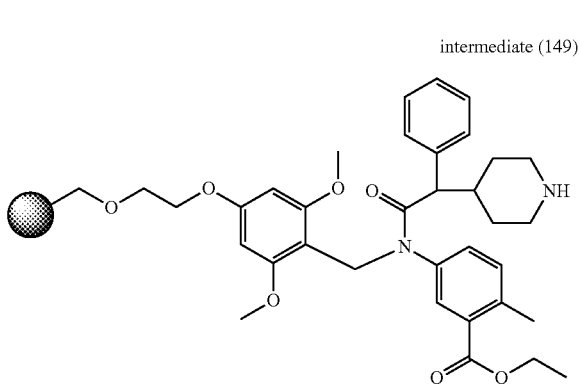
intermediate (149)

Intermediate (82) (0.000426 mol) was dissolved in DCM (5 ml). Thionyl chloride (0.0069 mol) was added. The mixture was heated, then stirred and refluxed for one hour. The solvent was evaporated and fresh DCM (5 ml) was added. The solvent was evaporated. The residue was dissolved in DCM (2 ml). This solution was added to a solution of intermediate (148) (0.000144 mol) in DCM (2 ml). N-ethyl-N-(1-methylethyl)-2-propanamine (0.00085 mol) was added and the mixture was agitated again at room temperature for 20 hours. The mixture was drained, washed with twice with [DCM (3×), methanol (3×)], then DCM (3×). A solution of piperidine in DMF (20%, (4 ml) was added and the mixture was agitated for 2 hours at room temperature. The reaction was drained, washed with twice with [DCM (3×), methanol (3×)], then DCM (3×), then dried under a gentle stream of nitrogen, yielding intermediate (149).

Example A.49 a) Preparation of

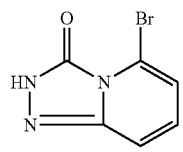
intermediate (150)

A mixture of 2-bromo-6-hydrazinopyridine (0.069 mol) and 1,1'-carbonylbis-1H-imidazole (0.207 mol) in DCM (150 ml) was stirred for 3 hours at room temperature, then cooled on an ice-bath. The precipitate was filtered off, washed with 2-propanol and dried, yielding 10 g of intermediate (150). The filtrate was evaporated and the residue was stirred in 2-propanol, filtered off and dried, yielding an additional 3 g of intermediate (150).

b) Preparation of

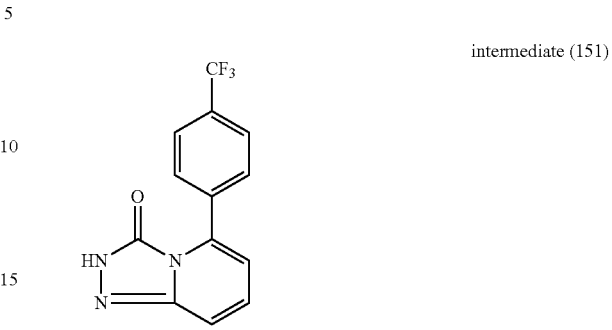
intermediate (151)

A mixture of intermediate (150) (0.01 mol), 4-(trifluoromethyl)phenylboronic acid (0.01 mol) and palladium tetra (triphenyl-phosphine) (0.00022 mol) in a $Na_2CO_3$ solution (1 M in water, 25 ml) and THF (35 ml) was stirred and refluxed (+65° C.) overnight. The solvent was evaporated. The residue was dissolved in DCM. The organic solution was washed with water, dried, filtered and the solvent evaporated. The residue was purified by column chromatography over silica gel (eluent: $CH_2Cl_2/CH_3OH$ 99/1). The product fractions were collected and the solvent was evaporated, yielding 1 g of intermediate (151).

c) Preparation of

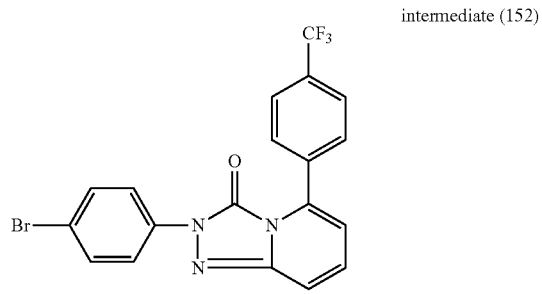
intermediate (152)

A mixture of intermediate (151) (0.0015 mol), 4-bromophenylboric acid (0.0030 mol), copper acetate (0.00225 mol) and a 1 M solution of potassium tert-butoxide in THF (0.00225 mol) in 1,2-dimethoxyethane (15 ml) was stirred overnight at room temperature. $NH_4OH$ (2 ml) was added and the mixture was stirred for 15 minutes. Water was added and this mixture was extracted with DCM. The organic layer was separated, washed with water, dried, filtered and the solvent evaporated. The residue was triturated under DIPE, filtered off, then crystallized from 2-propanol, filtered off and purified over silica gel on a glass filter (eluent:DCM). The desired fractions were collected and the solvent was evaporated. The residue was triturated under 2-propanol, filtered off and dried, yielding 0.125 g of intermediate (152).

Example A.50 a) Preparation of

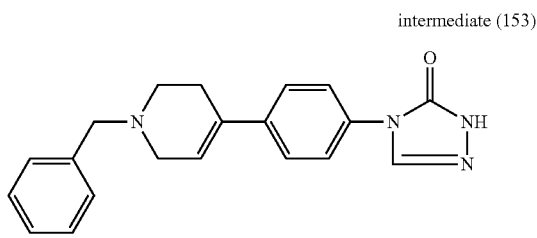
intermediate (153)

A mixture of 4-[1,2,3,6-tetrahydro-1-(phenylmethyl)-4-pyridinyl]benzenamine (prepared as intermediate (47) in WO-2002/081460) (0.085 mol) and ethyl [(dimethyl-amino)methylene]hydrazinecarboxylate (0.25 mol) in tetrahydrothiophene S,S-dioxide (50 ml) was stirred at 150° C. under nitrogen flow for 90 minutes. The mixture was stirred at room temperature overnight. 2-Propanone (50 ml) was added and the reaction mixture was stirred for 1 hour, filtered, and dried, yielding 17.4 g of intermediate (153).

b) Preparation of

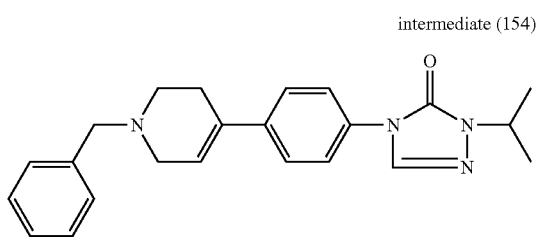
intermediate (154)

A mixture of mixture of intermediate (153) (0.052 mol) and potassium hydroxide (0.06 mol) in DMF (200 ml) was stirred for 20 minutes. Isopropyl bromide (0.15 mol) was added and the reaction mixture was stirred at 60° C. overnight. The reaction mixture was cooled and evaporated. The residue was dissolved in DCM and washed with water. The organic layer was separated, dried, filtered and evaporated. The residue was triturated in 2-propanol. The precipitate was filtered off and dried, yielding 11.6 g of intermediate (154).

c) Preparation of

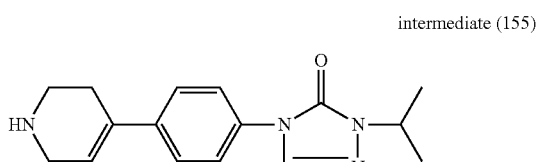
intermediate (155)

Intermediate (154) (0.13 mol) was suspended in dichloroethane (200 ml) and cooled on an ice bath. 1-Chloroethyl chloroformate (10 g) was added dropwise. The reaction mixture was stirred at room temperature for 1 hour, refluxed for 10 hours, and again stirred at room temperature overnight. The reaction mixture was evaporated and the residue was taken up in methanol (200 ml), stirred and refluxed for 1 hour. the solvent was removed by evaporation and the residue was triturated in 2-isopropanol. The precipitate was filtered off and dried, yielding 7.2 g of intermediate (155).

Example A.51

Preparation of

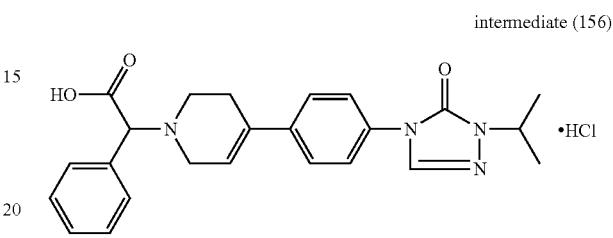
intermediate (156)

A mixture of compound (422) (0.0148 mol) in a concentrated HCl solution (100 ml) was stirred and refluxed for 6 hours and then stirred at room temperature overnight. the precipitate was filtered off, washed with water and dried yielding 4.8 g of intermediate (156) isolated as its hydrochloride acid addition salt.

For the preparation of the final compounds, also art known intermediates have been used such as, e.g. ethyl 2-bromopentanoate, α-bromo-2-thiopheneacetic acid ethyl ester, methyl 2-bromo-2-phenylacetate, ethyl 2-bromo-2-phenylacetate, α-bromo-α-phenylbenzeneacetic acid methyl ester

B. Preparation of the Final Compounds

Example B.1

A mixture of intermediate (18) (0.02 mol), intermediate (2) (0.01 mol), $Pd_2(dba)_3$ (0.05 g), [1,1'-binaphthalene]-2,2'-diylbis[diphenyl-phosphine (0.1 g) and $K_2CO_3/Cs_2CO_3$ (2 g) in toluene (50 ml) was stirred at 110° C. under argon flow for 2 days and then filtered. $Cs_2CO_3$ (4 g), $Pd_2(dba)_3$ (0.05 g) and [1,1'-binaphthalene]-2,2'-diylbis[diphenyl-phosphine (0.1 g) were added. The mixture was stirred at 110° C. overnight, then poured out into water and extracted with DCM. The organic layer was separated, dried, filtered and the solvent was evaporated. The residue was purified by column chromatography over silica gel (eluent: $CH_2Cl_2/CH_3OH$ 99/1). The pure fractions were collected and the solvent was evaporated. The residue was triturated in DIPE. The precipitate was filtered off and dried, yielding 1.05 g of compound (159).

Example B.2

A mixture of intermediate (57) (0.01 mol) and intermediate (12) (0.009 mol) in triethylamine (3 ml) and DMF (100 ml) was stirred at 60° C. for 6 hours. The mixture was cooled, poured into water, extracted with DCM and washed with water. The organic layer was dried, filtered off and evaporated. The residue was purified by column chromatography over silica gel (eluent: $CH_2Cl_2/CH_3OH$ 99/1). The pure fractions were collected and evaporated. The residue was dissolved in acetonitrile and converted into the ethanedioic acid salt (1:1). The precipitate was filtered off. The residue was crystallized from 2-propanol. The residue was recrystallized from 2-propanol and a few drops of water, yielding 0.7 g of compound (2), isolated as its ethanedioic acid salt (1:1), (mp. 165° C.).

Example B.3

A mixture of intermediate (93) (0.0002 mol) and PYBOP® (0.0004 mol) in triethylamine (0.1 ml) and DCM (5 ml) was stirred for 30 minutes, then ethanamine, hydrochloride (0.0004 mol) was added and the reaction mixture was stirred overnight at 40° C. Water (2 ml) was added, the mixture was stirred for 30 minutes and filtered through Extrelut™. The filtrates residue was purified by high-performance liquid chromatography, then the product fractions were collected and the solvent was evaporated, yielding 0.056 g of compound (113).

Example B.4

Intermediate (12) (0.0052 mol) and sodium carbonate (0.02 mol) were suspended in DMF (120 ml) under nitrogen flow. The mixture was heated to 60° C. A mixture of N-(dihydro-3,3-diphenyl-2(3H)-furanylidene)-N-methyl-methanaminium bromide (0.0058 mol) in DMF (20 ml) was added. The mixture was stirred at 90° C. for 3 hours and poured out on ice. The precipitate was filtered off and dissolved in 2-propanol. The mixture was boiled with active carbon and filtered over celite. Water was added. The precipitate was filtered off and dried. The residue was crystallized from a mixture of 2-propanol/water. The precipitate was filtered off and dried, yielding 2 g of compound (147).

Example B.5

A mixture of ethyl α-phenylacrylate (0.01 mol) and intermediate (12) (0.011 mol) in DMF (100 ml) was stirred for the weekend. The solvent was evaporated. The residue was purified by column chromatography over silica gel (eluent: $CH_2Cl_2/CH_3OH$ 99/1). The pure fractions were collected and the solvent was evaporated. The residue was triturated in DIPE, filtered off and dried, yielding 3 g of compound (138).

Example B.6

A mixture of α-(2-oxoethyl)-benzeneacetic acid methyl ester (0.06 mol), intermediate (12) (0.017 mol) and potassium acetate (20 g) in THF (50 ml) and methanol (50 ml) was stirred for two days under hydrogen. The mixture was filtered and the filtrate was evaporated. The residue was dissolved in DCM and washed with a sodium carbonate solution. The organic layer was separated, dried, filtered and the solvent was evaporated. The residue was triturated in 2-propanol, filtered off and dried, yielding 3.5 g of compound (169).

Example B.7

Intermediate (117) (0.00049 mol) was stirred in toluene (3 ml). Thionyl chloride (0.3 g) was added dropwise and the mixture was stirred for 3 hours at 60° C. The solvent was evaporated. Propanol (3 ml) was added and the reaction mixture was stirred for 3 hours. Triethylamine (0.2 ml) was added and the reaction mixture was stirred overnight. The solvent was evaporated. The residue was purified by column chromatography over silica gel (eluent: $CH_2Cl_2/CH_3OH$ 99/1). The desired fractions were collected and the solvent was evaporated, yielding 0.031 g of compound (38).

Example B.8

A mixture of intermediate (87) (0.0001 mol), N-(2,2-dimethoxyethyl)-α-methylbenzenemethanamine (0.0002 mol) and N,N-dimethyl-4-pyridinamine (0.0001 mol) in dioxane (3 ml) was shaken for 48 hours at 95° C. and the resulting mixture was blown dry with a stream of nitrogen. Trifluoroacetic acid (1 ml) and ethanol (1 ml) were added and the reaction mixture was warmed for 4 hours at 60° C., then the mixture was blown dry at 50° C. with a stream of nitrogen and the residue was purified by high-performance liquid chromatography. The product fractions were collected and the solvent was evaporated. The residue was dissolved in DCM (5 ml) and washed with a saturated aqueous. $NaHCO_3$ solution. The mixture was filtered through Extrelut™ and after evaporation off the separated organic layer, the desired product was dried, yielding 0.018 g of compound (222).

Example B.9

A mixture of intermediate (88) (0.000087 mol), intermediate (55) (0.0002 mol) and N,N-dimethyl-4-pyridinamine (0.0001 mol) in toluene (4 ml) was shaken for 48 hours at 100° C. and then Novabiochem 01-64-0169 methylisocyanate polystyrene resin (0.0003 mol, 1.5 mmol/g) and 3-(diethylenetriamino)propyl-functionalized silica gel (obtained from Sigma-Aldrich Corporation with Aldrich code 53, 792-6) (0.0002 mol; 1 mmol/g) were added. The reaction mixture was shaken for 2 hours at 100° C. and for 8 days at room temperature. The mixture was filtered, washed with toluene (2 ml) and sulfonic acid-2Ar functionalized silicagel (obtained from Across with Across code 36022) (0.0005 mol; 1 mmol/g) was added to the filtrate. The resulting mixture was shaken for 1 hour at 60° C., then cooled, filtered and washed 3 times with DCM (3 ml). The desired product was released from the reaction mixture by eluting it 3 times with $CH_2Cl_2/(CH_3OH/NH_3)$ (90/10, 2 ml). The solvent was evaporated at 50° C. under a stream of nitrogen and the residue was purified by high-performance liquid chromatography, yielding 0.007 g of compound (278).

Example B.10

A mixture of intermediate (92) (0.00027 mol) in trifluoroacetic acid (2 ml) and methanol (2 ml) was shaken at 60° C. for 20 hours and the solvent was evaporated, then the residue was dissolved in DCM (5 ml) and washed with a saturated aqueous $NaHCO_3$ solution. The mixture was filtered through Extrelut™ and the organic layer was evaporated. The aqueous residue was purified over silica gel (eluent: $CH_2Cl_2/CH_3OH$ 99/1) and the product fractions were collected. The solvent was evaporated and the residue was crystallised from DIPE, then the desired product was collected, yielding 0.0185 g of compound (264).

Example B.11

A mixture of intermediate (63) (0.000079 mol) and intermediate (55) (0.0002 mol) in toluene (4 ml) was shaken for 20 hours at 60° C. and the mixture was cooled, then Novabiochem 01-64-0169 methylisocyanate polystyrene resin (0.0003 mol, 1.5 mmol/g), followed by 3-(diethylenetriamino)propyl-functionalized silica gel (obtained from Sigma-Aldrich Corporation with Aldrich Code 53, 792-6) (0.0002 mol, 1 mmol/g) was added and the reaction mixture was shaken for 8 days. The mixture was filtered, washed with toluene (2 ml) and sulfonic acid-2Ar functionalized silicagel (obtained from Across with Across code 36022) (0.300 g, 1 mmol/g) was added. The resulting mixture was heated and shaken for 1 hour at 60° C., then cooled, filtered and washed 3 times with DCM (3 ml). The desired product was released from the reaction mixture by eluting it 3 times with $CH_2Cl_2$/($CH_3OH/NH_3$) (90/10, 2 ml). The solvent was evaporated at 50° C. under a nitrogen stream and the residue was purified by high-performance liquid chromatography. The product fractions were collected and the solvent was evaporated, yielding 0.023 g of compound (270).

Example B.12

Compound (265) (0.040 mol) was separated into its enantiomers by chiral separation on a Chiralpak AD 20 μm (Daicel) (eluent: ethanol/acetonitrile 80/20) column. Four product fractions were collected and the solvent was evaporated. Each fraction was then triturated under DIPE, filtered off and dried, yielding 3.75 g of compound (280), 3.77 g of compound (281), 3.94 g of compound (360), and 3.53 g of compound (304).

Example B.13

Sodium hydride 60% (0.0026 mol) was added to DMF (15 ml) and then compound (190) (0.0024 mol) was added. Ethyl bromoacetate (0.0024 mol) was added to the brown solution and the reaction mixture was heated at 80° C. (water bath) for 4 hours. The solution was cooled and carefully poured out into water (250 ml), the resulting solid was filtered off and washed with water, yielding 0.44 g of compound (210) (mp. 90-92° C.).

Example B.14

A mixture of intermediate (131) (0.000039 mol) in toluene (5 ml) was shaken for 30 minutes and then the mixture was filtered. A mixture of intermediate (6) (0.000525 mol) in toluene (2 ml) and then a suspension of [1,1'-binaphthalene]-2,2'-diylbis[diphenyl-phosphine (0.000035 mol) in toluene (1 ml), followed by a suspension of 2-methyl-2-propanol, sodium salt (0.00063 mol) in toluene (1 ml) were added and the reaction mixture was shaken for 30 minutes at 50° C. under a stream of nitrogen. A mixture of $Pd_2(dba)_3$ (0.0000087 mol) in toluene (1 ml) was added and the resulting mixture was shaken for 6 hours at 85° C. The product was filtered off hot and washed 2 times with DMF, once with water, 3 times with DMF, 3 times with water, 3 times with methanol, 3 times with DCM, 3 times with methanol and 3 times with DCM. A mixture of trifluoroacetic acid/dichloromethane/triisopropylsilane 49/49/2) (3 ml) was added and the reaction mixture was shaken for 1 hour at room temperature, then filtered and washed 3 times with DCM. Finally, the filtrate was evaporated and the residue was purified by high-performance liquid chromatography. The product fractions were collected and the solvent was evaporated, yielding 0.008 g of compound (207).

Example B.15

A solution of intermediate (88) (0.00036 mol) in dioxane/toluene (0.65/3.35 ml) (3 ml) was added to intermediate (135) (0.00012 mol) and a mixture of N,N-dimethyl-4-pyridinamine (0.00012 mol) in dioxane/toluene (0.65/3.35 ml) (1 ml) was added, then the reaction mixture was heated at 60° C. for 20 hours and was cooled. The mixture was filtered and washed 2×[3 times with DCM and 3 times with DMF] and finally 6 times with DCM. TFA/DCM (20/80) (4 ml) was added and the resulting mixture was shaken for 3 hours at room temperature. The mixture was filtered and washed with TFA/DCM (20/80) (2 ml). The filtrate was evaporated at 50° C. and the residue was purified by high-performance liquid chromatography. The product fractions were collected and the solvent was evaporated. The residue was dissolved in DCM and washed with an aqueous $NaHCO_3$. The organic layer was separated and evaporated, yielding 0.006 g of compound (223).

Example B.16

5-Indanylamine (0.00135 mol) and sodium hydride (catalytic quantity) were added to a solution of compound (302) (0.00111 mol) in xylene (50 ml) and then the reaction mixture was stirred and refluxed for 48 hours. The solvent was evaporated and the residue was dissolved in ether, then the resulting crude was purified by column chromatography (eluent:ethyl acetate). The product fractions were collected and the solvent was evaporated. The residue was triturated under 2-propanone and the product was filtered off and finally dried, yielding 0.2 g of compound (209) (mp.: 198-200° C.).

Example B.17

A solution of bromine (0.03451 mol) in DCM (30 ml) was added dropwise at −10° C. to a solution of ethyl 3-pyridineacetate (0.03027 mol) in DCM (70 ml), then the reaction mixture was stirred at room temperature for 90 minutes and the solvent was evaporated, to give an oily residue. Said residue was dissolved in DCM (50 ml) and added dropwise at 10° C. to a cold solution of intermediate (12) (0.03027 mol) and triethylamine (0.06054 mol) in DCM (100 ml). The reaction mixture was stirred overnight at room temperature and then the solvent was evaporated. The oily residue was purified by column chromatography (eluent:$CH_2Cl_2$/ethyl acetate 50/50). The product fractions were collected and the solvent was evaporated. The residue was crystallised from ether, then the resulting product was collected and dried, yielding 5 g of compound (302) (mp.: 142-143° C.).

Example B.18

A mixture of intermediate (117) (0.00025 mol) and N,N-carbonyldiimidazole (0.00075 mol) in DCM (5 ml) was stirred at room temperature. 2-Amino-5-methylthiazole (0.00025 mol) was added while stirring at room temperature and the reaction mixture was stirred overnight at room temperature. The reaction mixture was filtered through Extrelut™, evaporated and the residue was purified by HPLC, yielding 0.027 g of compound (125).

Example B.19

Intermediate (142) (0.000044 mol) was stirred in NMP (5 ml). A 1 M solution of $NaN[Si(CH_3)_3]_2$ in THF (0.4 ml) was added. The mixture was shaken for 30 minutes at room temperature. A solution of ethyl bromide (0.00042 mol) in 1 ml of THF was added. The mixture was shaken for 20 hours at room temperature, then filtered, washed with DMF (3 times), then 3 times with methanol followed by DMF, washed once with NMP. The reaction was done again The mixture was shaken for 24 hours, then filtered, washed with DMF (3 times), then with three times with methanol followed by DCM. A mixture of TFA/DCM/TIS (5/93/2) was added. The mixture was shaken for one hour at room temperature, filtered off, washed with a mixture of TFA/DCM/TIS (5/93/2) (2 ml) and DCM (1 ml). The filtrate was blown dry under nitrogen at 50° C. The desired compound was isolated/purified by high-performance liquid chromatography over RP BDS Spherical (100 g Hyperprep C18 (100 Å, 8 µm; eluent: [(0.5% NH$_4$OAc in H$_2$O)/CH$_3$CN 90/10)]/CH$_3$OH/CH$_3$CN (0 min) 75/25/0, (10 min) 0/50/50, (16 minutes) 0/0/100, (18.10-20 minutes) 75/25/0). The pure fractions were collected and the solvent was evaporated. Na$_2$CO$_3$ was added to the aqueous concentrate and this mixture was extracted with DCM. The extracts were blown dry with nitrogen at 50° C., then dried (vacuum, 60° C.), yielding 0.005 g of compound (179).

Example B.20

Intermediate (142) A (0.000054 mol) was stirred in NMP (5 ml). A 1 M solution of NaN[Si(CH$_3$)$_3$]$_2$ in THF (0.4 ml) was added. The mixture was shaken for 30 minutes at room temperature. A solution of 1-chloroethyl methyl ketone (0.00042 mol) in 1 ml of THF was added. The mixture was shaken for 20 hours at room temperature, then filtered, washed with DMF (3×), then with three times with methanol followed by DMF, washed once with NMP. The reaction was done again. The mixture was shaken for 24 hours, then filtered, washed with DMF (3×), then with three times methanol followed by DCM, then dried. THF (5 ml) was added. A 1 M solution of LiBH$_4$ in THF (0.5 ml) was added and the reaction mixture was shaken for 4 hours at room temperature. Methanol (1 ml) was added. The mixture was shaken for one hour, filtered, washed with methanol (3×) and then three times with DCM followed by methanol. A mixture of TFA/DCM/TIS (5/93/2) (4 ml) was added. The mixture was shaken for one hour at room temperature, filtered off, washed with a mixture of TFA/DCM/TIS (5/93/2) (2 ml) and DCM (1 ml). The filtrate was blown dry under nitrogen at 50° C. The desired compound was isolated/purified by high-performance liquid chromatography (100 g Hyperprep RP-C18 BDS (100 Å, 8 µm; eluent: [(0.5% NH$_4$OAc in H$_2$O)/CH$_3$CN 90/10)]/CH$_3$OH/CH$_3$CN (0 min) 75/25/0, (10 minutes) 0/50/50, (16 minutes) 0/0/100, (18.10-20 minutes) 75/25/0). The pure fractions were collected and the organic solvent was evaporated. The aqueous concentrate was treated with an aqueous K$_2$CO$_3$ solution and extracted with DCM. The extracts were blown dry with nitrogen at 50° C., yielding 0.003 g of compound (93).

Example B.21

A mixture of intermediate (146) (0.000054 mol) in a mixture of TFA/DCM/TIS (5/93/2) (4 ml) was shaken for 30 minutes at room temperature, then filtered, washed with a mixture of TFA/DCM/TIS (5/93/2) (2 ml) and DCM (2 ml), then blown dry with nitrogen at 50° C., yielding 0.037 g of compound (99).

Example B.22

A mixture of intermediate (138) (0.03 mol), and 5-indanylamine (0.045 mol) in DCM (2 ml) was stirred for 4 hours at room temperature. Methylisocyanate polystyrene resin (Novabiochem 01-64-0169) (0.1 g) and MP-Carbonate resin (polystyrene-linked-CH$_2$—N(Et)$_3$$^+$)$_2$/(CO$_3$)$_2$— resin obtained from Argonaut (New Road, Hengoed, CF82 8AU Mid Glamorgan, United Kingdom) with product code 800268) (0.150 g) were added and the reaction mixture was stirred overnight, filtered and blown dry, yielding 0.012 g of compound (191).

Example B.23

A solution of 5-amino-1-methyl-2-phenyl-benzimidazole (0.0001 mol) in DMF (1 ml) and DCM (1 ml) was added to a mixture of intermediate (147) (0.0001 mol) in DCM (1 ml). Morpholinomethyl PS HL resin (Novabiochem 01-64-0171) (0.1 g) was added and the reaction mixture was shaken at room temperature. Then methylisocyanate polystyrene resin (Novabiochem 01-64-0169) (0.100 g) and MP-Carbonate resin (Argonaut resin with product code 800268) (0.1 g) were added The resulting mixture was shaken for 24 hours at room temperature and was filtered. The residue was washed with DCM (5 ml) and the filtrate was evaporated. The residue was dissolved in DCM (3 ml) and TFA (1.5 ml), then the solution was stood overnight and the solvent was evaporated. The residue was purified by high-performance liquid chromatography (eluent: (NH$_4$OAc/H$_2$O)/CH$_3$OH/CH$_3$CN). The product fractions were collected and the solvent was evaporated, yielding 0.015 g of compound (199).

Example B.24

3-(Trimethylammonium)propyl-functionalized silica gel, carbonate (obtained from Sigma-Aldrich Corporation with Aldrich code 55, 288-7) (0.000378 mol) was added to a solution of intermediate (43) (0.000189 mol) in DMF (2.5 ml). N,N-(diisopropyl)-amino-methylpolystyrene (PS-DIEA) (0.000378 mol) was added in the reaction vessel of a 24-position MiniBlock™ reaction vessel (obtained from Mettler-Toledo), then a solution of intermediate (20) (0.000126 mol) in DMF (2.5 ml) was added and the reaction mixture was shaken (600 rpm) at 40° C. for 18 hours. The mixture was shaken (650 rpm) at 60° C. for 72 hours and then shaken (600 rpm) at 80° C. for 72 hours. After cooling to room temperature, methylisocyanate polystyrene resin (Novabiochem 01-64-0169) (0.100 g) was added and the resulting mixture was shaken (600 rpm) at 20° C. for 18 hours. The mixture was filtered and the residue was washed with DMF (2 ml) and filtered off into the same tubes. The solvent was evaporated and the residue was purified by high-performance liquid chromatography over RP-18. The product fractions were collected and the solvent was evaporated. The residue was dissolved in DCM (9 ml) and washed with an aqueous 10% Na$_2$CO$_3$ solution. The mixture was filtered through Extrelut™ and the Extrelut™-filters were washed 2 times with DCM (3 ml). Finally, the solvent was evaporated, yielding 0.030 g of compound (282).

Example B.25

A solution of intermediate (43) (0.000100 mol) in DMF (4 ml) was added to the MiniBlock™ reaction vessel (obtained from Mettler-Toledo), MP-Carbonate resin (Argonaut resin with product code 800268) (0.08 g equivalent to 0.000300 mol) was added, and PS-DIEA (N,N-(diisopropyl)aminomethylpolystyrene resin obtained from Argonaut with product code 800279) (0.000300 mol) was added. Methyl α-bromo-2-chlorophenylacetate (0.000100 mol) was added and the reaction mixture was shaken at 600 rpm for 70 hours at 70° C. The mixture was filtered and the resulting residue was washed with DMF (2 ml), then the mixture was filtered again and the solvent was evaporated. The residue was purified by reversed phase high-performance liquid chromatography, yielding 0.019 g of compound (307).

Example B.26

4-(4-Bromophenyl)-2-(1-phenylethyl)-2,4-dihydro[1,2,4]triazol-3-one (0.00108 mol) was dissolved in toluene (2 ml). This solution was added to a solution of intermediate (149) (0.000072 mol) in toluene (1 ml). A suspension of BINAP (0.00007 mol) in toluene (2 ml) was added, followed by the addition of a suspension of sodium tert-butoxide (0.001296 mol) in toluene (2 ml). The reaction mixture was heated to 5° C., and agitated under nitrogen flow for 30 minutes. A solution of $Pd_2(dba)_3$ (0.0000144 mol) in toluene (1 ml) was added and the reaction mixture was heated and agitated for 6 hours at 90° C. The reactions were drained while still warm, then washed with DMF (3×), water (3×), DMF (3×), methanol (3×), DCM (3×), methanol (3×) and DCM (3×). Then a mixture of TFA/TIS/$CH_2Cl_2$ (2 ml) was added and the reaction mixture was stirred for 2 hours at room temperature. More TFA/TIS/$CH_2Cl_2$ (2 ml) was added and the mixture was stirred for 15 minutes. The mixture was filtered, then the filter residue was washed with DCM (2 ml). The filtrate was evaporated in vacuo. The residue was dissolved in DCM (1 ml). Thionyl chloride (0.100 ml) was added and the mixture was heated for one hour at 40° C., then concentrated at 50° C. under a stream of nitrogen. Ethanol (1 ml) was added. The mixture was heated for one hour at 40° C., then the solvent was evaporated. The residue was purified by reversed-phase high-performance liquid chromatography using a $NH_4HCO_3$ buffer, yielding 0.011 g of compound (369).

Example B.27 a) A solution of NaOH (2N, 13.5 ml) was added portion wise to a solution of compound (386) (0.02 mol) in methanol (45 ml). The reaction mixture was stirred for 1 hour at 20° C. and for 1 hour at 40° C. The reaction mixture was cooled to 10° C. and the mixture was neutralised with an Amberlyst resin to a pH of 6 to 7. The resin was filtered off, washed with methanol and the filtrate was evaporated, yielding 5.5 g of (1-{4-[5-oxo-1-(1-phenyl-ethyl)-1,5-dihydro-[1,2,4]triazol-4-yl]-phenyl}-piperidin-4-yl)-acetic acid. b) (1-{4-[5-Oxo-1-(1-phenyl-ethyl)-1,5-dihydro-[1,2,4]triazol-4-yl]-phenyl}-piperidin-4-yl)-acetic acid (0.000075 mol) was dissolved in dichloromethane (2 ml) was added to the MiniBlock™ reaction vessel (obtained from Mettler-Toledo), then PS-DCC (1.38 mmol/g; 2 equivalents) was added and the Miniblocks were shaken at 650 rpm for 1 hour at room temperature. PS-DIPEA (3.50 mmol/g; 1.5 equivalents) was added and then a solution of (R)-2-(ethoxycarbonyl)piperidine (0.0001125 mol; 1.5 equivalents) in DMF (0.5 ml) was added. The reaction mixture was shaken at 650 rpm for 20 hours at room temperature and filtered. the solvent was evaporated and the residue was purified by reversed phase HPLC, yielding 0.002 g of compound (387).

Example B.28

A mixture of intermediate (155) (0.02 mol) and $Na_2CO_3$ (0.02 mol) in DMF (100 ml) was stirred at room temperature. Methyl 2-bromophenylacetate (0.02 mol) was added dropwise and the mixture was stirred for two days. The solvent was evaporated and the residue was taken up in DCM, washed, filtered and evaporated. The residue was triturated in DIPE, the precipitate was filtered off and dried, yielding 6.4 g of compound (422).

Example B.29

A mixture of intermediate (156) (0.0002 mol), PyBOP (0.3 g), and triethylamine (0.5 ml) in DCM (5 ml) was stirred for 20 minutes. Ethylamine (0.0004 mol) was added and the reaction mixture was stirred overnight at 40° C. The reaction mixture was evaporated and the residue was purified by reversed phase HPLC, yielding 0.065 g of compound (414).

Tables F-1a and F-1b list the compounds that were prepared according to one of the above Examples. Some compounds have been obtained as a single enantiomer without knowing their absolute configuration. In those cases the stereochemically isomeric form which was first isolated by liquid chromatography is designated as "A-isomer", the second as "B-isomer", the third one as "C-isomer" and the fourth one as "D-isomer", without further reference to the actual stereochemical configuration. The stereochemical configuration for some compounds has been designated as R*, or S* indicating a relative stereochemistry since the absolute stereochemistry is unknown.

TABLE F-1a

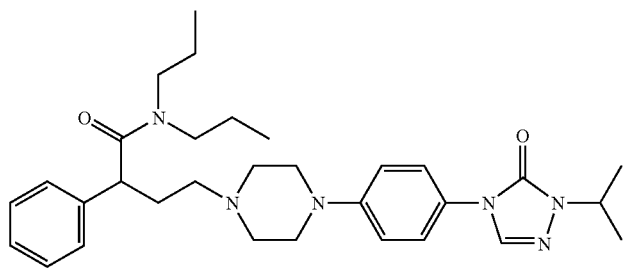

Co. No. 1; Ex. B.2; m.p. 165.0° C.

TABLE F-1a-continued
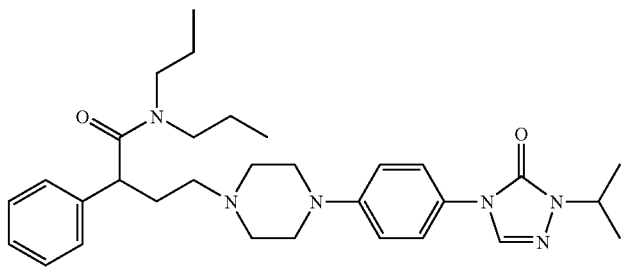
Co. No. 2; Ex. B.2; •C$_2$H$_2$O$_4$; m.p. 165.0° C.
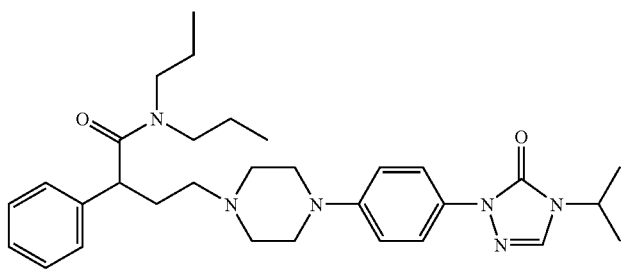
Co. No. 3; Ex. B.2; m.p. 146.2° C.
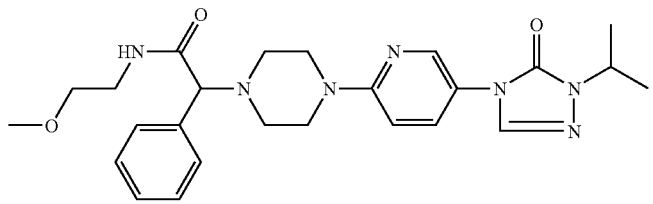
Co. No. 4; Ex. B.3
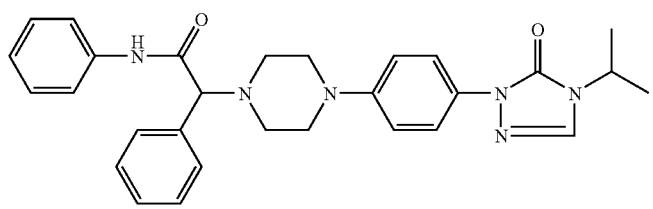
Co. No. 5; Ex. B.3
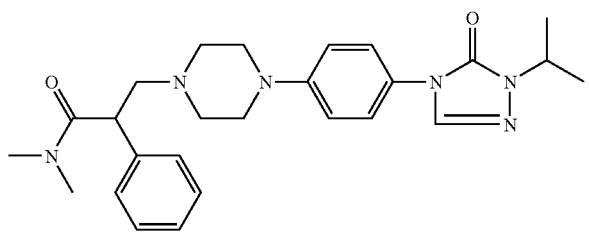
Co. No. 6; Ex. B.3

TABLE F-1a-continued
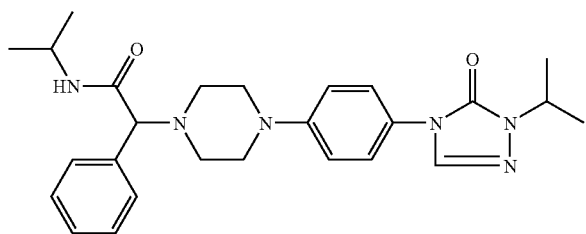
Co. No. 7; Ex. B.3
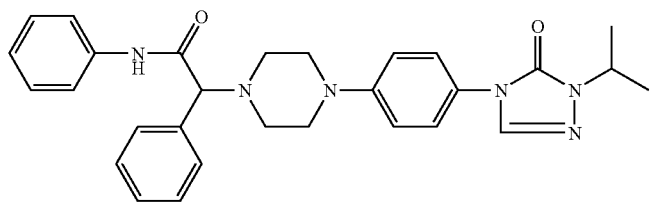
Co. No. 8; Ex. B.3
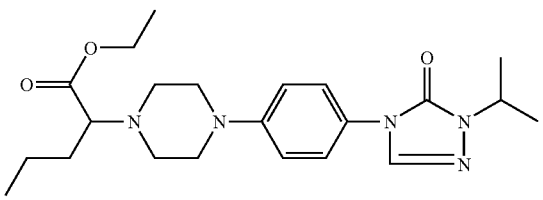
Co. No. 9; Ex. B.2; m.p. 104° C.
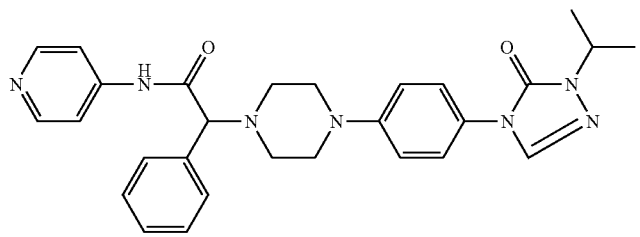
Co. No. 10; Ex. B.3; m.p. 150° C.
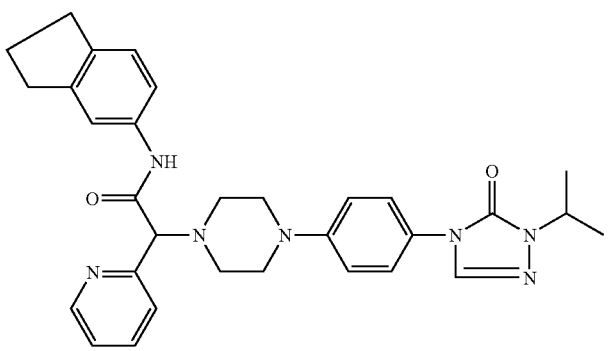
Co. No. 11; Ex. B.16, m.p. 193° C.

TABLE F-1a-continued
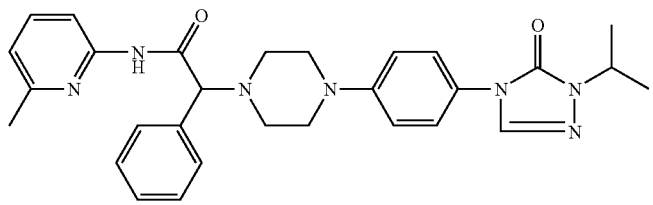
Co. No. 12; Ex. B.3; m.p. 198° C.
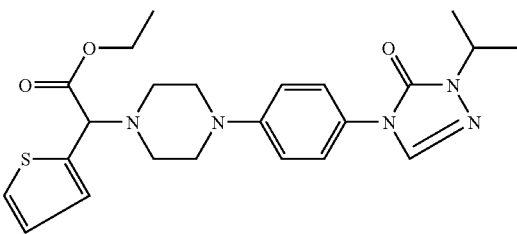
Co. No. 13; Ex. B.2; m.p. 148° C.
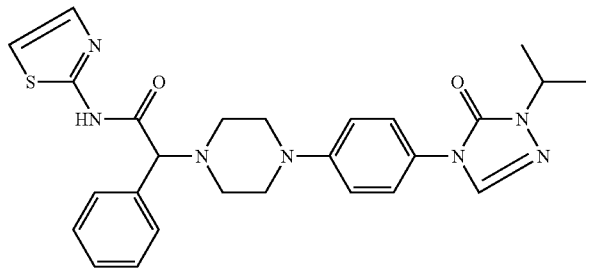
Co. No. 14; Ex. B.3; m.p. 106° C.
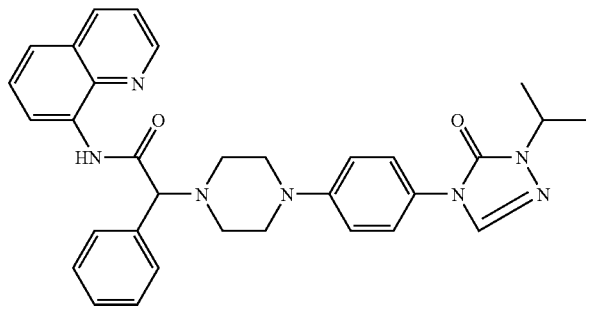
Co. No. 15; Ex. B.3; m.p. 204° C.
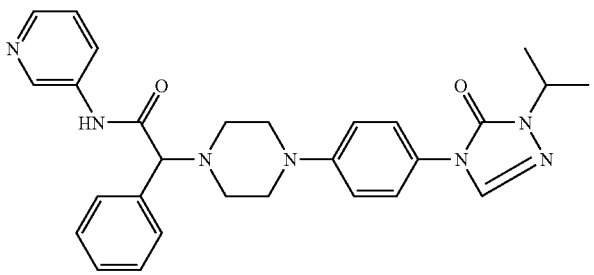
Co. No. 16; Ex. B.3; m.p. 154° C.

TABLE F-1a-continued
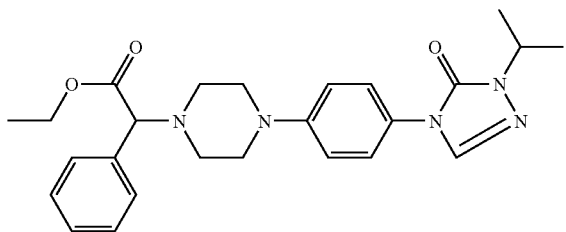
Co. No. 17; Ex. B.2; m.p. 98-101° C.
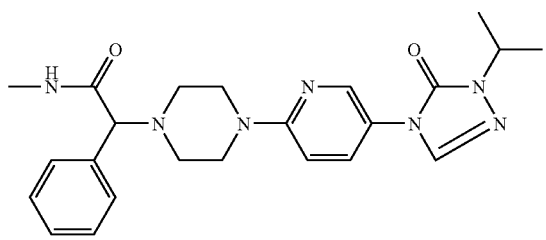
Co. No. 18; Ex. B.3
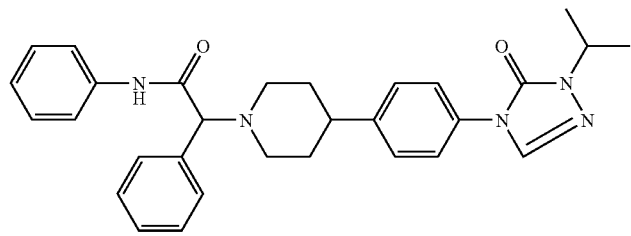
Co. No. 19; Ex. B.3
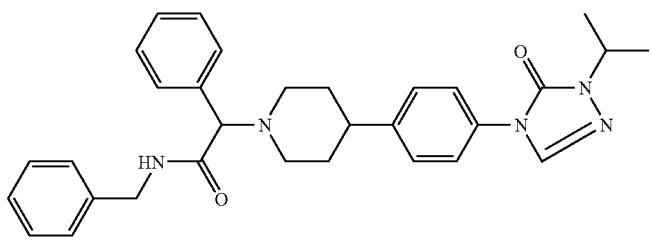
Co. No. 20; Ex. B.3
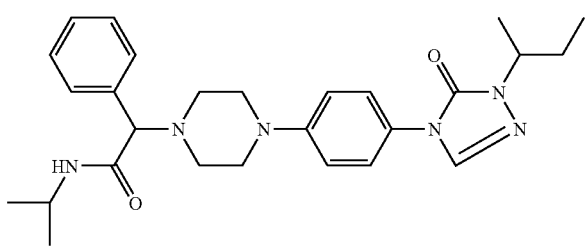
Co. No. 21; Ex. B.3

TABLE F-1a-continued
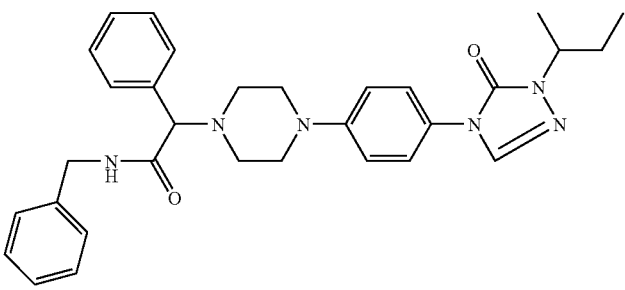
Co. No. 22; Ex. B.3
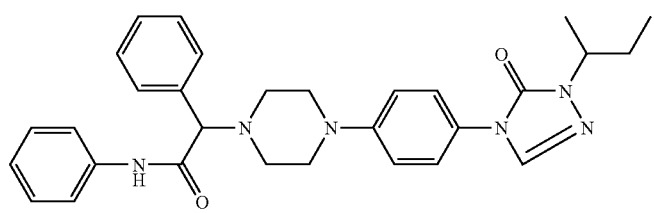
Co. No. 23; Ex. B.3
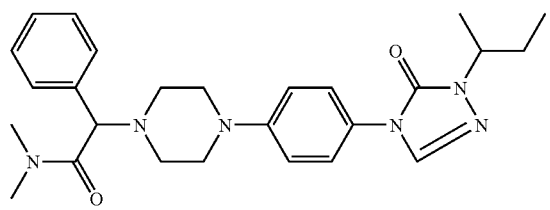
Co. No. 24; Ex. B.3
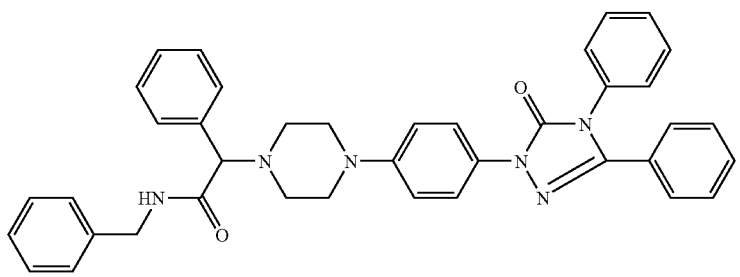
Co. No. 25; Ex. B.3
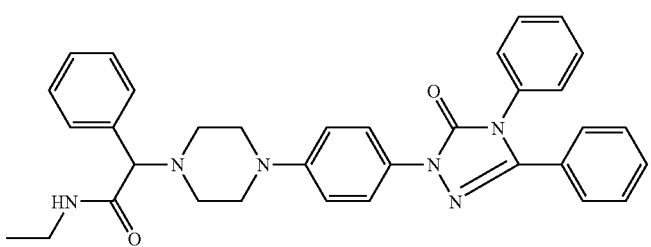
Co. No. 26; Ex. B.3

TABLE F-1a-continued
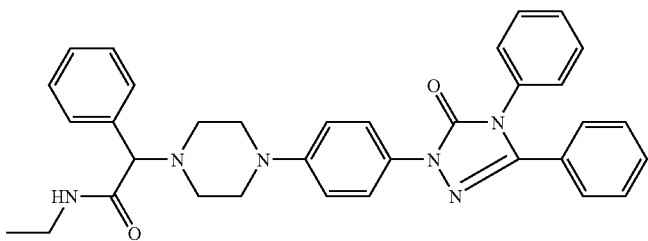
Co. No. 27; Ex. B.3
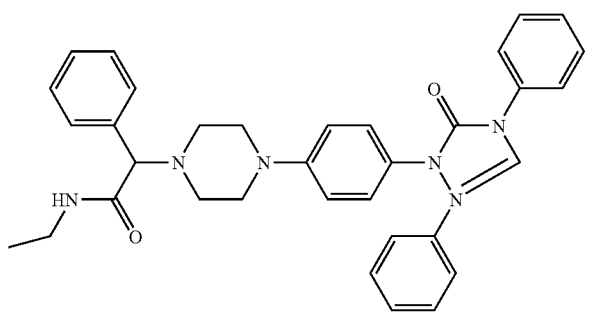
Co. No. 28; Ex. B.3
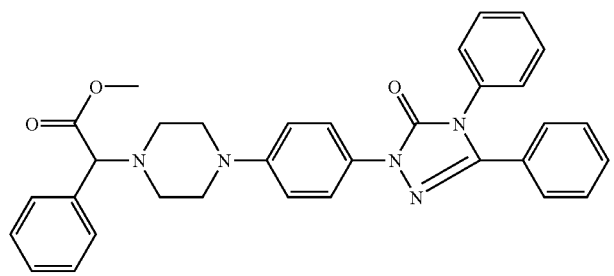
Co. No. 29; Ex. B.2
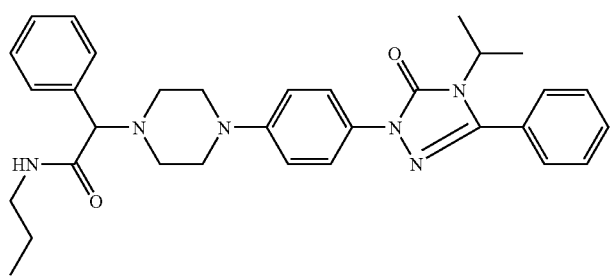
Co. No. 30; Ex. B.3
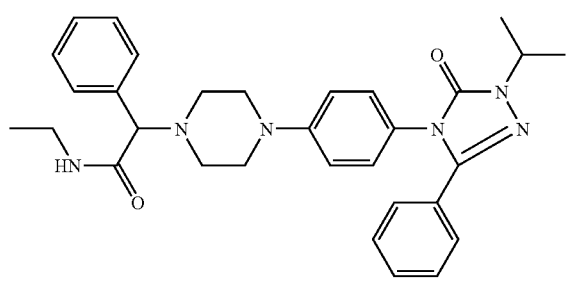
Co. No. 31; Ex. B.3

TABLE F-1a-continued
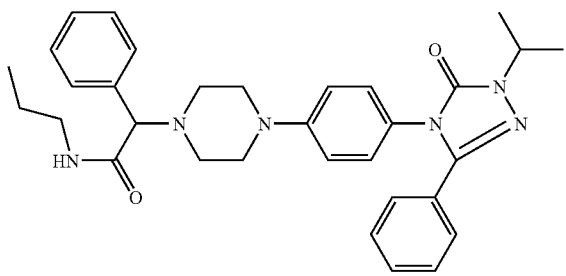
Co. No. 32; Ex. B.3
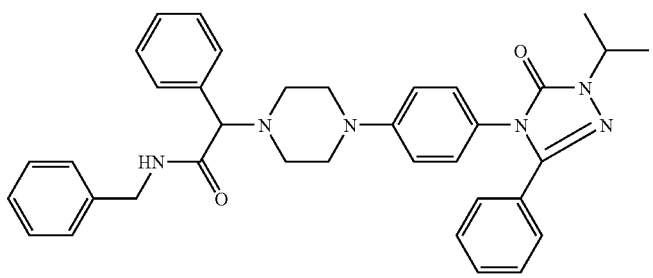
Co. No. 33; Ex. B.3
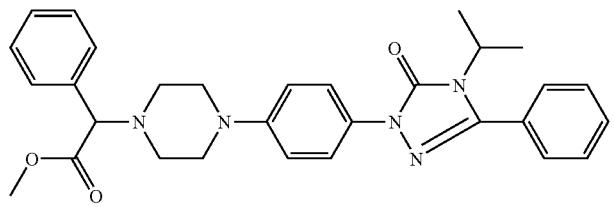
Co. No. 34; Ex. B.2
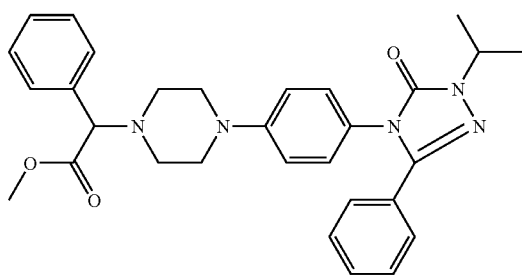
Co. No. 35; Ex. B.2
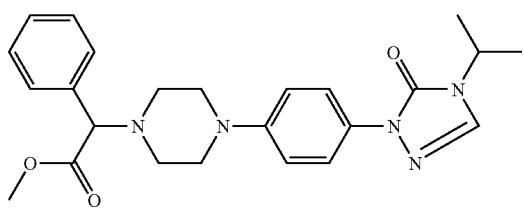
Co. No. 36; Ex. B.2

TABLE F-1a-continued
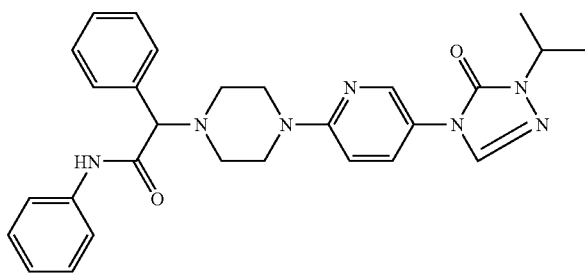
Co. No. 37; Ex. B.3
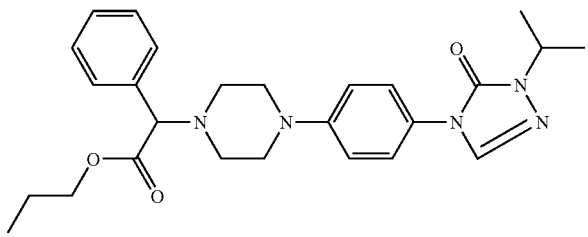
Co. No. 38; Ex. B.7
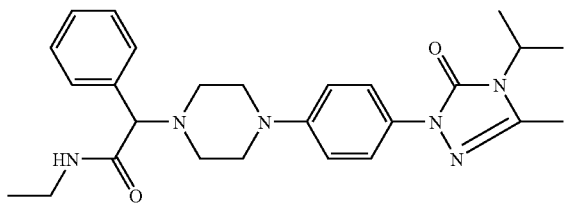
Co. No. 39; Ex. B.3
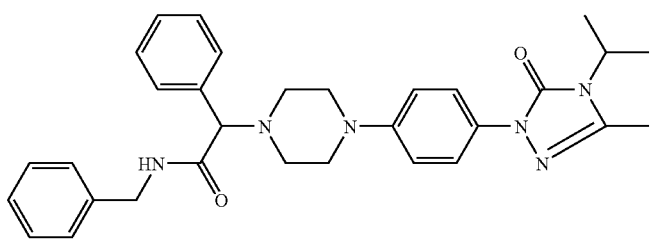
Co. No. 40; Ex. B.3
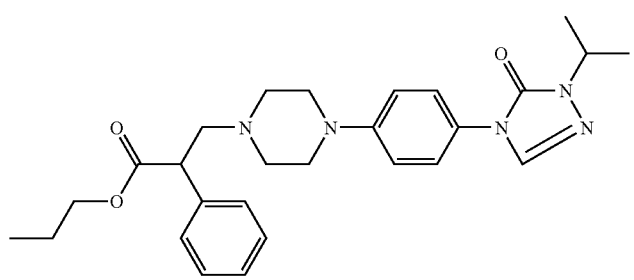
Co. No. 41; Ex. B.3

TABLE F-1a-continued
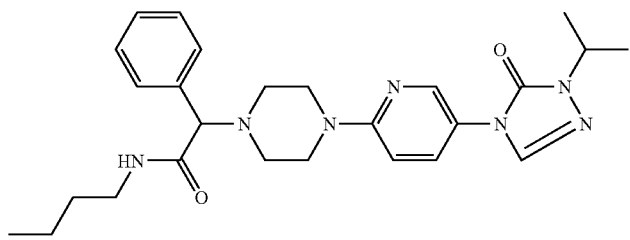
Co. No. 42; Ex. B.3
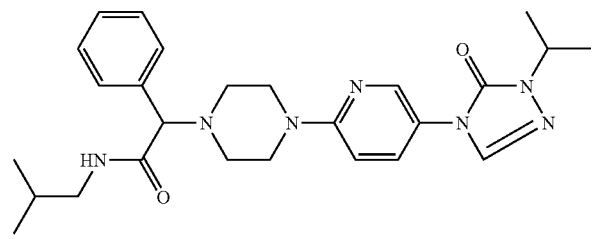
Co. No. 43; Ex. B.3
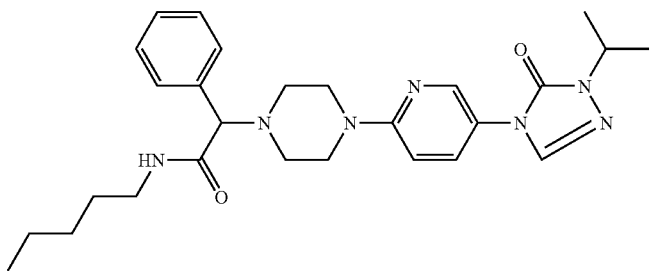
Co. No. 44; Ex. B.3
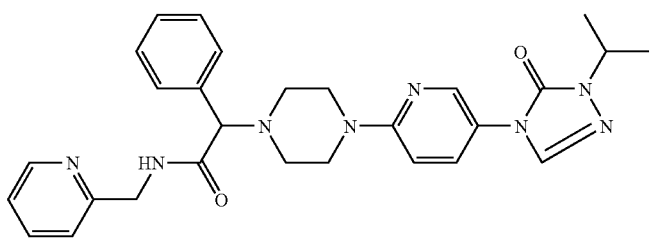
Co. No. 45; Ex. B.3
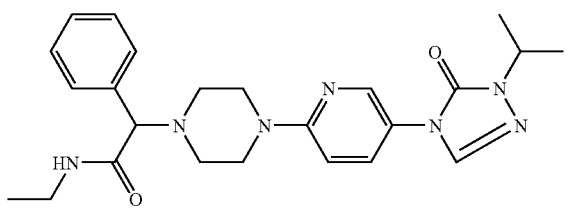
Co. No. 46; Ex. B.3

TABLE F-1a-continued
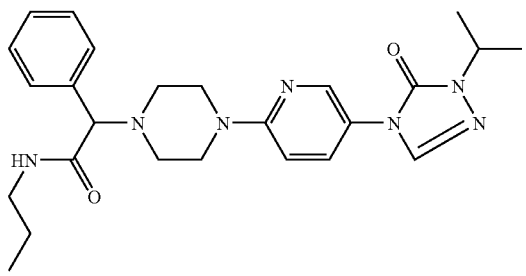
Co. No. 47; Ex. B.3
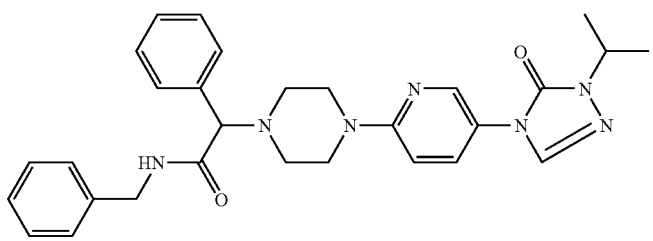
Co. No. 48; Ex. B.3
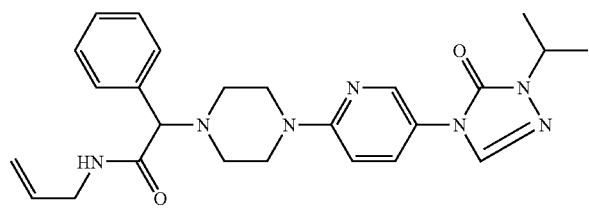
Co. No. 49; Ex. B.3
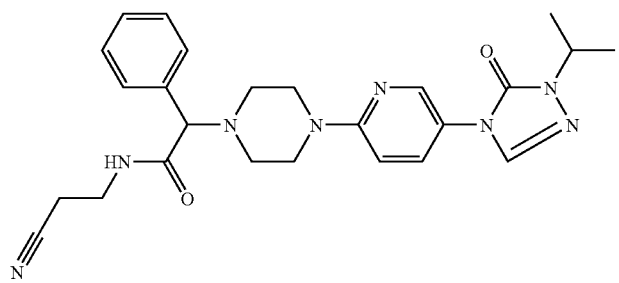
Co. No. 50; Ex. B.3
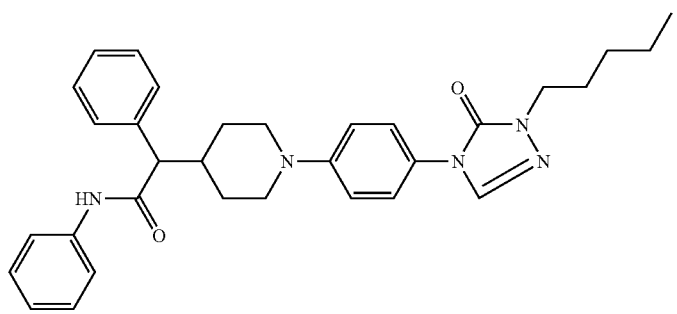
Co. No. 51; Ex. B.19

TABLE F-1a-continued
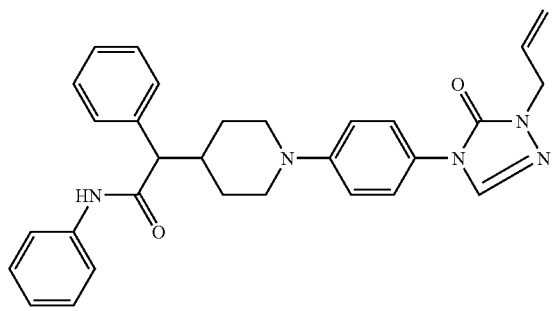
Co. No. 52; Ex. B.19
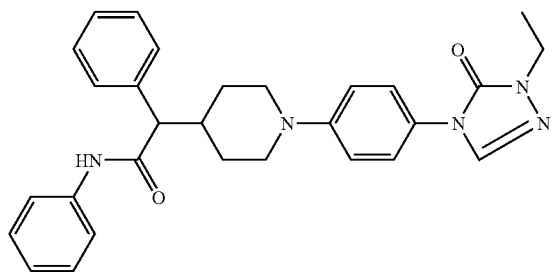
Co. No. 53; Ex. B.19
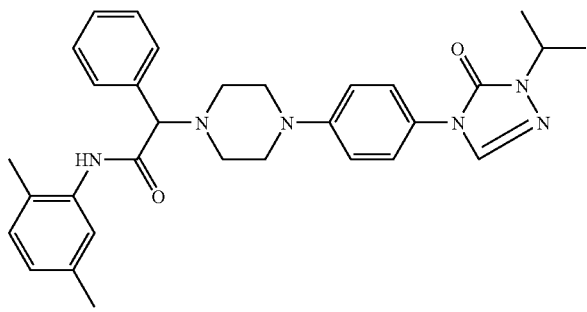
Co. No. 54; Ex. B.18
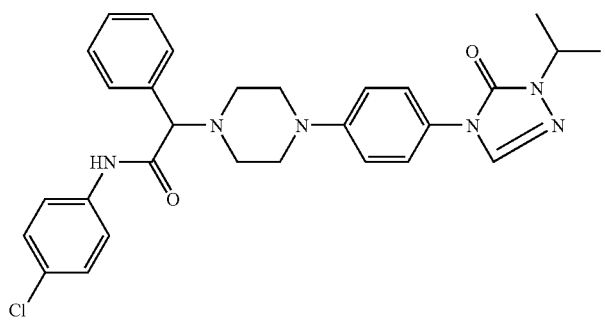
Co. No. 55; Ex. B.18

TABLE F-1a-continued
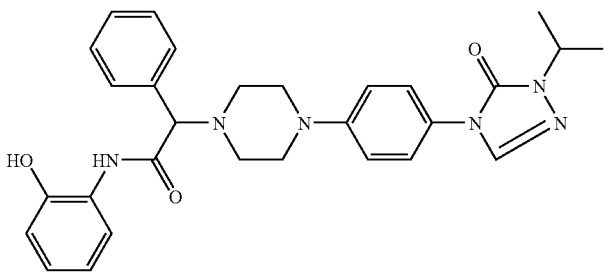
Co. No. 56; Ex. B.18
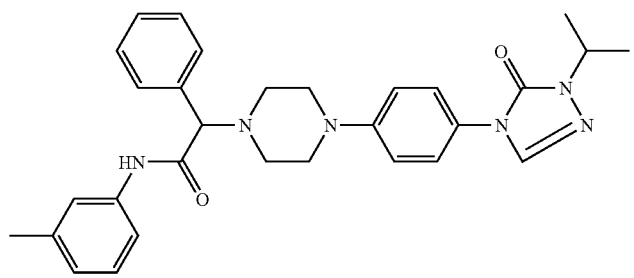
Co. No. 57; Ex. B.18
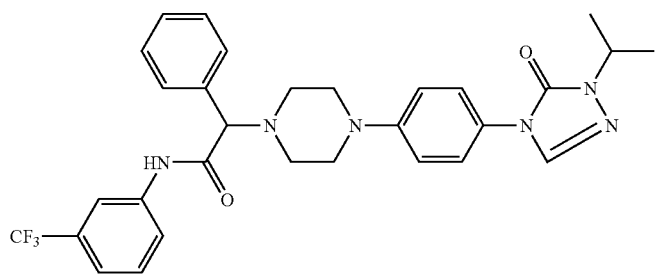
Co. No. 58; Ex. B.18
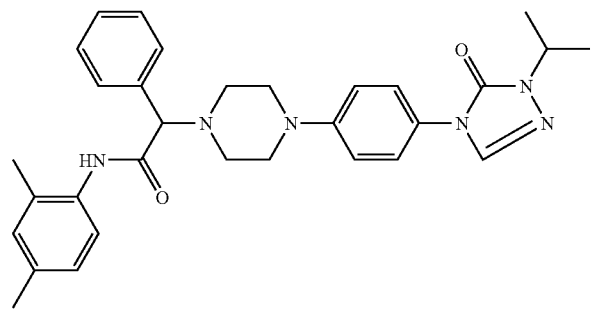
Co. No. 59; Ex. B.18

TABLE F-1a-continued
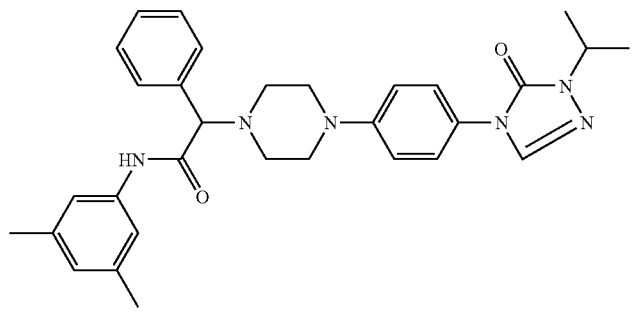
Co. No. 60; Ex. B.18
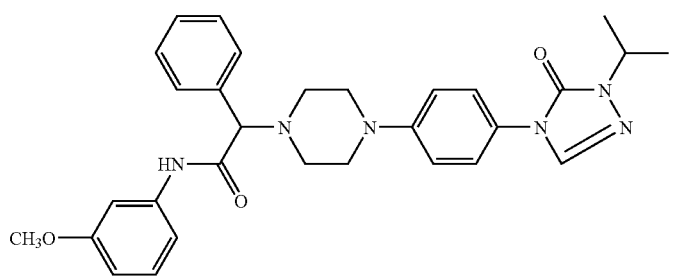
Co. No. 61; Ex. B.18
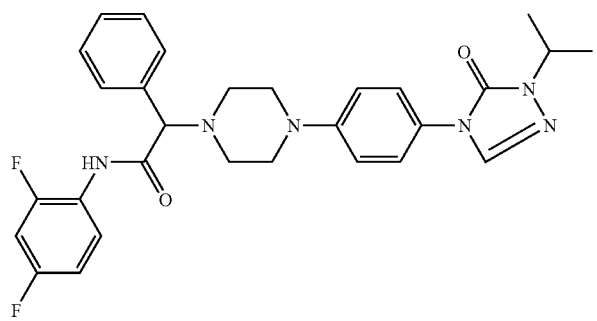
Co. No. 62; Ex. B.18
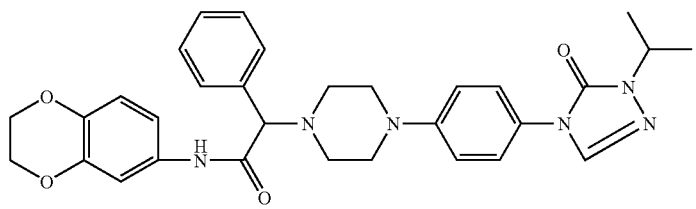
Co. No. 63; Ex. B.18
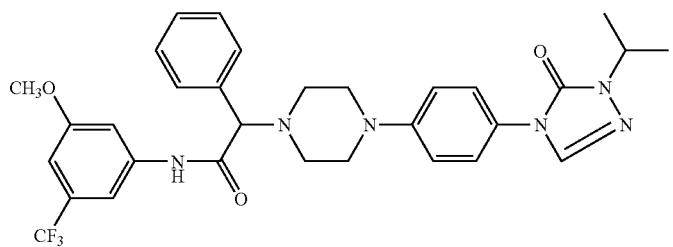
Co. No. 64; Ex. B.18

TABLE F-1a-continued
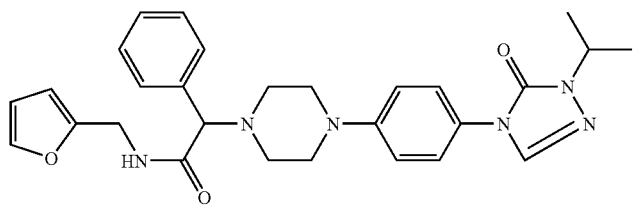
Co. No. 65; Ex. B.18
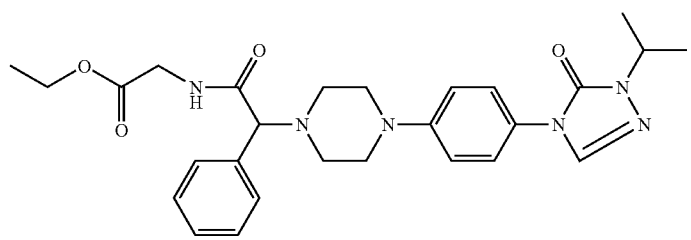
Co. No. 66; Ex. B.18
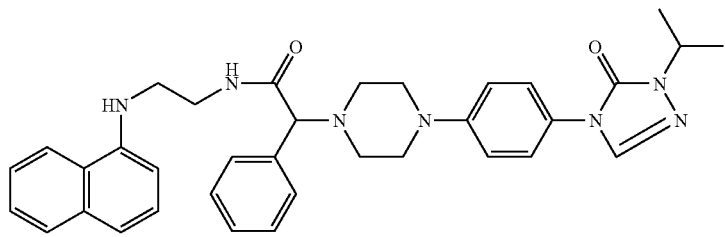
Co. No. 67; Ex. B.15
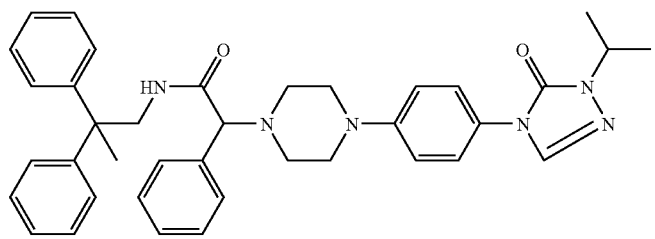
Co. No. 68; Ex. B.18
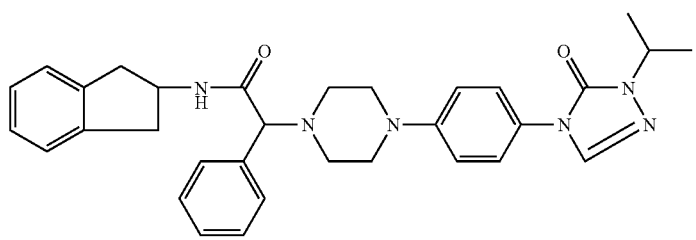
Co. No. 69; Ex. B.18

TABLE F-1a-continued
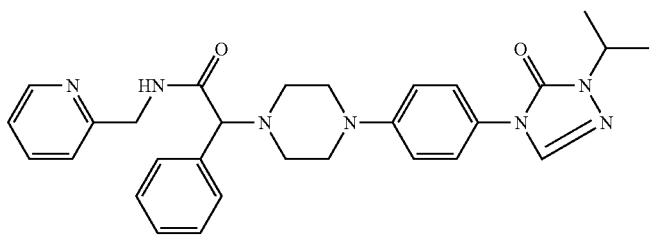
Co. No. 70; Ex. B.18
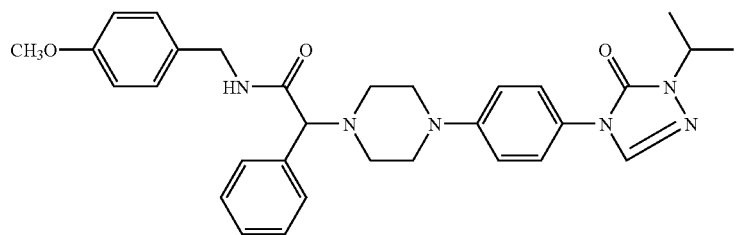
Co. No. 71; Ex. B.18
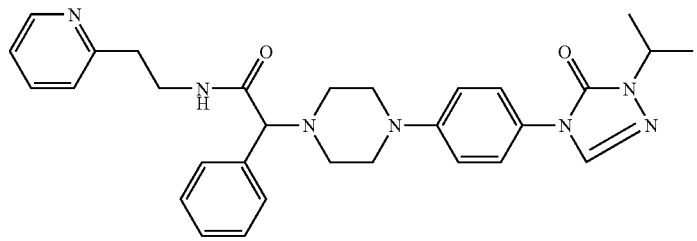
Co. No. 72; Ex. B.18
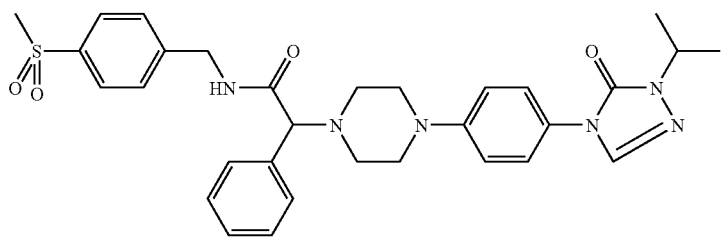
Co. No. 73; Ex. B.18
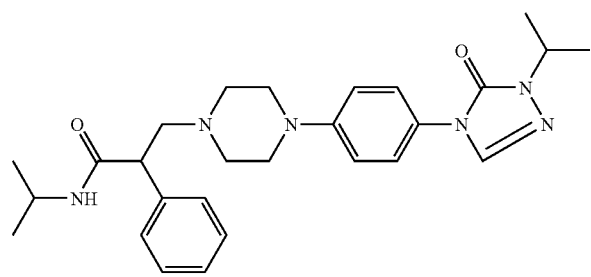
Co. No. 74; Ex. B.18

TABLE F-1a-continued
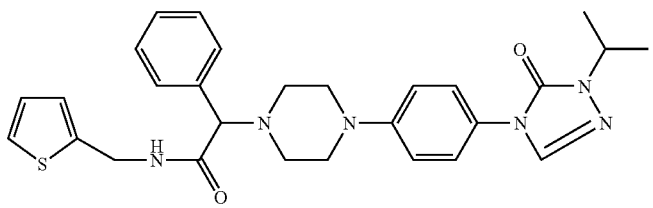
Co. No. 75; Ex. B.18
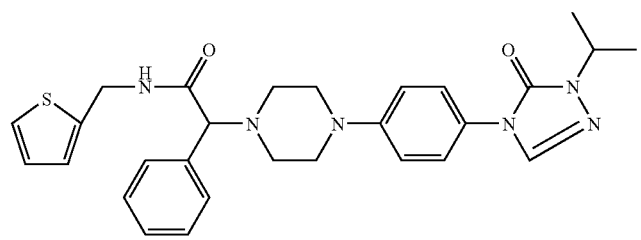
Co. No. 76; Ex. B.18
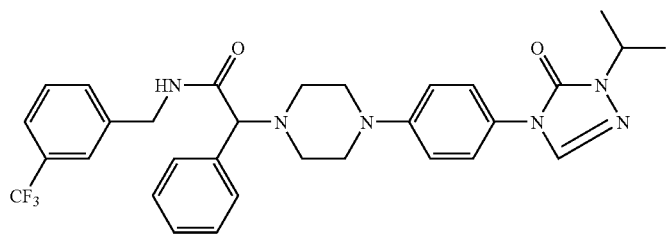
Co. No. 77; Ex. B.18
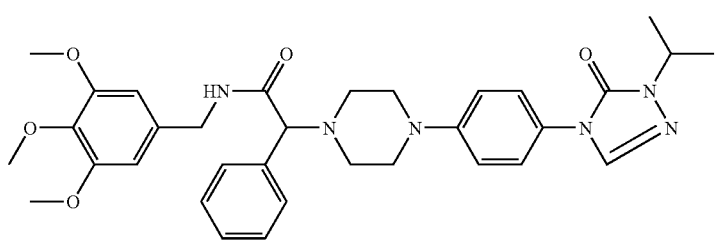
Co. No. 78; Ex. B.18
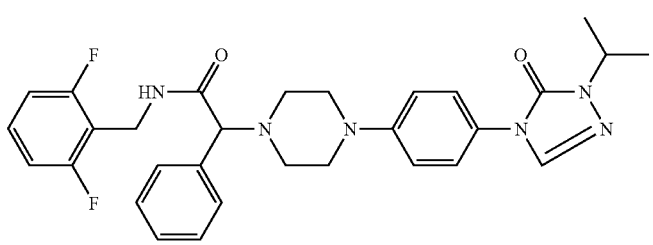
Co. No. 79; Ex. B.18

TABLE F-1a-continued
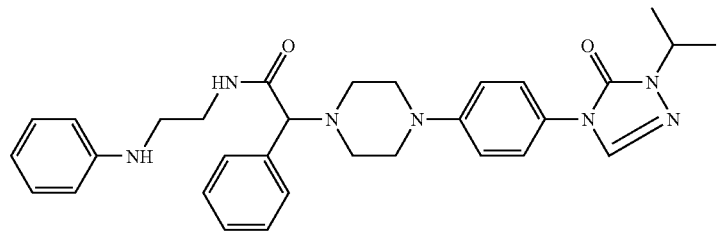
Co. No. 80; Ex. B.18
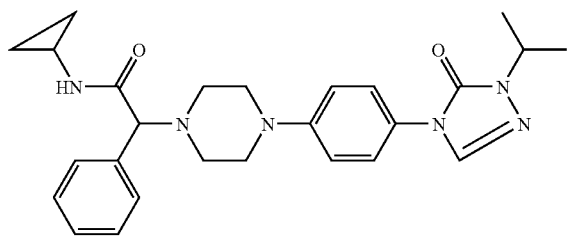
Co. No. 81; Ex. B.18
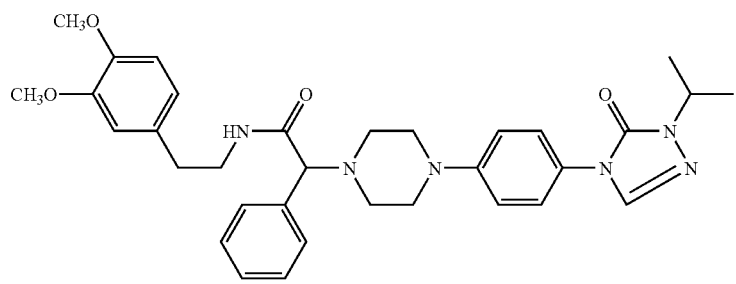
Co. No. 82; Ex. B.18
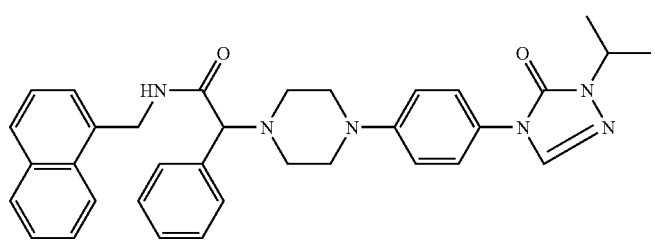
Co. No. 83; Ex. B.18
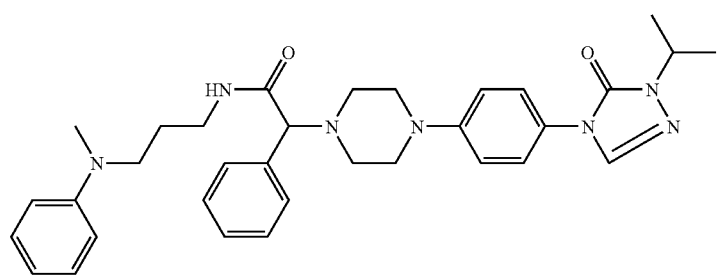
Co. No. 84; Ex. B.18

TABLE F-1a-continued
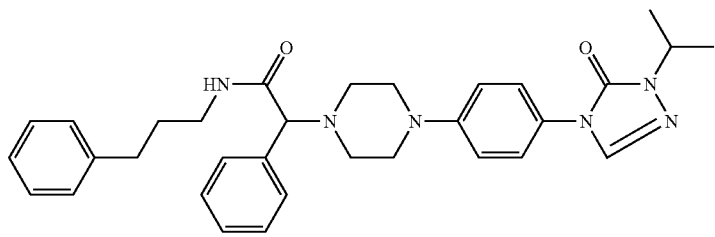
Co. No. 85; Ex. B.18
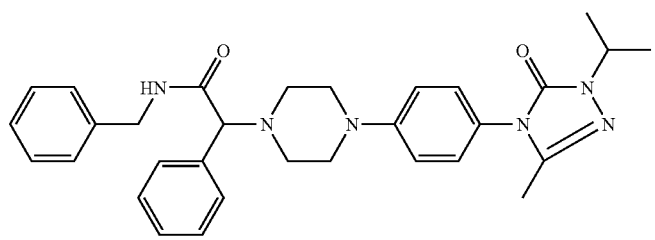
Co. No. 86; Ex. B.3
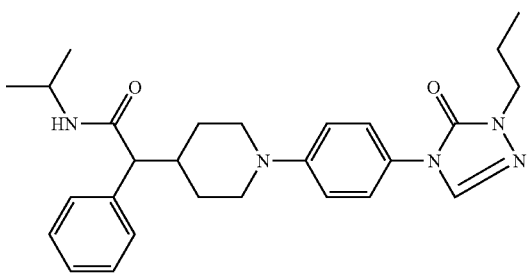
Co. No. 87; Ex. B.19
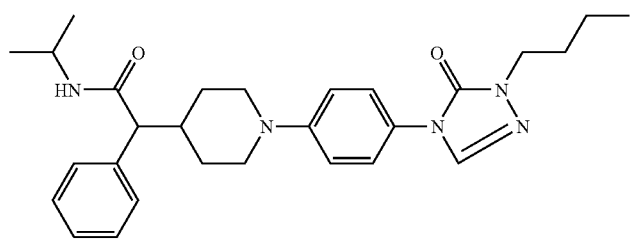
Co. No. 88; Ex. B.19
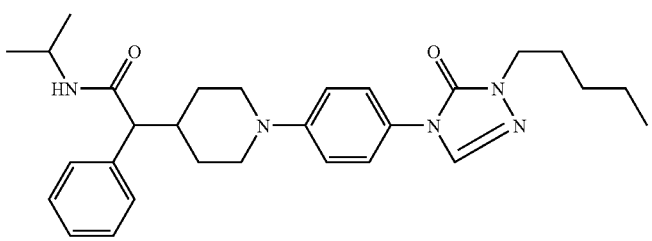
Co. No. 89; Ex. B.

TABLE F-1a-continued
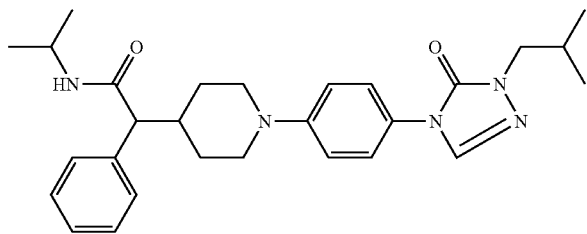
Co. No. 90; Ex. B.19
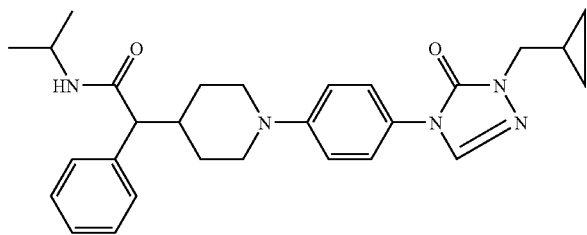
Co. No. 91; Ex. B.19
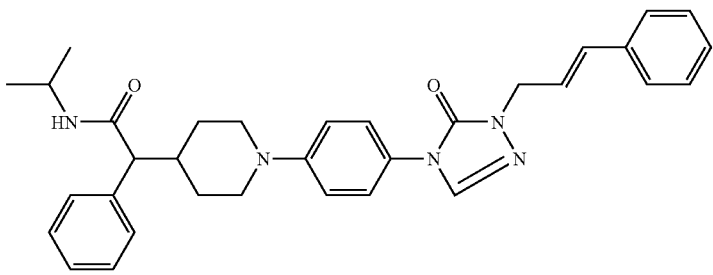
Co. No. 92; Ex. B.19
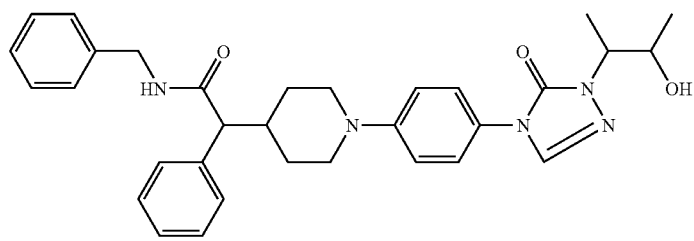
Co. No. 93; Ex. B.20
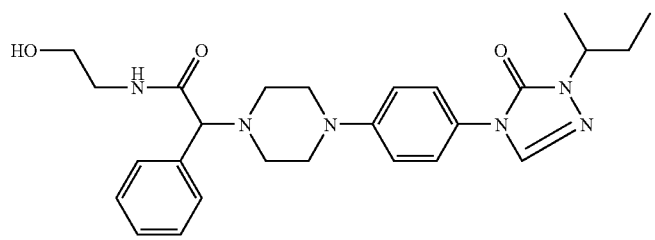
Co. No. 94; Ex. B.3

TABLE F-1a-continued
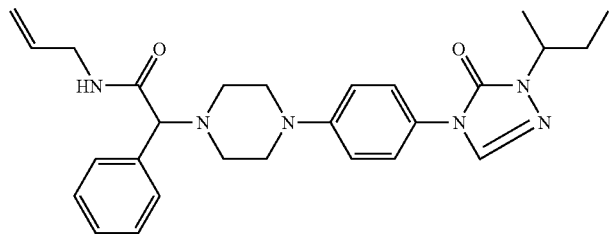
Co. No. 95; Ex. B.3
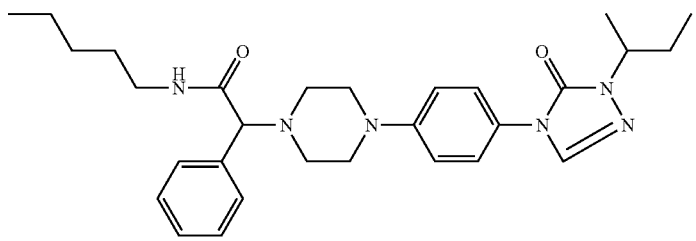
Co. No. 96; Ex. B.3
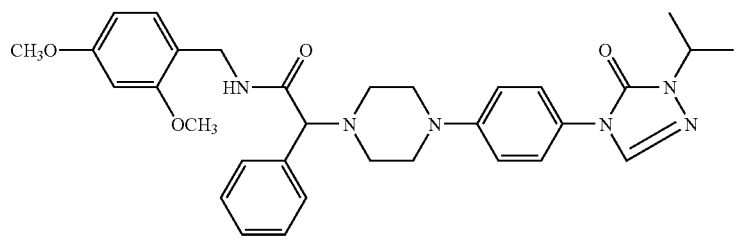
Co. No. 97; Ex. B.18
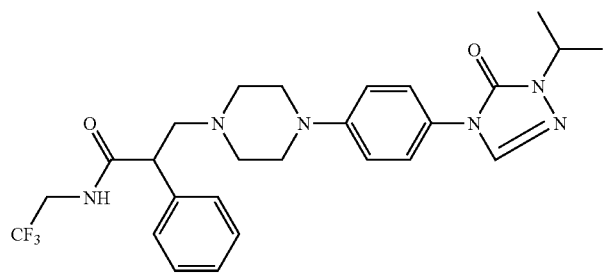
Co. No. 98; Ex. B.18
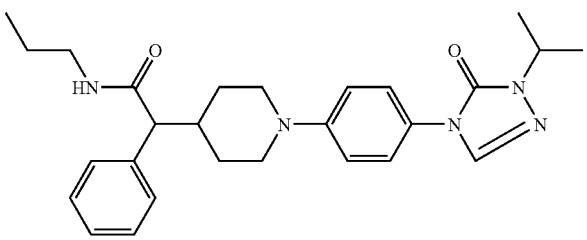
Co. No. 99; Ex. B.21; •C$_2$HF$_3$O$_2$ TABLE F-1a-continued
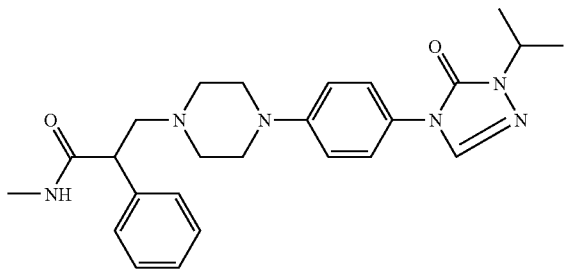
Co. No. 100; Ex. B.18
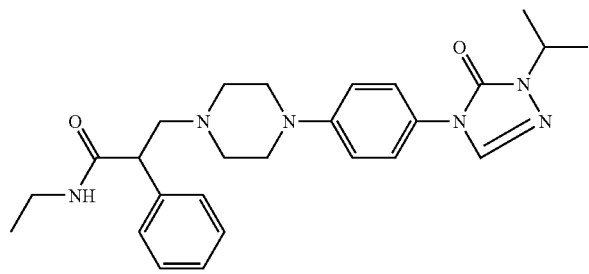
Co. No. 101; Ex. B.18
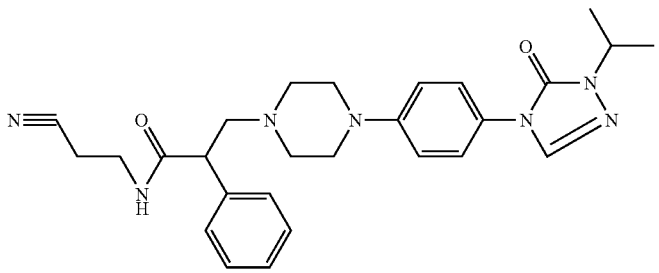
Co. No. 102; Ex. B.3
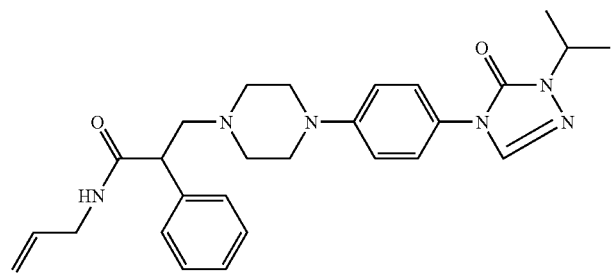
Co. No. 103; Ex. B.3
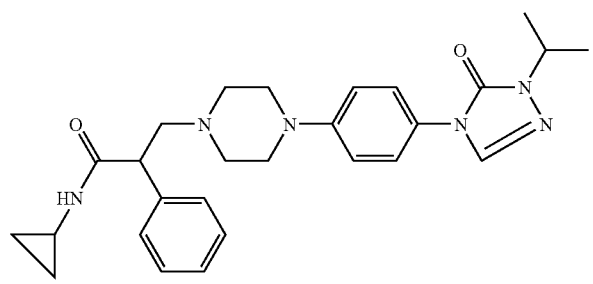
Co. No. 104; Ex. B.3

TABLE F-1a-continued
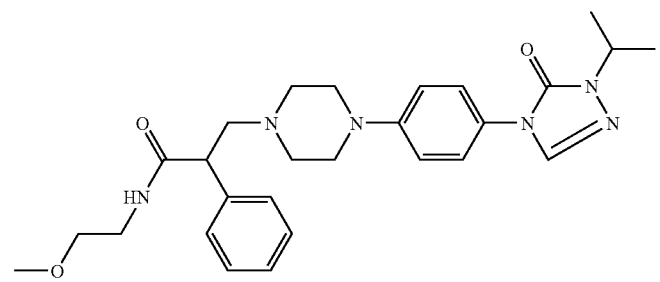
Co. No. 105; Ex. B.3
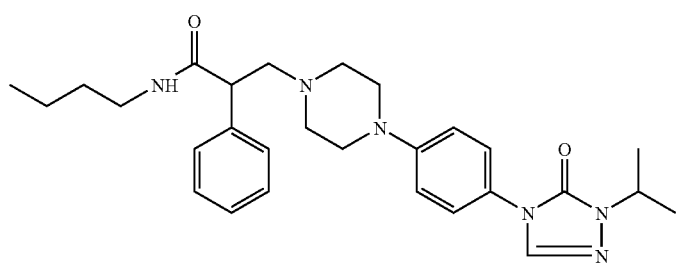
Co. No. 106; Ex. B.3
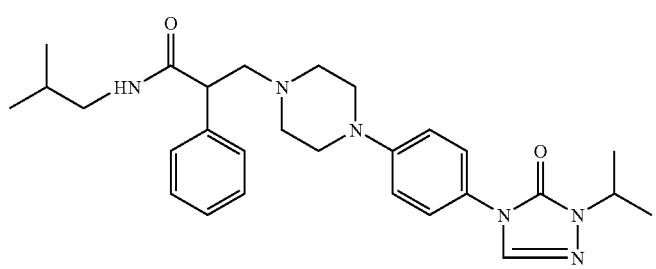
Co. No. 107; Ex. B.3
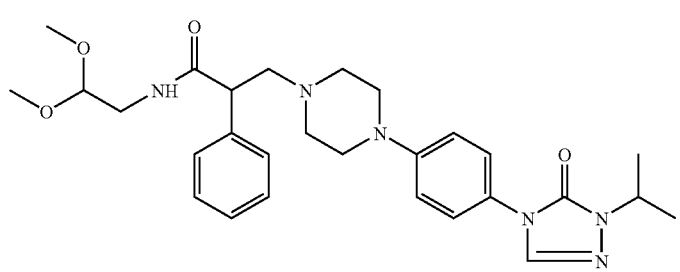
Co. No. 108; Ex. B.3
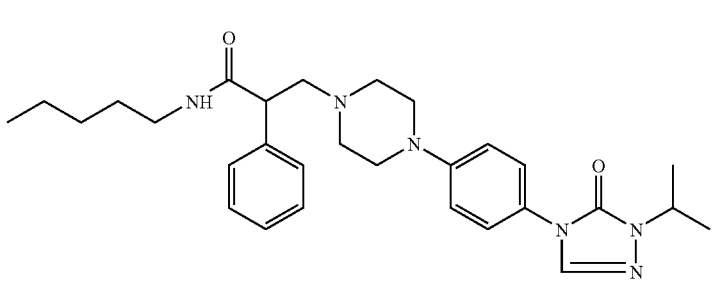
Co. No. 109; Ex. B.3

TABLE F-1a-continued
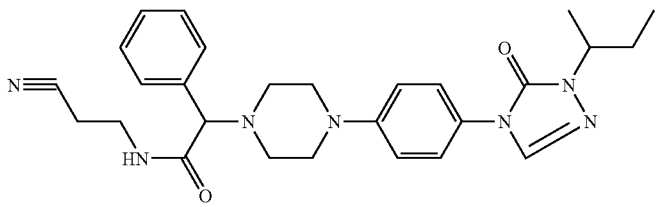
Co. No. 110; Ex. B.3
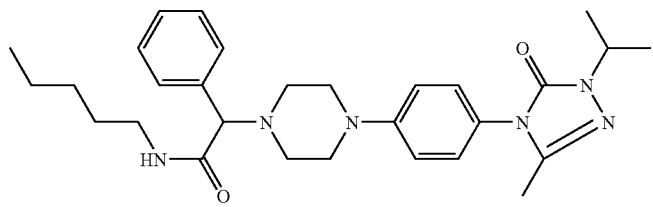
Co. No. 111; Ex. B.3
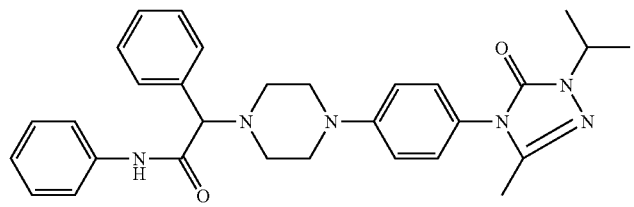
Co. No. 112; Ex. B.3
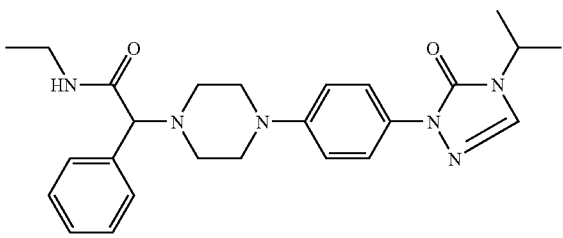
Co. No. 113; Ex. B.3
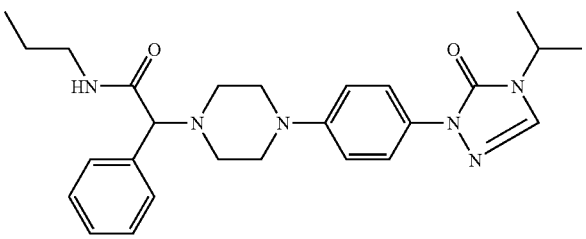
Co. No. 114; Ex. B.3
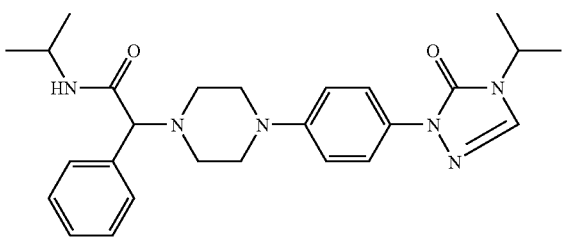
Co. No. 115; Ex. B.3

TABLE F-1a-continued
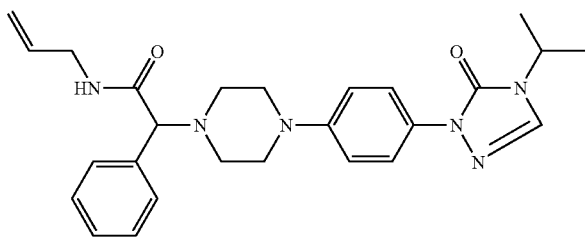
Co. No. 116; Ex. B.3
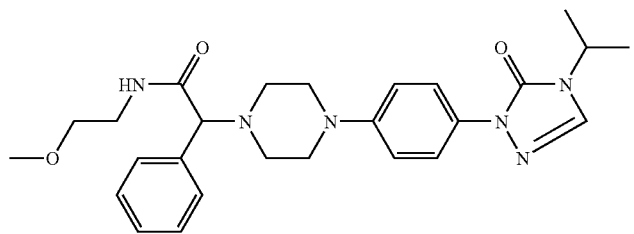
Co. No. 117; Ex. B.3
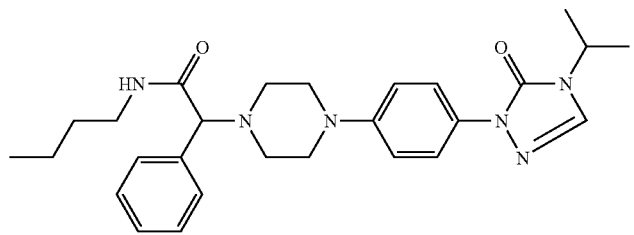
Co. No. 118; Ex. B.3
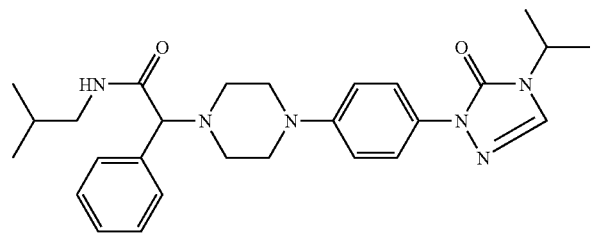
Co. No. 119; Ex. B.3
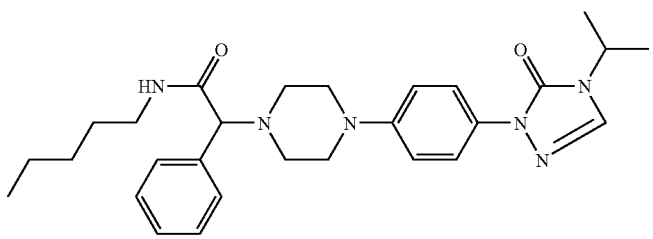
Co. No. 120; Ex. B.3

TABLE F-1a-continued
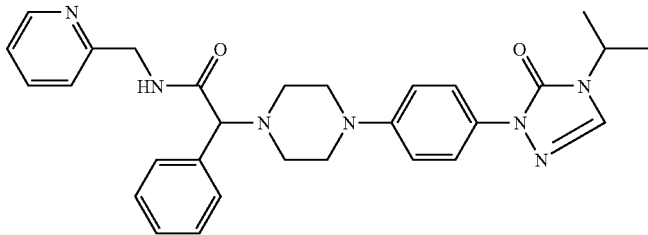
Co. No. 121; Ex. B.3
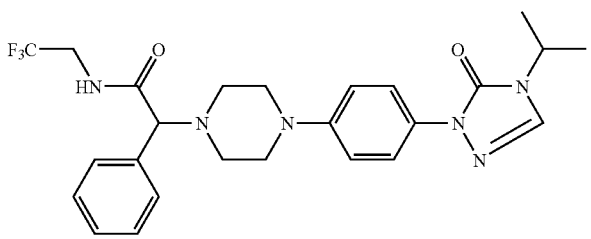
Co. No. 122; Ex. B.3
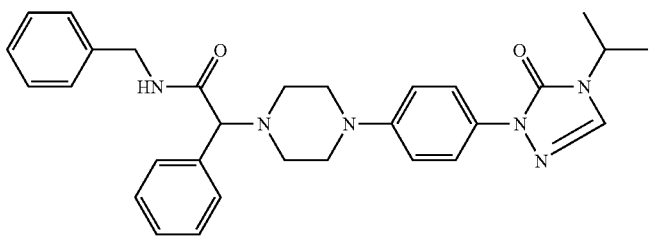
Co. No. 123; Ex. B.3
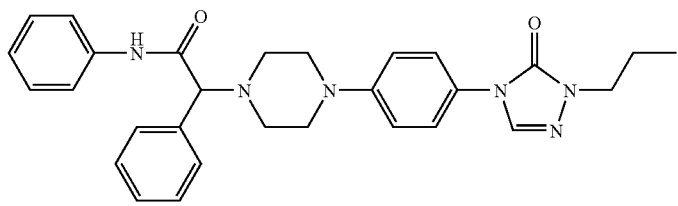
Co. No. 124; Ex. B.19
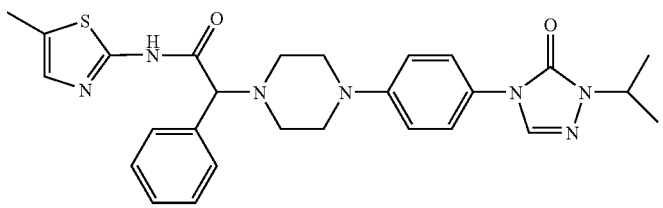
Co. No. 125; Ex. B.18
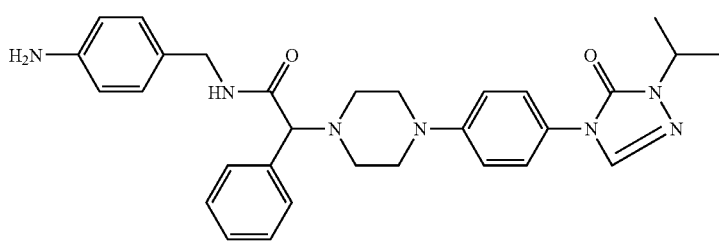
Co. No. 126; Ex. B.18

TABLE F-1a-continued
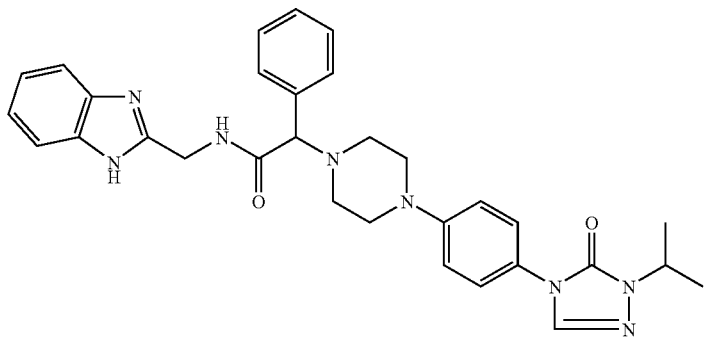
Co. No. 127; Ex. B.18
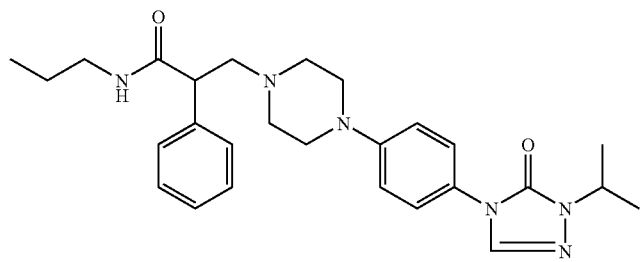
Co. No. 128; Ex. B.18
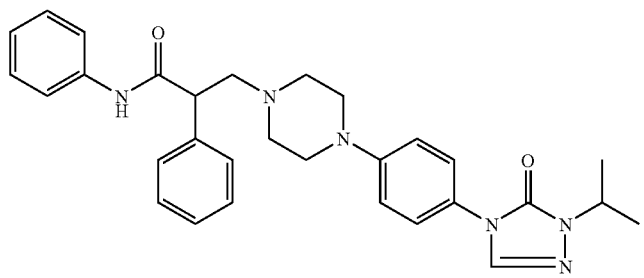
Co. No. 129; Ex. B.18
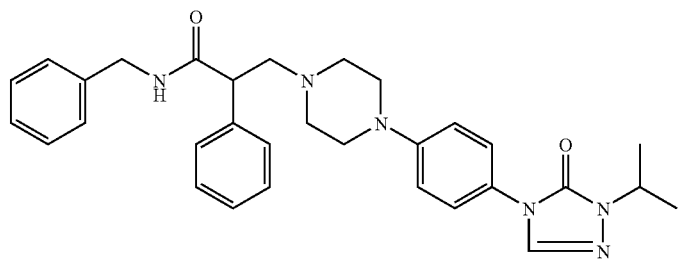
Co. No. 130; Ex. B.18

TABLE F-1a-continued
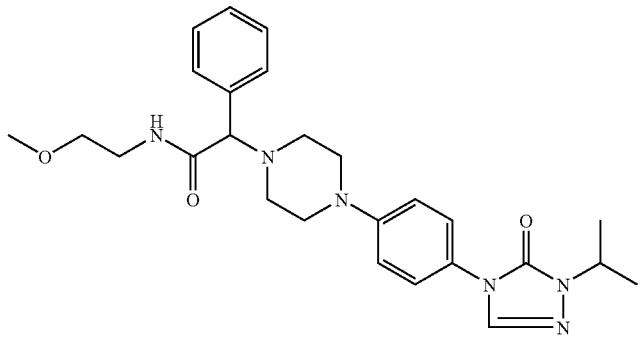
Co. No. 131; Ex. B.18
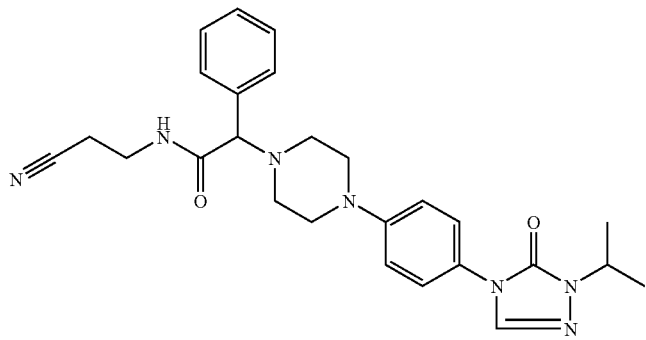
Co. No. 132; Ex. B.18
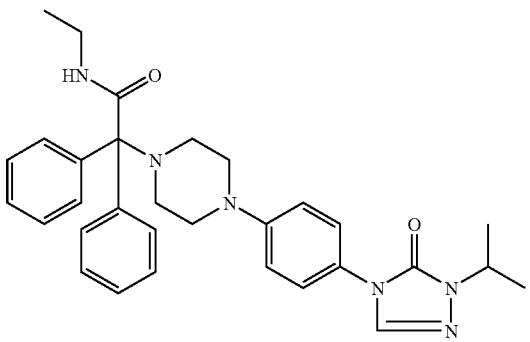
Co. No. 133; Ex. B.18
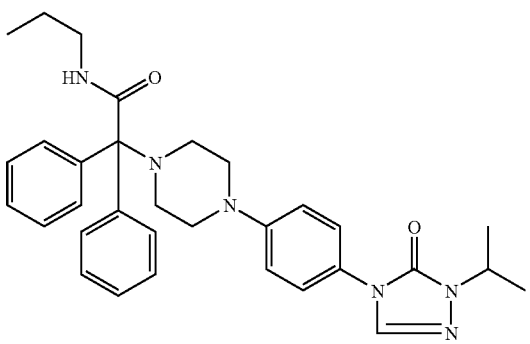
Co. No. 134; Ex. B.3

TABLE F-1a-continued
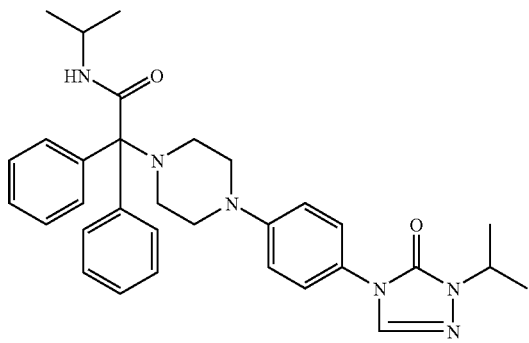
Co. No. 135; Ex. B.18
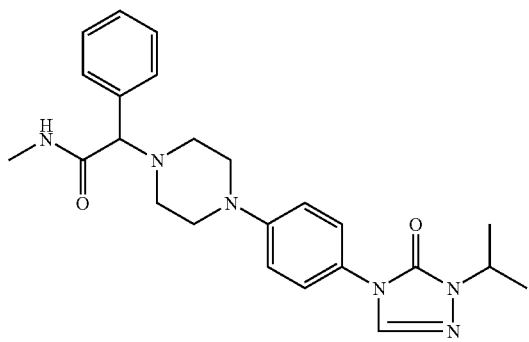
Co. No. 136; Ex. B.18
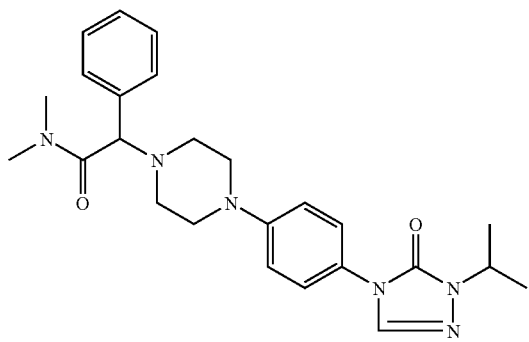
Co. No. 137; Ex. B.18
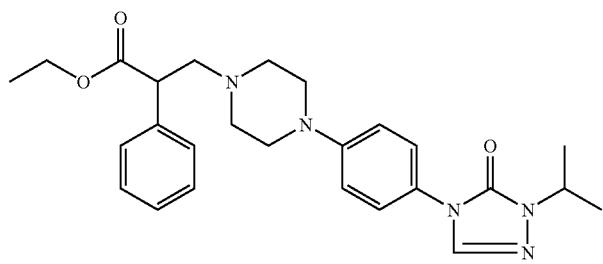
Co. No. 138; Ex. B.5

TABLE F-1a-continued
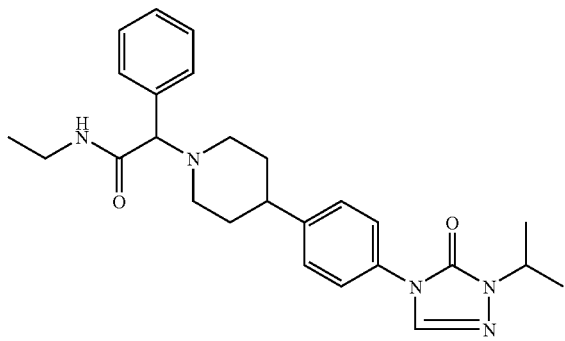
Co. No. 139; Ex. B.3
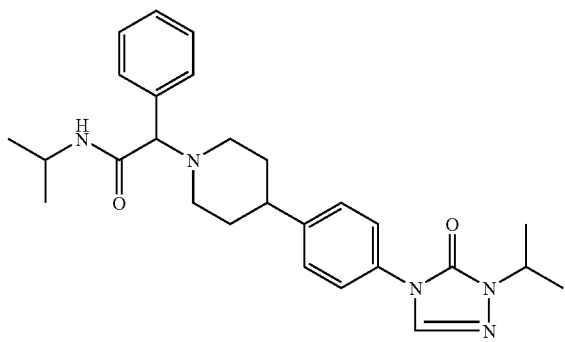
Co. No. 140; Ex. B.18
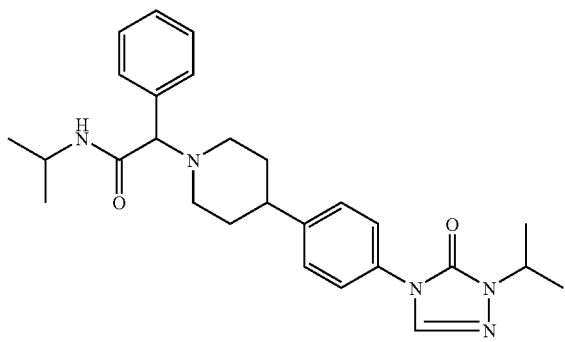
Co. No. 141; Ex. B.18
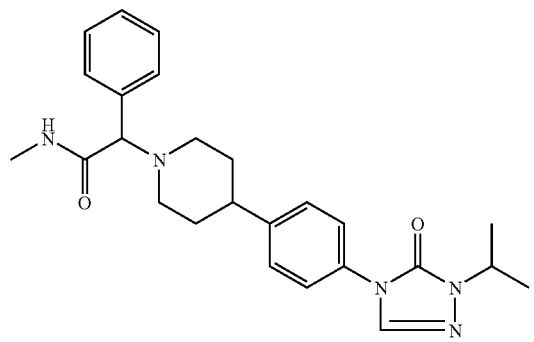
Co. No. 142; Ex. B.18

TABLE F-1a-continued
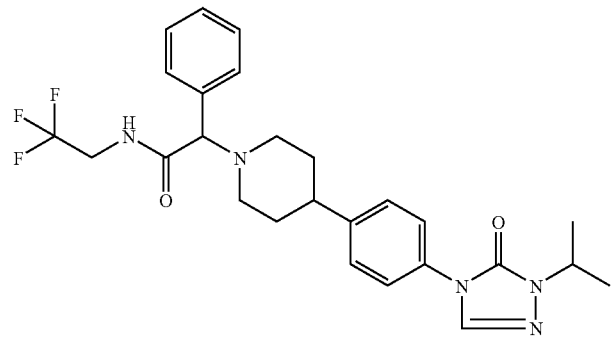
Co. No. 143; Ex. B.18
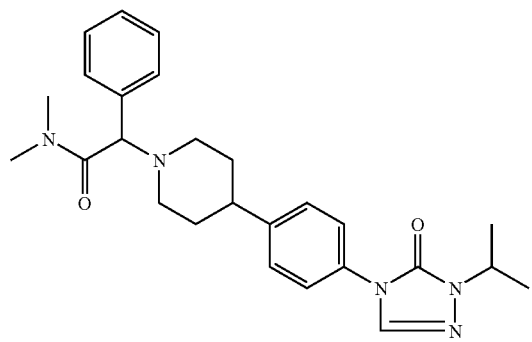
Co. No. 144; Ex. B.18
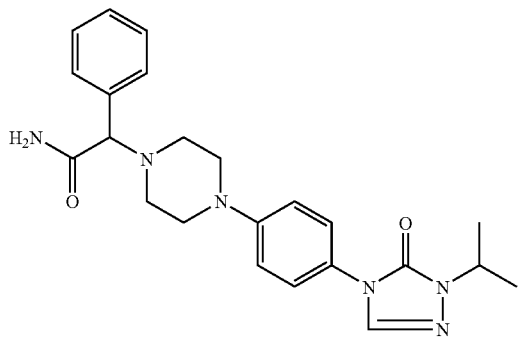
Co. No. 145; Ex. B.18
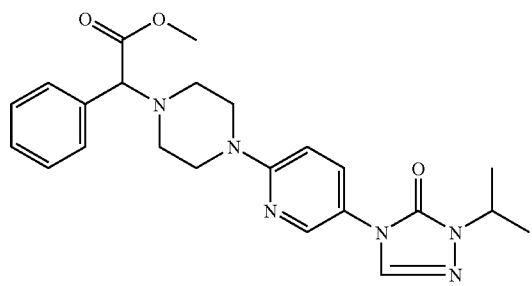
Co. No. 146; Ex. B.2; •HCON(CH$_3$)$_2$ TABLE F-1a-continued
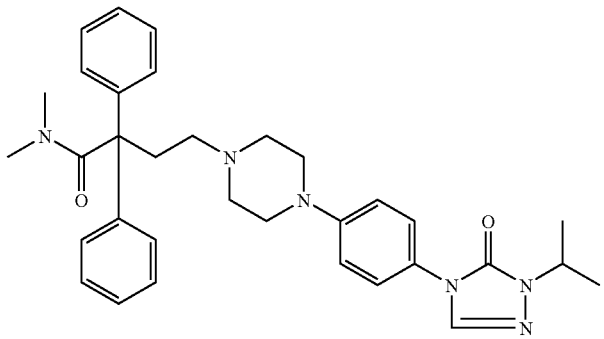
Co. No. 147; Ex. B.4
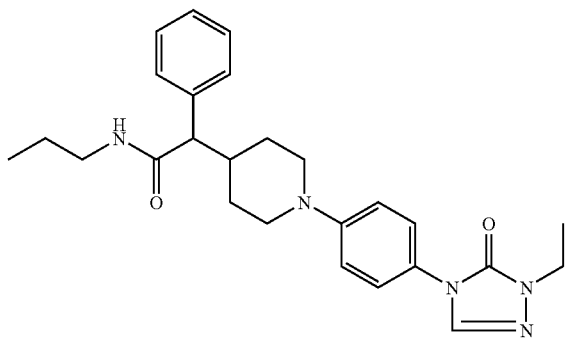
Co. No. 148; Ex. B.19
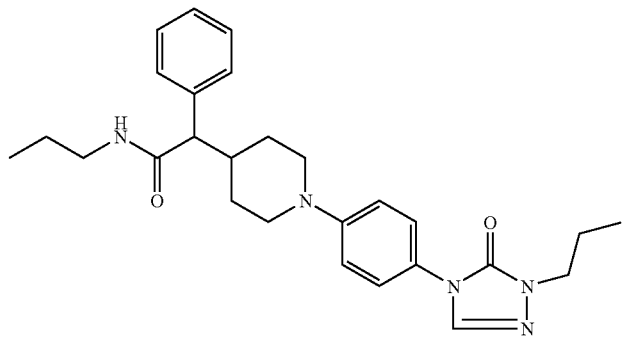
Co. No. 149; Ex. B.19
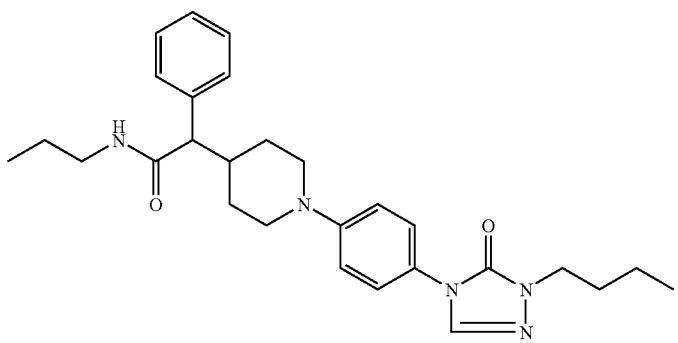
Co. No. 150; Ex. B.19

TABLE F-1a-continued
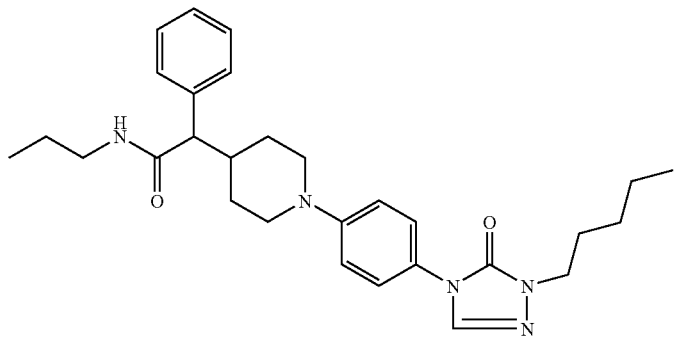
Co. No. 151; Ex. B.19
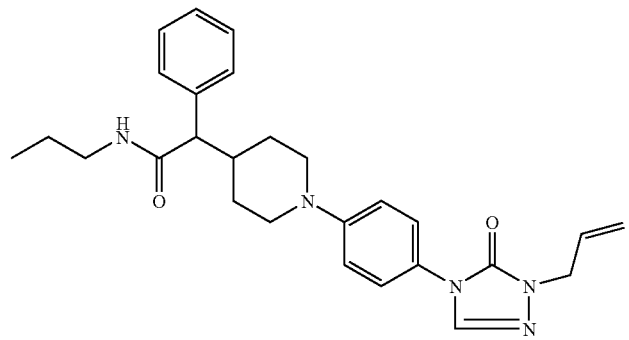
Co. No. 152; Ex. B.19
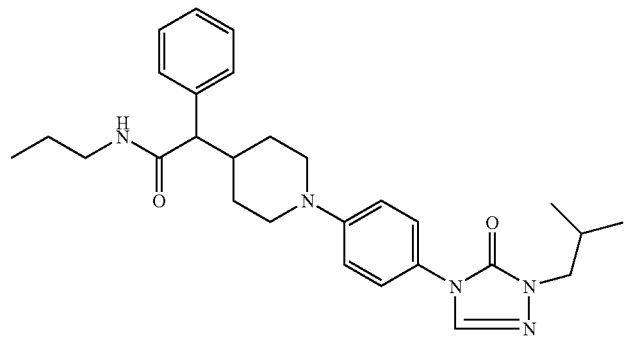
Co. No. 153; Ex. B.19
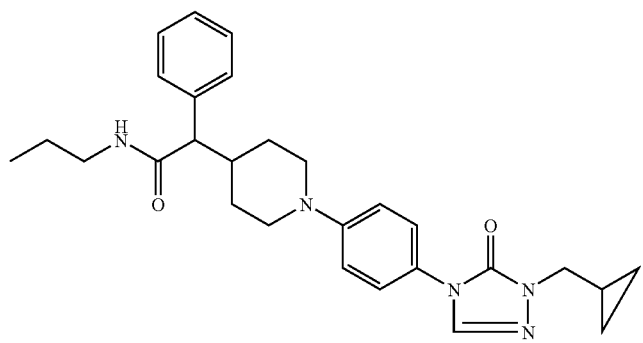
Co. No. 154; Ex. B.19

TABLE F-1a-continued
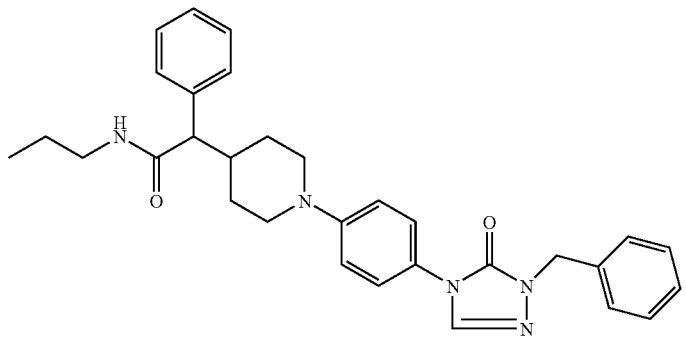
Co. No. 155; Ex. B.19
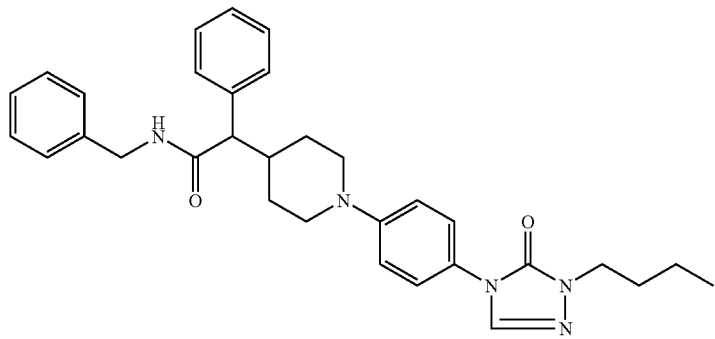
Co. No. 156; Ex. B.19
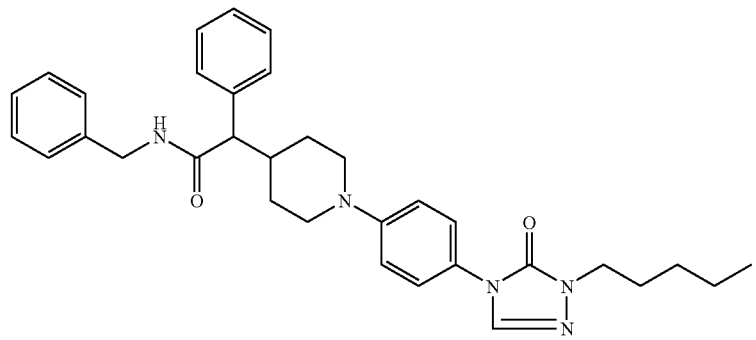
Co. No. 157; Ex. B.19
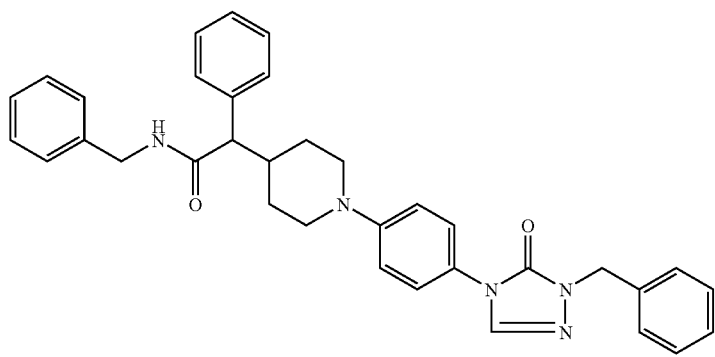
Co. No. 158; Ex. B.19

TABLE F-1a-continued
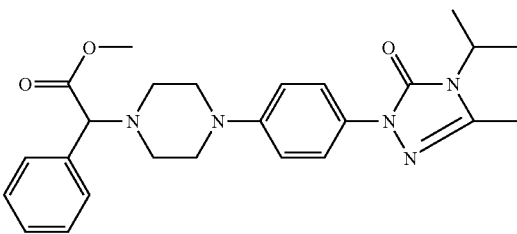
Co. No. 159; Ex. B.1
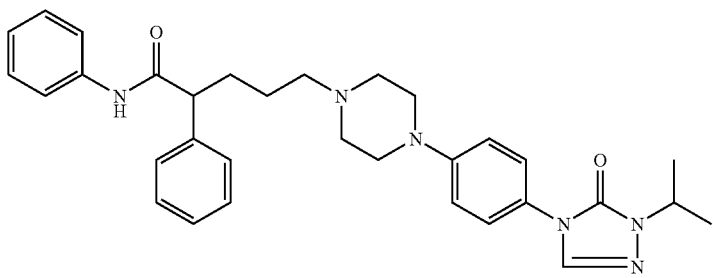
Co. No. 160; Ex. B.18
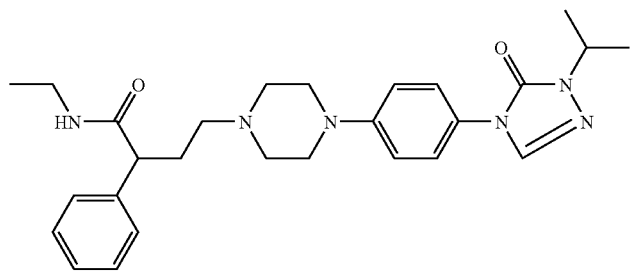
Co. No. 161; Ex. B.18
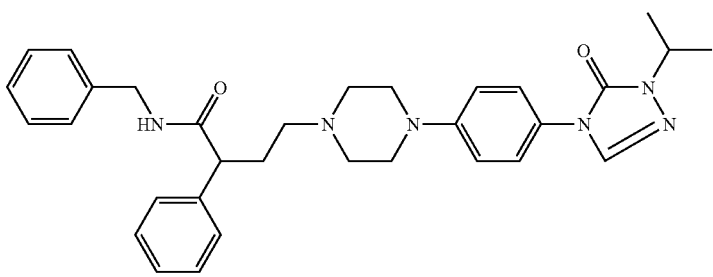
Co. No. 162; Ex. B.18
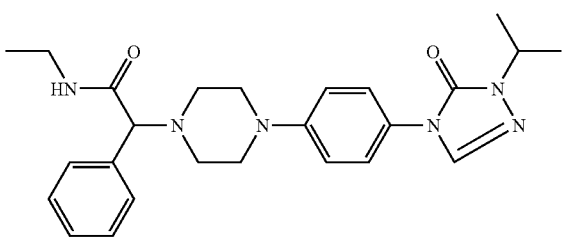
Co. No. 163; Ex. B.18

TABLE F-1a-continued
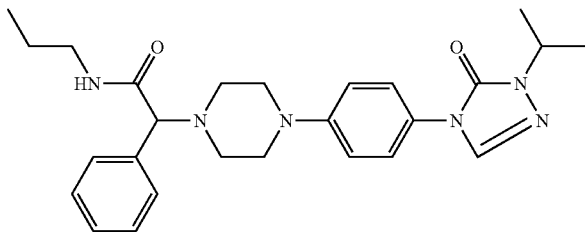
Co. No. 164; Ex. B.18
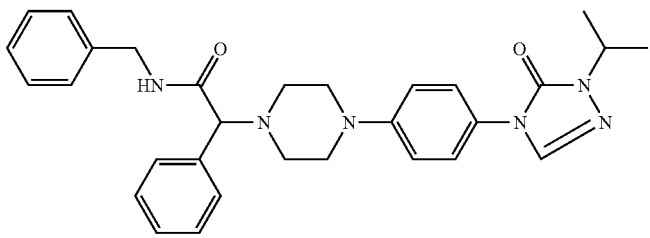
Co. No. 165; Ex. B.18
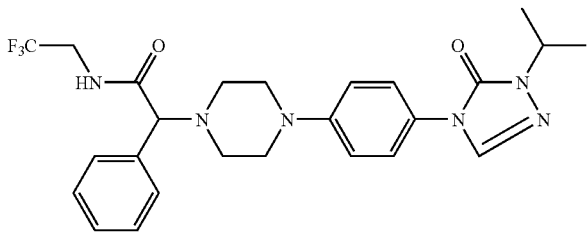
Co. No. 166; Ex. B.18
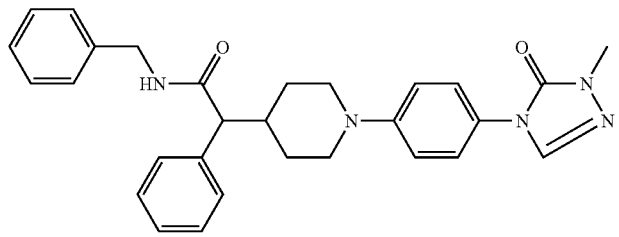
Co. No. 167; Ex. B.21
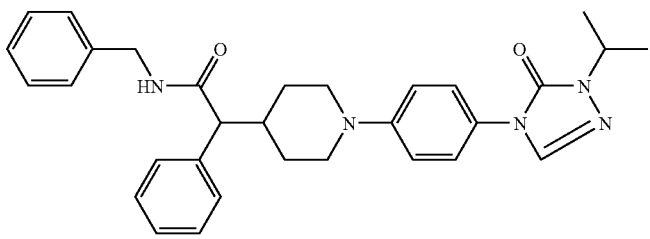
Co. No. 168; Ex. B.21

TABLE F-1a-continued
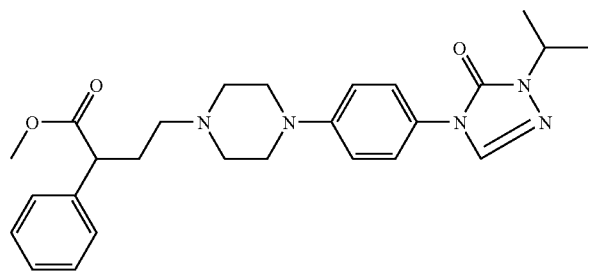
Co. No. 169; Ex. B.6
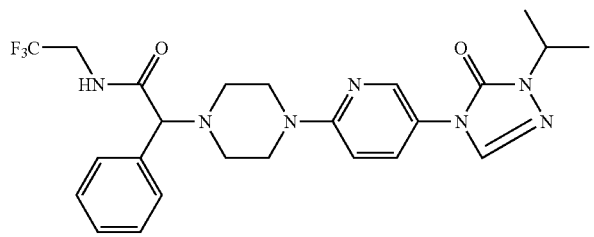
Co. No. 170; Ex. B.3
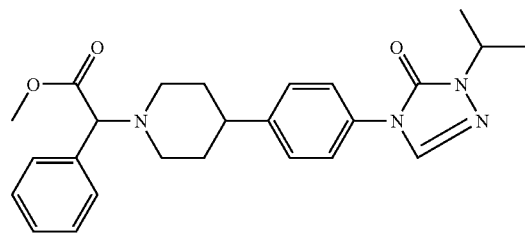
Co. No. 171; Ex. B.2
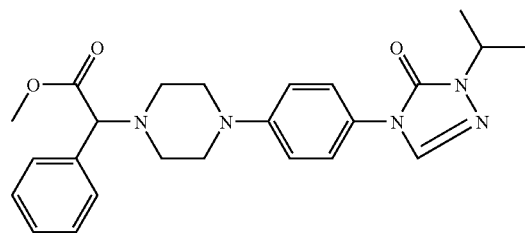
Co. No. 172; Ex. B.2
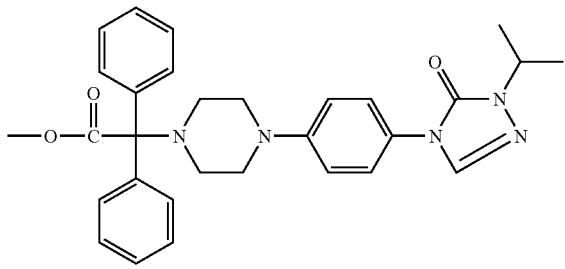
Co. No. 173; Ex. B.2

TABLE F-1a-continued
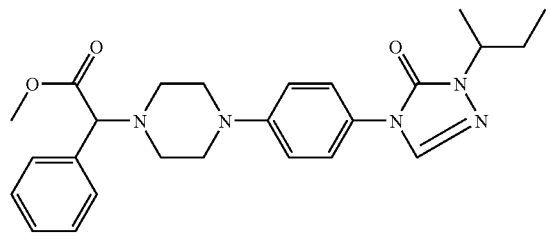
Co. No. 174; Ex. B.2; •HCl (1:1)
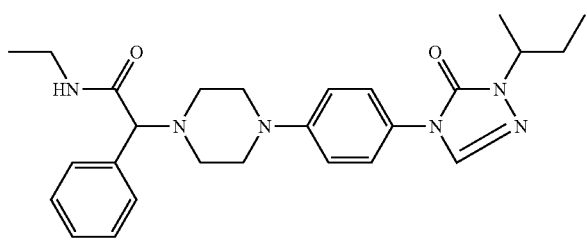
Co. No. 175; Ex. B.3
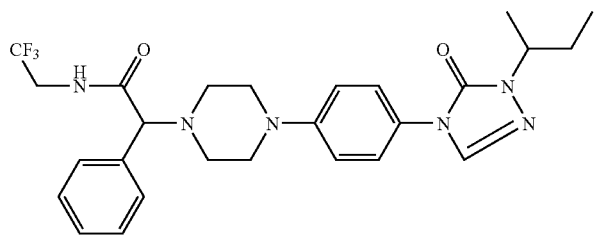
Co. No. 176; Ex. B.3
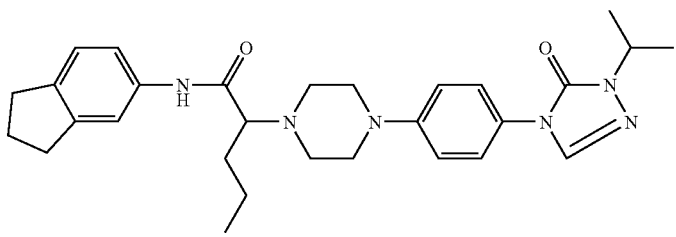
Co. No. 177; Ex. B.3; m.p. 153° C.
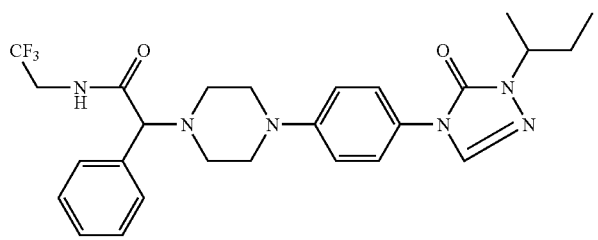
Co. No. 178; Ex. B.3

TABLE F-1a-continued
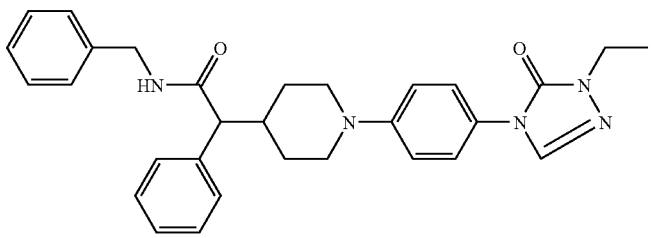
Co. No. 179; Ex. B.20
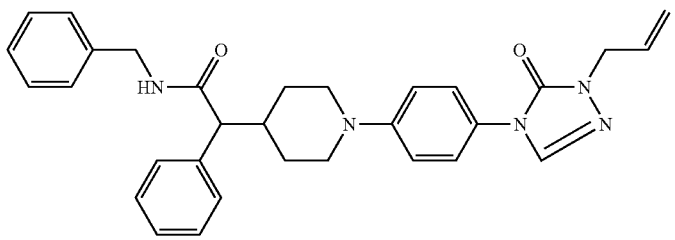
Co. No. 180; Ex. B.20
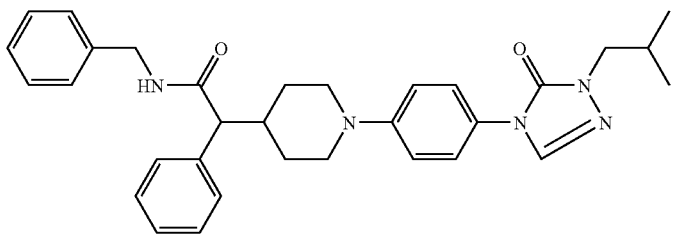
Co. No. 181; Ex. B.20
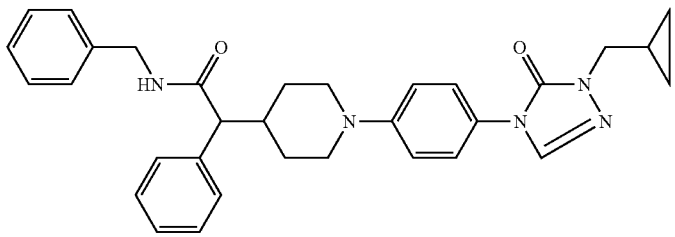
Co. No. 182; Ex. B.19
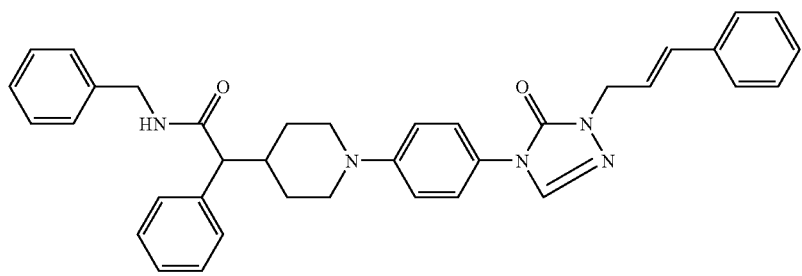
Co. No. 183; Ex. B.19

TABLE F-1a-continued
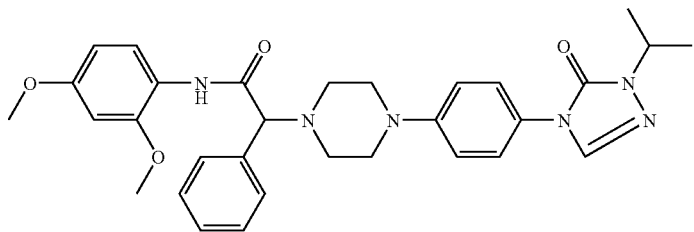
Co. No. 184; Ex. B.18
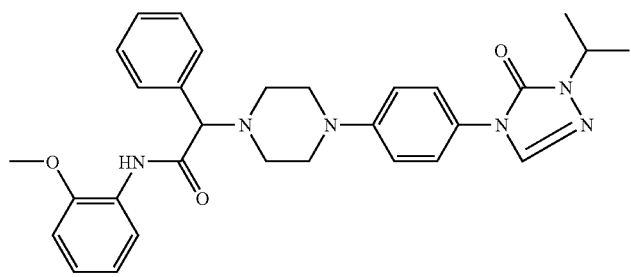
Co. No. 185; Ex. B.18
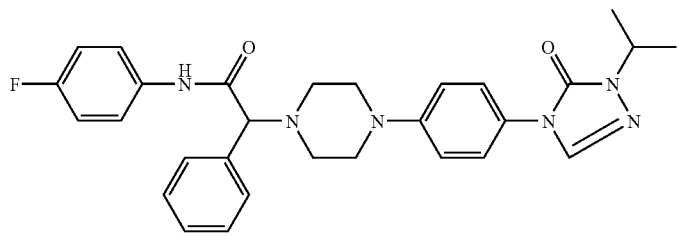
Co. No. 186; Ex. B.18
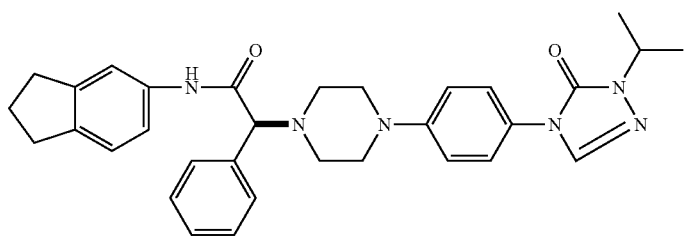
Co. No. 187; Ex. B.3; (A-isomer)
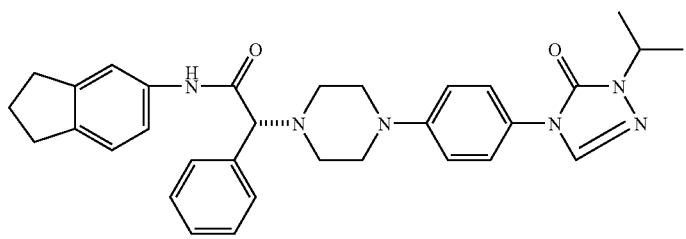
Co. No. 188; Ex. B.3; (B-isomer)

TABLE F-1a-continued
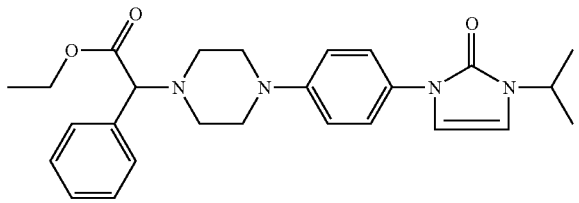
Co. No. 189; Ex. B.2
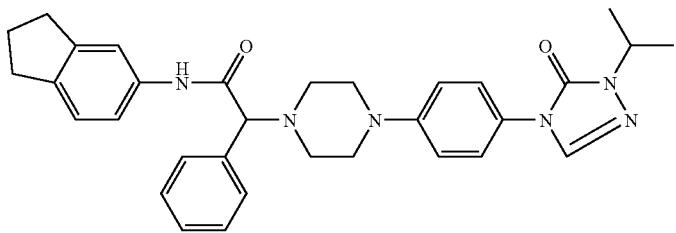
Co. No. 190; Ex. B.3; m.p. 182° C.
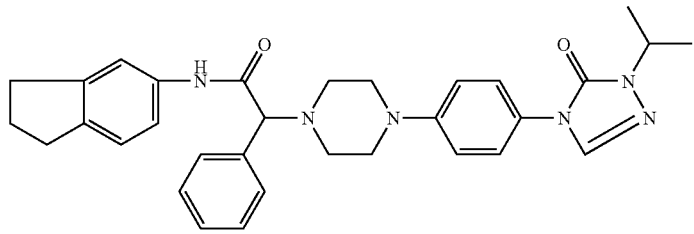
Co. No. 191; Ex. B.22
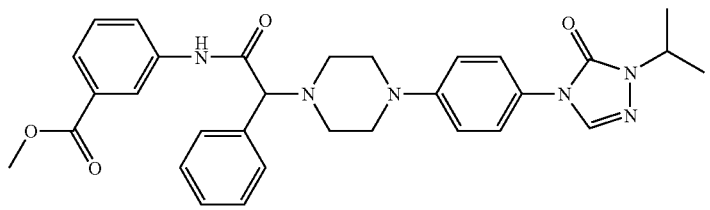
Co. No. 192; Ex. B.23
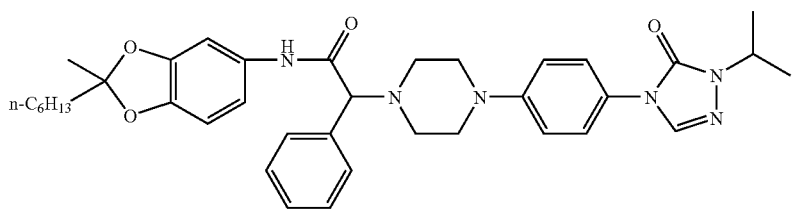
Co. No. 193; Ex. B.23
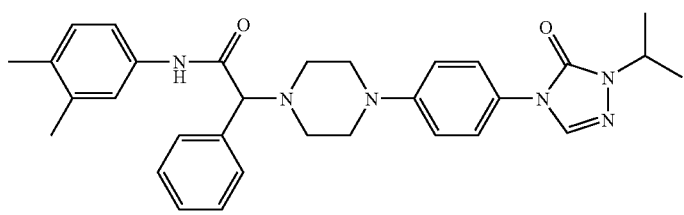
Co. No. 194; Ex. B.23

TABLE F-1a-continued
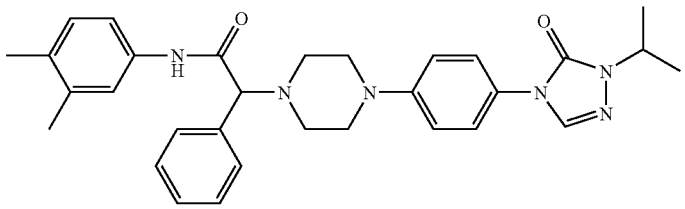
Co. No. 195; Ex. B.23
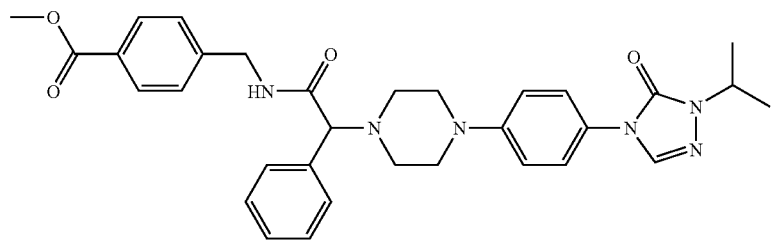
Co. No. 196; Ex. B.23
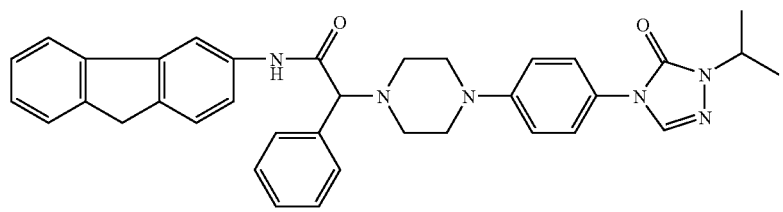
Co. No. 197; Ex. B.23
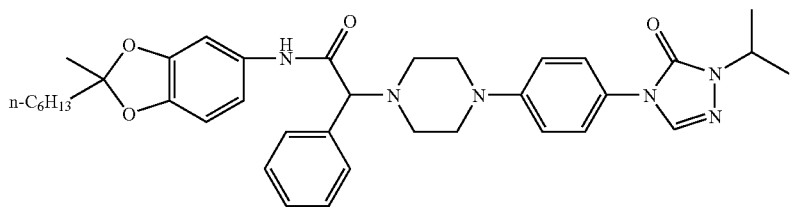
Co. No. 198; Ex. B.23
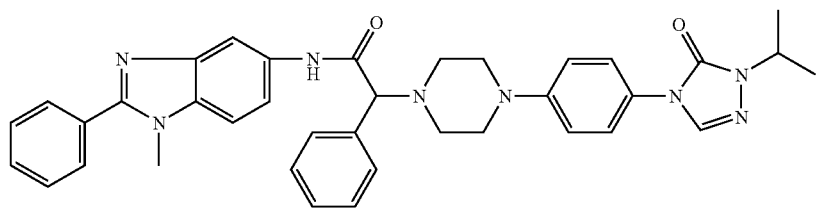
Co. No. 199; Ex. B.23
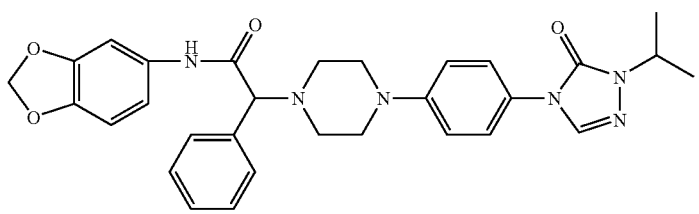
Co. No. 200; Ex. B.23

TABLE F-1a-continued
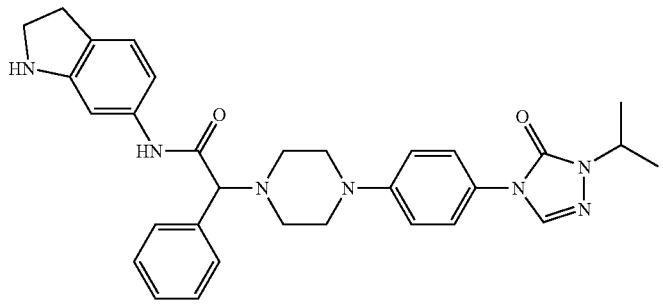
Co. No. 201; Ex. B.23
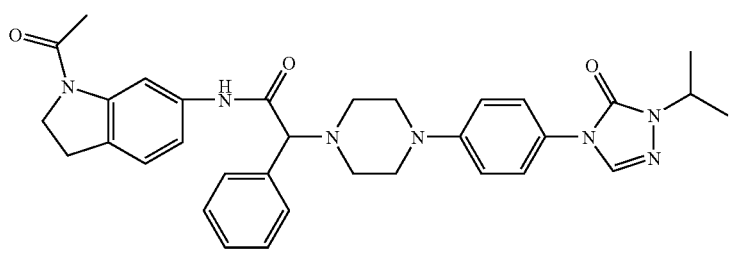
Co. No. 202; Ex. B.23
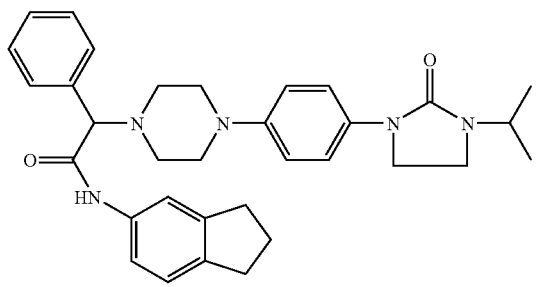
Co. No. 203; Ex. B.2; m.p. 215-217° C.
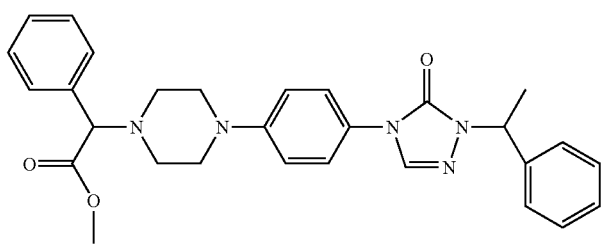
Co. No. 204; Ex. B.2
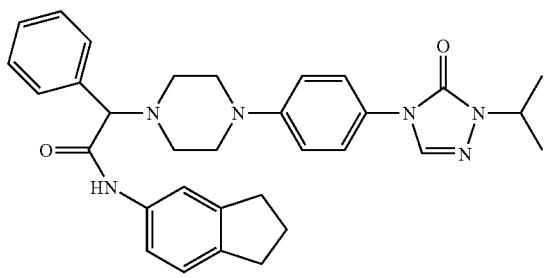
Co. No. 205; Ex. B.2; m.p. 199-201° C.

TABLE F-1a-continued
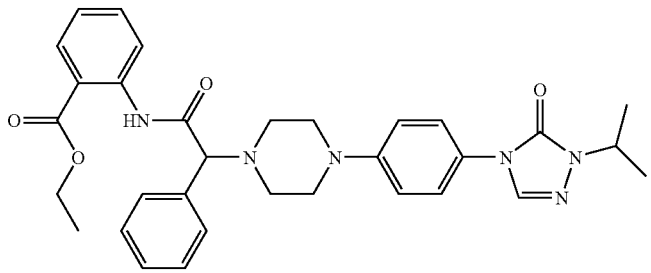
Co. No. 206; Ex. B.2; m.p. 211.5=213.5° C.
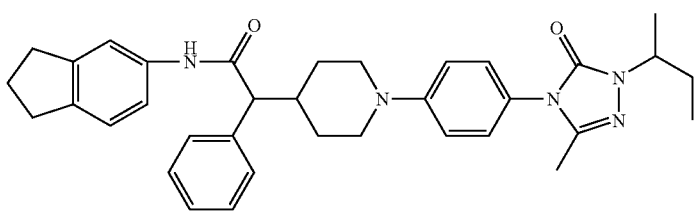
Co. No. 207; Ex. B.14
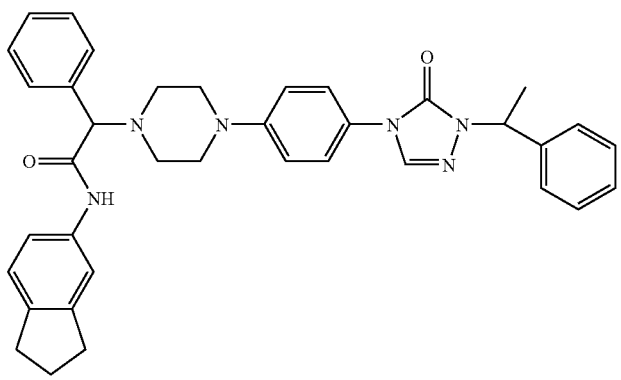
Co. No. 208; Ex. B.2; m.p. 188-190° C.
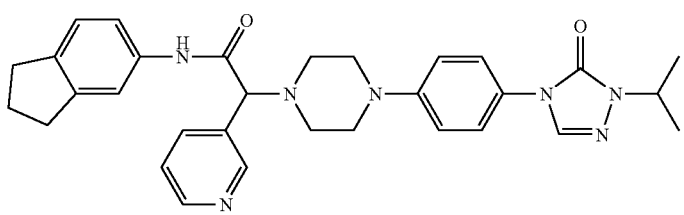
Co. No. 209; Ex. B.16
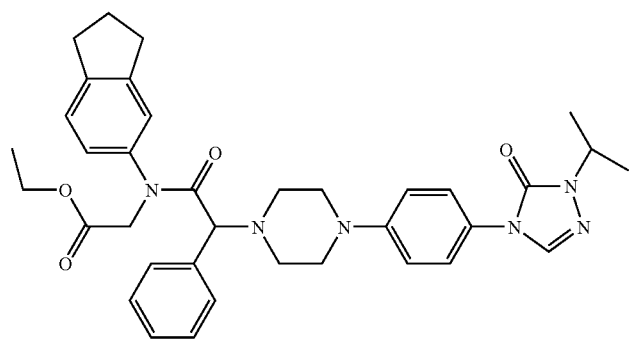
Co. No. 210; Ex. B.13

TABLE F-1a-continued
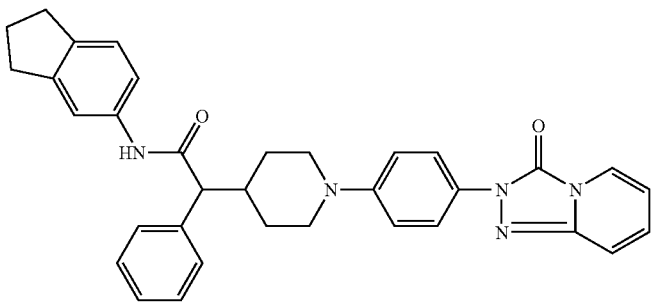
Co. No. 211; Ex. B.14
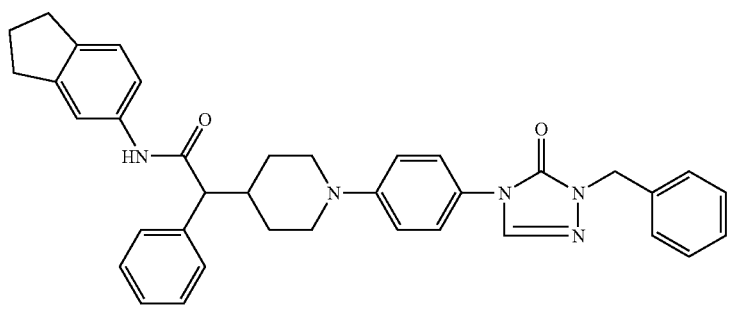
Co. No. 212; Ex. B.14
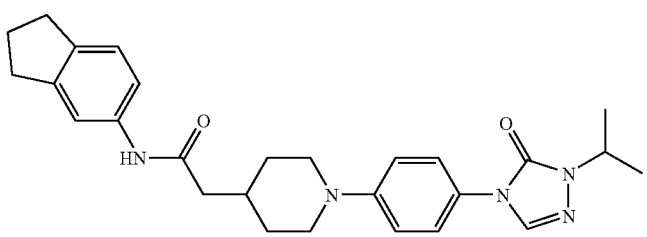
Co. No. 213; Ex. B.14
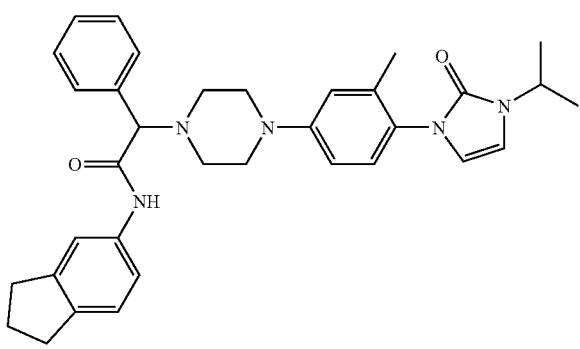
Co. No. 214; Ex. B.2; m.p. 111-112° C.

TABLE F-1a-continued
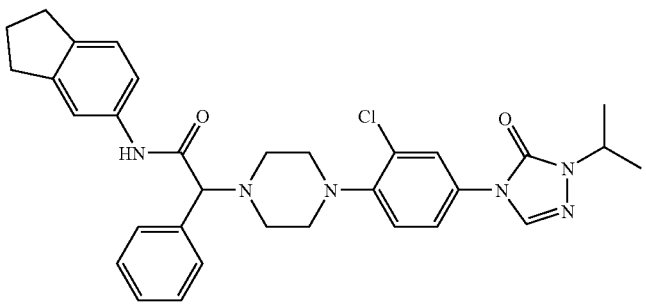
Co. No. 215; Ex. B.2; m.p. 199-200° C.
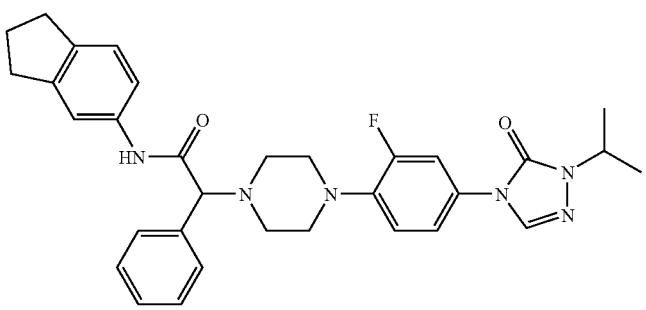
Co. No. 216; Ex. B.2
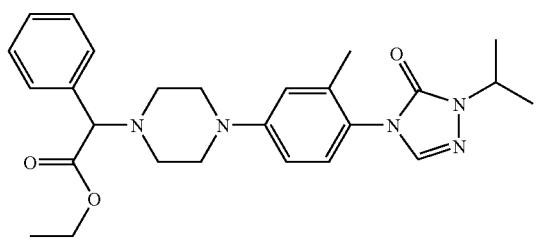
Co. No. 217; Ex. B.2
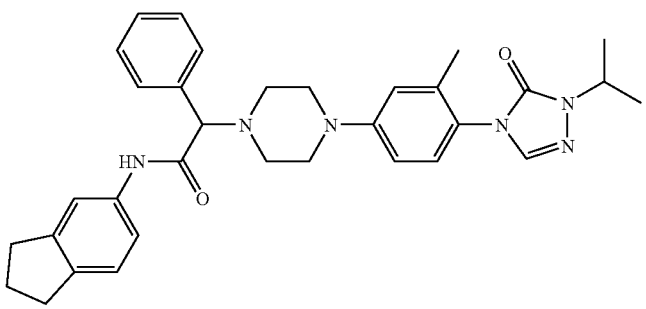
Co. No. 218; Ex. B.2; m.p. 233-235° C.
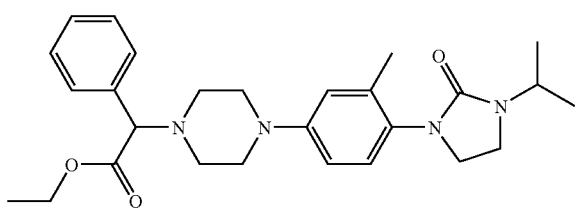
Co. No. 219; Ex. B.2

TABLE F-1a-continued
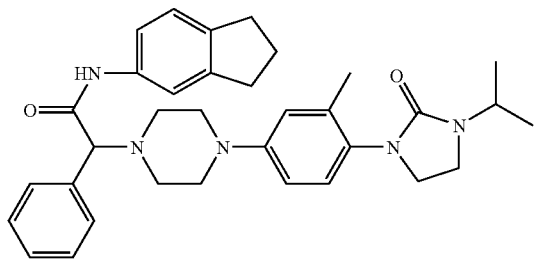
Co. No. 220; Ex. B.2; m.p. 177-179° C.
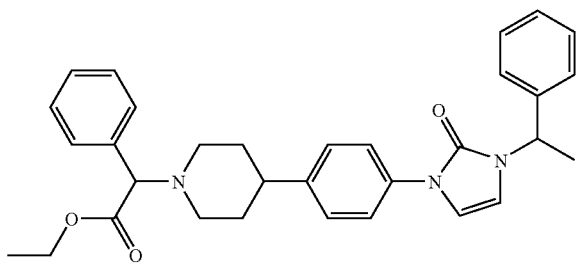
Co. No. 221; Ex. B.8
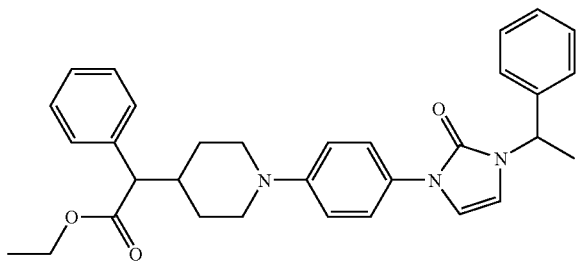
Co. No. 222; Ex. B.8
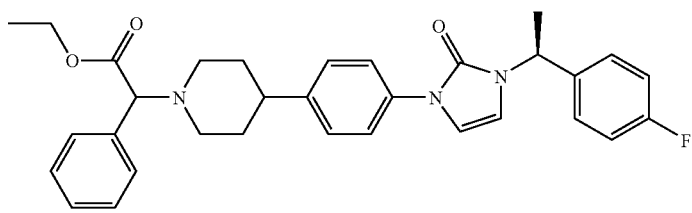
Co. No. 223; Ex. B.14; (S)
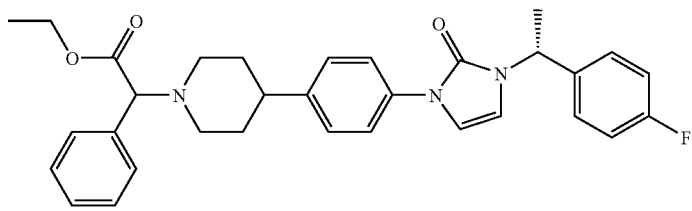
Co. No. 224; Ex. B.15; (R)

TABLE F-1a-continued
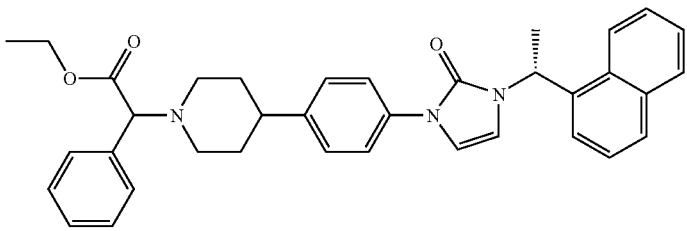
Co. No. 225; Ex. B.15; (R)
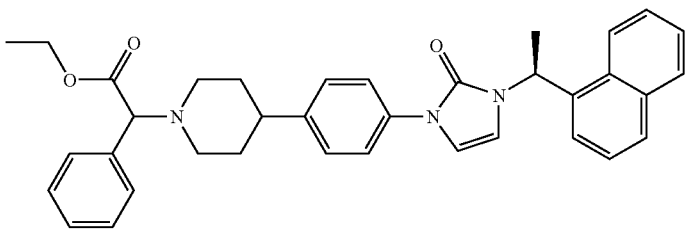
Co. No. 226; Ex. B.15; (S)
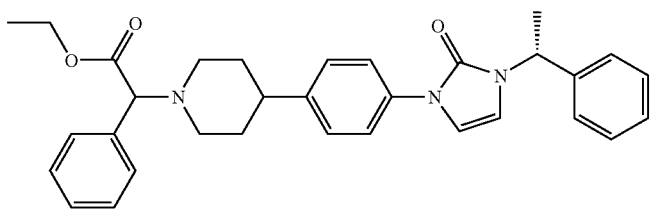
Co. No. 227; Ex. B.15; (R)
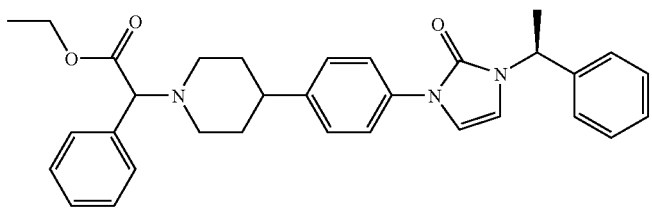
Co. No. 228; Ex. B.15; (S)
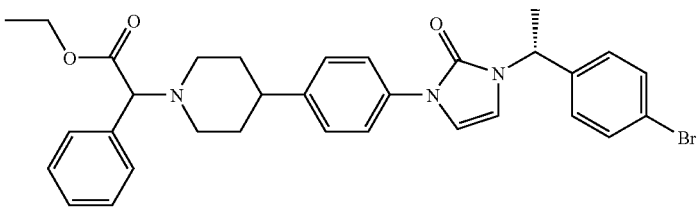
Co. No. 229; Ex. B.15; (R)
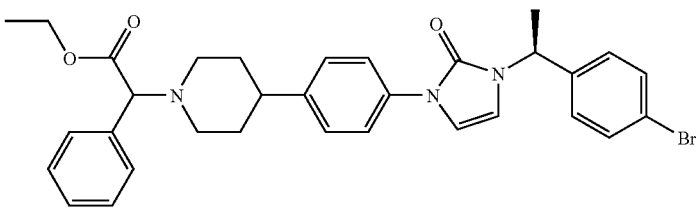
Co. No. 230; Ex. B.15; (S)

TABLE F-1a-continued
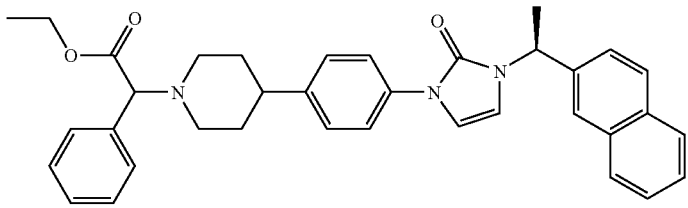
Co. No. 231; Ex. B.15; (S)
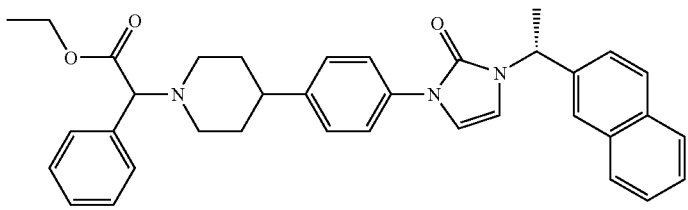
Co. No. 232; Ex. B.15; (R)
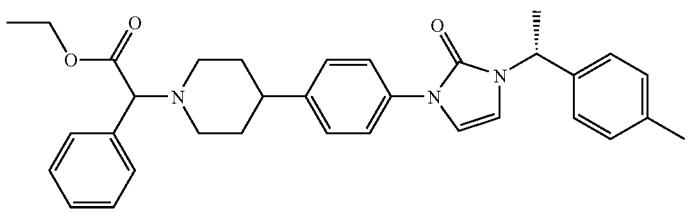
Co. No. 233; Ex. B.15; (R)
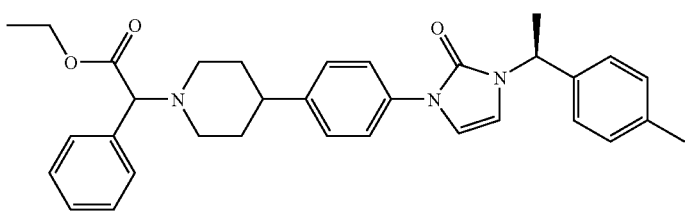
Co. No. 234; Ex. B.15; (S)
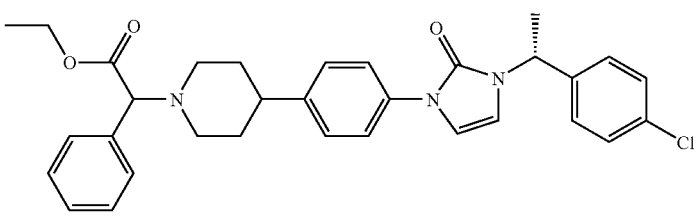
Co. No. 235; Ex. B.15; (R)
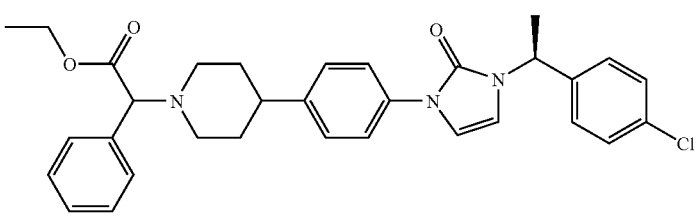
Co. No. 236; Ex. B.15; (S)

TABLE F-1a-continued
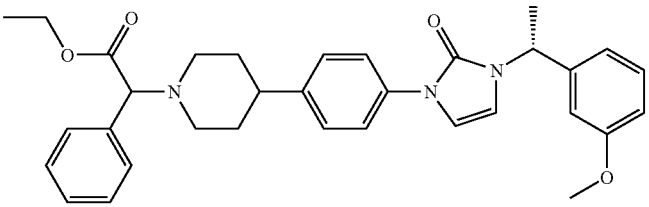
Co. No. 237; Ex. B.15; (R)
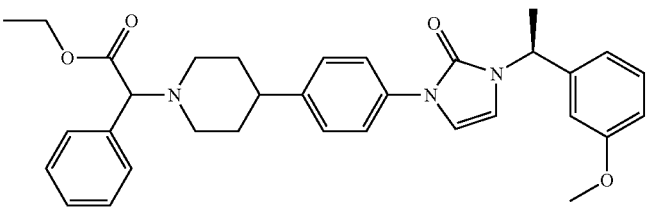
Co. No. 238; Ex. B.15; (S)
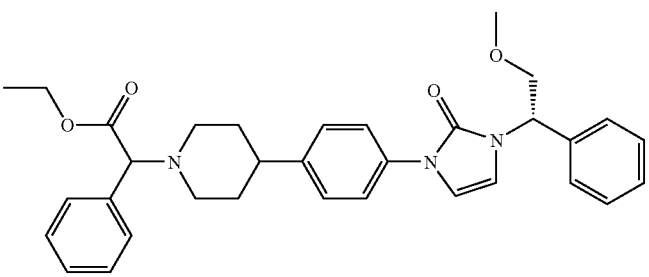
Co. No. 239; Ex. B.15; (S)
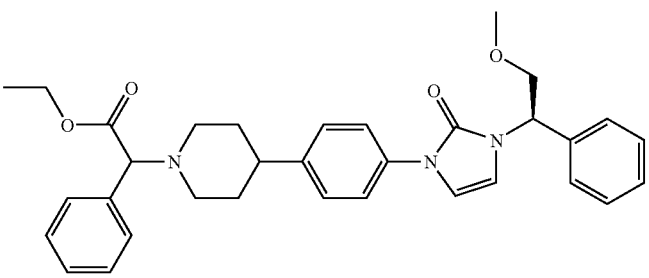
Co. No. 240; Ex. B.15; (R)
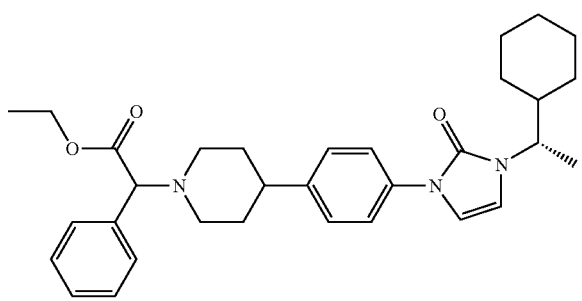
Co. No. 241; Ex. B.15; (S)

TABLE F-1a-continued
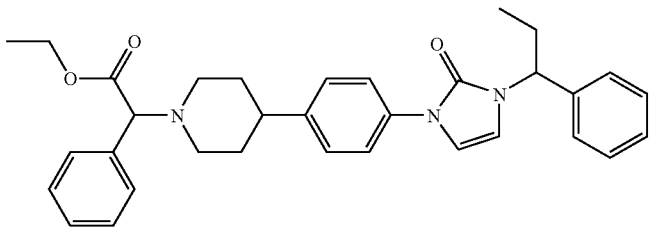
Co. No. 242; Ex. B.15
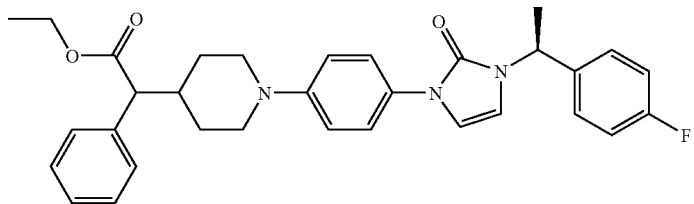
Co. No. 243; Ex. B.15; (S)
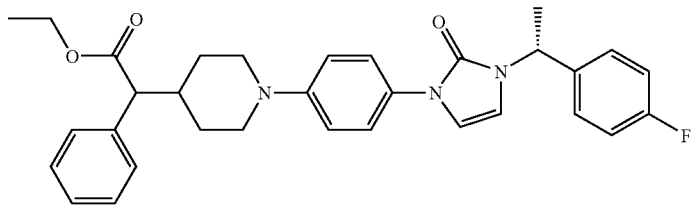
Co. No. 244; Ex. B.15; (R)
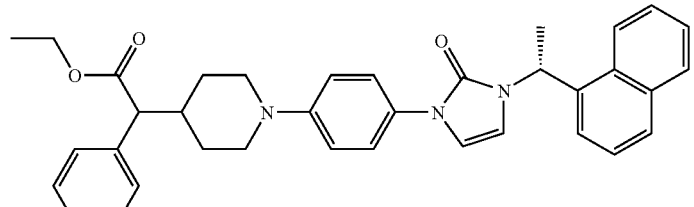
Co. No. 245; Ex. B.15; (R)
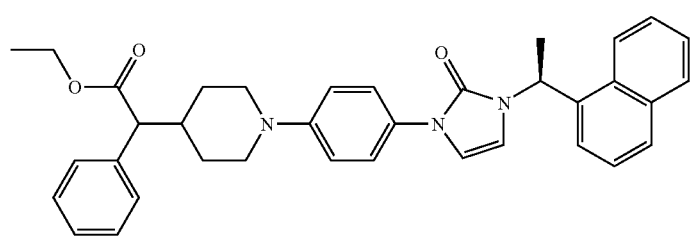
Co. No. 246; Ex. B.15; (S)
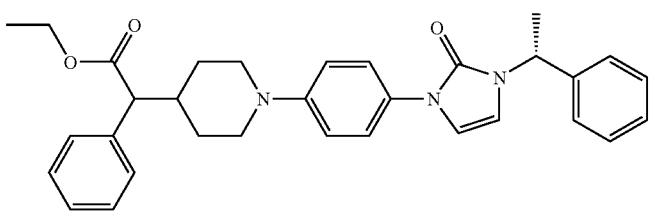
Co. No. 247; Ex. B.15; (R)

TABLE F-1a-continued
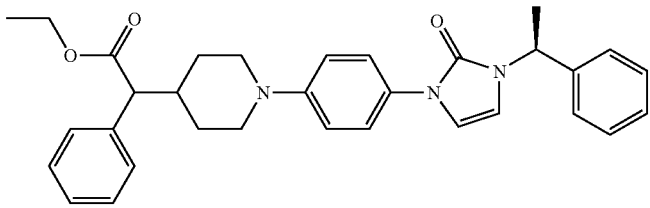
Co. No. 248; Ex. B.15; (S)
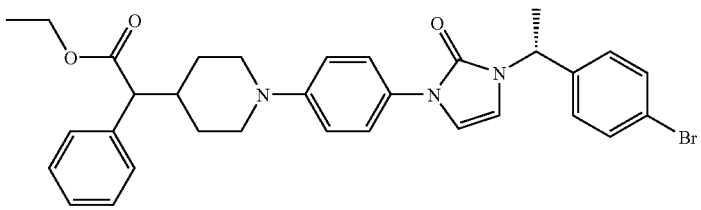
Co. No. 249; Ex. B.15; (R)
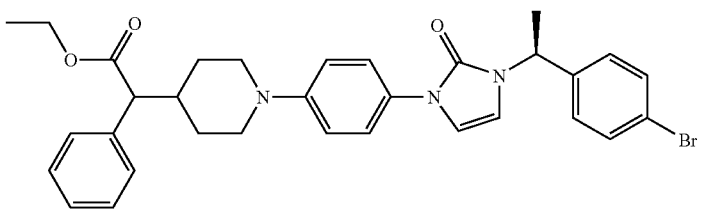
Co. No. 250; Ex. B.15; (S)
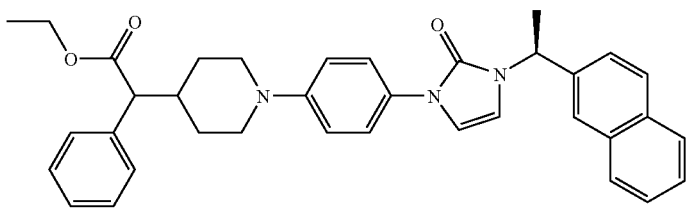
Co. No. 251; Ex. B.15; (S)
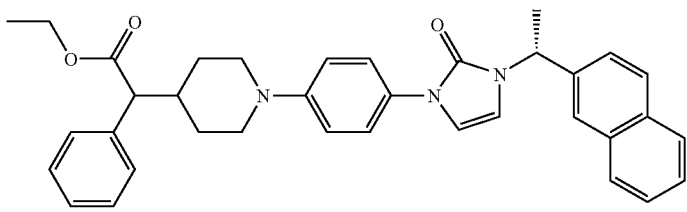
Co. No. 252; Ex. B.15; (R)
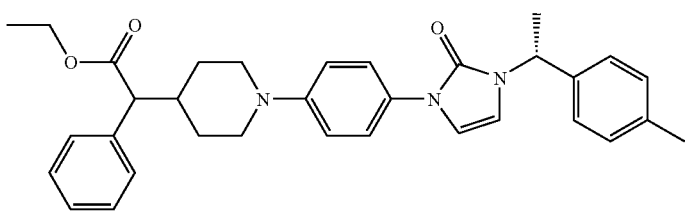
Co. No. 253; Ex. B.15; (R)

TABLE F-1a-continued
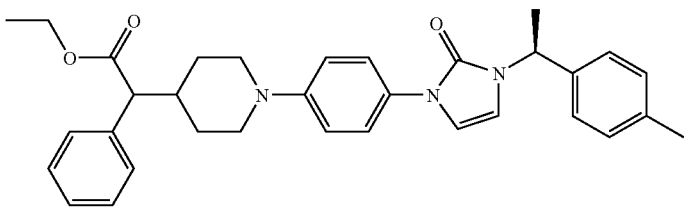
Co. No. 254; Ex. B.15; (S)
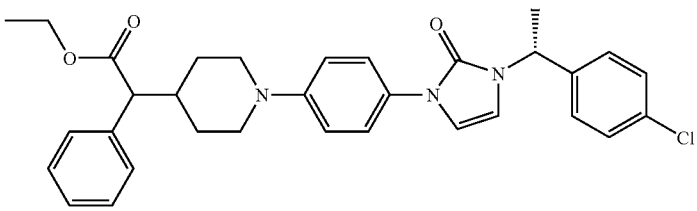
Co. No. 255; Ex. B.15; (R)
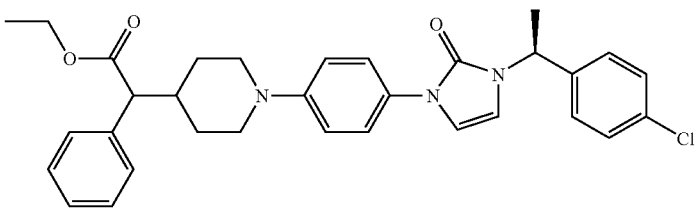
Co. No. 256; Ex. B.15; (S)
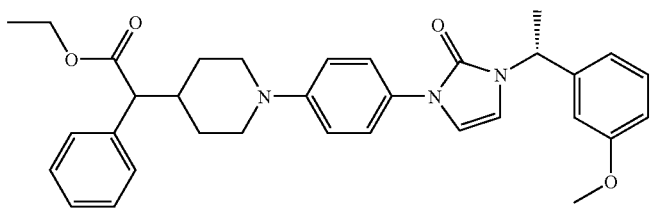
Co. No. 257; Ex. B.15; (R)
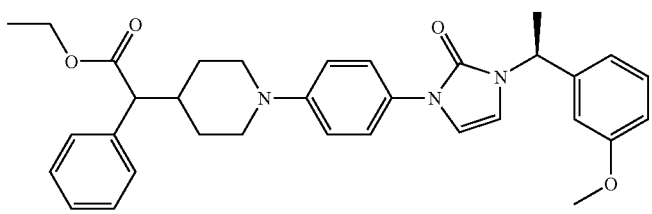
Co. No. 258; Ex. B.15; (S)
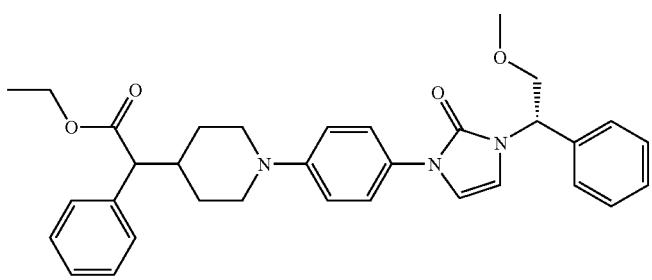
Co. No. 259; Ex. B.15; (R)

TABLE F-1a-continued
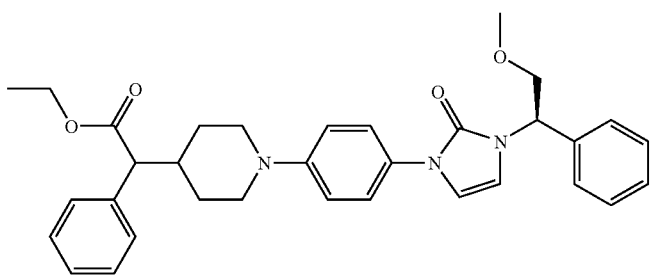
Co. No. 260; Ex. B.15
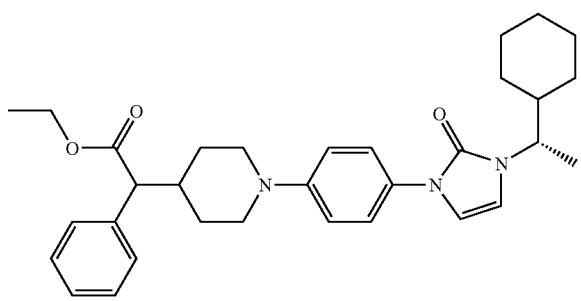
Co. No. 261; Ex. B.15; (S)
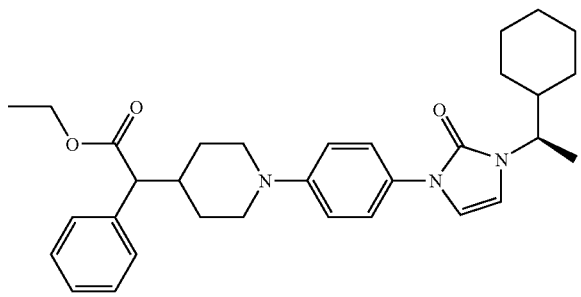
Co. No. 262; Ex. B.15; (R)
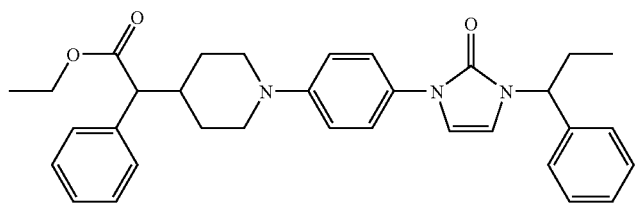
Co. No. 263; Ex. B.15
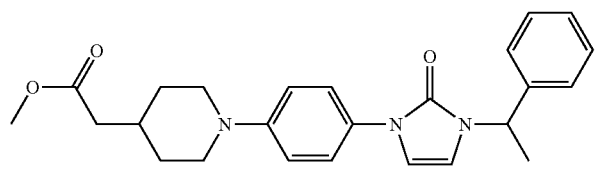
Co. No. 264; Ex. B.10

TABLE F-1a-continued
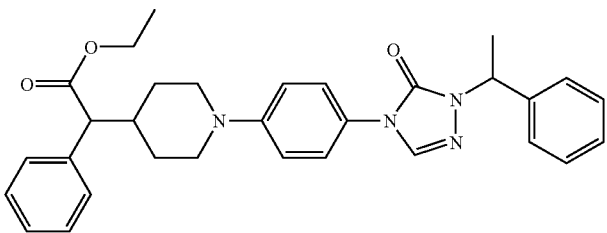
Co. No. 265; Ex. B.2; m.p. 102-104° C.
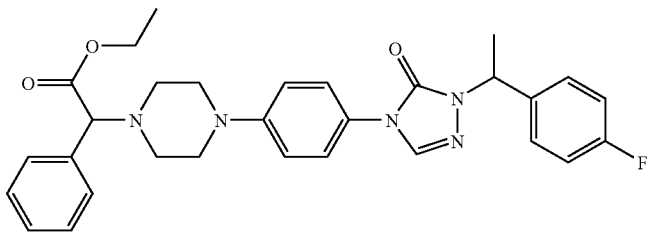
Co. No. 266; Ex. B.2; m.p. 52-55° C.
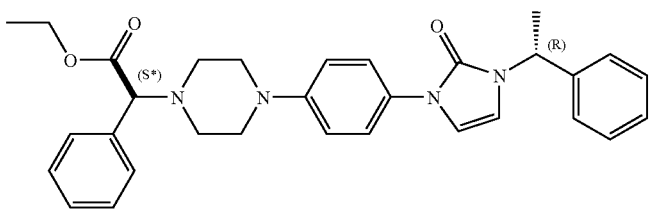
Co. No. 267; Ex. B.11; (S*, R)
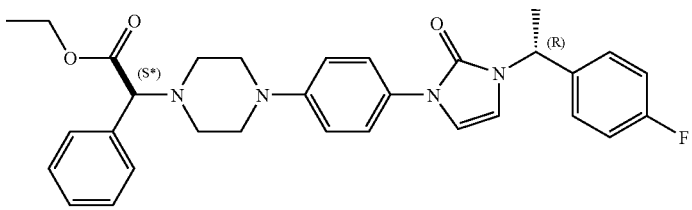
Co. No. 268; Ex. B.11; (S*, R)
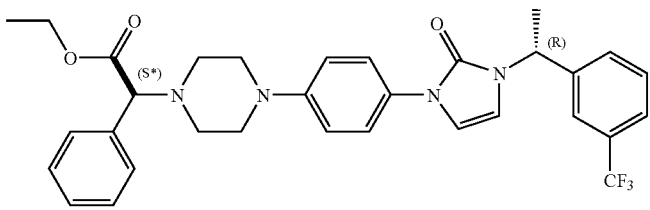
Co. No. 269; Ex. B.11; (S*, R)
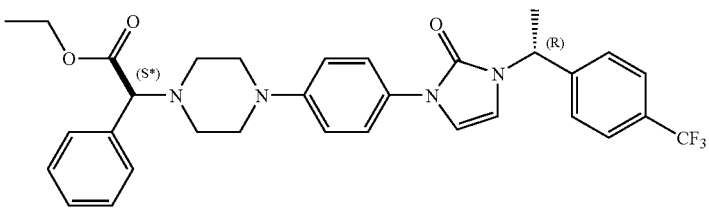
Co. No. 270; Ex. B.11; (S*, R)

TABLE F-1a-continued
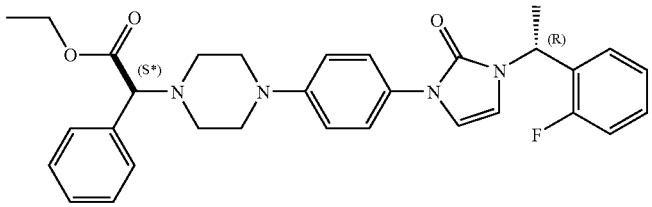
Co. No. 271; Ex. B.11; (S*, R)
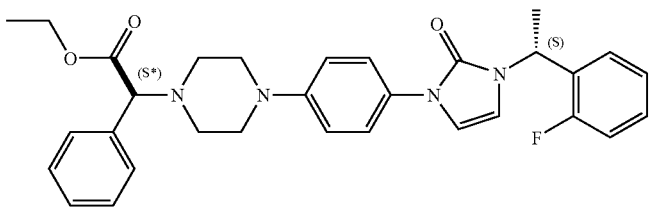
Co. No. 272; Ex. B.11; (S*, S)
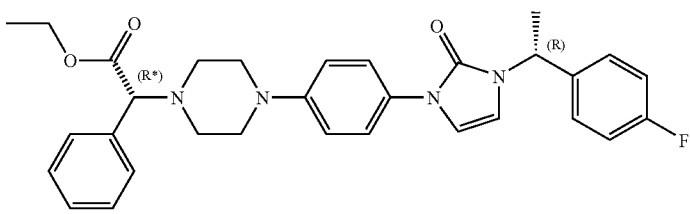
Co. No. 273; Ex. B.11; (R*, R)
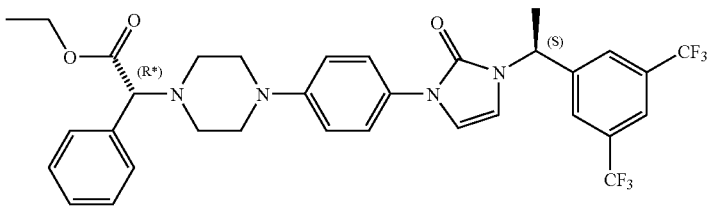
Co. No. 274; Ex. B.11; (R*, S)
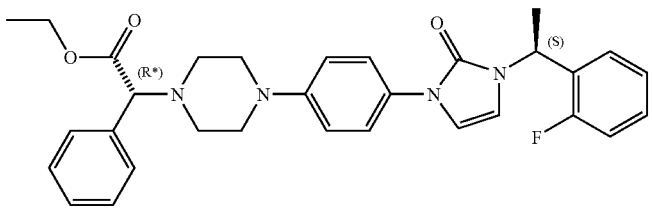
Co. No. 275; Ex. B.11; (R*, S)
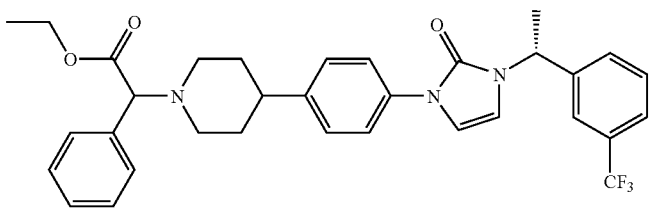
Co. No. 276; Ex. B.11; (R)

TABLE F-1a-continued
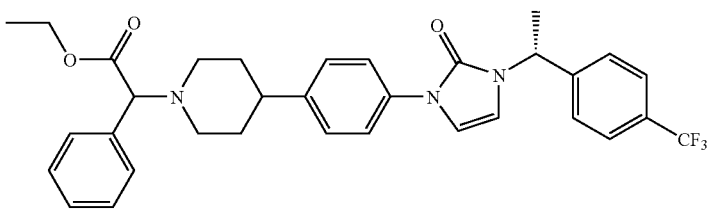
Co. No. 277; Ex. B.11; (R)
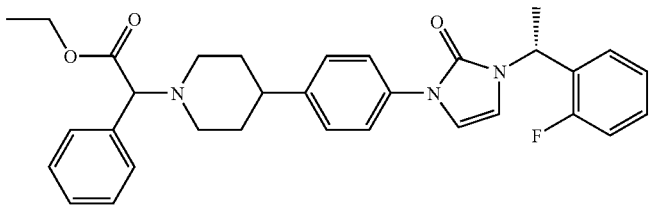
Co. No. 278; Ex. B.9; (R)
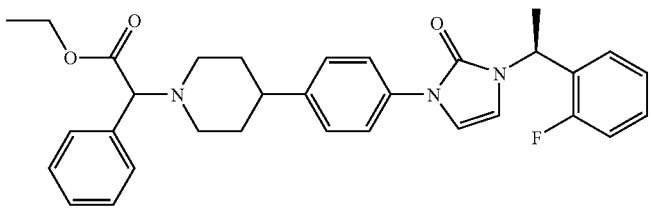
Co. No. 279; Ex. B.11; (S)
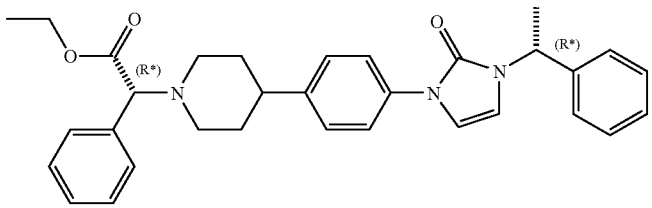
Co. No. 280; Ex. B.12; (R*, R*); (A-isomer); m.p. 117.2-120.0° C.;
$[\alpha]_D^{20}$ = +72.99° (ethanol)
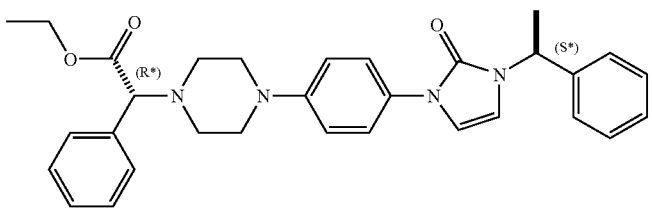
Co. No. 281; Ex. B.12; m.p. 125.4-127.8° C.;
$[\alpha]_D^{20}$ = +145.95° (ethanol); (R*, S*); (B-isomer)
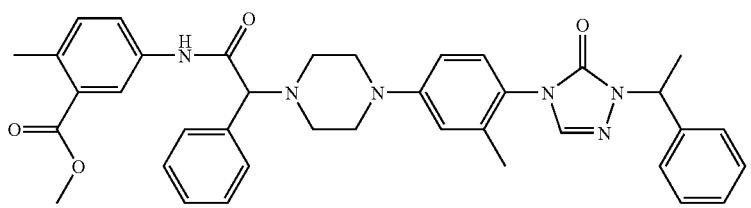
Co. No. 282; Ex. B.24

TABLE F-1a-continued
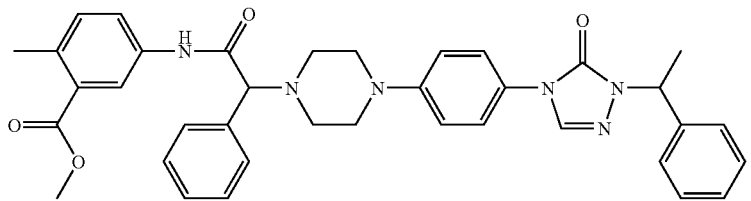
Co. No. 283; Ex. B.24
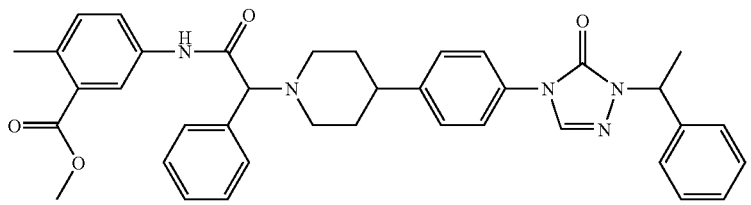
Co. No. 284; Ex. B.24
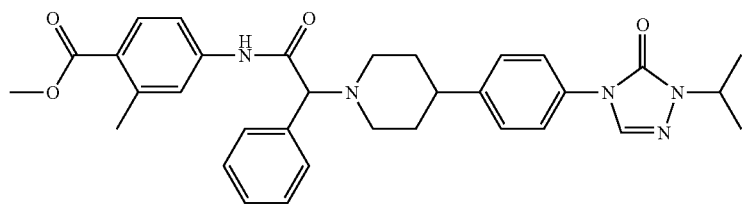
Co. No. 285; Ex. B.24
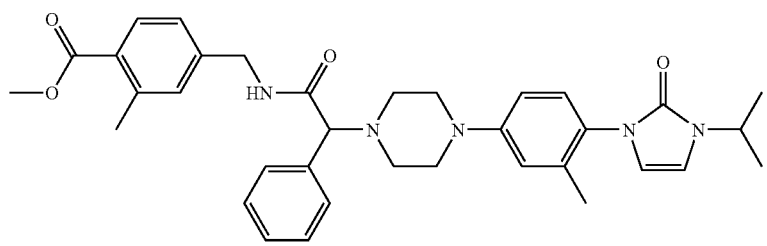
Co. No. 286; Ex. B.24
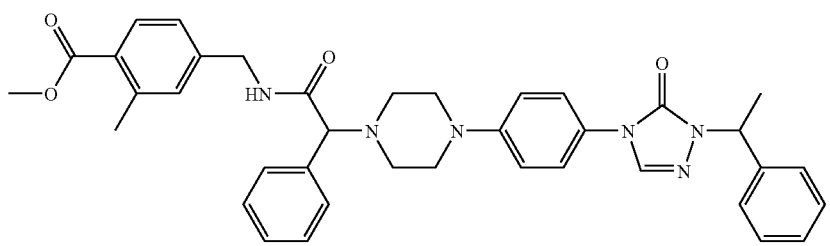
Co. No. 287; Ex. B.24
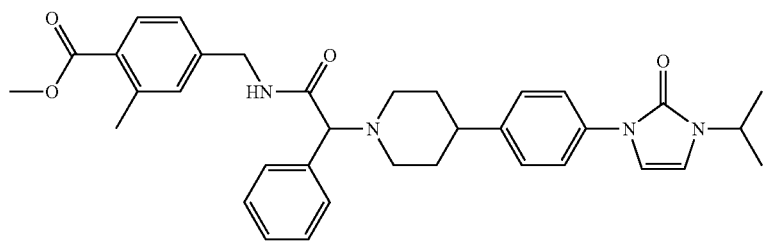
Co. No. 288; Ex. B.24

TABLE F-1a-continued
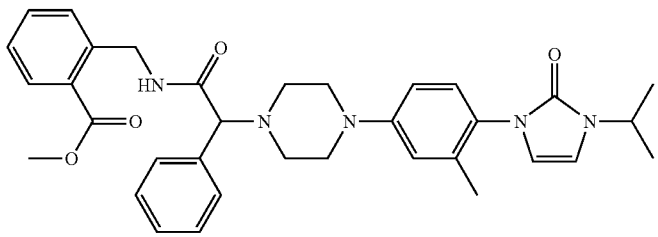
Co. No. 289; Ex. B.24
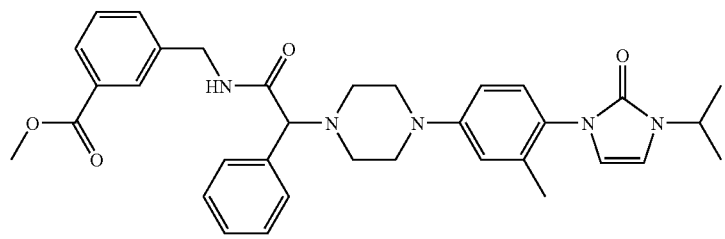
Co. No. 290; Ex. B.24
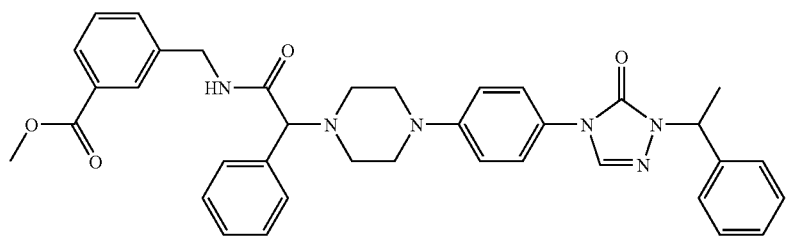
Co. No. 291; Ex. B.24
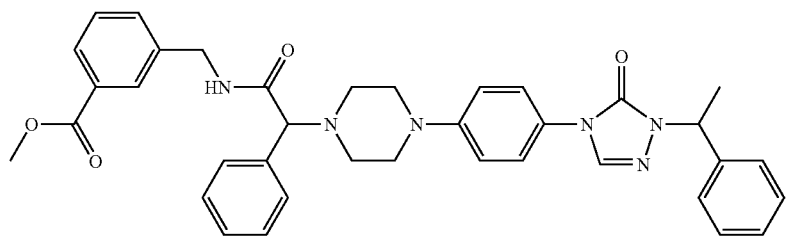
Co. No. 292; Ex. B.24
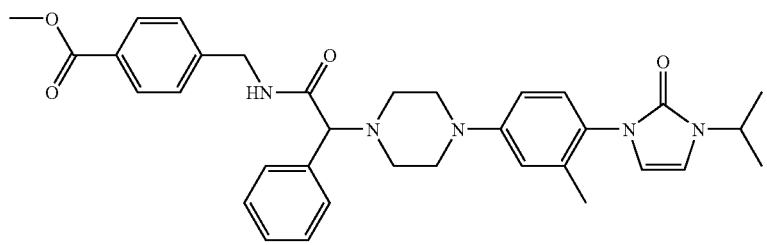
Co. No. 293; Ex. B.24

TABLE F-1a-continued
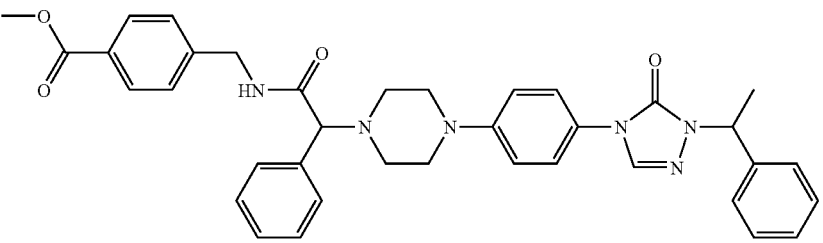
Co. No. 294; Ex. B.24
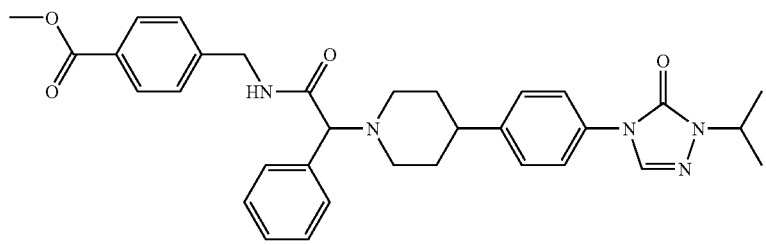
Co. No. 295; Ex. B.24
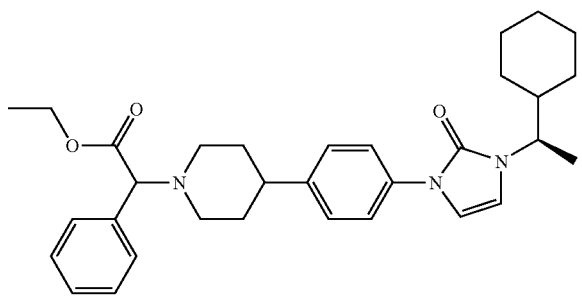
Co. No. 296; Ex. B.15; (R)
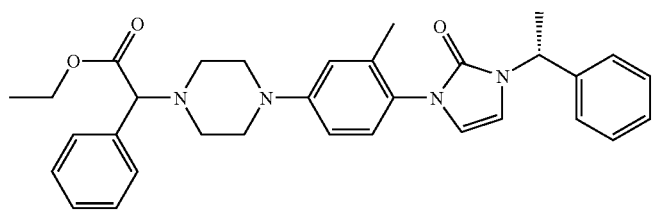
Co. No. 297; Ex. B.2; mp. 30-40° C.; (R)
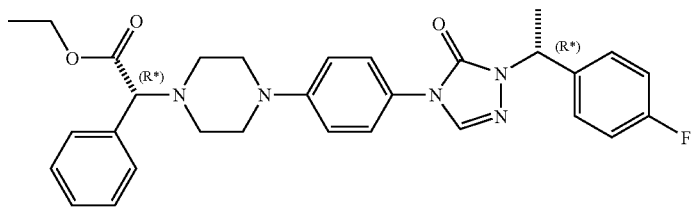
Co. No. 298; Ex. B.12; m.p. 116.2-132.4° C.;
$[\alpha]_D^{20}$ = +58.58° (DMF); (R*, R*)

TABLE F-1a-continued
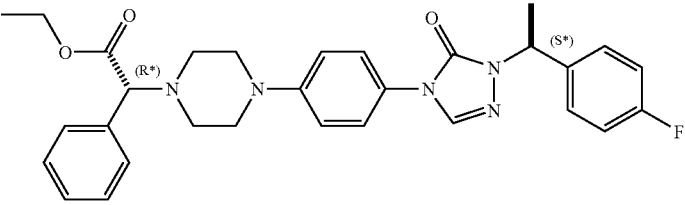
Co. No. 299; Ex. B.12; m.p. 130.5-145.0° C.;
$[\alpha]_D^{20} = +109.71°$ (DMF); (R*, S*)
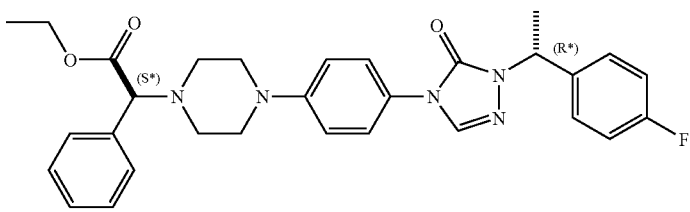
Co. No. 300; Ex. B.12; m.p. 119.4-127.8° C.;
$[\alpha]_D^{20} = -106.59°$ (DMF); (S*, R*)
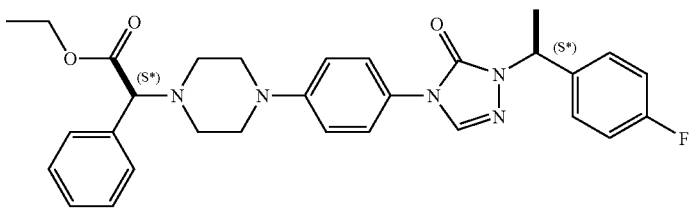
Co. No. 301; Ex. B.12; m.p. 115.4-129.9° C.;
$[\alpha]_D^{20} = -57.61°$ (DMF); (S*, S*)
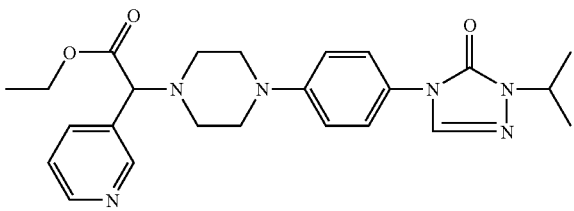
Co. No. 302; Ex. B.17
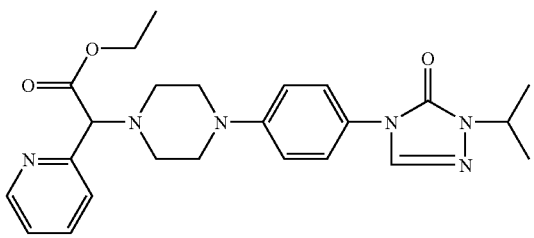
Co. No. 303; Ex. B.5; m.p. 138° C.
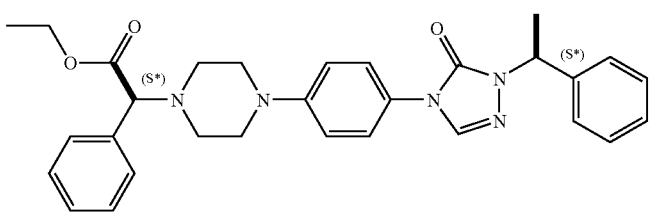
Co. No. 304; Ex. B.12; m.p. 122.5-123.8° C.;
$[\alpha]_D^{20} = -71.57°$ (ethanol); (S*, S*)

TABLE F-1a-continued
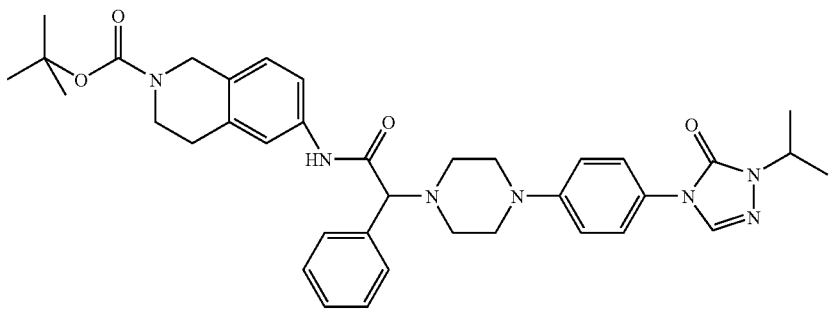
Co. No. 305; Ex. B.23
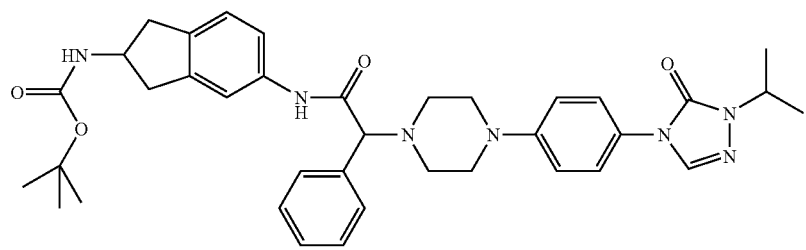
Co. No. 306; Ex. B.23
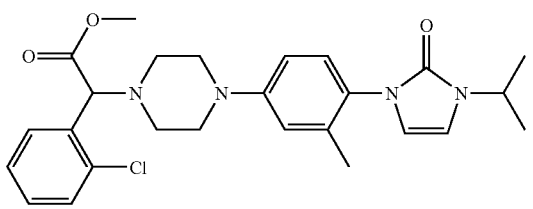
Co. No. 307; Ex. B.25
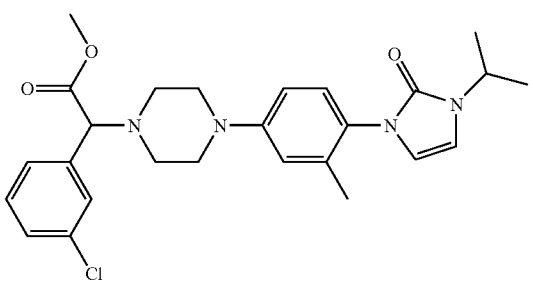
Co. No. 308; Ex. B.25
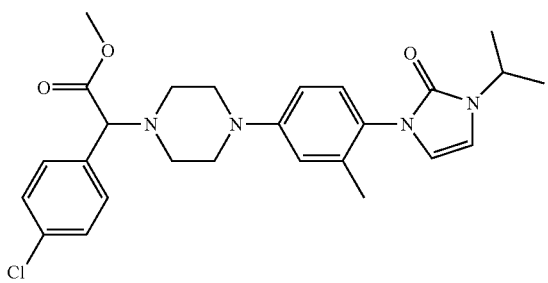
Co. No. 309; Ex. B.25

TABLE F-1a-continued
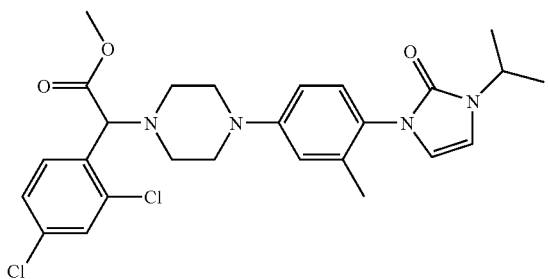
Co. No. 310; Ex. B.25
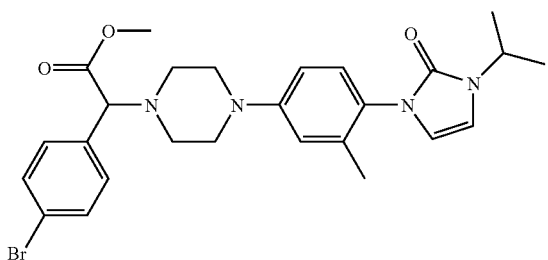
Co. No. 311; Ex. B.25
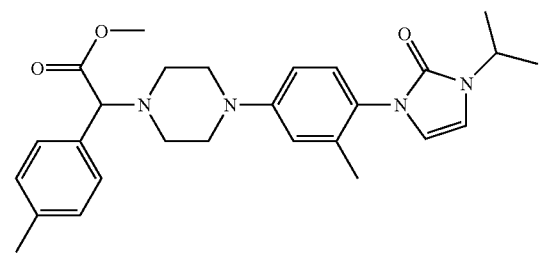
Co. No. 312; Ex. B.25
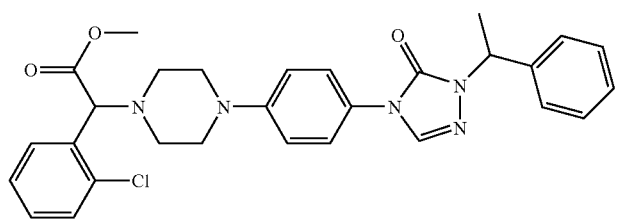
Co. No. 313; Ex. B.25
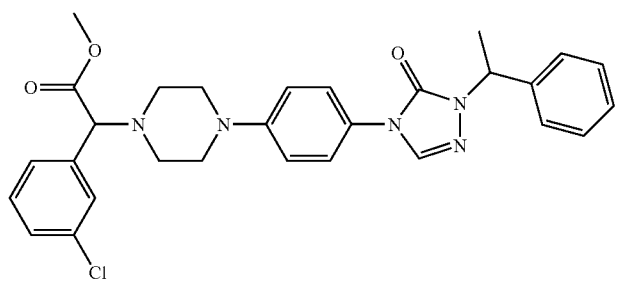
Co. No. 314; Ex. B.25

TABLE F-1a-continued
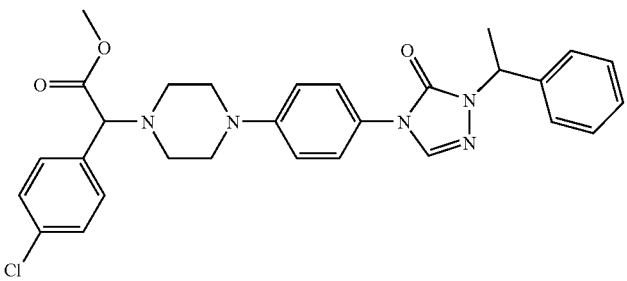
Co. No. 315; Ex. B.25
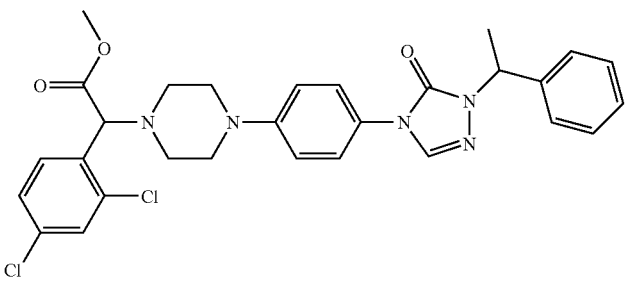
Co. No. 316; Ex. B.25
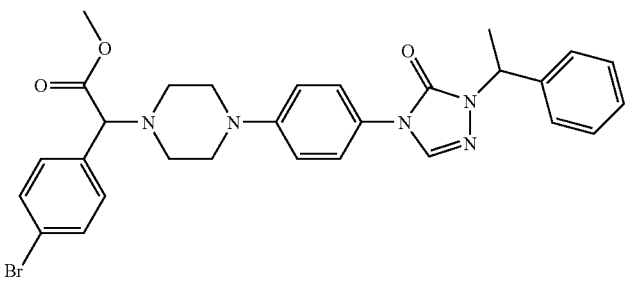
Co. No. 317; Ex. B.25
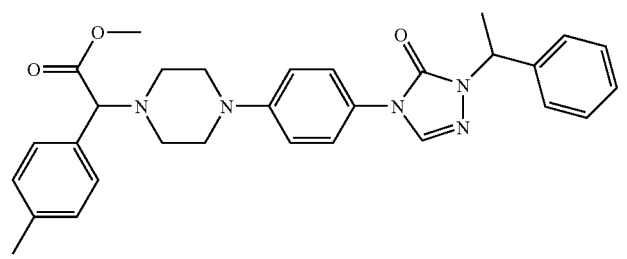
Co. No. 318; Ex. B.25
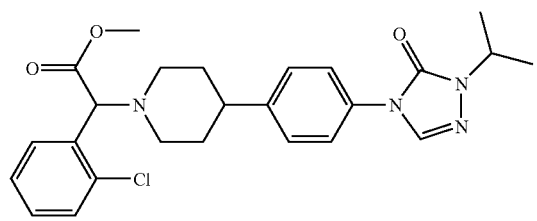
Co. No. 319; Ex. B.25

TABLE F-1a-continued
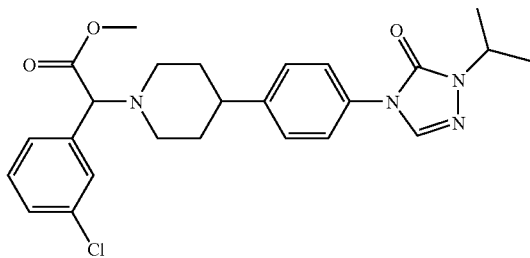
Co. No. 320; Ex. B.25
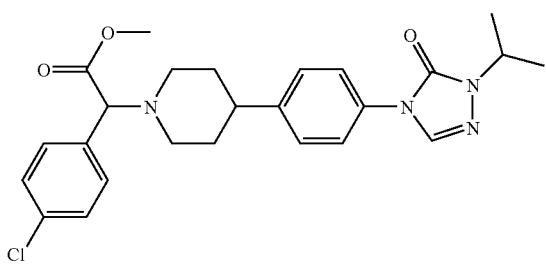
Co. No. 321; Ex. B.25
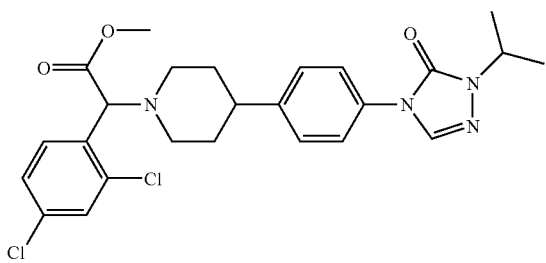
Co. No. 322; Ex. B.25
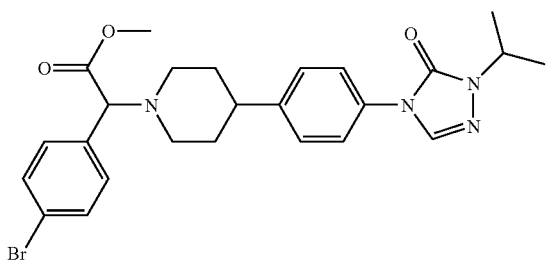
Co. No. 323; Ex. B.25
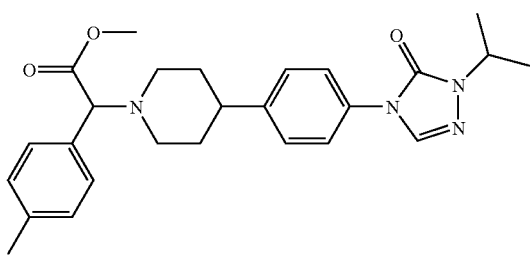
Co. No. 324; Ex. B.25

TABLE F-1a-continued
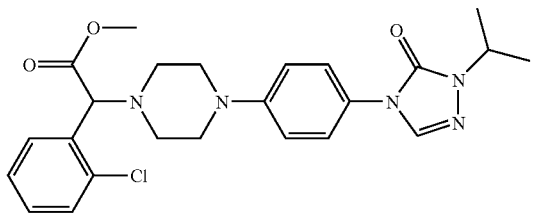
Co. No. 325; Ex. B.25
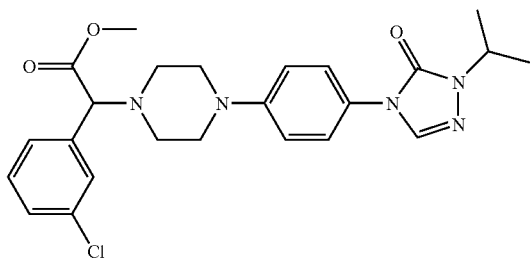
Co. No. 326; Ex. B.25
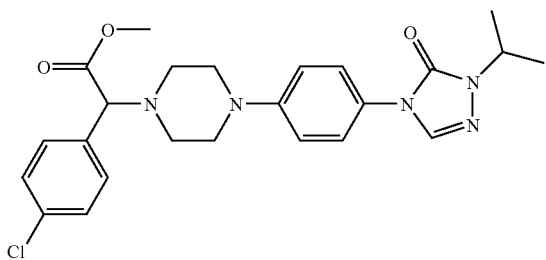
Co. No. 327; Ex. B.25
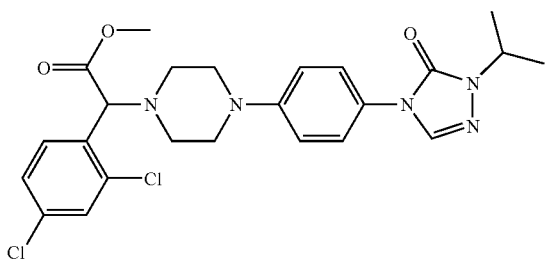
Co. No. 328; Ex. B.25
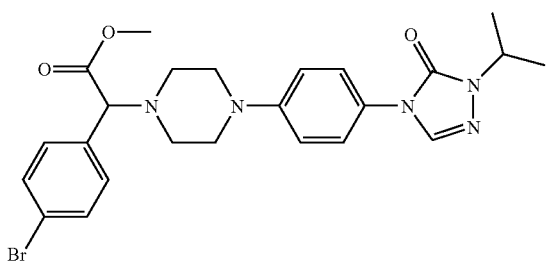
Co. No. 329; Ex. B.25

TABLE F-1a-continued
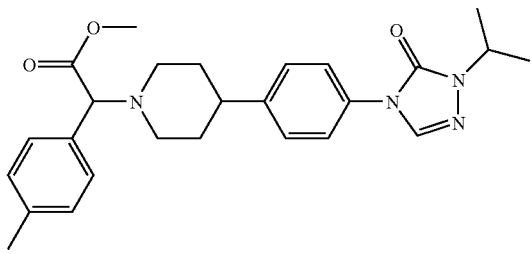
Co. No. 330; Ex. B.25
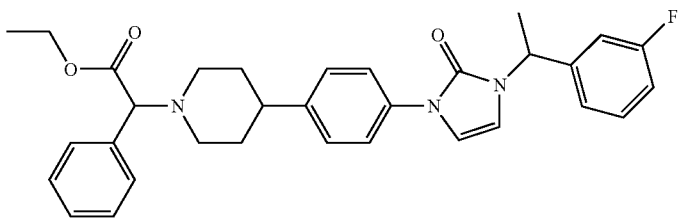
Co. No. 331; Ex. B.9
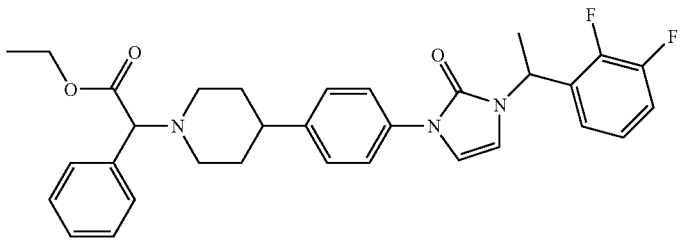
Co. No. 332; Ex. B.9
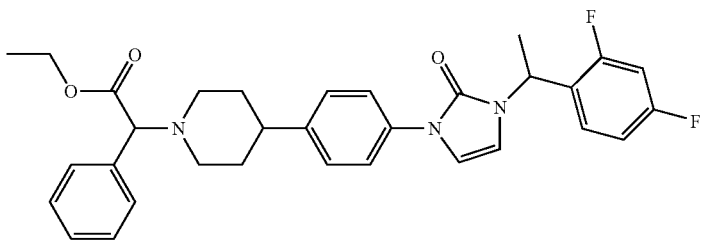
Co. No. 333; Ex. B.9
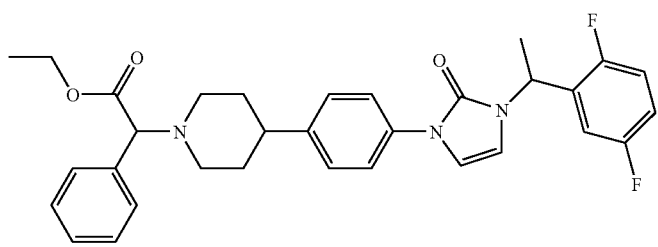
Co. No. 334; Ex. B.9

TABLE F-1a-continued
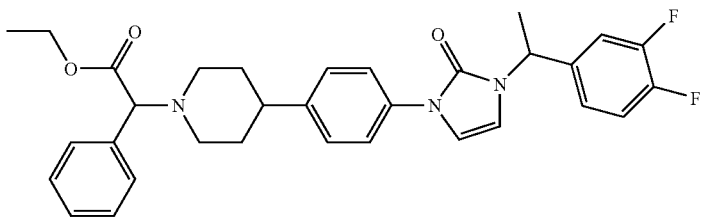
Co. No. 335; Ex. B.9
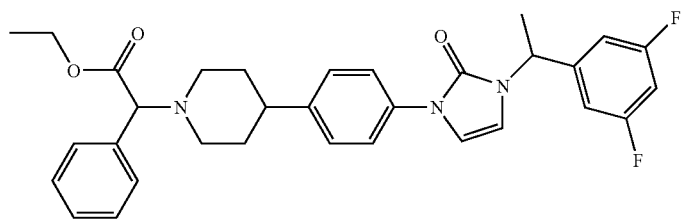
Co. No. 336; Ex. B.9
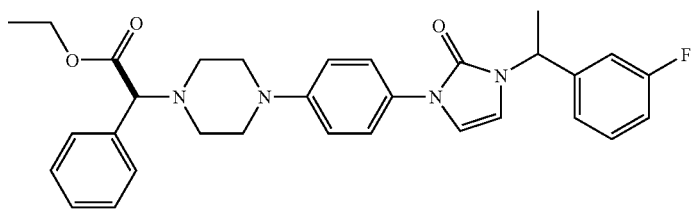
Co. No. 337; Ex. B.9; (S*)
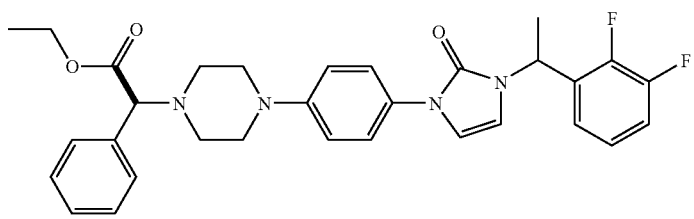
Co. No. 338; Ex. B.9; (S*)
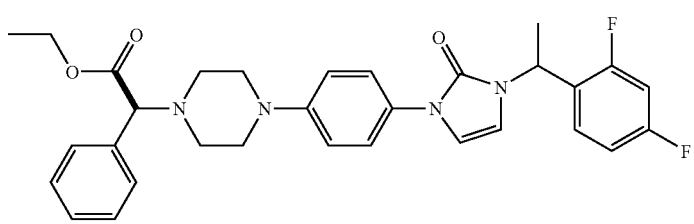
Co. No. 339; Ex. B.9; (S*)
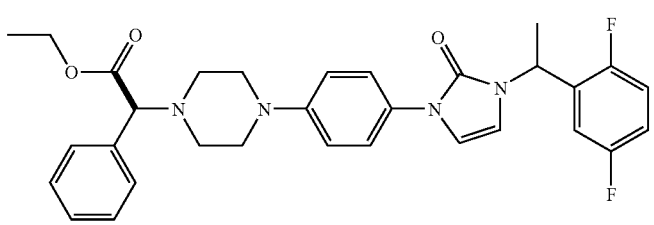
Co. No. 340; Ex. B.9; (S*)

TABLE F-1a-continued
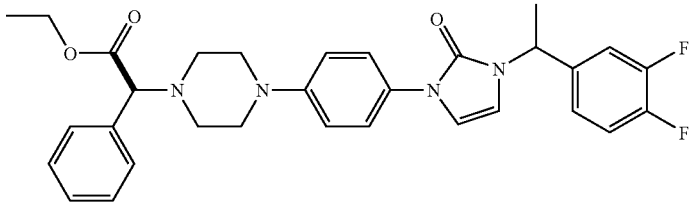
Co. No. 341; Ex. B.9; (S*)
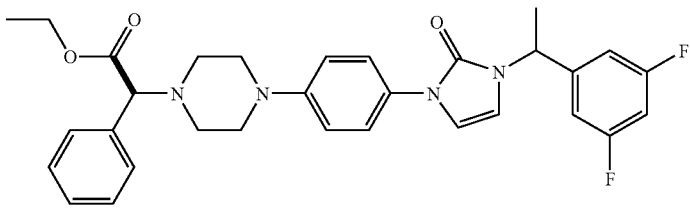
Co. No. 342; Ex. B.9; (S*)
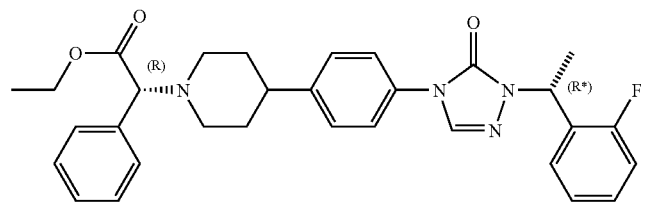
Co. No. 343; Ex. B.2; m.p. 119.1-120.9° C.;
$[\alpha]_D^{20}$ = +44.47° (c = 0.389 w/v % in ethanol); (R, R*)
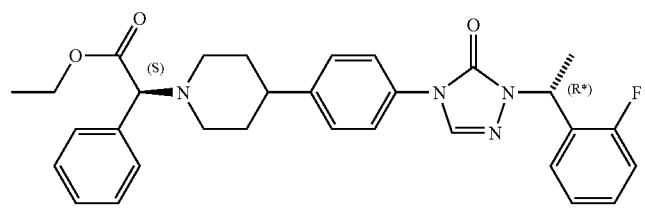
Co. No. 344; Ex. B.2; m.p. 89.3-93.5° C.;
$[\alpha]_D^{20}$ = +86.02° (c = 0.4534 w/v % in ethanol) (S, R*)
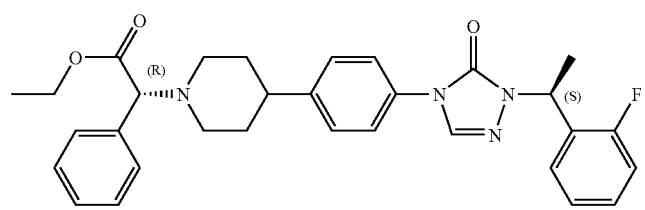
Co. No. 345; Ex. B.2; m.p. 83.7-88.5° C.;
$[\alpha]_D^{20}$ = -85.06° (ethanol); (R,S)
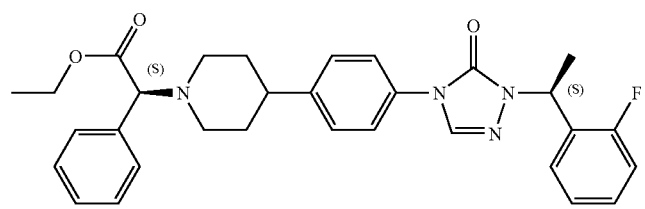
Co. No. 364; Ex. B.2; m.p. 117.2-122.5° C.;
$[\alpha]_D^{20}$ = -44.93° (ethanol); (S, S)

TABLE F-1a-continued
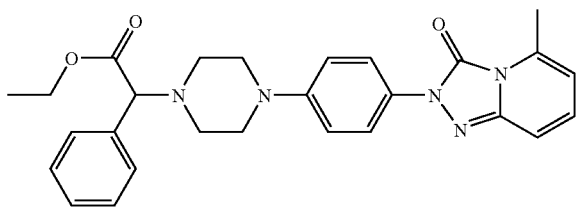
Co. No. 347; Ex. B.1
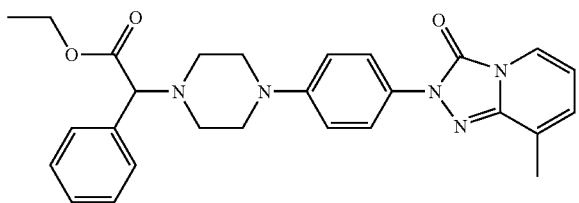
Co. No. 348; Ex. B.1
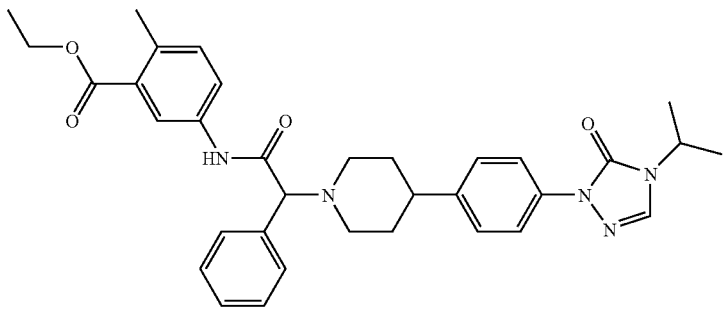
Co. No. 349; Ex. B.2
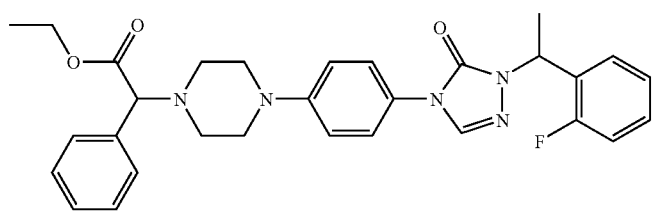
Co. No. 350; Ex. B.2
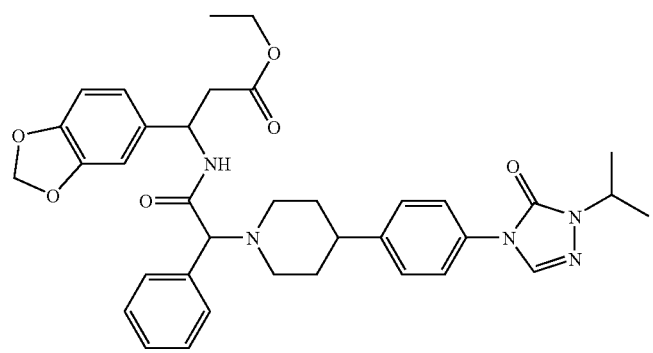
Co. No. 351; Ex. B.3

TABLE F-1a-continued
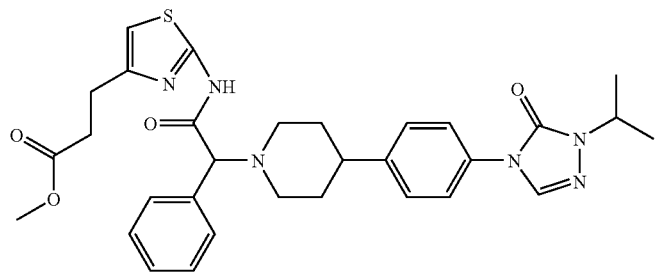
Co. No. 352; Ex. B.3
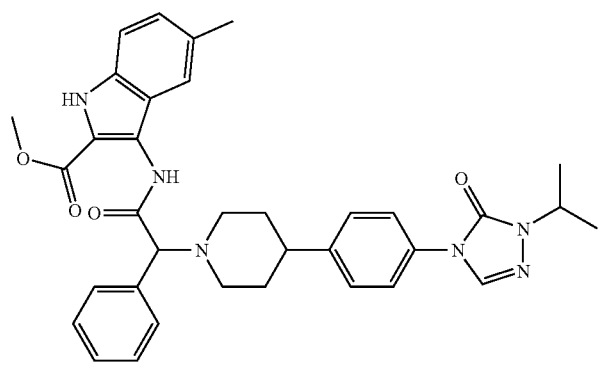
Co. No. 353; Ex. B.3
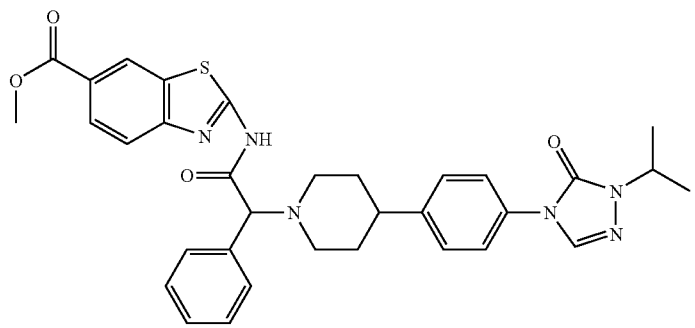
Co. No. 354; Ex. B.3
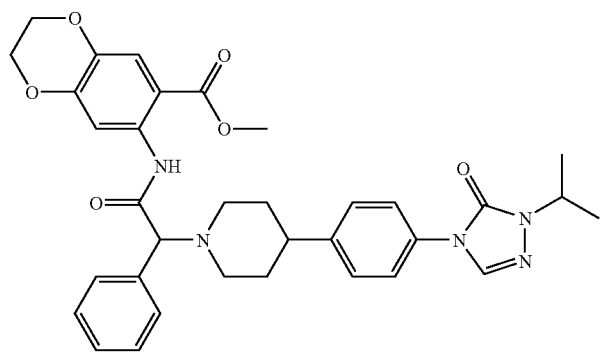
Co. No. 355; Ex. B.3

TABLE F-1a-continued
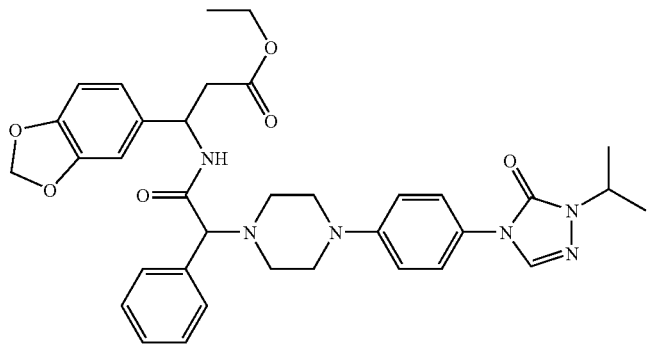
Co. No. 356; Ex. B.3
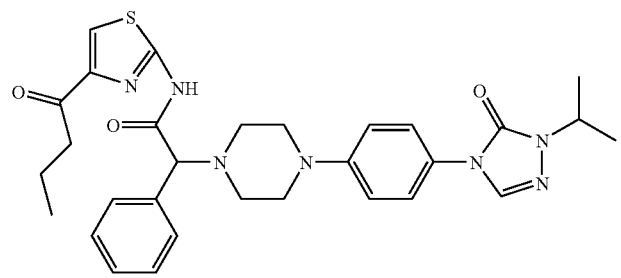
Co. No. 357; Ex. B.3
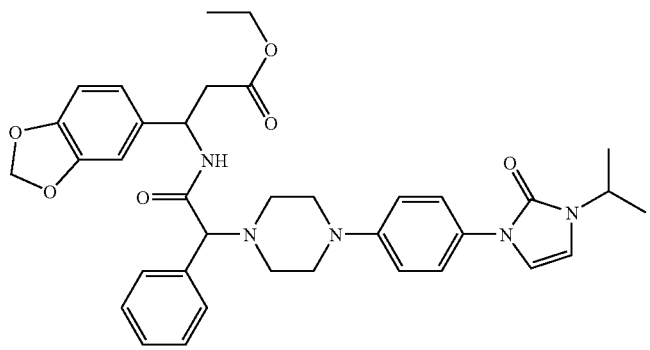
Co. No. 358; Ex. B.3
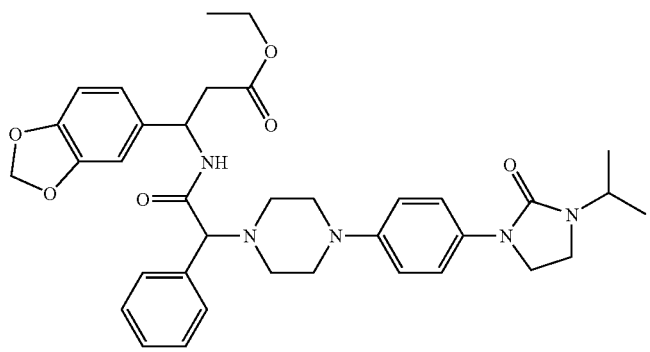
Co. No. 359; Ex. B.3

TABLE F-1a-continued
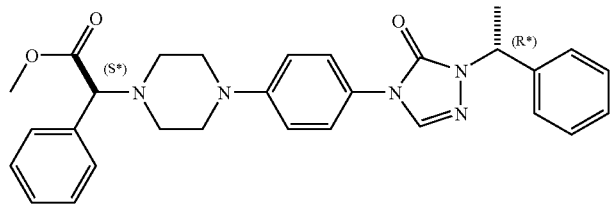
Co. No. 360; Ex. B.12; m.p. 130.9-131.4° C.;
$[\alpha]_D^{20}$ = -147.46° (ethanol); (S*, R*), (C-isomer)
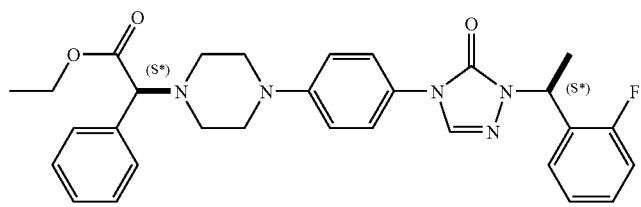
Co. No. 361; Ex. B.2; m.p. 110° C.;
$[\alpha]_D^{20}$ = +34.46° (c = 0.4266 w/v % in ethanol); (S*, S*)
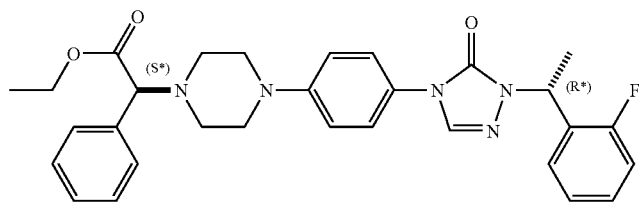
Co. No. 362; Ex. B.2; •HCl (1:1); m.p. 150° C.;
$[\alpha]_D^{20}$ = +95.57° (c = 0.4112 w/v % in DMF); (S*, R*)
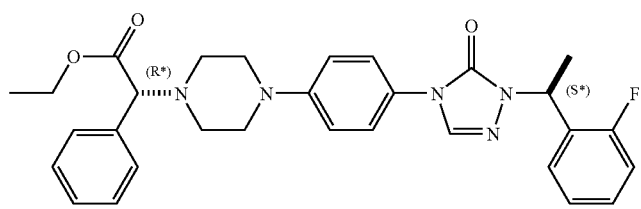
Co. No. 363; Ex. B.2; •HCl (1:1); m.p. 145° C.;
$[\alpha]_D^{20}$ = -97.27° (c = 0.403 w/v % in DMF); (R*, S*)
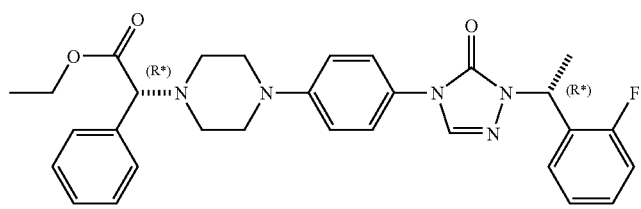
Co. No. 364; Ex. B.2; m.p. 108° C.;
$[\alpha]_D^{20}$ = -25° (c = 0.392 w/v % in ethanol); (R*, R*)

TABLE F-1a-continued
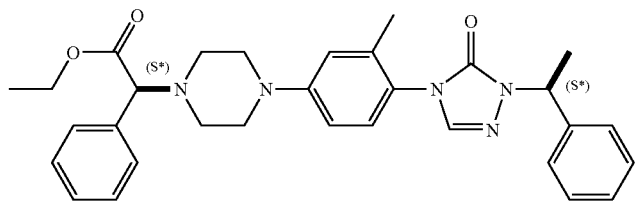
Co. No. 365; Ex. B.2;
$[\alpha]_D^{20}$ = +134.64° (c = 0.4122 w/v % in ethanol); (S*, S*)
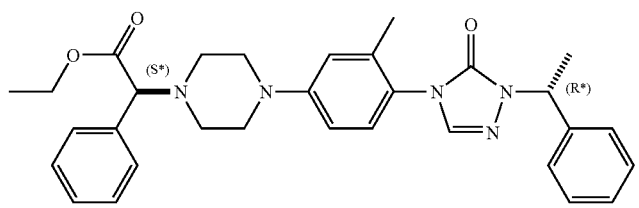
Co. No. 366; Ex. B.2;
$[\alpha]_D^{20}$ = +58.36° (c = 0.4352 w/v % in ethanol); (S*, R*)
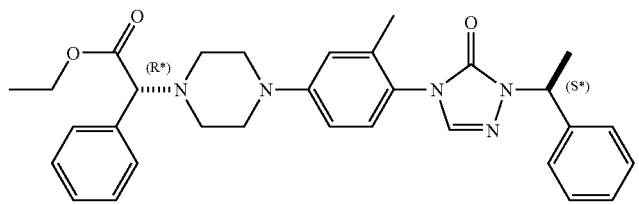
Co. No. 367; Ex. B.2;
$[\alpha]_D^{20}$ = -22.96° (c = 0.4094 w/v % in ethanol); (R*, S*)
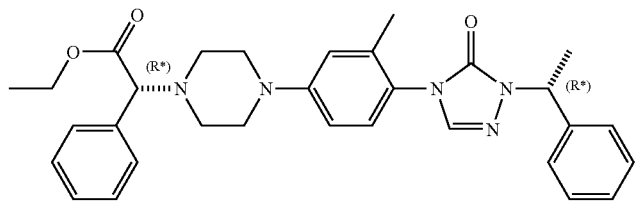
Co. No. 368; Ex. B.2;
$[\alpha]_D^{20}$ = -134.01° (c = 0.4328 w/v % in ethanol); (R*, R*)
TABLE F-1b
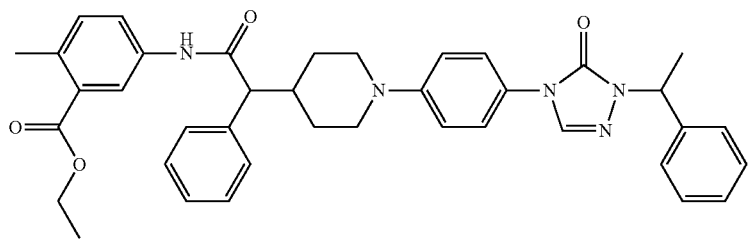
Co. No. 369; Ex. B.26

TABLE F-1b-continued
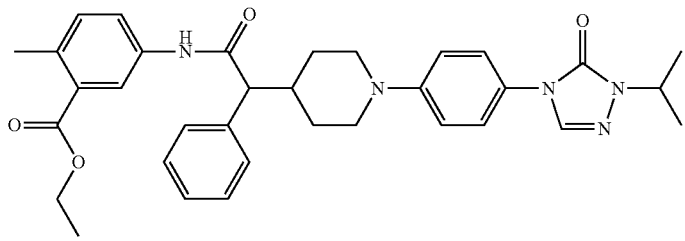
Co. No. 370; Ex. B.26
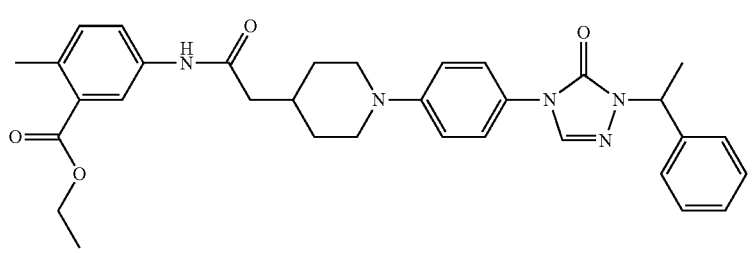
Co. No. 371; Ex. B.26
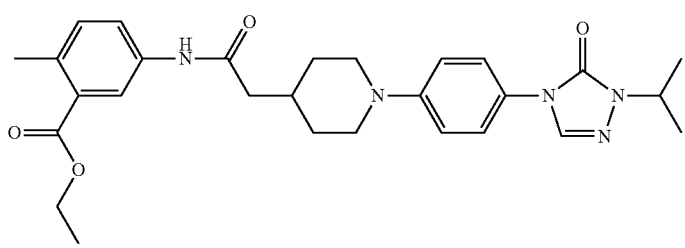
Co. No. 372; Ex. B.26
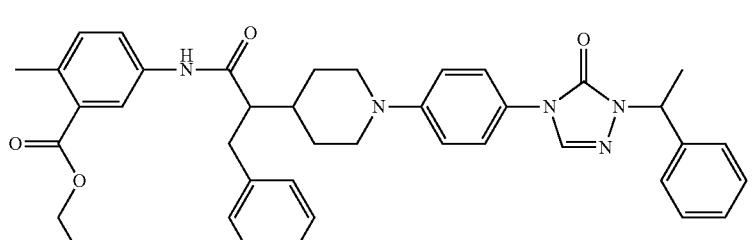
Co. No. 373; Ex. B.26
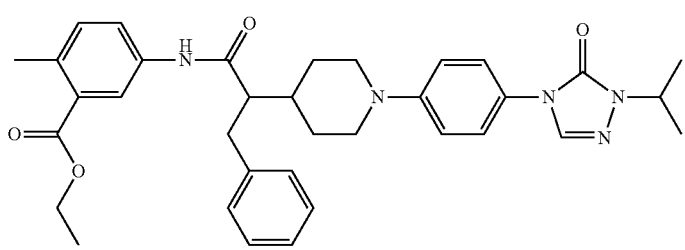
Co. No. 374; Ex. B.26
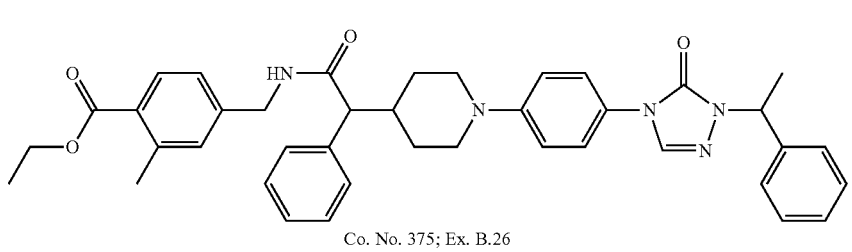
Co. No. 375; Ex. B.26

TABLE F-1b-continued
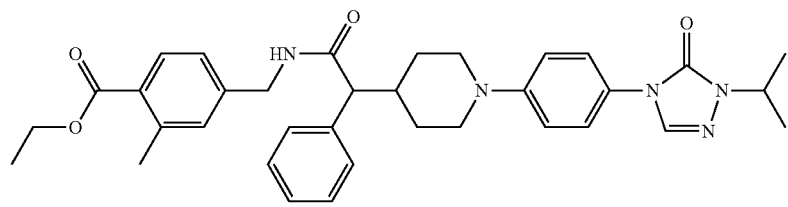
Co. No. 376; Ex. B.26
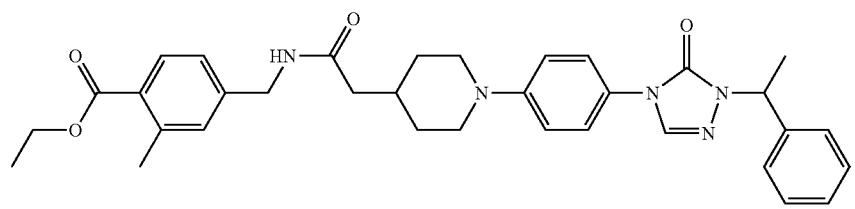
Co. No. 377; Ex. B.26
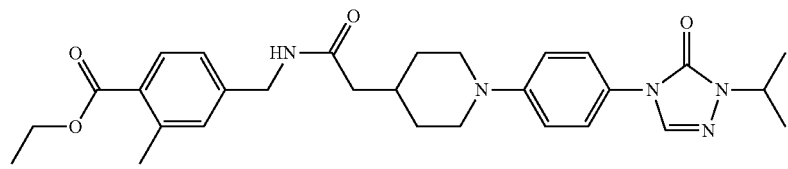
Co. No. 378; Ex. B.26
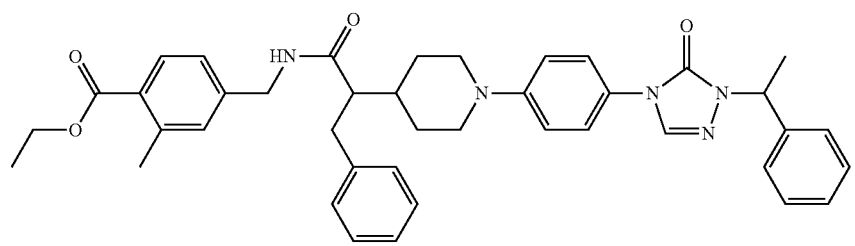
Co. No. 379; Ex. B.26
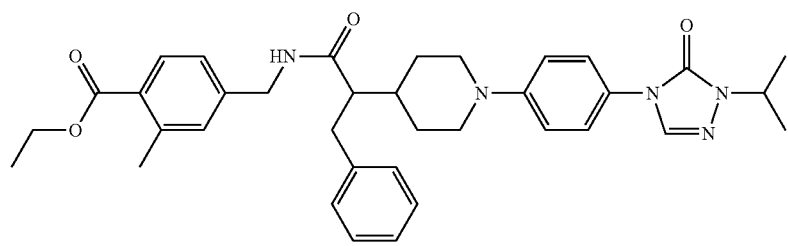
Co. No. 380; Ex. B.26
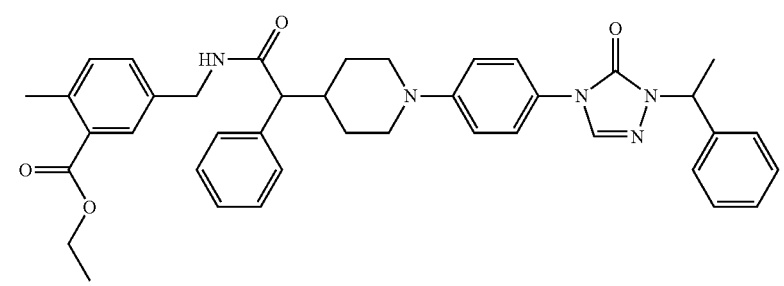
Co. No. 381; Ex. B.26

TABLE F-1b-continued
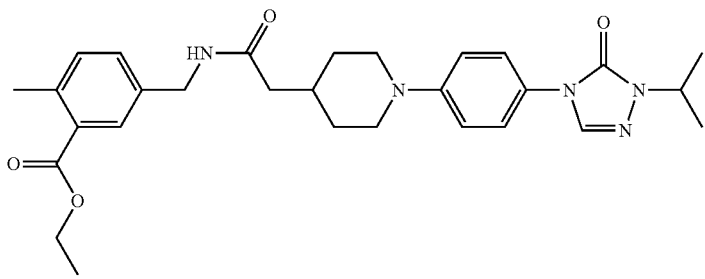
Co. No. 382; Ex. B.26
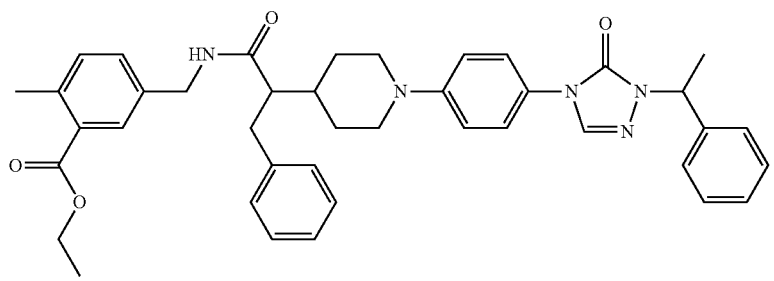
Co. No. 383; Ex. B.26
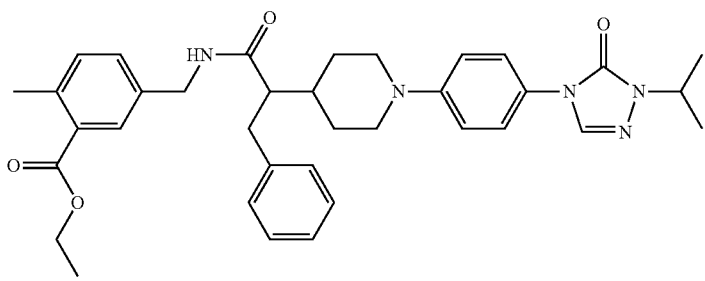
Co. No. 384; Ex. B.26
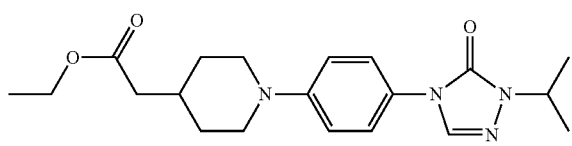
Co. No. 385; Ex. B.7
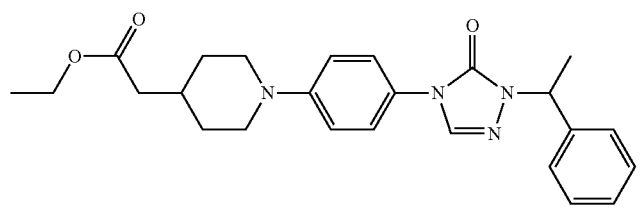
Co. No. 386; Ex. B.7
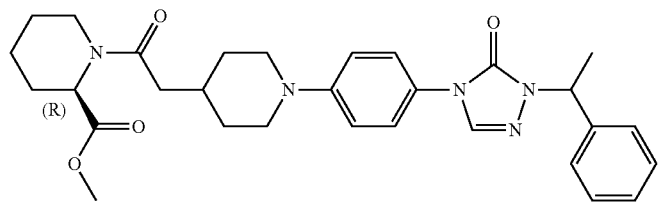
Co. No. 387; Ex. B.27; (R)

TABLE F-1b-continued
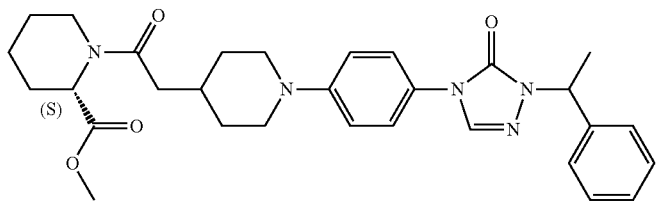
Co. No. 388; Ex. B.27; (S)
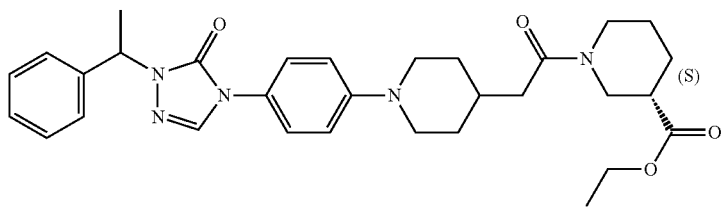
Co. No. 389; Ex. B.27; (S)
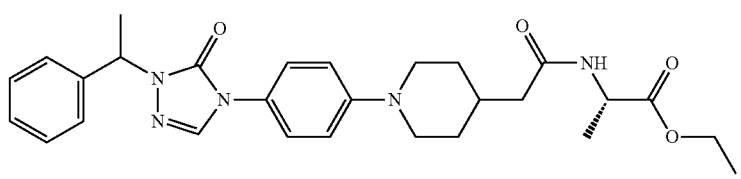
Co. No. 390; Ex. B.27; (S)
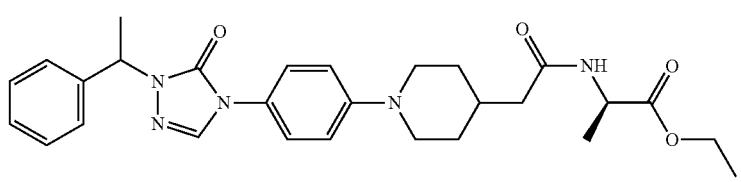
Co. No. 391; Ex. B.27; (R)
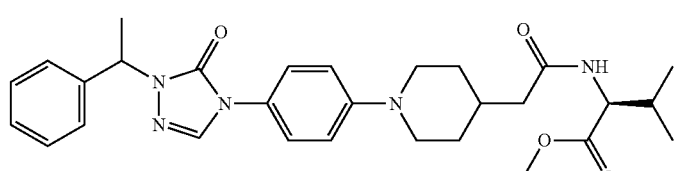
Co. No. 392; Ex. B.27; (S)
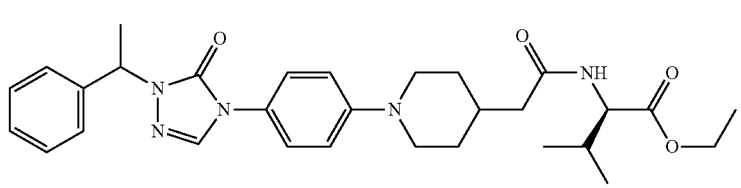
Co. No. 393; Ex. B.27; (R)
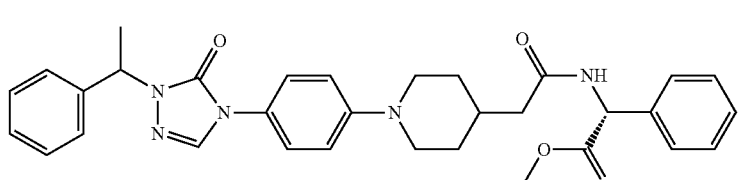
Co. No. 394; Ex. B.27; (R)

TABLE F-1b-continued
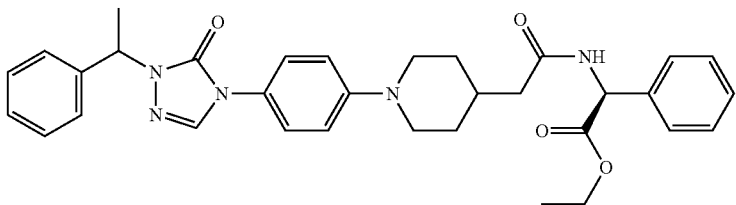
Co. No. 395; Ex. B.27; (S)
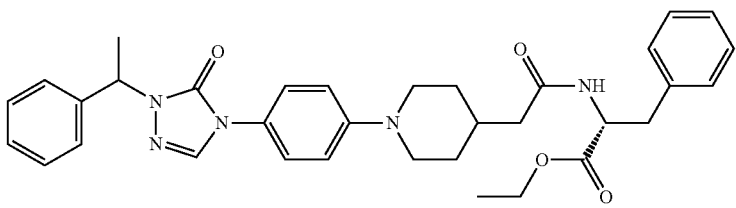
Co. No. 396; Ex. B.27; (R)
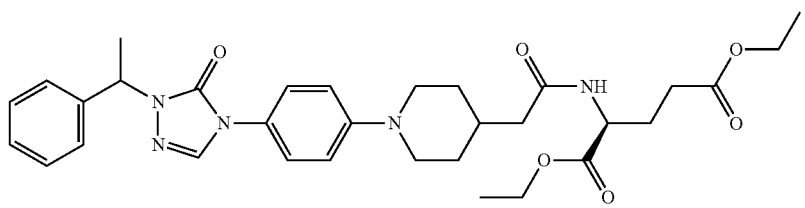
Co. No. 397; Ex. B.27; (S)
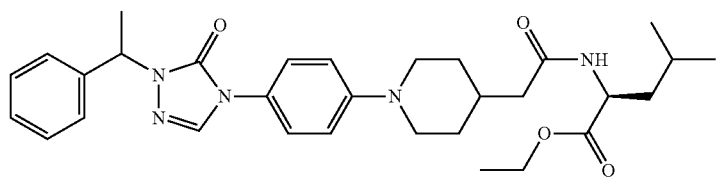
Co. No. 398; Ex. B.27; (S)
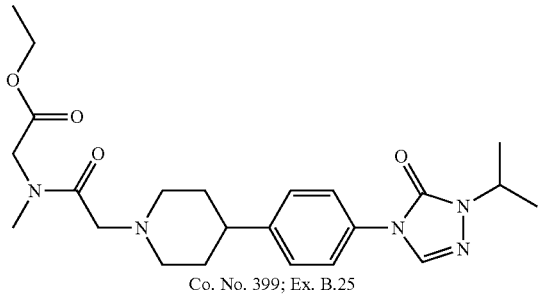
Co. No. 399; Ex. B.25
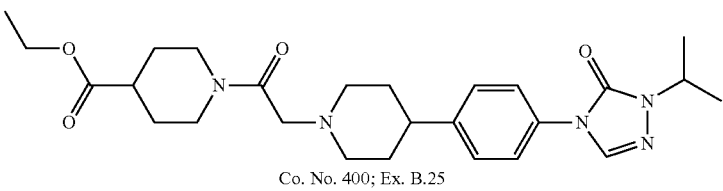
Co. No. 400; Ex. B.25
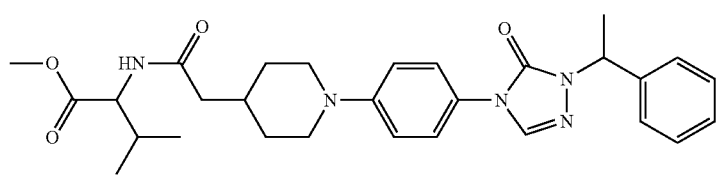
Co. No. 401; Ex. B.27

TABLE F-1b-continued
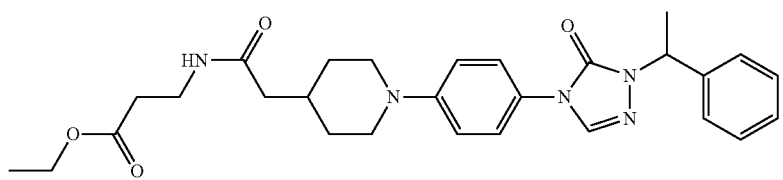
Co. No. 402; Ex. B.27
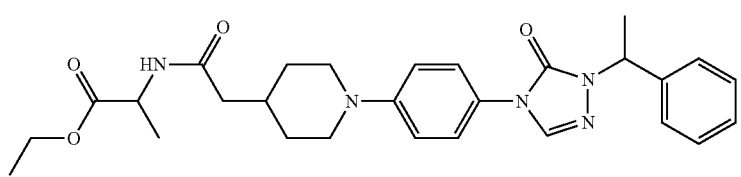
Co. No. 403; Ex. B.27
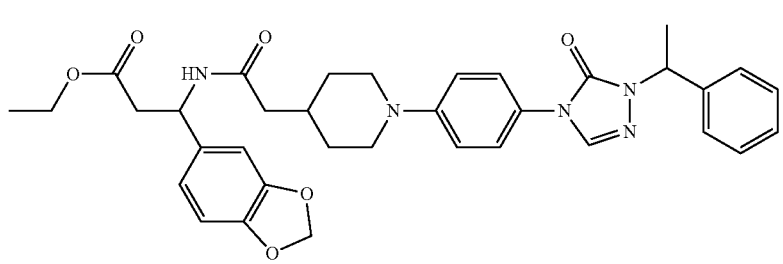
Co. No. 404; Ex. B.27
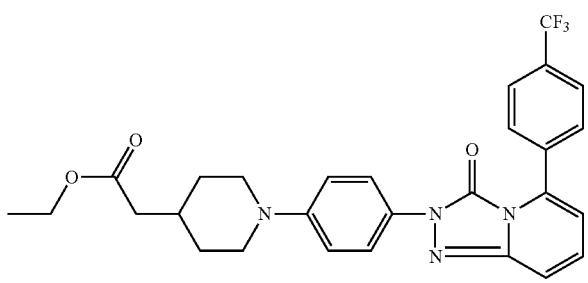
Co. No. 405; Ex. B.1
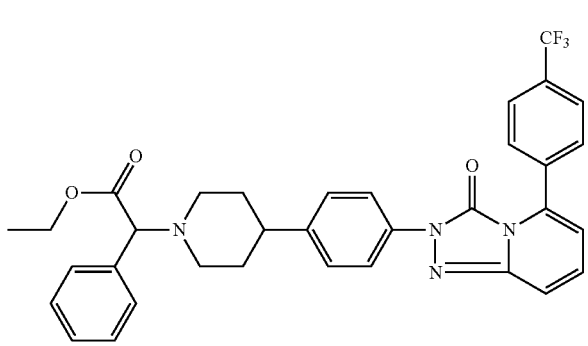
Co. No. 406; Ex. B.1
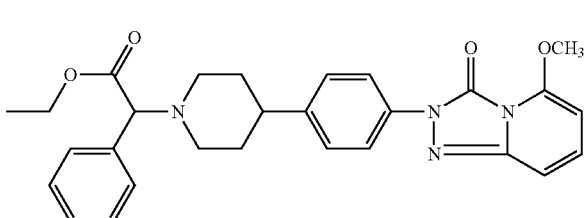
Co. No. 407; Ex. B.1

TABLE F-1b-continued
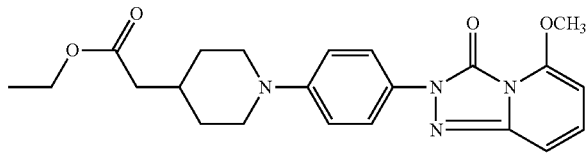
Co. No. 408; Ex. B.1
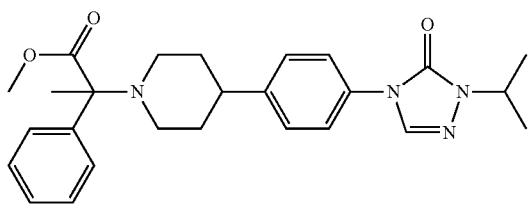
Co. No. 409; Ex. B.1
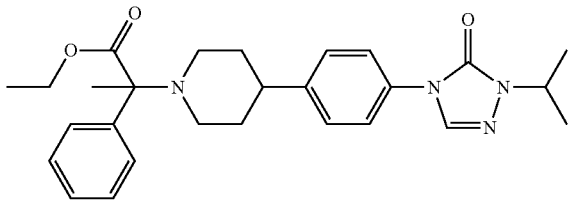
Co. No. 410; Ex. B.1
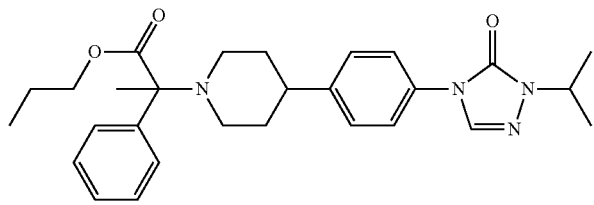
Co. No. 411; Ex. B.1
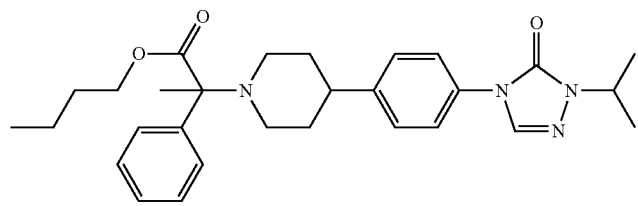
Co. No. 412; Ex. B.1
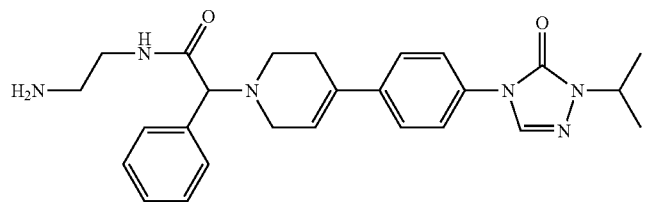
Co. No. 413; Ex. B.29
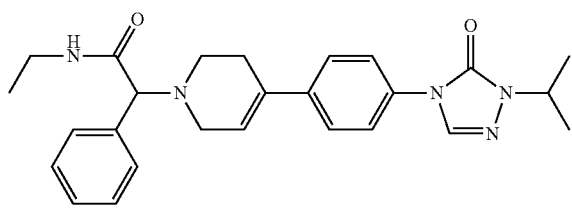
Co. No. 414; Ex. B.29

TABLE F-1b-continued
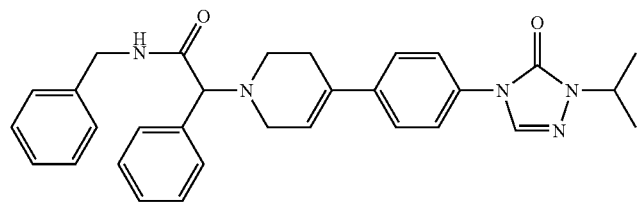
Co. No. 415; Ex. B.29
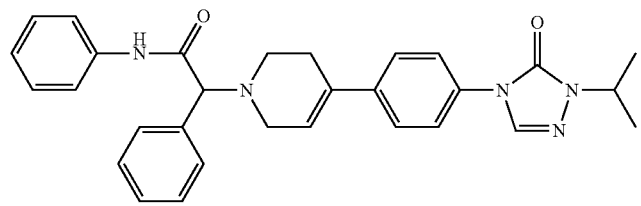
Co. No. 416; Ex. B.29
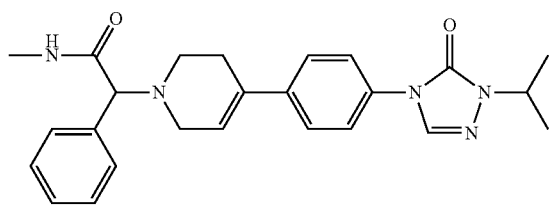
Co. No. 417; Ex. B.29
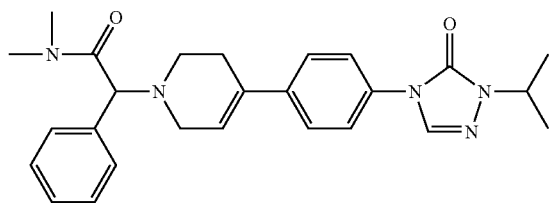
Co. No. 418; Ex. B.29
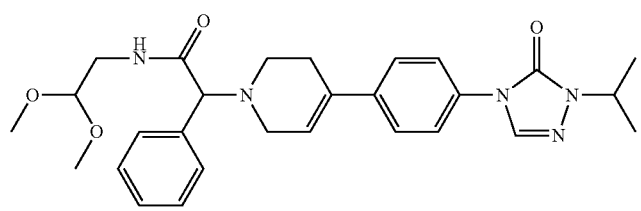
Co. No. 419; Ex. B.29
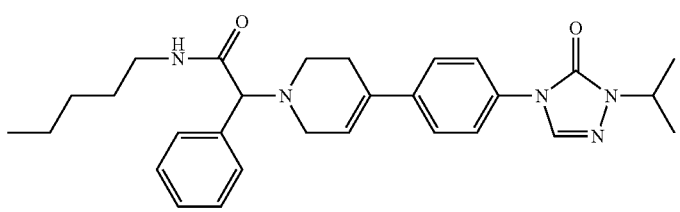
Co. No. 420; Ex. B.29
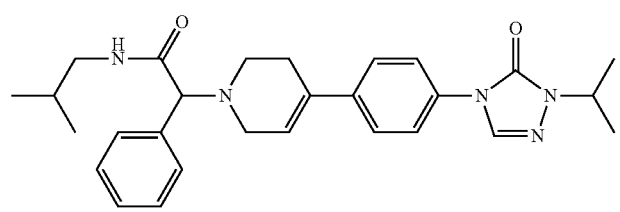
Co. No. 421; Ex. B.29

TABLE F-1b-continued
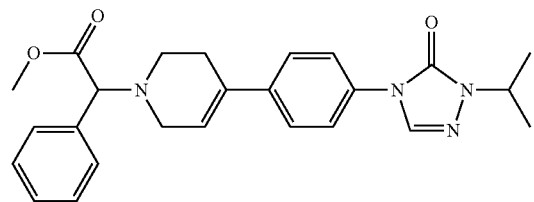
Co. No. 422; Ex. B.28
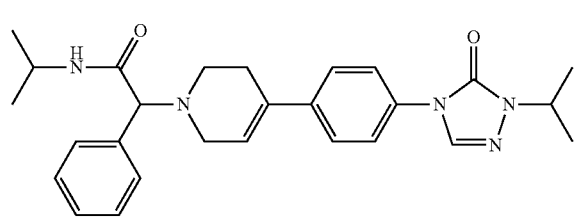
Co. No. 423; Ex. B.29
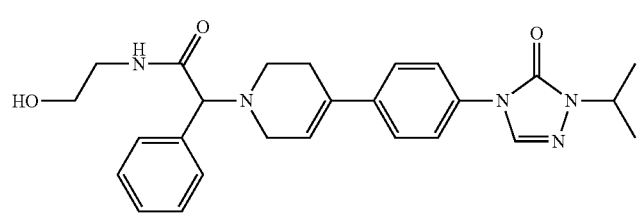
Co. No. 424; Ex. B.29
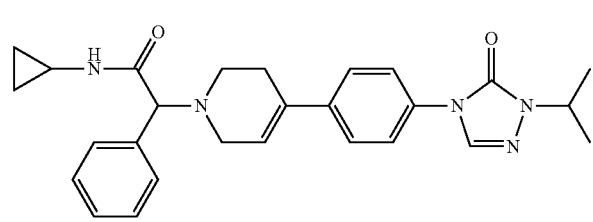
Co. No. 425; Ex. B.29
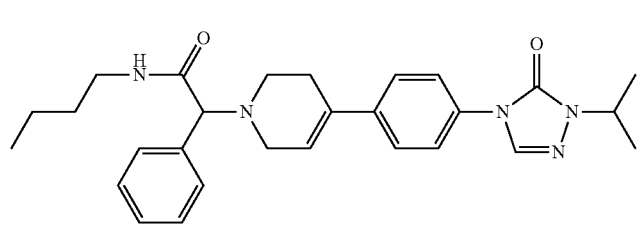
Co. No. 426; Ex. B.29
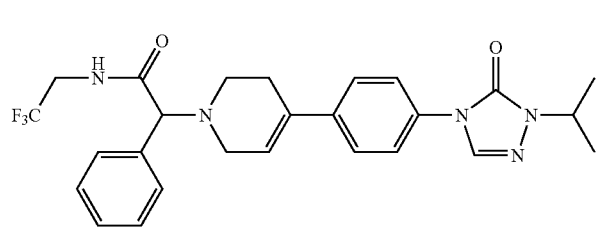
Co. No. 427; Ex. B.29

TABLE F-1b-continued

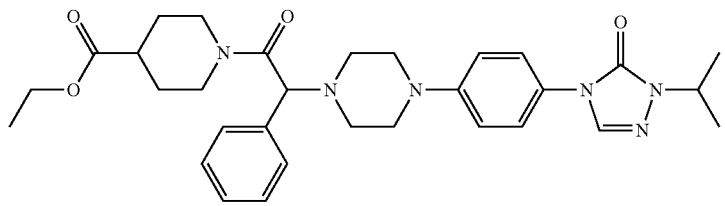

Co. No. 428; Ex. B.18

Compound Identification

Procedure 1

The compounds were identified by LC/MS using a gradient elution system on a reversed phase HPLC. The compounds are identified by their specific retention time and their protonated molecular ion $MH^+$ peak. The HPLC gradient was supplied by a Waters Alliance HT 2790 system with a columnheater set at 40° C. Flow from the column was split to a Waters 996 photodiode array (PDA) detector and a Waters-Micromass ZQ mass spectrometer with an electrospray ionization source operated in positive and negative ionization mode. Reversed phase HPLC was carried out on a Xterra MS C18 column (3.5 μm, 4.6×100 mm) with a flow rate of 1.6 ml/min. Three mobile phases (mobile phase A 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 1 minute, 100% B for 1 minute and reequilibrate with 100% A for 1.5 minutes. An injection volume of 10 μL was used.

Mass spectra were acquired by scanning from 100 to 1000 in 1 s using a dwell time of 0.1 s. The capillary needle voltage was 3 kV and the source temperature was maintained at 140° C. Nitrogen was used a the nebulizer gas. Cone voltage was 10 V for positive ionzation mode and 20 V for negative ionization mode. Data acquisition was performed with a Waters-Micromass MassLynx-Openlynx data system.

TABLE F-2a retention time (RT in minutes) and molecular weight as the $MH^+$

| Co. No. | Rt | MW ($MH^+$) |
|---|---|---|
| 2 | 5.91 | 533 |
| 3 | 5.9 | 533 |
| 4 | 4.56 | 480 |
| 5 | 5.5 | 497 |
| 6 | 4.91 | 463 |
| 7 | 5.05 | 463 |
| 8 | 5.41 | 497 |
| 9 | 5.58 | 416 |
| 10 | 4.88 | 498 |
| 11 | 5.57 | 538 |
| 12 | 5.56 | 512 |
| 13 | 5.4 | 456 |
| 14 | 5.13 | 504 |
| 15 | 6.05 | 548 |
| 16 | 4.84 | 498 |
| 17 | 5.49 | 450 |
| 18 | 4.27 | 436 |
| 19 | 5.76 | 496 |
| 20 | 5.67 | 510 |
| 21 | 5.32 | 477 |
| 22 | 5.56 | 525 |
| 23 | 5.62 | 511 |

TABLE F-2a-continued retention time (RT in minutes) and molecular weight as the $MH^+$

| Co. No. | Rt | MW ($MH^+$) |
|---|---|---|
| 24 | 5 | 463 |
| 25 | 6.19 | 621 |
| 26 | 5.92 | 559 |
| 27 | 6.08 | 573 |
| 28 | 6.17 | 559 |
| 29 | 6.21 | 546 |
| 30 | 5.99 | 539 |
| 31 | 5.66 | 525 |
| 32 | 5.83 | 539 |
| 33 | 5.98 | 587 |
| 34 | 6.12 | 512 |
| 36 | 5.23 | 436 |
| 37 | 4.71 | 498 |
| 38 | 5.83 | 464 |
| 43 | 5.07 | 478 |
| 44 | 5.39 | 492 |
| 46 | 4.62 | 450 |
| 48 | 5.13 | 512 |
| 50 | 4.38 | 475 |
| 51 | 6.11 | 524 |
| 53 | 5.41 | 482 |
| 54 | 5.87 | 525 |
| 55 | 5.8 | 531 |
| 56 | 5.28 | 513 |
| 57 | 5.73 | 511 |
| 58 | 5.9 | 565 |
| 59 | 5.84 | 525 |
| 60 | 5.93 | 525 |
| 61 | 5.47 | 527 |
| 62 | 5.68 | 533 |
| 63 | 5.31 | 555 |
| 64 | 5.93 | 595 |
| 65 | 5.15 | 501 |
| 66 | 5.01 | 507 |
| 67 | 5.85 | 590 |
| 68 | 6.22 | 615 |
| 69 | 5.61 | 537 |
| 70 | 4.93 | 512 |
| 71 | 5.39 | 541 |
| 72 | 4.94 | 526 |
| 73 | 4.83 | 589 |
| 74 | 5.06 | 477 |
| 75 | 5.32 | 517 |
| 76 | 5.45 | 529 |
| 78 | 5.19 | 601 |
| 79 | 5.44 | 547 |
| 80 | 5.45 | 540 |
| 81 | 4.88 | 461 |
| 82 | 5.26 | 585 |
| 83 | 5.81 | 561 |
| 84 | 5.79 | 568 |
| 85 | 5.72 | 539 |
| 86 | 5.35 | 525 |
| 93 | 4.7 | 479 |
| 99 | 4.08 | 462 |
| 101 | 4.83 | 463 |
| 102 | 4.69 | 488 |

TABLE F-2a-continued retention time (RT in minutes) and molecular weight as the MH+

| Co. No. | Rt | MW (MH+) |
|---|---|---|
| 103 | 4.98 | 475 |
| 104 | 4.87 | 475 |
| 105 | 4.8 | 493 |
| 106 | 5.35 | 491 |
| 107 | 5.32 | 491 |
| 108 | 4.92 | 523 |
| 111 | 5.61 | 505 |
| 112 | 5.45 | 511 |
| 115 | 5.14 | 463 |
| 116 | 4.98 | 461 |
| 118 | 5.41 | 477 |
| 119 | 5.39 | 477 |
| 120 | 5.66 | 491 |
| 121 | 4.9 | 512 |
| 122 | 5.15 | 503 |
| 123 | 5.41 | 511 |
| 124 | 5.67 | 496 |
| 125 | 5.39 | 518 |
| 126 | 4.81 | 526 |
| 127 | 5.04 | 551 |
| 129 | 5.51 | 511 |
| 130 | 5.31 | 525 |
| 131 | 4.83 | 479 |
| 132 | 4.57 | 474 |
| 133 | 5.79 | 525 |
| 134 | 5.9 | 539 |
| 135 | 5.92 | 539 |
| 136 | 4.61 | 435 |
| 137 | 4.8 | 449 |
| 138 | 5.65 | 464 |
| 139 | 5.22 | 448 |
| 140 | 5.42 | 462 |
| 141 | 5.42 | 462 |
| 142 | 5.02 | 434 |
| 143 | 5.46 | 502 |
| 144 | 4.94 | 448 |
| 145 | 4.46 | 421 |
| 146 | 4.97 | 437 |
| 147 | 5.57 | 553 |
| 157 | 5.93 | 538 |
| 159 | 5.42 | 450 |
| 160 | 5.42 | 539 |
| 161 | 4.64 | 477 |
| 162 | 5.25 | 539 |
| 164 | 5.08 | 463 |
| 165 | 5.06 | 511 |
| 166 | 5.09 | 503 |
| 167 | 5.02 | 482 |
| 169 | 5.35 | 464 |
| 170 | 4.85 | 504 |
| 171 | 5.6 | 435 |
| 172 | 5.21 | 436 |
| 173 | 5.98 | 512 |
| 175 | 5.07 | 463 |
| 176 | 5.3 | 477 |
| 177 | 5.92 | 503 |
| 178 | 5.38 | 517 |
| 179 | 5.26 | 496 |
| 180 | 5.33 | 508 |
| 185 | 5.74 | 527 |
| 186 | 4.73 | 515 |
| 188 | 5.93 | 537 |
| 189 | 5.32 | 449 |
| 190 | 5.92 | 537 |
| 191 | 5.96 | 537 |
| 192 | 5.46 | 555 |
| 193 | 5.69 | 569 |
| 195 | 5.81 | 525 |
| 196 | 5.27 | 569 |
| 197 | 6.1 | 585 |
| 198 | 6.64 | 639 |
| 199 | 5.46 | 627 |
| 200 | 5.32 | 541 |
| 202 | 5.16 | 580 |
| 203 | 6.13 | 538 |
| 204 | 5.7 | 498 |
| 205 | 6 | 536 |
| 206 | 6.22 | 569 |
| 209 | 5.56 | 538 |
| 210 | 6.34 | 623 |
| 212 | 6.14 | 584 |
| 213 | 5.47 | 460 |
| 214 | 6.08 | 550 |
| 215 | 6.22 | 571 |
| 216 | 6.05 | 555 |
| 217 | 5.58 | 464 |
| 218 | 5.99 | 551 |
| 219 | 5.81 | 465 |
| 220 | 5.95 | 552 |
| 221 | 6.24 | 510 |
| 222 | 6.25 | 510 |
| 223 | 6.23 | 528 |
| 224 | 6.23 | 528 |
| 225 | 6.51 | 560 |
| 226 | 6.52 | 560 |
| 227 | 6.23 | 510 |
| 228 | 6.24 | 510 |
| 229 | 6.45 | 588 |
| 231 | 6.5 | 560 |
| 232 | 6.5 | 560 |
| 233 | 6.4 | 524 |
| 234 | 6.4 | 524 |
| 235 | 6.42 | 544 |
| 236 | 6.41 | 544 |
| 238 | 6.22 | 540 |
| 239 | 5.78 | 540 |
| 242 | 6.34 | 524 |
| 243 | 6.24 | 528 |
| 244 | 6.24 | 528 |
| 245 | 6.52 | 560 |
| 246 | 6.5 | 560 |
| 247 | 6.17 | 510 |
| 248 | 6.25 | 510 |
| 249 | 6.47 | 588 |
| 251 | 6.5 | 560 |
| 252 | 6.5 | 560 |
| 253 | 6.41 | 524 |
| 254 | 6.41 | 524 |
| 255 | 6.41 | 544 |
| 256 | 6.41 | 544 |
| 257 | 6.28 | 540 |
| 258 | 6.27 | 540 |
| 259 | 6.16 | 540 |
| 260 | 6.15 | 540 |
| 262 | 6.68 | 516 |
| 263 | 6.36 | 524 |
| 264 | 5.51 | 420 |
| 267 | 5.97 | 511 |
| 268 | 5.96 | 529 |
| 269 | 6.15 | 579 |
| 270 | 6.17 | 579 |
| 271 | 5.98 | 529 |
| 272 | 5.96 | 529 |
| 273 | 5.96 | 529 |
| 275 | 5.95 | 529 |
| 276 | 6.37 | 578 |
| 277 | 6.39 | 578 |
| 278 | 6.22 | 528 |
| 279 | 6.23 | 528 |
| 280 | 5.91 | 512 |
| 281 | 5.91 | 512 |
| 282 | 5.8 | 582 |
| 283 | 5.96 | 631 |
| 285 | 5.73 | 568 |
| 286 | 5.65 | 596 |
| 287 | 5.82 | 645 |
| 288 | 5.76 | 582 |
| 289 | 5.7 | 582 |

TABLE F-2a-continued retention time (RT in minutes) and molecular weight as the MH+

| Co. No. | Rt | MW (MH+) |
|---|---|---|
| 290 | 5.22 | 582 |
| 291 | 5.71 | 631 |
| 292 | 5.62 | 568 |
| 293 | 5.49 | 582 |
| 294 | 5.7 | 631 |
| 295 | 5.59 | 568 |
| 296 | 6.61 | 516 |
| 298 | 5.93 | 530 |
| 299 | 5.93 | 530 |
| 300 | 5.93 | 530 |
| 301 | 5.94 | 530 |
| 302 | 4.69 | 451 |
| 303 | 4.68 | 451 |
| 304 | 5.91 | 512 |
| 305 | 6.01 | 652 |
| 306 | 5.81 | 652 |
| 307 | 5.82 | 483 |
| 308 | 5.81 | 483 |
| 309 | 5.83 | 483 |
| 310 | 6.23 | 517 |
| 311 | 5.91 | 527 |
| 312 | 5.73 | 463 |
| 313 | 5.99 | 532 |
| 314 | 5.98 | 532 |
| 315 | 6.01 | 532 |
| 316 | 6.35 | 566 |
| 317 | 6.07 | 576 |
| 318 | 5.92 | 512 |
| 319 | 5.94 | 469 |
| 320 | 5.93 | 469 |
| 321 | 5.96 | 469 |
| 322 | 6.36 | 503 |
| 323 | 6.02 | 513 |
| 324 | 5.86 | 449 |
| 325 | 5.6 | 470 |
| 326 | 5.6 | 470 |
| 327 | 5.63 | 470 |
| 328 | 6.07 | 504 |
| 329 | 5.72 | 514 |
| 330 | 5.53 | 450 |
| 331 | 6.23 | 528 |
| 332 | 6.24 | 546 |
| 333 | 6.26 | 546 |
| 334 | 6.22 | 546 |
| 335 | 6.27 | 546 |
| 336 | 6.28 | 546 |
| 337 | 5.98 | 529 |
| 338 | 6 | 547 |
| 339 | 5.99 | 547 |
| 340 | 5.98 | 547 |
| 341 | 6.02 | 547 |
| 342 | 6.03 | 547 |
| 343 | 6.17 | 529 |
| 344 | 6.17 | 529 |
| 345 | 6.16 | 529 |
| 346 | 6.17 | 529 |
| 347 | 5.98 | 472 |
| 348 | 6.04 | 472 |
| 351 | 5.74 | 640 |
| 352 | 5.74 | 589 |
| 353 | 6.07 | 607 |
| 354 | 6.15 | 611 |
| 355 | 6.3 | 612 |
| 356 | 5.48 | 641 |
| 357 | 5.59 | 576 |
| 358 | 5.54 | 640 |
| 359 | 5.68 | 642 |
| 360 | 5.91 | 512 |

Procedure 2

The following compounds were identified by LC/MS using a gradient elution system on a reversed phase HPLC. The compounds are identified by their specific retention time and their protonated molecular ion MH+ peak. The HPLC gradient was supplied by a Waters 600 system with a columnheater set at 45° C. Flow from the column was split to a Waters 2996 photodiode array (PDA) detector and a Waters-Micromass LCT mass spectrometer with an electrospray ionization source operated in positive ionization mode. Reversed phase HPLC was carried out on a Xterra MS C18 column (3.5 µm, 4.6×100 mm) with a flow rate of 1.6 ml/min. Three mobile phases (mobile phase: A 95% 10 mM ammoniumacetate+5% acetonitrile; mobile phase B: acetonitrile; mobile phase C: methanol) were employed to run a gradient condition from 100% A to 35% A 35% B and 35% C in 3.5 minutes, to 50% B and 50% C in 3 minutes, to 100% B in 1 minute, 100% B for 1 minute and reequilibrate with 100% A for 1.5 minutes. An injection volume of 10 µL was used. Mass spectra were acquired by scanning from 100 to 1000 in 1 s using a dwell time of 0.1 s. The capillary needle voltage was 3 kV and the source temperature was maintained at 140° C. Nitrogen was used a the nebulizer gas. Cone voltage was 10 V for positive ionization mode and 20 V for negative ionization mode. Data acquisition was performed with a Waters-Micromass Mass-Lynx-Openlynx data system.

TABLE F-2b retention time (RT in minutes) and molecular weight as the MH+

| Co. No. | Rt | MW (MH+) |
|---|---|---|
| 369 | 7.81 | 644 |
| 370 | 7.81 | 582 |
| 371 | 7.04 | 568 |
| 372 | 6.61 | 506 |
| 373 | 7.72 | 658 |
| 374 | 7.35 | 596 |
| 375 | 7.42 | 658 |
| 376 | 7.04 | 596 |
| 377 | 6.97 | 582 |
| 378 | 6.52 | 520 |
| 379 | 7.49 | 672 |
| 380 | 7.11 | 610 |
| 381 | 7.55 | 658 |
| 382 | 6.37 | 520 |
| 383 | 7.65 | 672 |
| 384 | 7.29 | 610 |

Procedure 3

The following compounds were identified by LC/MS using a gradient elution system on a reversed phase HPLC. The compounds are identified by their specific retention time and their protonated molecular ion MH+ peak. The HPLC gradient was supplied by a Waters Alliance HT 2790 system with a columnheater set at 40° C. Flow from the column was split to a Waters 996 photodiode array (PDA) detector and a Waters-Micromass ZQ mass spectrometer with an electrospray ionization source operated in positive and negative ionization mode.

Reversed phase HPLC was carried out on a Xterra MS C18 column (3.5 µm, 4.6×100 mm) with a flow rate of 1.2 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 10 minutes, to 100% B in 1 minute, 100% B for 3 minutes and reequilibrate with 100% A for 1.5 minutes. An injection volume of 10 µL was used. Mass spectra were acquired by scanning from 100 to 1000 in 1 s using a dwell time of 0.1 s. The capillary needle voltage was 3 kV and the source temperature was maintained at 140° C. Nitrogen was used a the nebulizer gas.

Cone voltage was 10 V for positive ionzation mode and 20 V for negative ionization mode. Data acquisition was performed with a Waters-Micromass MassLynx-Openlynx data system.

TABLE F-2c retention time (RT in minutes) and molecular weight as the MH+

| Co. No. | Rt | MW (MH+) |
|---|---|---|
| 387 | 8.1 | 532 |
| 388 | 8.1 | 532 |
| 389 | 8.13 | 546 |
| 390 | 7.53 | 506 |
| 391 | 7.52 | 506 |
| 392 | 8.19 | 534 |
| 393 | 8.19 | 534 |
| 394 | 8.35 | 568 |
| 395 | 8.35 | 568 |
| 396 | 8.51 | 582 |
| 397 | 7.97 | 592 |
| 398 | 8.48 | 548 |
| 401 | 7.88 | 520 |
| 402 | 7.36 | 506 |
| 403 | 7.53 | 506 |
| 404 | 8.36 | 626 |

C. Pharmacological Examples

C.1. Quantification of the secretion of ApoB

HepG2 cells were cultured in 24-well plates in MEM Rega 3 containing 10% fetal calf serum. At 70% confluency, the medium was changed and the test compound or carrier (DMSO, 0.4% final concentration) was added. After 24 hours of incubation, the medium was transferred to Eppendorf tubes and cleared by centrifugation. A sheep antibody directed against either apoB was added to the supernatant and the mixture was kept at 8° C. for 24 hours. Then, rabbit anti-sheep antibody was added and the immune complex was allowed to precipitate for 24 hours at 8° C. The immunoprecipitate was pelleted by centrifugation for 25 minutes at 1320 g and washed twice with a buffer containing 40 mM Mops, 40 mM $NaH_2PO_4$, 100 mM NaF, 0.2 mM DTT, 5 mM EDTA, 5 mM EGTA, 1% Triton-X-100, 0.5% sodium deoxycholate (DOC), 0.1% SDS, 0.2 µM leupeptin and 0.2 µM PMSF. Radioactivity in the pellet was quantified by liquid scintillation counting. The $IC_{50}$ values are usually converted to pIC50 values (=-log $IC_{50}$ value) for ease of use.

The following compounds have a pIC50 value from 5.5 to 6.5:2, 4, 5, 9, 10, 12, 13, 14, 15, 16, 17, 18, 25, 26, 27, 28, 29, 30, 31, 32, 33, 34, 35, 36, 37, 38, 39, 40, 41, 42, 43, 45, 46, 47, 49, 50, 52, 53, 56, 65, 67, 68, 70, 71, 72, 73, 75, 76, 78, 79, 81, 84, 86, 87, 89, 90, 91, 92, 93, 94, 102, 104, 105, 107, 108, 111, 112, 114, 115, 116, 117, 118, 119, 120, 121, 122, 126, 127, 129, 130, 131, 132, 133, 134, 135, 136, 137, 138, 144, 145, 146, 147, 148, 149, 152, 159, 160, 161, 162, 165, 166, 167, 169, 170, 172, 185, 189, 195, 196, 199, 208, 213, 219, 223, 226, 228, 230, 231, 234, 236, 238, 239, 240, 241, 243, 245, 246, 248, 250, 251, 252, 254, 256, 257, 258, 259, 260, 264, 265, 266, 272, 273, 274, 275, 279, 280, 287, 290, 291, 293, 294, 298, 318, 320, 321, 323, 324, 326, 327, 329, 330, 347, 351, 352, 354, 356, 357, 358, 359, 372, 373, 374, 379, 380, 383, 384, 385, 386, 391, 392, 395, 396, 397, 398, 401, 402, 403 and 404.

The following compounds have a pIC50 value from 6.5 to 7.5:1, 3, 6, 7, 8, 19, 20, 21, 22, 23, 24, 44, 48, 51, 54, 55, 57, 58, 59, 60, 61, 62, 63, 64, 66, 69, 74, 77, 80, 82, 83, 85, 88, 95, 96, 97, 98, 99, 100, 101, 103, 106, 109, 110, 113, 123, 124, 125, 128, 139, 140, 141, 142, 143, 150, 151, 153, 154, 155, 156, 157, 158, 163, 164, 168, 171, 173, 174, 175, 176, 177, 178, 179, 180, 181, 182, 183, 184, 186, 191, 192, 193, 194, 197, 198, 200, 201, 202, 204, 206, 209, 210, 216, 217, 221, 222, 224, 225, 227, 229, 232, 233, 235, 237, 242, 244, 247, 249, 253, 255, 261, 262, 263, 268, 269, 270, 271, 276, 277, 278, 281, 286, 288, 289, 292, 295, 296, 297, 299, 304, 305, 319, 322, 325, 328, 331, 332, 333, 334, 335, 336, 337, 338, 339, 340, 341, 342, 350, 353, 369, 370, 371, 375, 376, 377, 378, 382, 393 and 394.

The following compounds have a pIC50 value higher than 7.5:11, 187, 188, 190, 203, 205, 207, 211, 212, 214, 215, 218, 220, 267, 282, 283, 284, 285, 306, 349 and 381.

C.2. MTP Assay

MTP activity was measured using an assay similar to one described by J. R. Wetterau and D. B. Zilversmit in *Chemistry and Physics of Lipids,* 38, 205-222 (1985). To prepare the donor and acceptor vesicles, the appropriate lipids in chloroform were put into a glass test tube and dried under a stream of $N_2$. A buffer containing 15 mM Tris-HCl pH 7.5, 1 mM EDTA, 40 mM NaCl, 0.02% $NaN_3$ (assay buffer) was added to the dried lipid. The mixture was vortexed briefly and the lipids were then allowed to hydrate for 20 min on ice. Vesicles were then prepared by bath sonication (Branson 2200) at room temperature for maximum 15 min. Butylated hydroxytoluene was included in all vesicle preparations at a concentration of 0.1%. The lipid transfer assay mixture contained donor vesicles (40 nmol phosphatidylcholine, 7.5 mol % of cardiolipin and 0.25 mol % glycerol tri [1-$^{14}$C]-oleate), acceptor vesicles (240 nmol phosphatidylcholine) and 5 mg BSA in a total volume of 675 µl in a 1.5 ml microcentrifuge tube. Test compounds were added dissolved in DMSO (0.13% final concentration). After 5 minutes of pre-incubation at 37° C., the reaction was started by the addition of MTP in 100 µl dialysis buffer. The reaction was stopped by the addition of 400 µl DEAE-52 cellulose pre-equilibrated in 15 mM Tris-HCl pH 7.5, 1 mM EDTA, 0.02% $NaN_3$ (1:1, vol/vol). The mixture was agitated for 4 min and centrifuged for 2 min at maximum speed in an Eppendorf centrifuge (4° C.) to pellet the DEAE-52-bound donor vesicles. An aliquot of the supernatant containing the acceptor liposomes was counted and the [$^{14}$C]-counts were used to calculate the percent triglyceride transfer from donor to acceptor vesicles.

The invention claimed is:
1. A compound of formula (I)

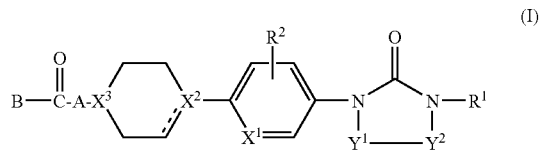

the N-oxides, the pharmaceutically acceptable acid addition salts and the stereochemically isomeric forms thereof, wherein
the dotted line is an optional bond and is absent when $X^2$ represents nitrogen;
the radical —$Y^1$—$Y^2$— is a radical of formula —N=CH—   (a-1), —CH=N—   (a-2), —$CH_2$—$CH_2$—   (a-3), —CH=CH—   (a-4), wherein in the bivalent radicals of formula (a-1) or (a-2) the hydrogen atom may optionally be replaced by $C_{1-6}$alkyl or phenyl; or in the bivalent radicals of formula (a-3) or (a-4) one or two hydrogen atoms may optionally be replaced by $C_{1-6}$alkyl or phenyl;

$X^1$ is carbon or nitrogen;

at least one of $X^2$ or $X^3$ represents nitrogen and the other $X^2$ or $X^3$ represents CH or carbon when the dotted line represents a bond, or both $X^2$ and $X^3$ represent nitrogen;

$R^1$ is $C_{1-6}$alkyl;
   aryl$^1$;
   $C_{1-6}$alkyl substituted with hydroxy, $C_{3-6}$cycloalkyl, aryl$^1$ or naphthalenyl;
   $C_{3-6}$cycloalkyl;
   $C_{3-6}$cycloalkenyl;
   $C_{3-6}$alkenyl;
   $C_{3-6}$alkenyl substituted with aryl$^1$;
   $C_{3-6}$alkynyl;
   $C_{3-6}$alkynyl substituted with aryl$^1$;
   $C_{1-4}$alkyloxy$C_{1-4}$alkanediyl optionally substituted with aryl$^1$;
   or when —$Y^1$—$Y^2$— is a radical of formula (a-1) than $R^1$ may be taken together with $Y^2$ to form a radical of formula —CH=CH—CH=CH— wherein each hydrogen may optionally be replaced by a substituent independently selected from $C_{1-4}$alkyl, $C_{1-4}$alkyloxy, polyhalo$C_{1-4}$alkyl, halo, cyano, trifluoromethyl or aryl';
   wherein aryl' is phenyl; or phenyl substituted with from one or five substituents each independently selected from $C_{1-4}$alkyl, $C_{1-4}$alkyloxy, polyhalo$C_{1-4}$alkyl, halo, cyano, or trifluoromethyl;

$R^2$ is hydrogen, $C_{1-4}$alkyl, or halo;

A is $C_{1-6}$alkanediyl;
   $C_{1-6}$alkanediyl substituted with one or two groups selected from aryl$^2$, heteroaryl$^1$ and $C_{3-8}$cycloalkyl;
   or provided $X^3$ represents CH said radical A may also represent NH optionally substituted with aryl$^2$, heteroaryl$^1$ or $C_{3-8}$cycloalkyl;
   wherein aryl$^2$ is phenyl; or phenyl substituted with from one to five substituents each independently selected from $C_{1-4}$-alkyl, $C_{1-4}$-alkyloxy, halo, cyano or trifluoromethyl;
      heteroaryl$^1$ is furanyl, thienyl, pyridinyl, pyrazinyl, pyrimidinyl, or pyridazinyl; and said heteroaryl$^1$ is optionally substituted with one or two substituents each independently selected from $C_{1-4}$alkyl, $C_{1-4}$alkyloxy, halo, cyano or trifluoromethyl;

B is $NR^3R^4$, or
OR$^9$;
wherein each $R^3$ and $R^4$ are independently selected from
   hydrogen,
   $C_{1-8}$alkyl,
   $C_{1-8}$alkyl substituted with one, two or three substituents each independently from one another selected from hydroxy, halo, cyano, $C_{1-4}$-alkyloxy, $C_{1-4}$alkyloxycarbonyl, $C_{3-8}$cycloalkyl, polyhalo$C_{1-4}$alkyl, $NR^5R^6$, $CONR^7R^8$, aryl$^3$, polycyclic aryl, or heteroaryl$^2$;
   $C_{3-8}$cycloalkyl;
   $C_{3-8}$cycloalkenyl;
   $C_{3-8}$alkenyl;
   $C_{3-8}$alkynyl;
   aryl$^3$;
   polycyclic aryl;
   heteroaryl$^2$; or
   $R^3$ and $R^4$ combined with the nitrogen atom bearing $R^3$ and $R^4$ may form an azetidinyl, pyrrolidinyl, piperidinyl, morpholinyl, azepanyl, or azocanyl ring wherein each of these rings may optionally be substituted by $C_{1-4}$alkyloxycarbonyl, $C_{1-4}$alkyloxycarbonyl$C_{1-4}$alkyl, carbonylamino, $C_{1-4}$alkylcarbonylamino, $CONR^7R^8$ or $C_{1-4}$alkyl$CONR^7R^8$;

wherein
   $R^5$ is hydrogen, $C_{1-4}$alkyl, aryl$^3$, polycyclic aryl, or heteroaryl$^2$;
   $R^6$ is hydrogen or $C_{1-4}$-alkyl;
   $R^7$ is hydrogen, $C_{1-4}$alkyl or phenyl;
   $R^8$ is hydrogen, $C_{1-4}$alkyl or phenyl; or
   $R^9$ is $C_{1-6}$alkyl, or $C_{1-6}$alkyl substituted with one, two or three substituents each independently from one another selected from hydroxy, halo, cyano, $C_{1-4}$alkyloxy, $C_{1-4}$alkyloxycarbonyl, $C_{3-8}$cycloalkyl, $C_{3-8}$cycloalkenyl, trifluoromethyl, $NR^5R^6$, $CONR^7R^8$, aryl$^3$, polycyclic aryl, or heteroaryl$^2$;
   wherein
      aryl$^3$ is phenyl; phenyl substituted with one to five substituents each independently selected from $C_{1-4}$alkyl, $C_{1-4}$alkyloxy, halo, hydroxy, trifluoromethyl, cyano, $C_{1-4}$alkyloxycarbonyl, $C_{1-4}$alkyloxycarbonyl$C_{1-4}$alkyl, methylsulfonylamino, methylsulfonyl, $NR^5R^6$, $C_{1-4}$alkyl$NR^5R^6$, $CONR^7R^8$ or $C_{1-4}$alkyl$CONR^7R^8$;
      polycyclic aryl is naphthalenyl, indanyl, fluorenyl, or 1,2,3,4-tetrahydronaphtalenyl, and said polycyclic aryl is optionally substituted with one or two substituents each independently selected from $C_{1-6}$alkyl, $C_{1-6}$alkyloxy, phenyl, halo, cyano, $C_{1-4}$alkylcarbonyl, $C_{1-4}$alkyloxycarbonyl, $C_{1-4}$alkyloxycarbonyl$C_{1-4}$alkyl, $NR^5R^6$, $C_{1-4}$alkyl$NR^5R^6$, $CONR^7R^8$, $C_{1-4}$alkyl$CONR^7R^8$ or $C_{1-4}$alkyloxycarbonylamino and
      heteroaryl$^2$ is pyridinyl, pyrazinyl, pyrimidinyl, pyridazinyl, triazinyl, triazolyl, imidazolyl, pyrazolyl, thiazolyl, isothiazolyl, oxazolyl, pyrrolyl, furanyl, thienyl; quinolinyl; isoquinolinyl; 1,2,3,4-tetrahydro-isoquinolinyl; benzothiazolyl; benzo[1,3]dioxolyl; 2,3-dihydro-benzo[1,4]dioxinyl; indolyl; 2,3-dihydro-1H-indolyl; 1H-benzoimidazolyl; and said heteroaryl$^2$ is optionally substituted with one or two substituents each independently selected from $C_{1-6}$alkyl, $C_{1-6}$alkyloxy, phenyl, halo, cyano, $C_{1-4}$alkylcarbonyl, $C_{1-4}$alkyloxycarbonyl, $C_{1-4}$alkyloxycarbonyl$C_{1-4}$alkyl, $NR^5R^6$, $C_{1-4}$alkyl$NR^5R^6$, $CONR^7R^8$ or $C_{1-4}$alkyl$CONR^7R^8$.

2. A compound as claimed in claim 1 wherein $X^2$ represents nitrogen and $X^3$ represents CH.

3. A compound as claimed in claim 1 wherein $X^2$ represents CH and $X^3$ represents nitrogen.

4. A compound as claimed in claim 1 wherein both $X^2$ and $X^3$ represent nitrogen.

5. A compound as claimed in claim 1 wherein radical A represents $C_{1-6}$alkanediyl substituted with aryl$^2$.

6. A compound as claimed in claim 1 wherein radical B represents OR$^9$ wherein R$^9$ is $C_{1-6}$alkyl or $NR^3R^4$ wherein $R^3$ is hydrogen.

7. A pharmaceutical composition comprising a pharmaceutically acceptable carrier and a therapeutically active amount of a compound as claimed in claim 1.

8. A process for preparing a pharmaceutical composition comprising intimately mixing a therapeutically effective amount of a compound of claim 1 with a pharmaceutically acceptable carrier.

9. A process for preparing a compound of formula (I) of claim 1 wherein an intermediate of formula (II), wherein $X^1$, $X^2$, $X^3$, $R^2$, A, and B are as defined in claim 1 and Q is selected from bromo, iodo and trifluoromethylsulfonate, is reacted with an intermediate of formula (III), wherein $Y^1$, $Y^2$ and $R^1$ are defined as in claim 1, in a reaction-inert solvent and optionally in the presence of at least one transition metal coupling reagent and/or at least one suitable catalyst such as palladium associated with triphenylphosphine, or triphenylarsine; to prepare as compound for formula (I) as follows:

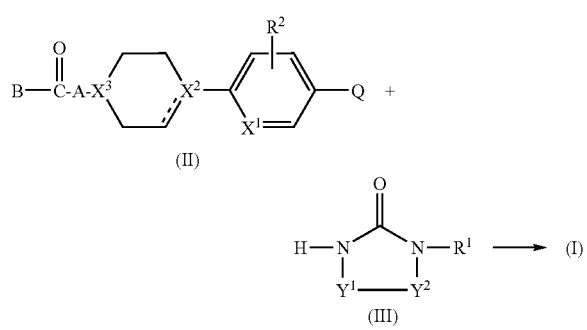

10. The process according to claim 9, further comprising converting the compound of formula (I) into an acid addition salt.

11. A method of treating a warm-blooded animal suffering from a disorder selected from the group consisting of atherosclerosis, pancreatitis, obesity, hypertriglyceridemia, hypercholesterolemia, hyperlipidemia, diabetes and type II diabetes comprising administering to the animal a therapeutically effective amount of a compound of claim 1.

12. The method of treatment according to claim 11 wherein the disorder is hyperlipidemia, obesity, atherosclerosis or type II diabetes.

13. The compound of formula (I) which is selected from the group consisting of:

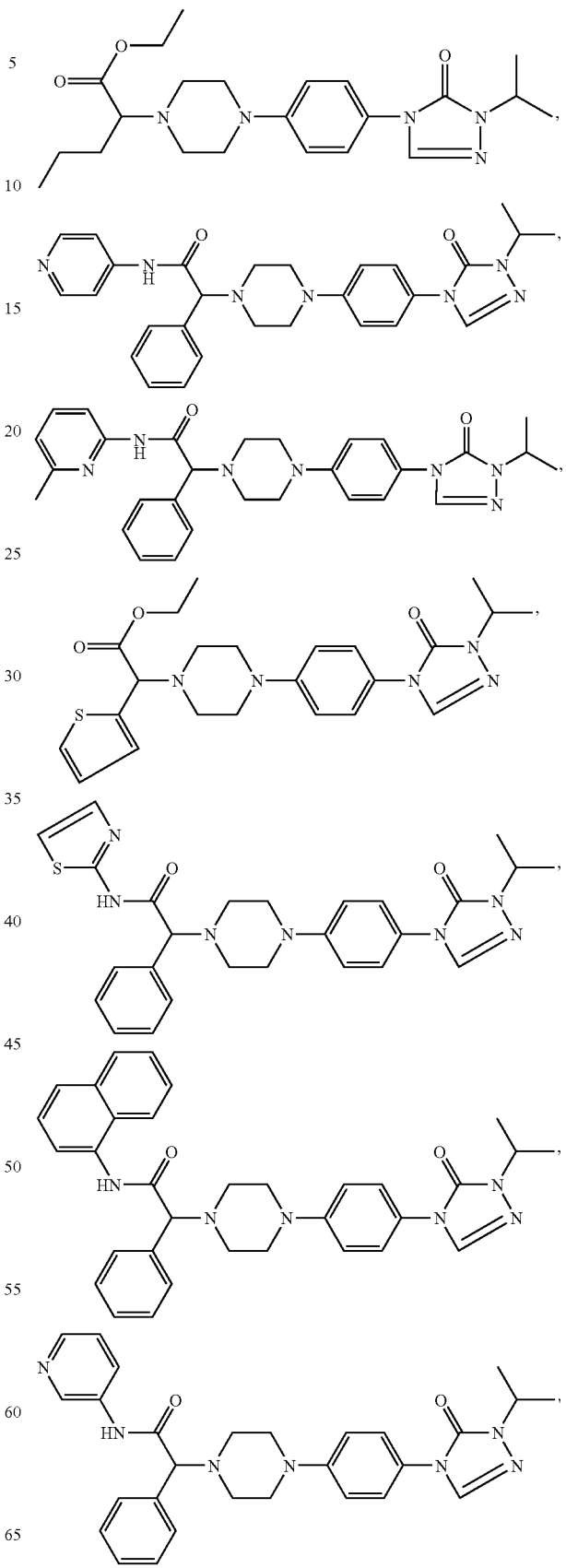

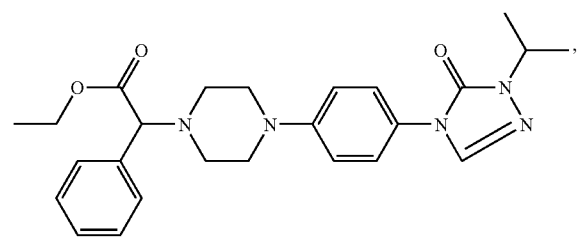
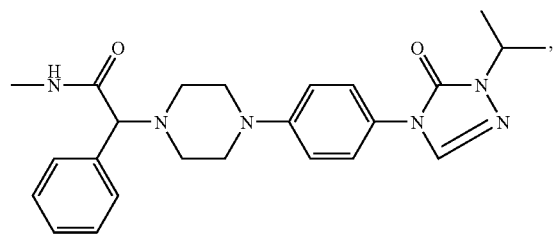
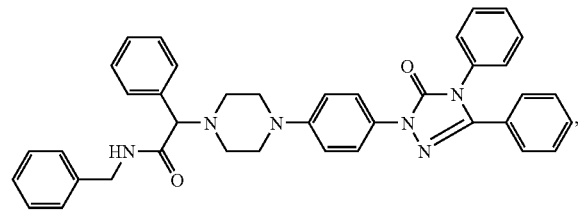
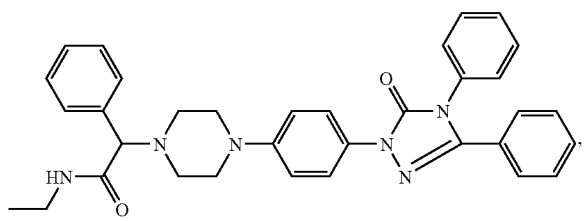
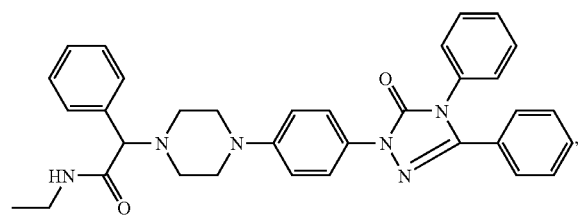
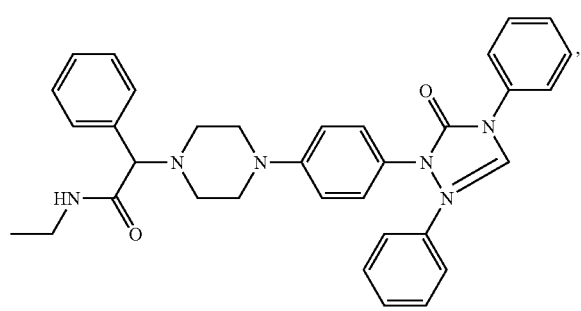
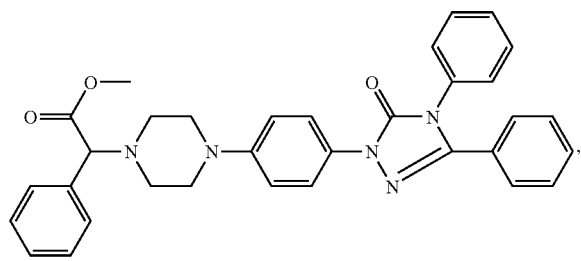
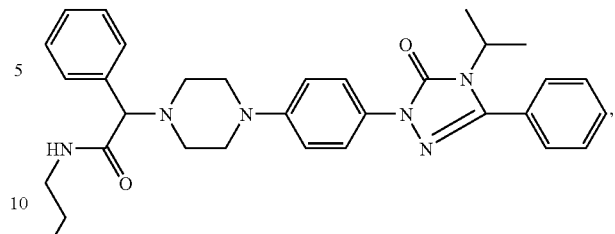
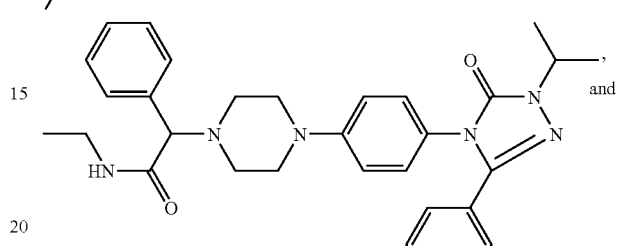
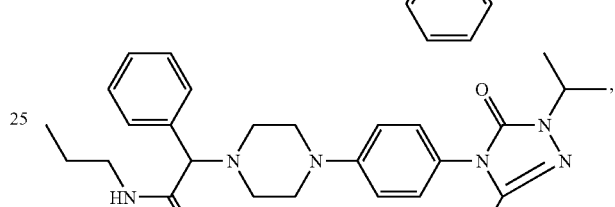
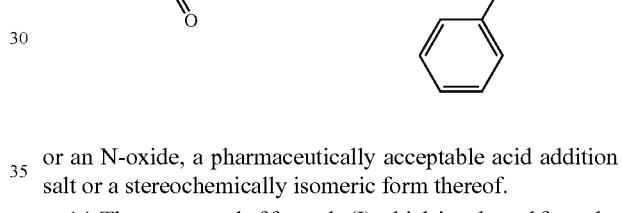
or an N-oxide, a pharmaceutically acceptable acid addition salt or a stereochemically isomeric form thereof.
14. The compound of formula (I) which is selected from the group consisting of
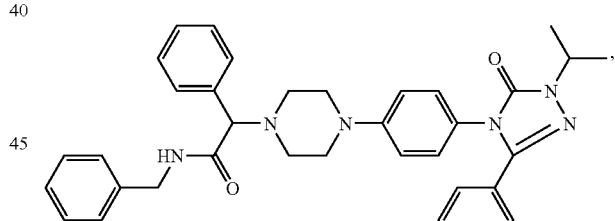
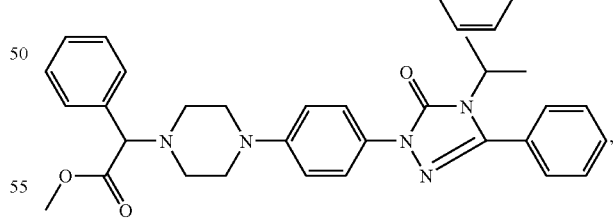
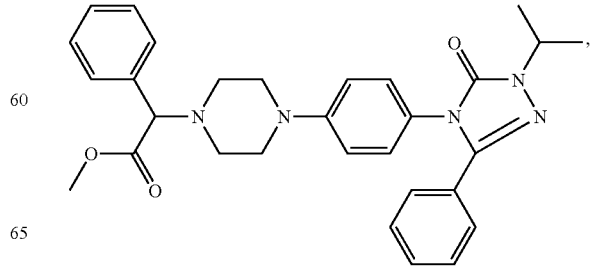

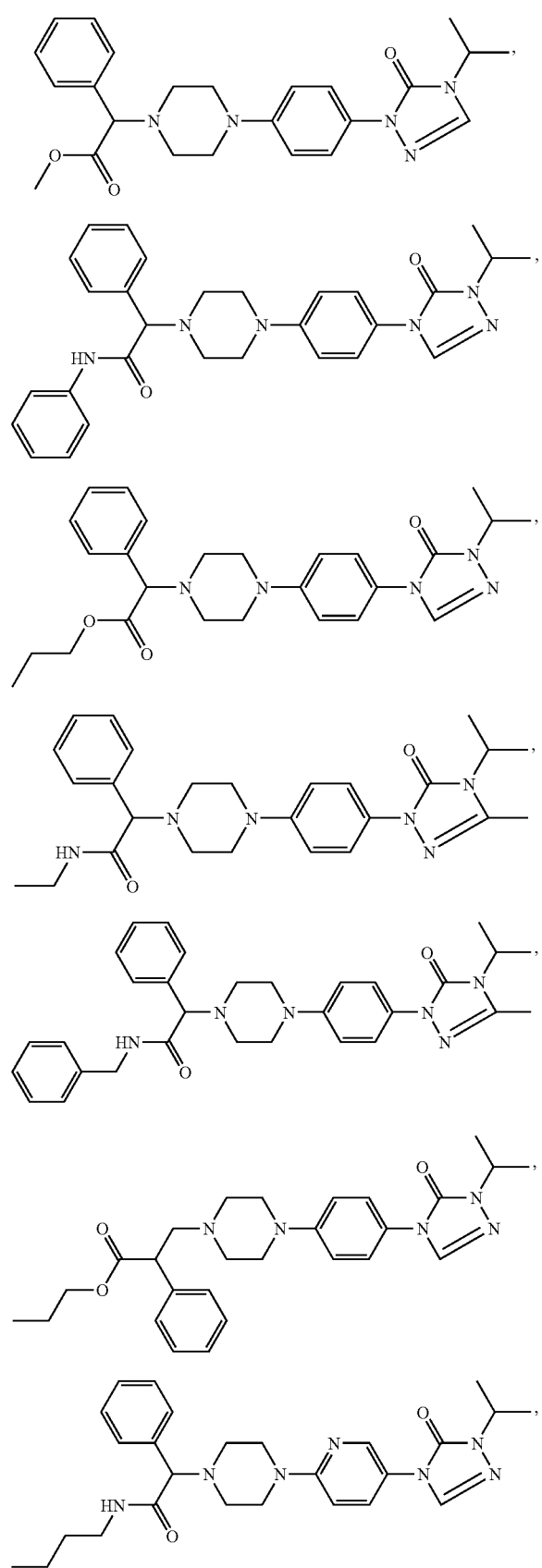
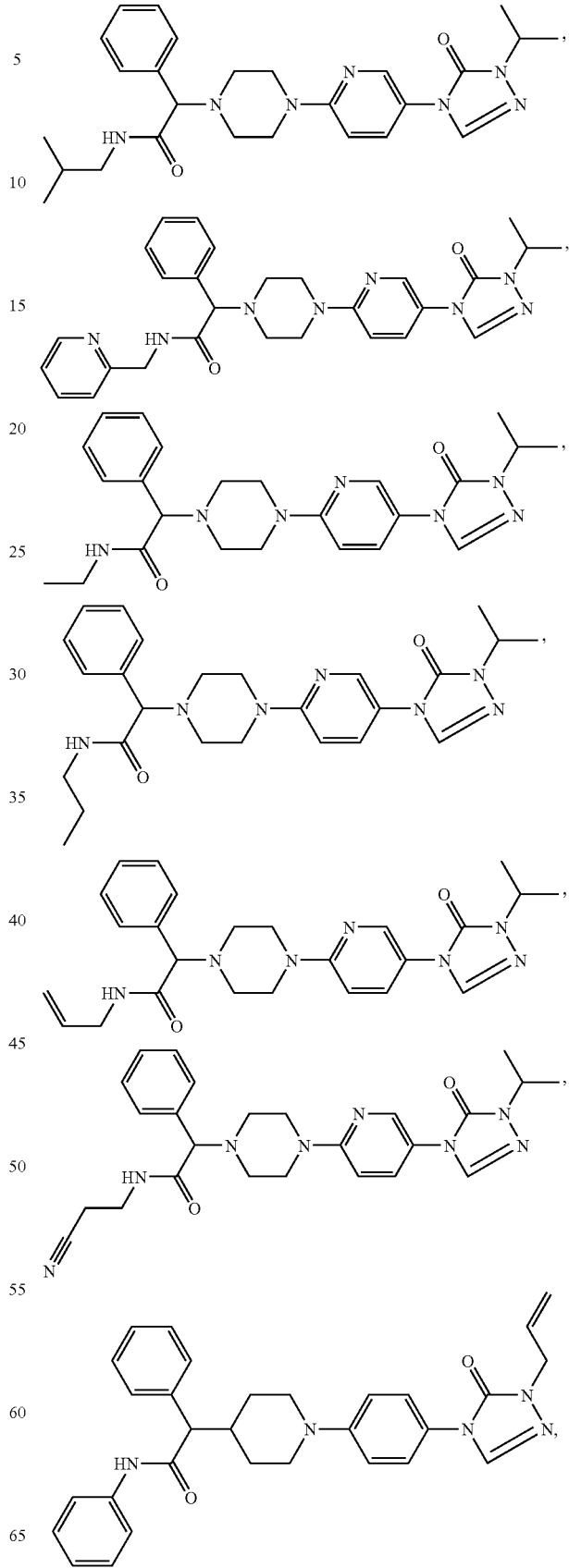

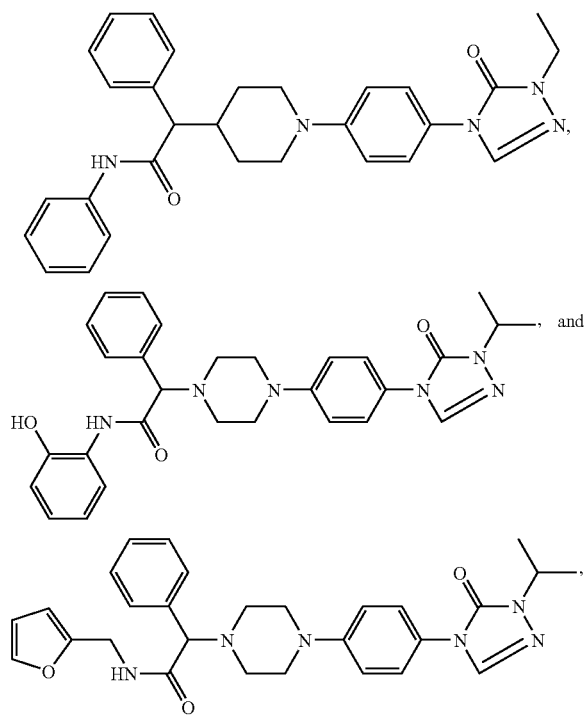
or an N-oxide, a pharmaceutically acceptable acid addition salt or a stereochemically isomeric form thereof.
15. The compound of formula (I) which is selected from the group consisting of:
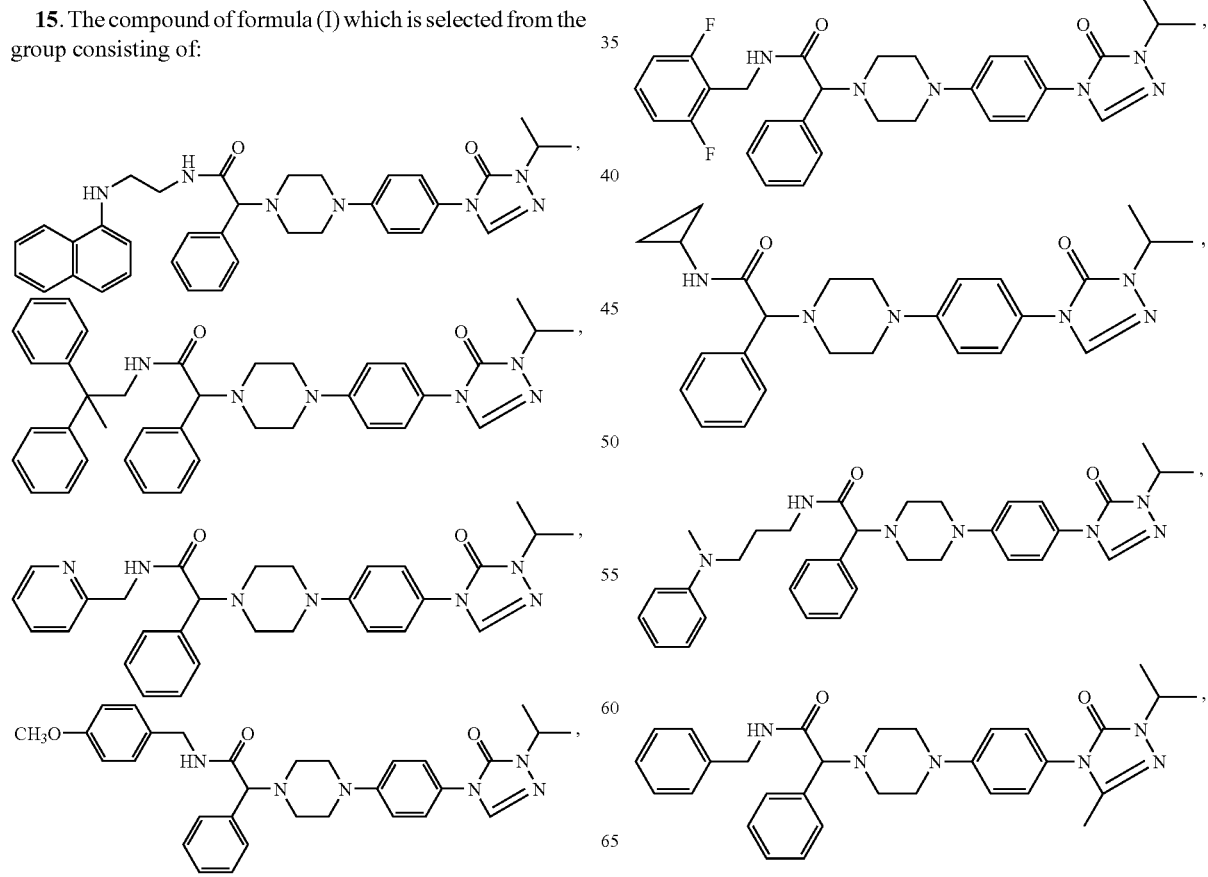
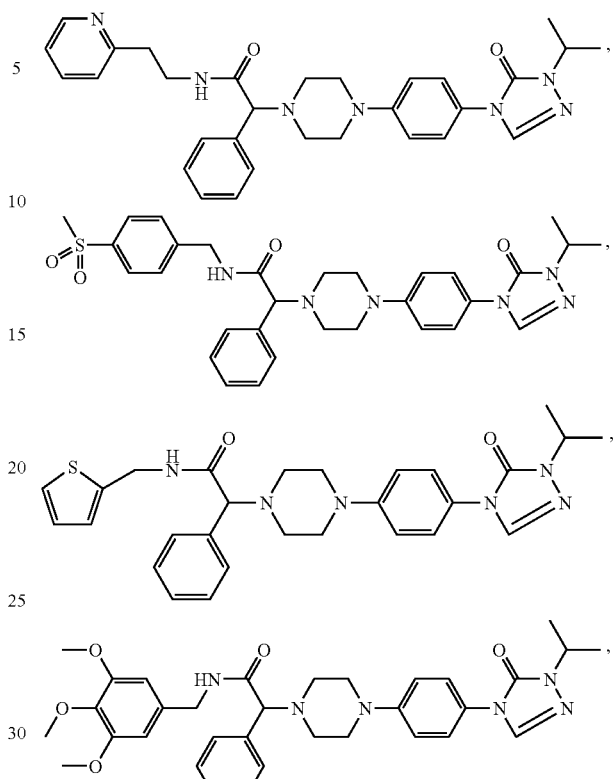

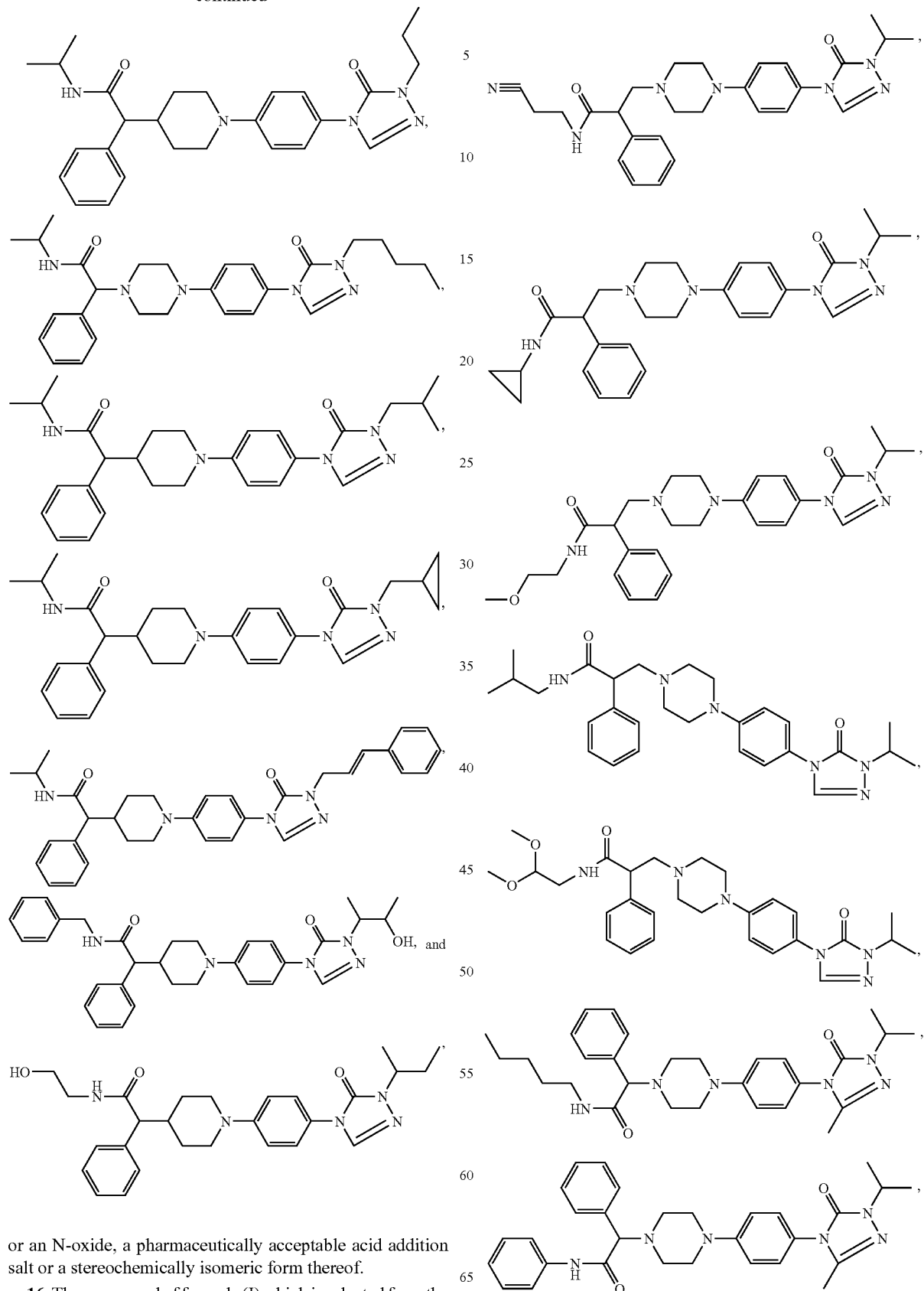
or an N-oxide, a pharmaceutically acceptable acid addition salt or a stereochemically isomeric form thereof.
16. The compound of formula (I) which is selected from the group consisting of

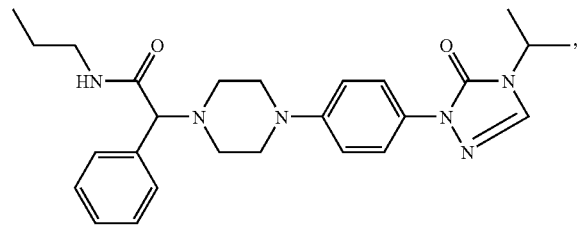
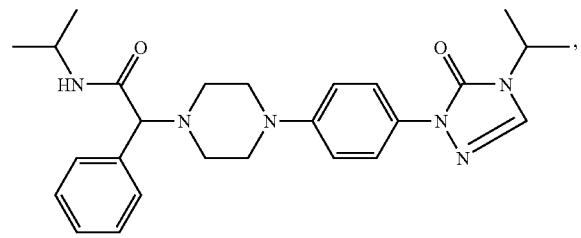
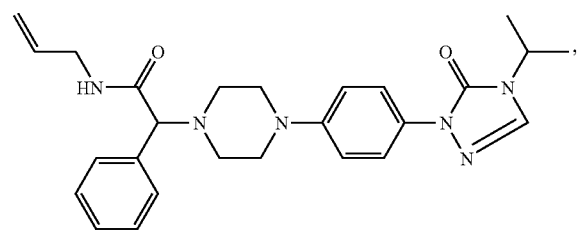
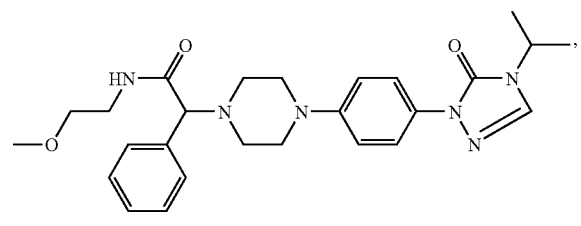
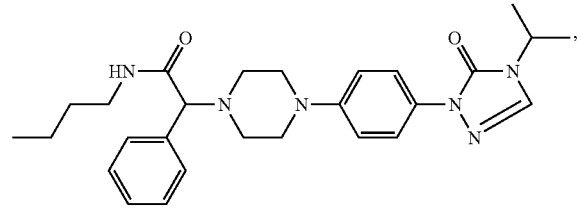
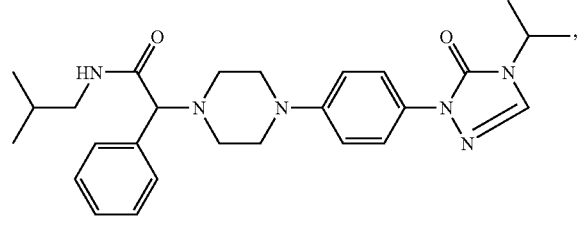
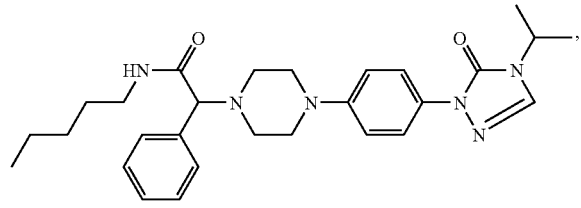
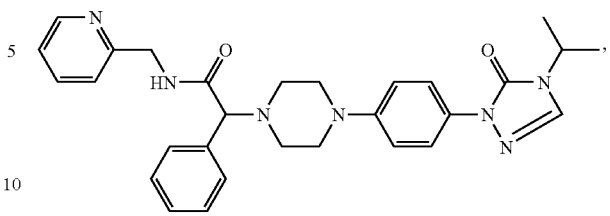
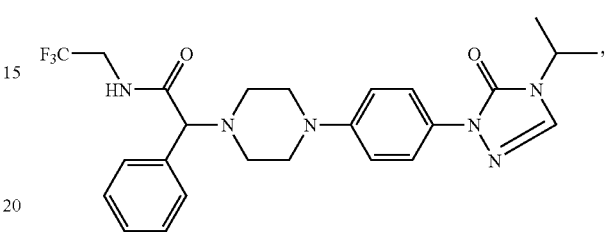
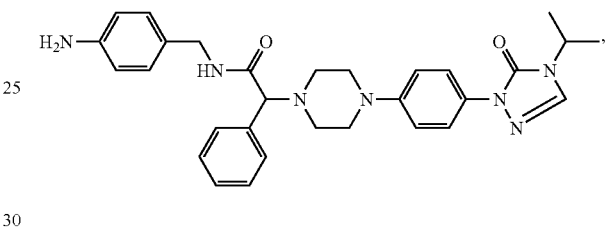
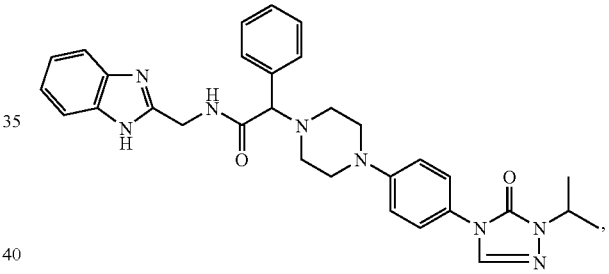
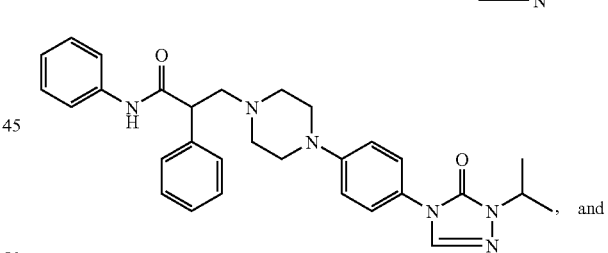
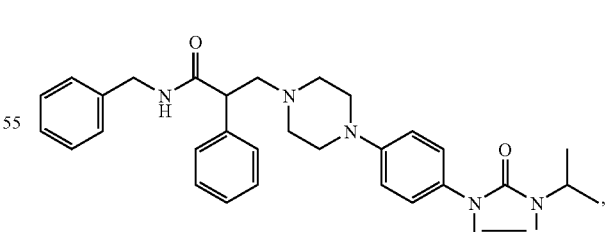
or an N-oxide, a pharmaceutically acceptable acid addition salt or a stereochemically isomeric form thereof.
17. The compound of formula (I) which is selected from the group consisting of 265
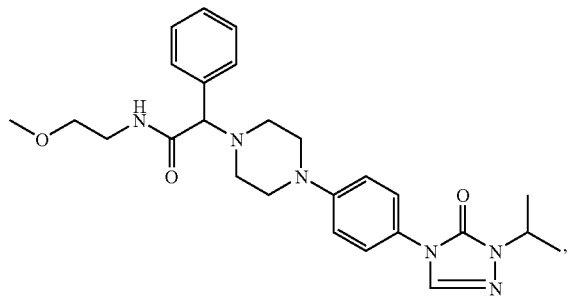
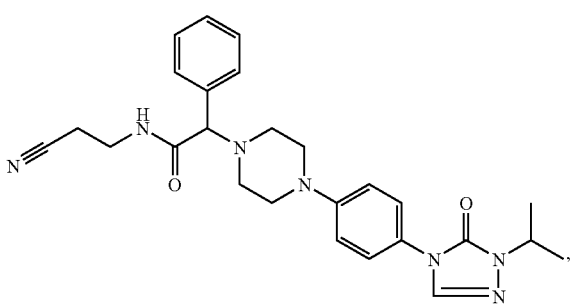
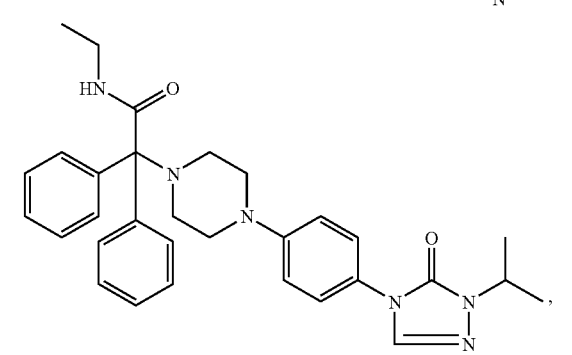
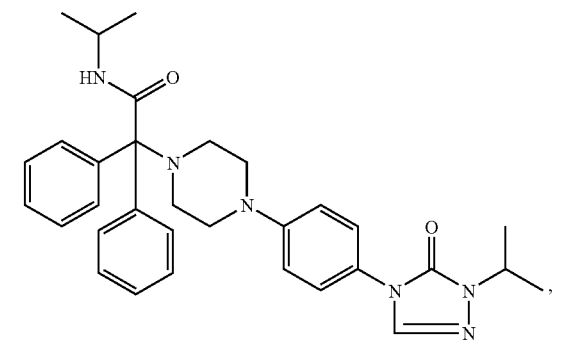
266
-continued
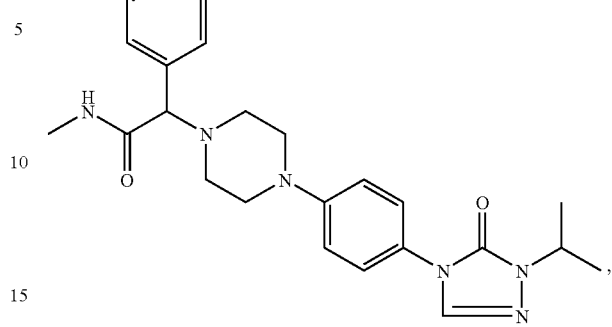
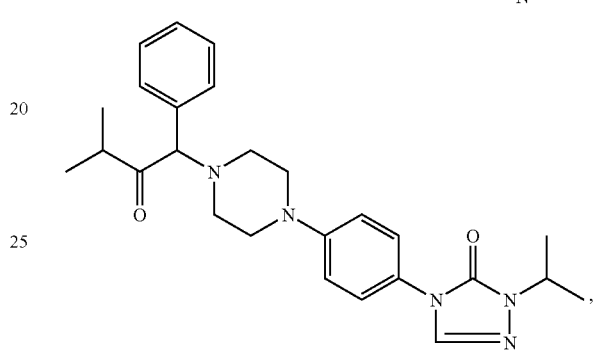
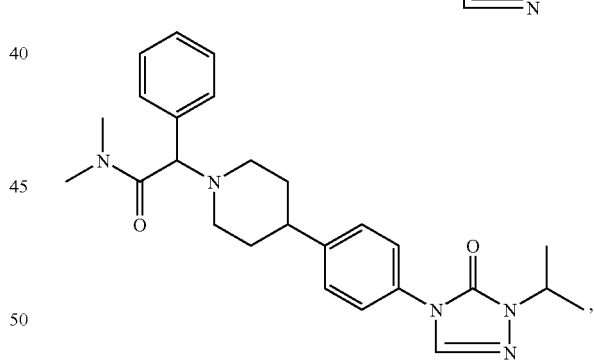
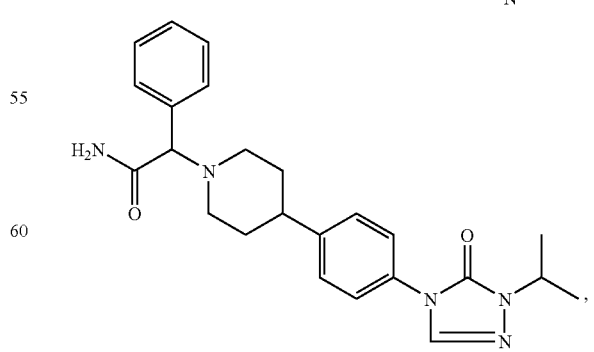

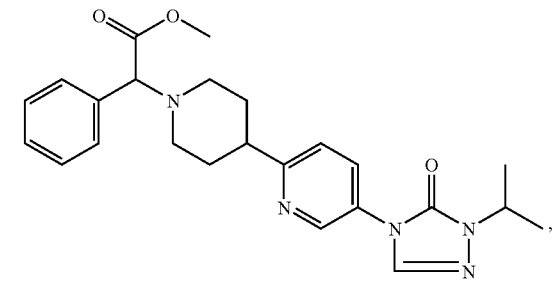
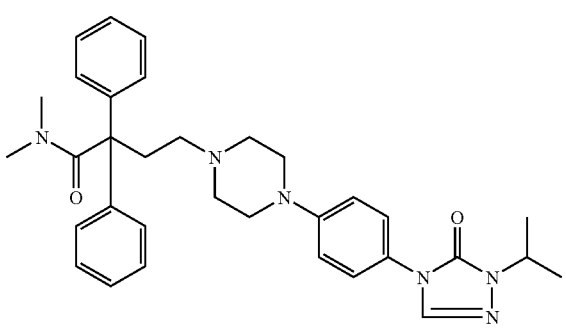
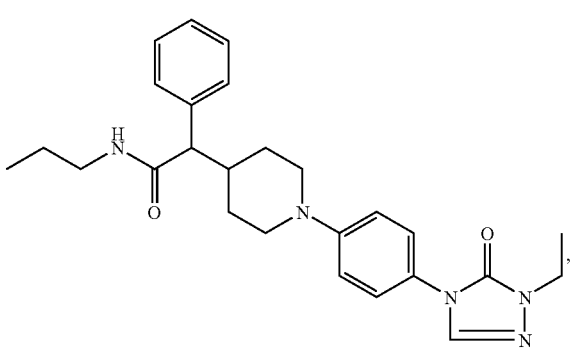
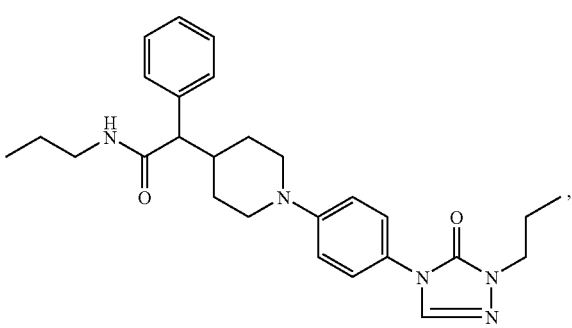
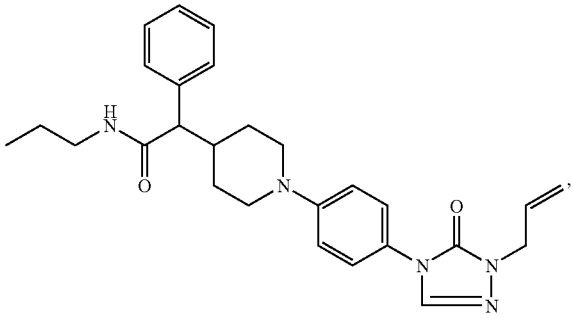
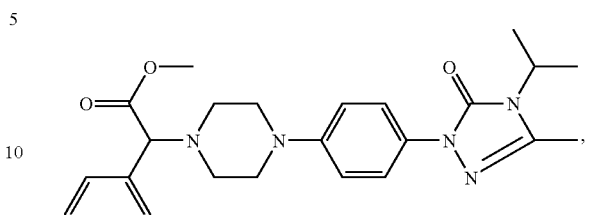
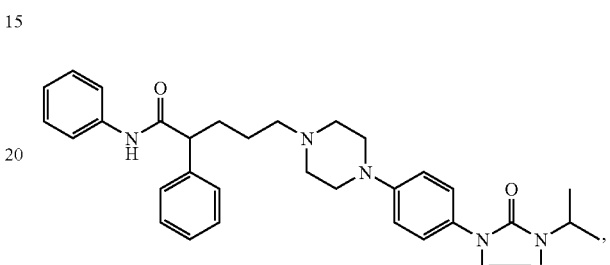
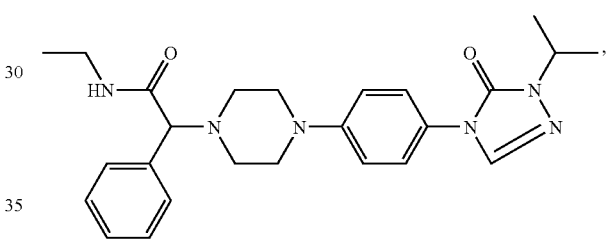
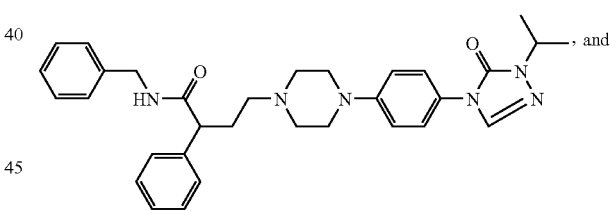
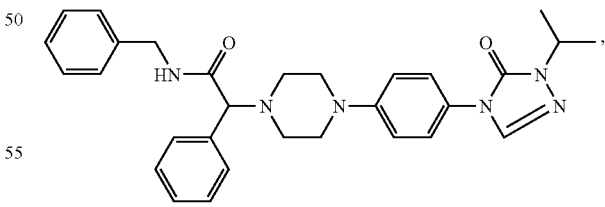
or an N-oxide, a pharmaceutically acceptable acid addition salt or a stereochemically isomeric form thereof.
18. The compound of formula (I) which is selected from the group consisting of

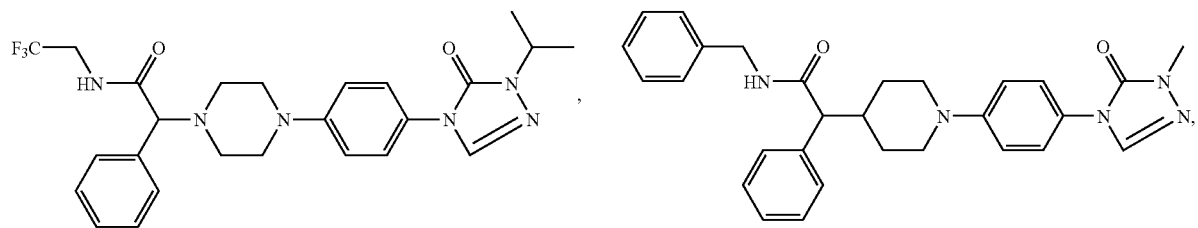
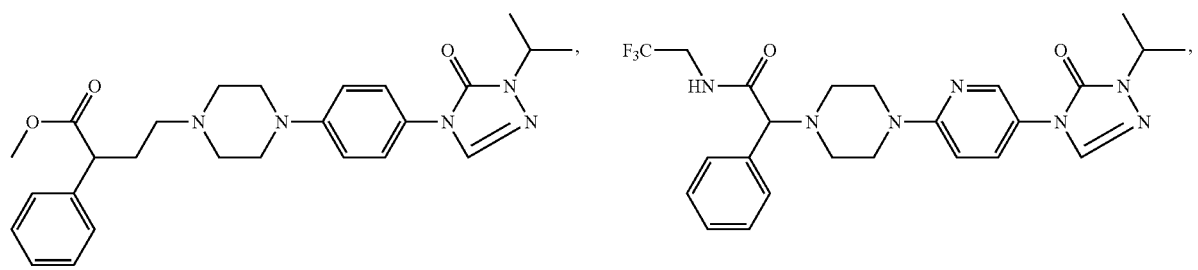
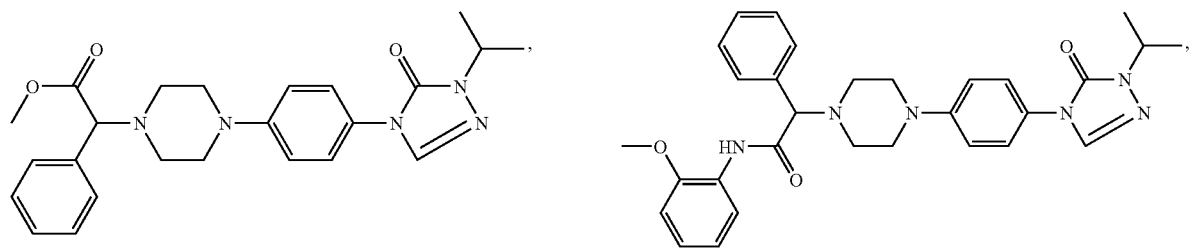
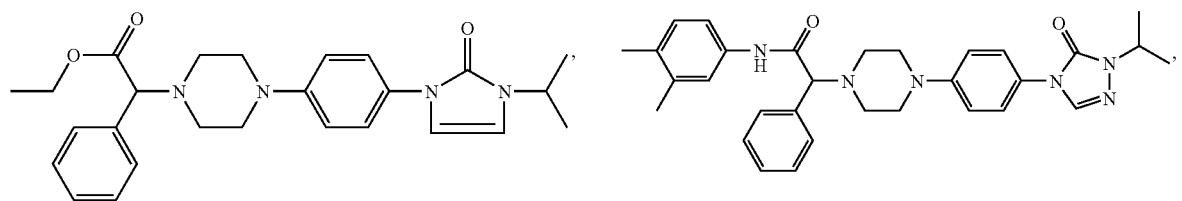
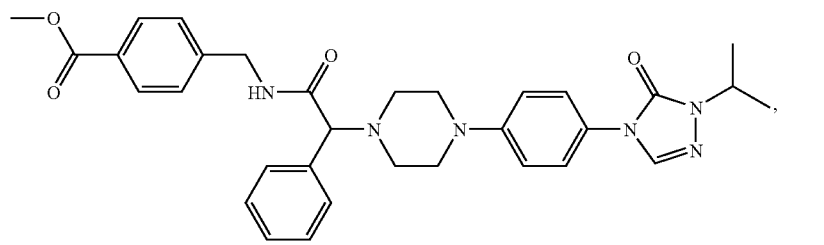
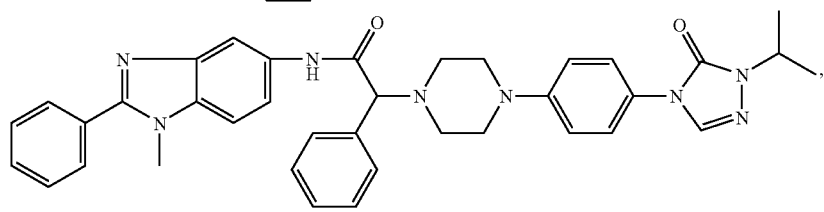

-continued
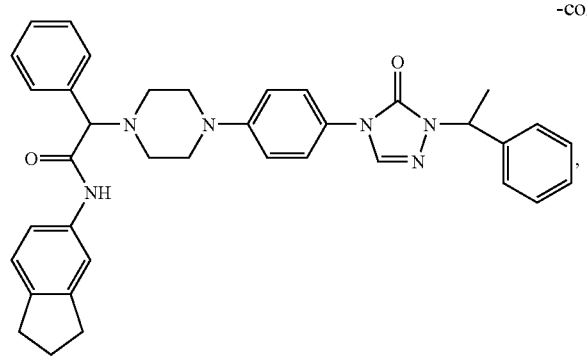
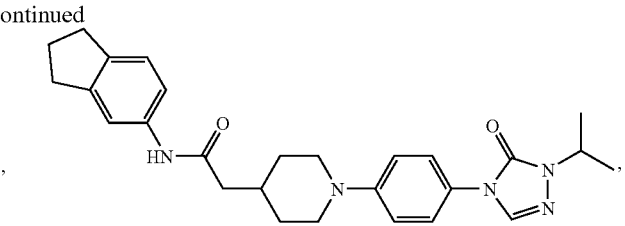
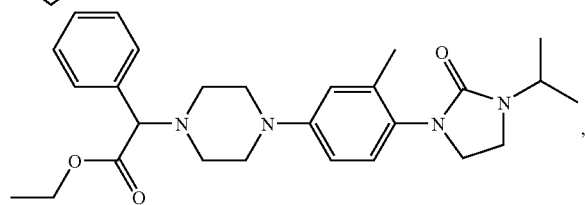
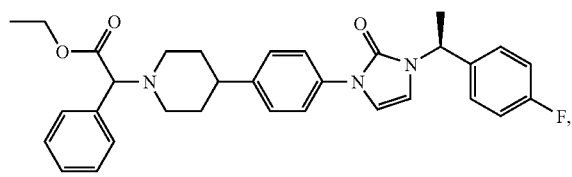
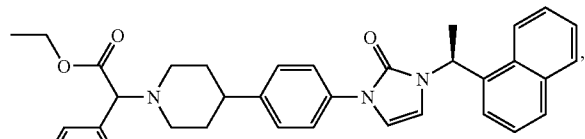
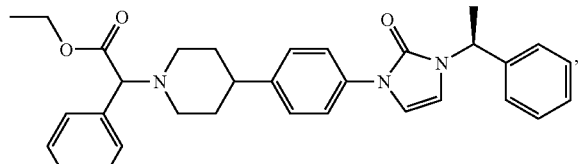
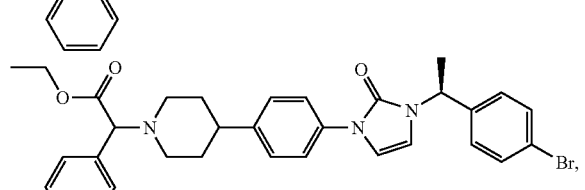
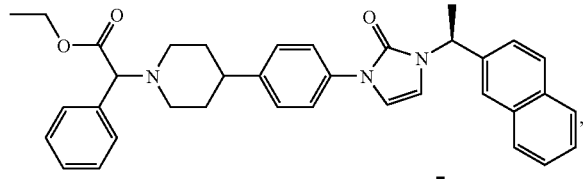
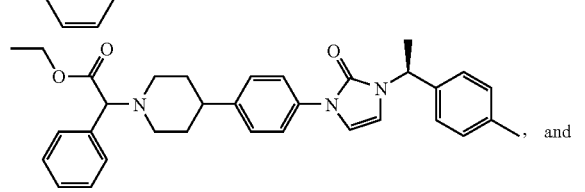, and
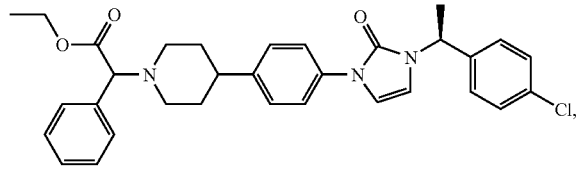
or an N-oxide, a pharmaceutically acceptable acid addition salt or a stereochemically isomeric form thereof.
19. The compound of formula (I) which is selected from the group consisting of
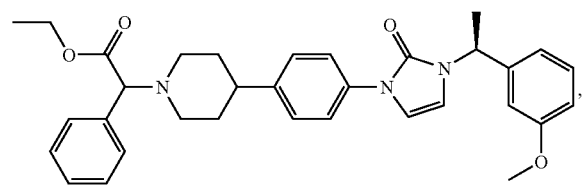
-continued
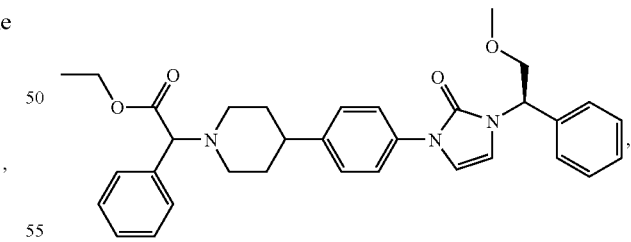
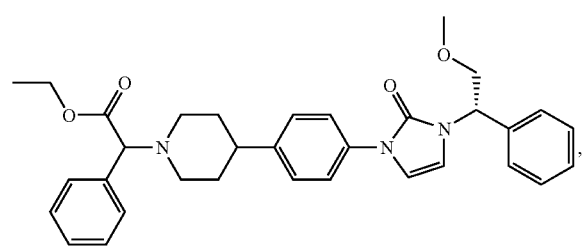
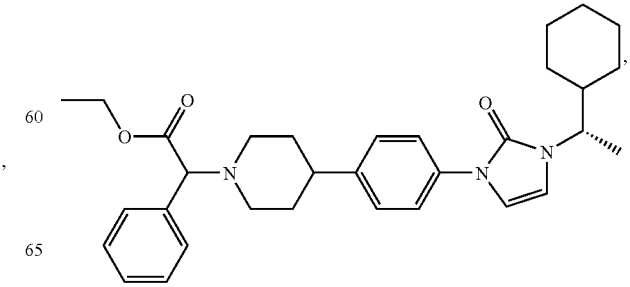

-continued
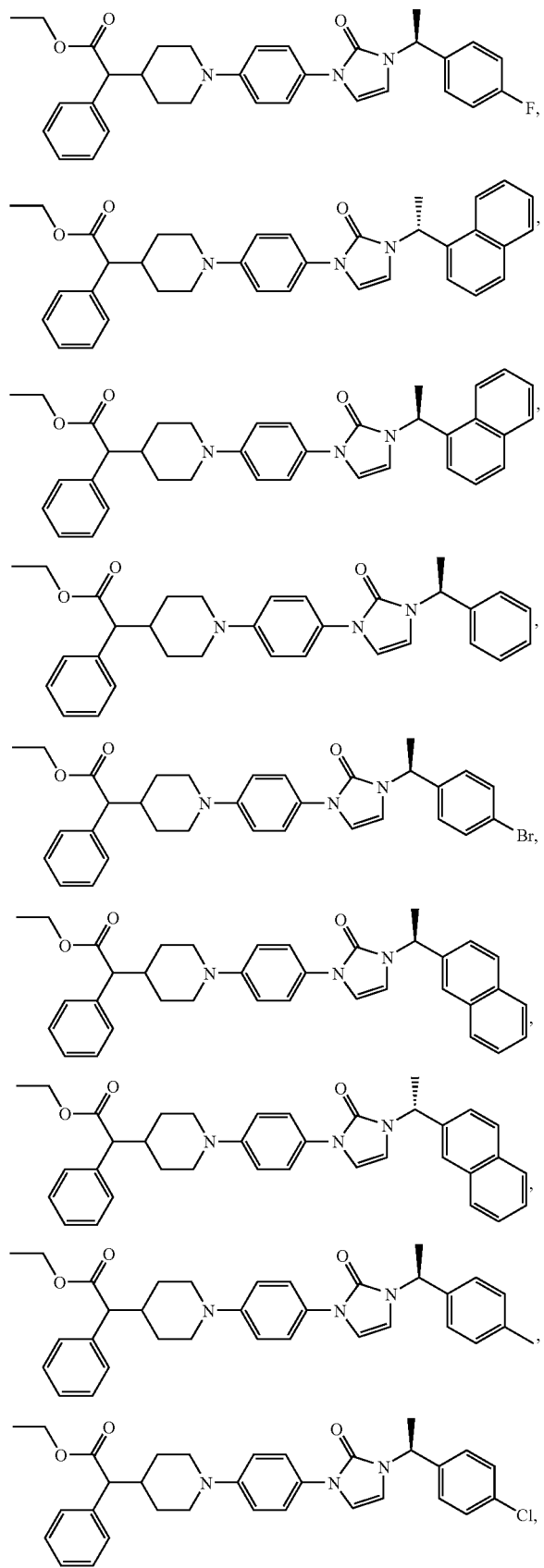
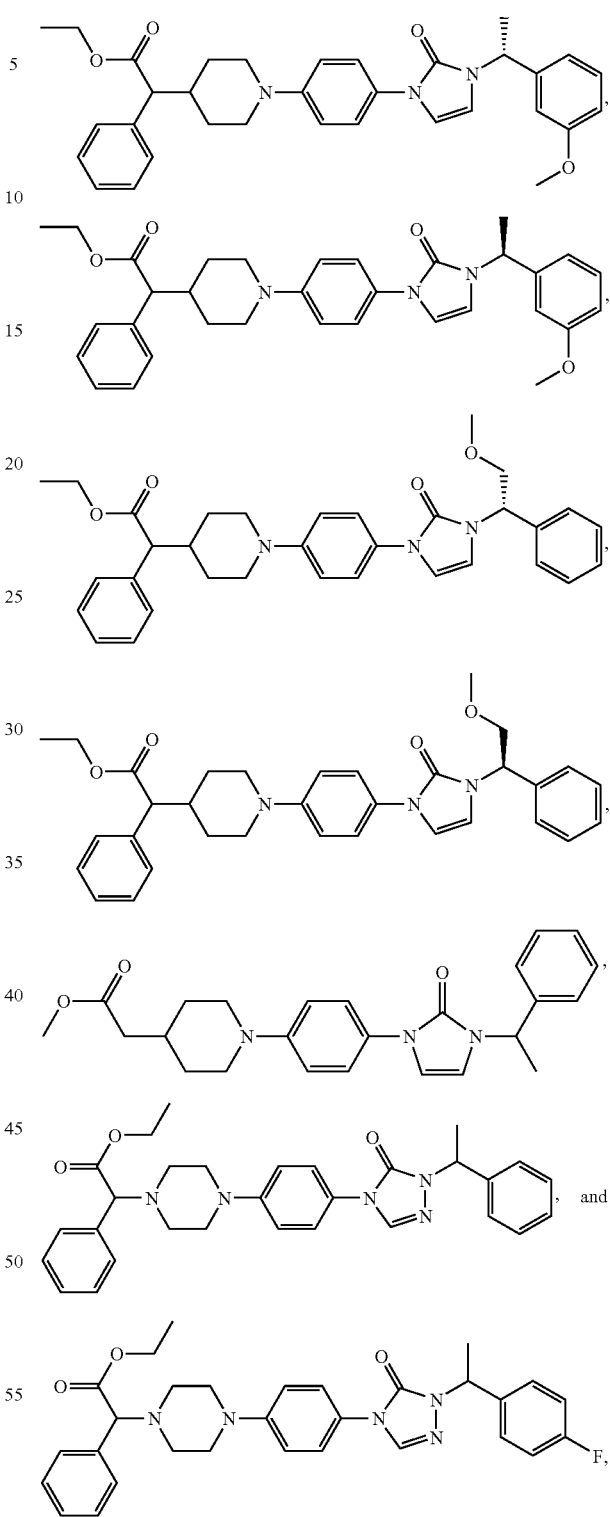
or an N-oxide, a pharmaceutically acceptable acid addition salt or a stereochemically isomeric form thereof.
20. The compound of formula (I) which is selected from the group consisting of 275 276
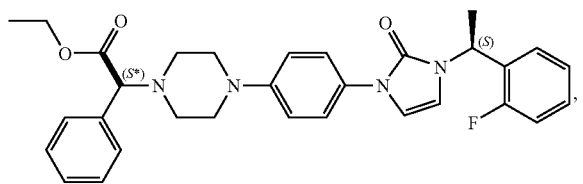 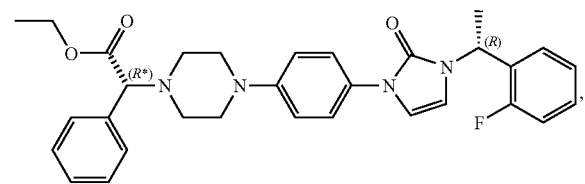
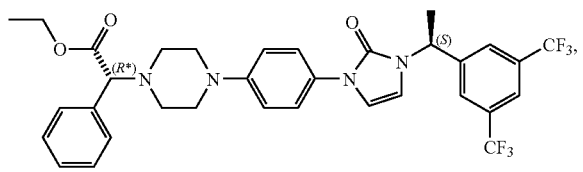 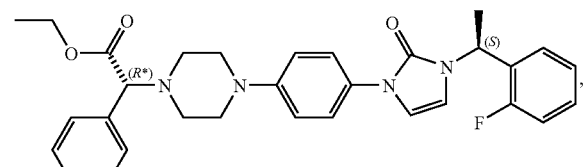
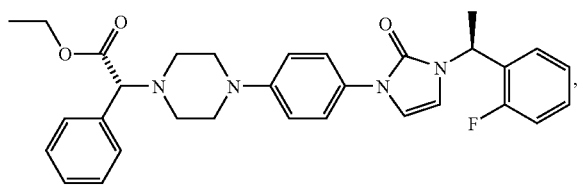 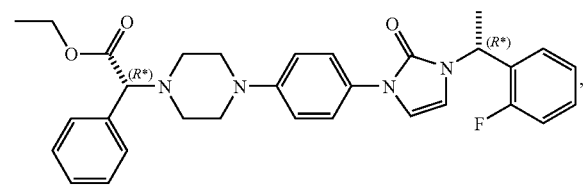
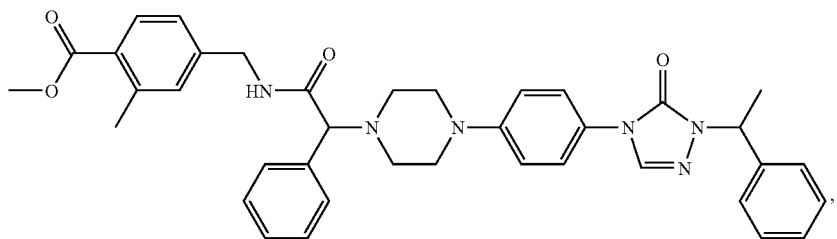
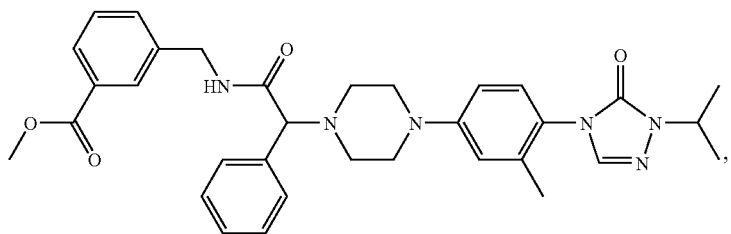
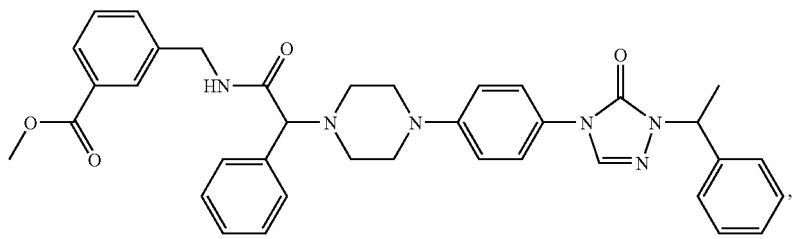
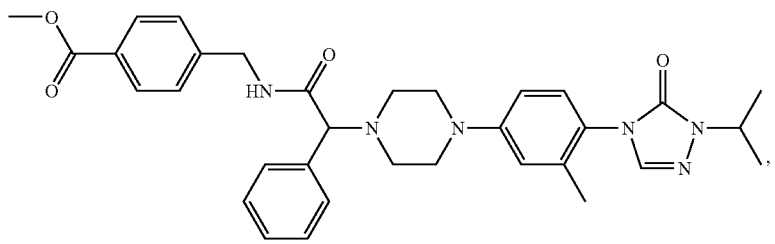

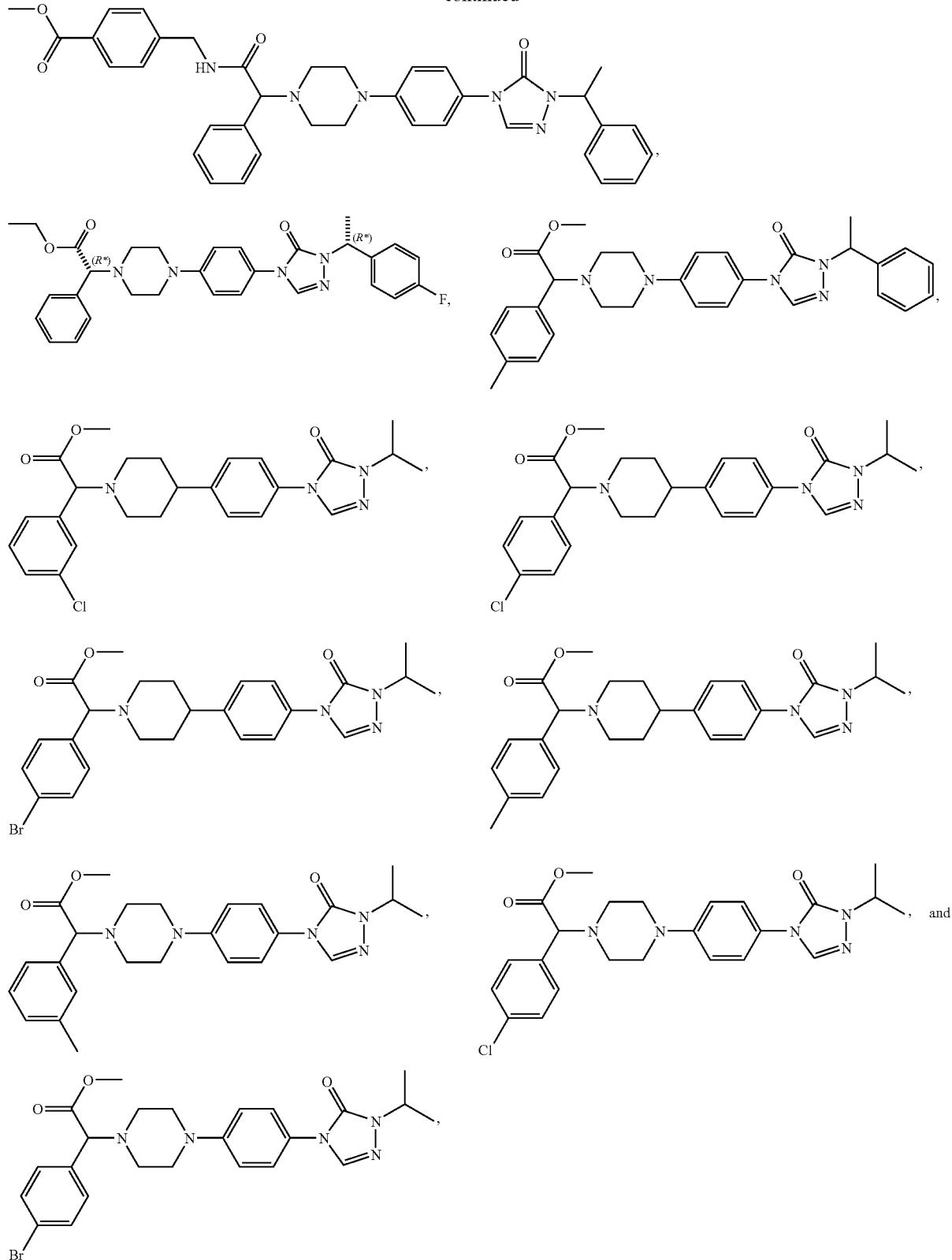
or an N-oxide, a pharmaceutically acceptable acid addition salt or a stereochemically isomeric form thereof.
21. The compound of formula (I) which is selected from the group consisting of 279                                       280
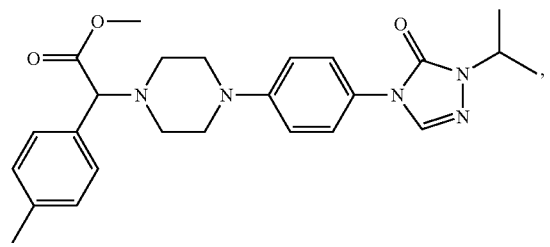
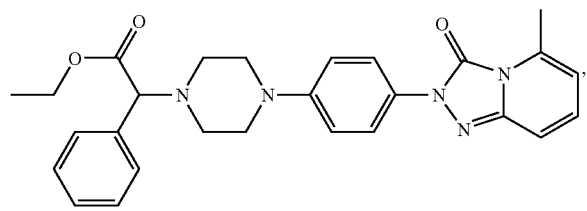
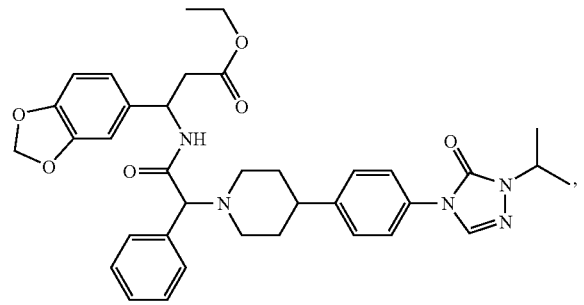
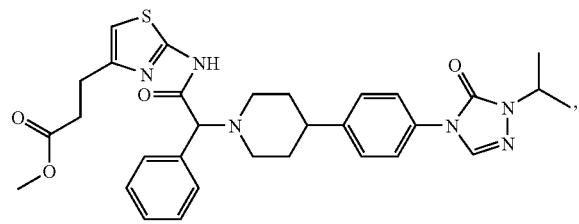
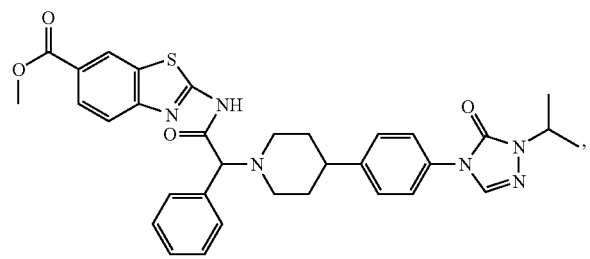
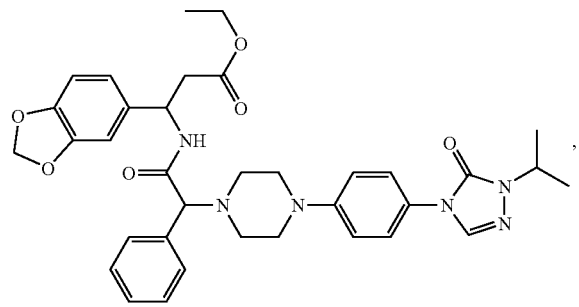
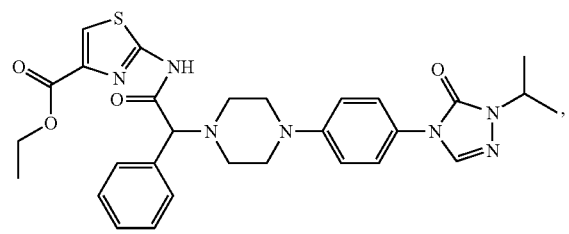
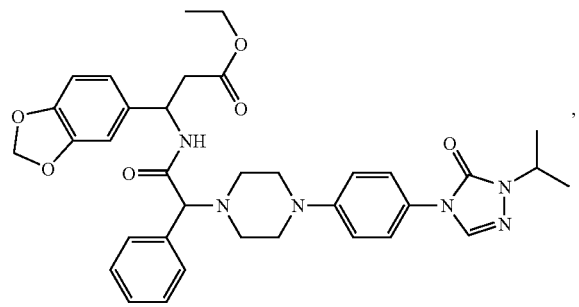
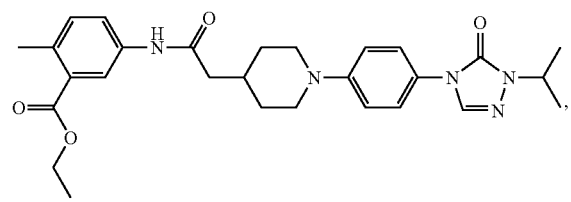
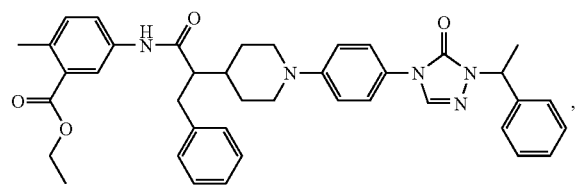
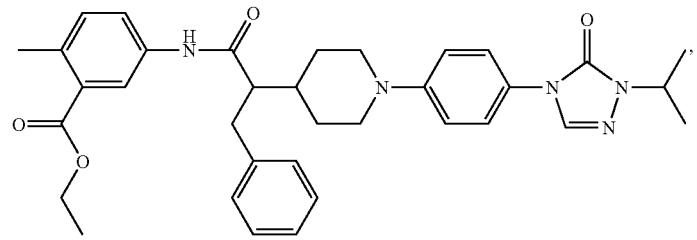

-continued
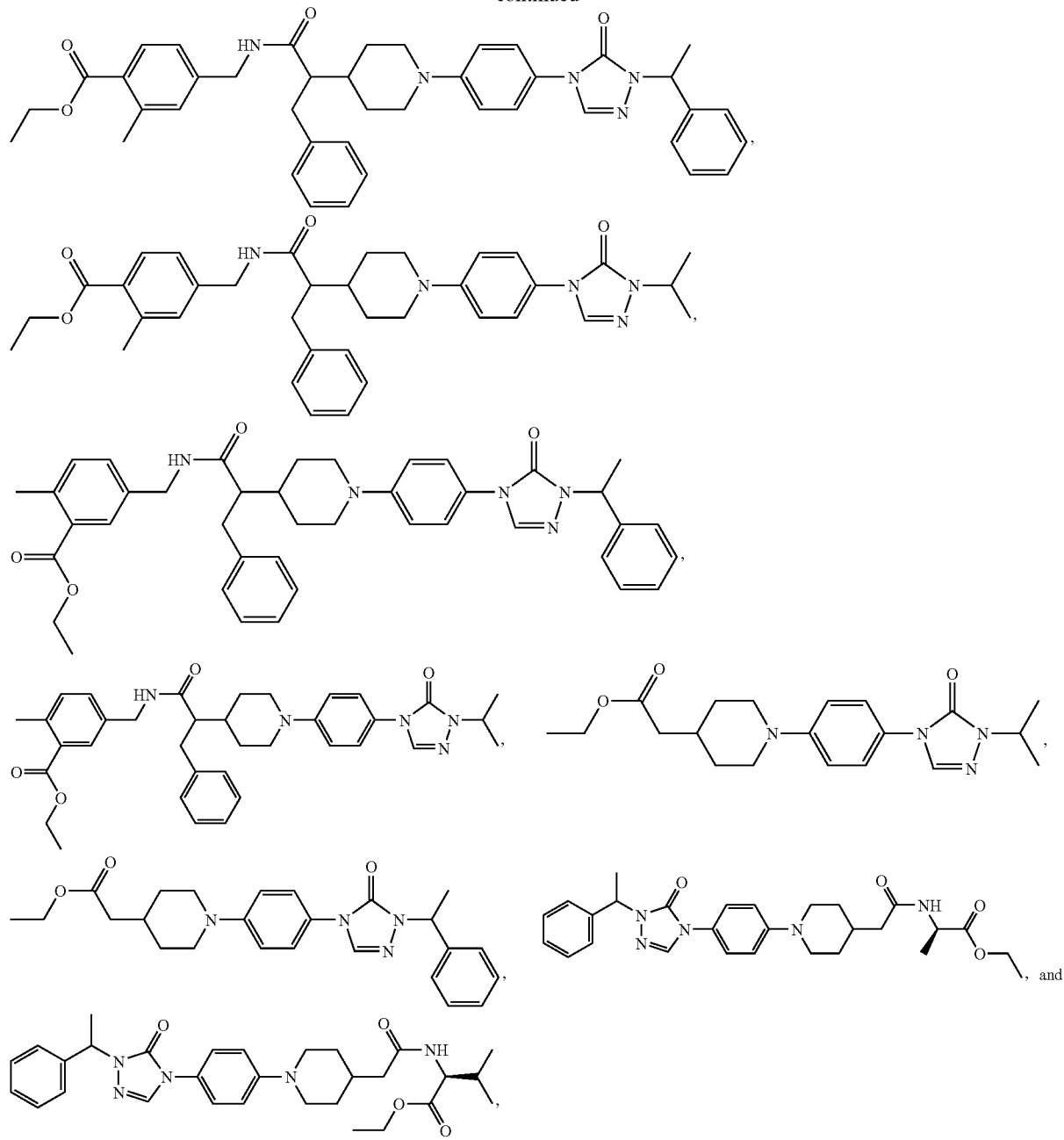
or an N-oxide, a pharmaceutically acceptable acid addition salt or a stereochemically isomeric form thereof.
22. The compound of formula (I) which is selected from the group consisting of

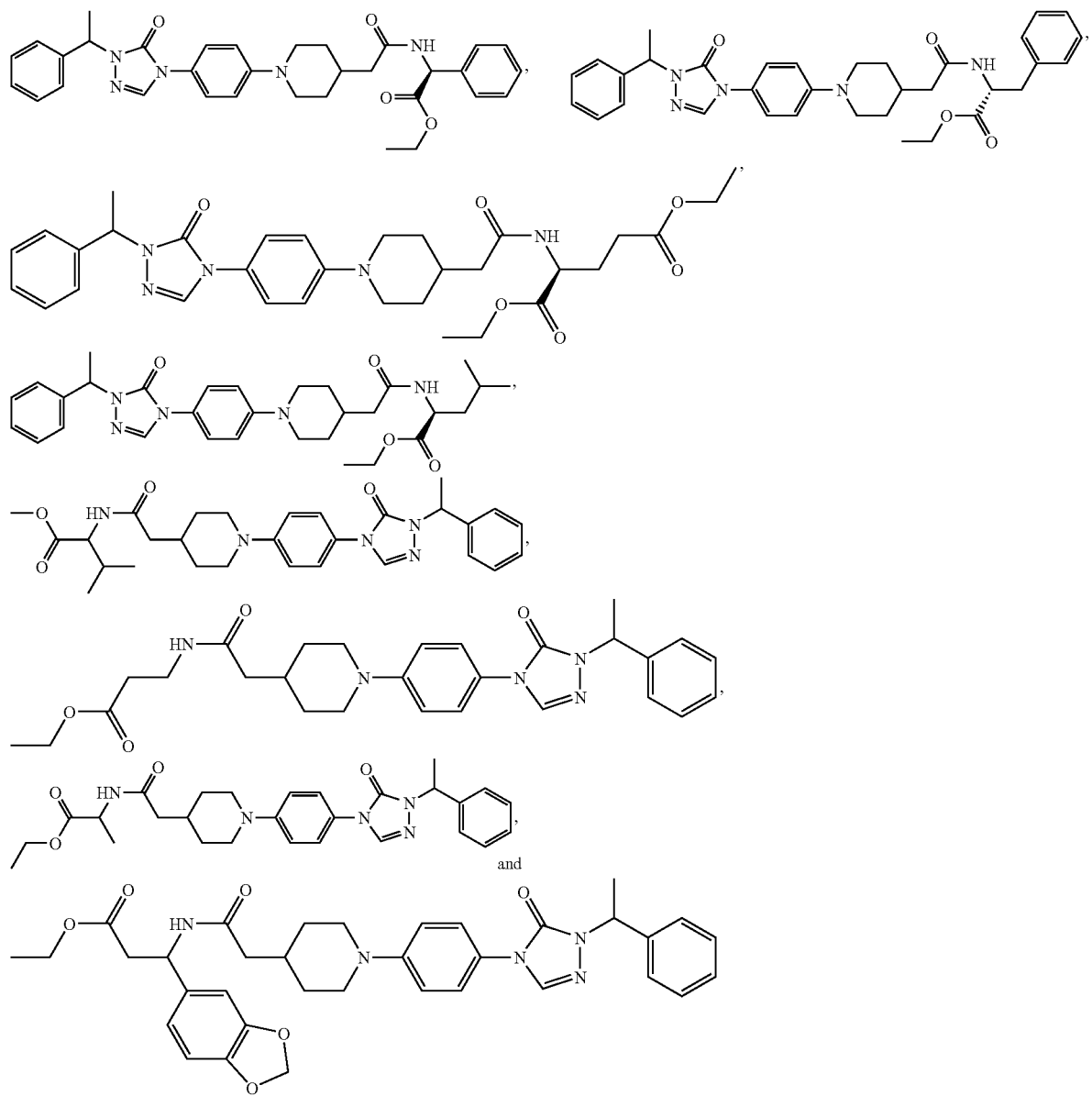
or an N-oxide, a pharmaceutically acceptable acid addition salt or a stereochemically isomeric form thereof.
23. A compound which is
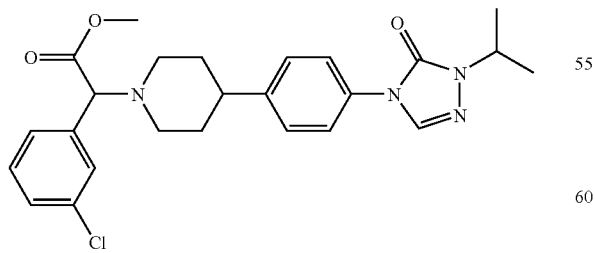
an N-oxide, a pharmaceutically acceptable acid addition salt or a stereochemically isomeric form thereof.
* * * * *